(12) United States Patent
Scheres et al.

(10) Patent No.: US 7,563,946 B2
(45) Date of Patent: Jul. 21, 2009

(54) PLANT DEVELOPMENT REGULATING GENE AND ITS USES

(75) Inventors: Ben Scheres, Utrecht (NL); Ikram Blilou, Utrecht (NL); Saskia Folmer, Amsterdam (NL)

(73) Assignee: CropDesign, N.V., Ghent (BE)

( * ) Notice: Subject to any disclaimer, the term of this patent is extended or adjusted under 35 U.S.C. 154(b) by 591 days.

(21) Appl. No.: 10/416,621

(22) PCT Filed: Nov. 13, 2001

(86) PCT No.: PCT/EP01/13116

§ 371 (c)(1),
(2), (4) Date: Nov. 28, 2003

(87) PCT Pub. No.: WO02/38599

PCT Pub. Date: May 16, 2002

(65) Prior Publication Data

US 2004/0172686 A1    Sep. 2, 2004

Related U.S. Application Data

(60) Provisional application No. 60/250,402, filed on Nov. 30, 2000.

(30) Foreign Application Priority Data

Nov. 13, 2000   (EP) .................................. 00870271

(51) Int. Cl.
*C12N 15/82* (2006.01)
*C12N 15/63* (2006.01)
*C12N 15/29* (2006.01)
*C12N 15/11* (2006.01)

(52) U.S. Cl. .................... 800/290; 800/284; 435/320.1; 435/468; 536/23.1; 536/23.6

(58) Field of Classification Search .................. None
See application file for complete search history.

(56) References Cited

U.S. PATENT DOCUMENTS 6,114,602 A * 9/2000 Barg et al. .................. 800/290

FOREIGN PATENT DOCUMENTS

EP          1 033 405        9/2000
WO       WO 01/02430        1/2001
WO       WO 0102430     *  1/2001

OTHER PUBLICATIONS

Hughes D.A. et al. Molecular cloning and sequence analysis of cdc27+ required for the G2-M transition in the fission yeast *Schizosaccharomyces pombe*. Mol Gen Genet. Feb. 1992;231(3):401-10.*
Tugendreich S. et al. CDC27Hs colocalizes with CDC16Hs to the centrosome and mitotic spindle and is essential for the metaphase to anaphase transition. Cell. Apr. 21, 1995;81(2):261-8.*
Balasubramanian et al 2004 Current Biology 14:806-818.*
Willemsen et al 1998 Development 125:521-531.*
Iturriaga et al 1992 Plant Molecular Biology 20:555-558.*
Blilou et al 2002 Genes and Development 16:2566-2575.*
Friml et al. (2002) "AtPIN4 Mediates Sink-Driven Auxin Gradients and Root Patterning in *Arabidopsis*", Cell, 108(5):661-673.
Grebe et al. (2002) "Cell Polarity Signaling in *Arabidopsis* Involves a BFA-Sensitive Auxin Influx Pathway", Current Biology, 12(4):329-334.
Harada (1999) "Signaling in plant embryogenesis" Curr. Opin. Plant Biol., 2(1):23-27.
Lin et al. (1998), *Arabidopsis thaliana* chromosome II section 115 of 255 of the complete sequence. Sequence from clones F6F22, T2G17, *EMBL*, Accession No. AC006081.
Lin et al. (2000) CDC27/NUC2-like protein. *Swall* Accession No. Q9SL81.
Sato, et al. (2000) "Structural Analysis of *Arabidopsis thaliana* Chromosome 3.1. Sequence Features of the Regions of 4,504,864 bp Covered by Sixty P1 and TAC Clones", DNA Research, 7(2):131-135.
Willemsen, et al. (1998) "The Hobbit gene is required for formation of the root meristem in the *Arabidopsis* embryo" Development 125:521-531.
Wolkenfelt et al. (1997) "The role of the HBT gene in *Arabidopsis* Embryogenesis" Development Biology 186:272.

* cited by examiner

*Primary Examiner*—Anne Kubelik
*Assistant Examiner*—Brent Page
(74) *Attorney, Agent, or Firm*—Ann R. Pokalsky; Dilworth & Barrese, LLP

(57) ABSTRACT

The present invention is situated in the field of plant development. More specifically the invention relates to the identification and characterization of plant development regulating proteins (cdc27B) required for correct plant development as well as to mutants (hbt, HOBBIT) thereof. The present invention thus relates to isolated nucleic acid sequences and protein sequences, and to vectors and host cells comprising said nucleic acid sequences. The invention further relates to transgenic cells and plants comprising and expressing said sequences and to methods for obtaining said cells and plants. The present invention further relates to the use of said wild type or mutant genes and proteins in methods to modify plant development. Said genes and proteins can furthermore be used in methods for mimicking or modifying auxin-related effects.

12 Claims, 22 Drawing Sheets

Figure 1:
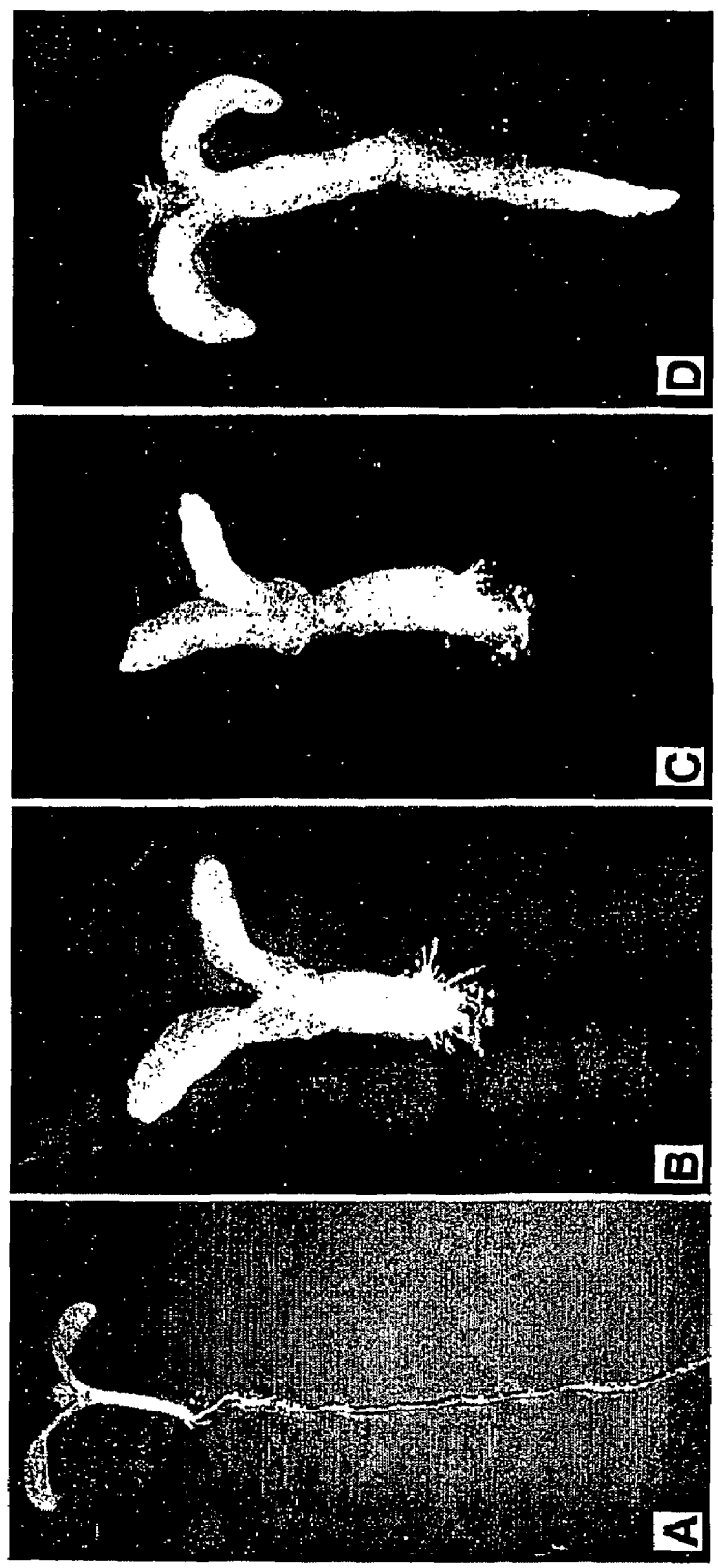

```
Cdc27A       1-  MMENLLANCVQKNLNHFMFTNAIFLCELLLAQPPSE---------------
HBT/Cdc27B   1-  MEAMLV-DCVNNSLRHFVYKNAIFMCERLCAEFPSEVNLQLLATSYLQNN
                                    SEQ ID NO 3

Cdc27A      37-  --------------SRYLFAFSCFKLDLLGEAEAALLP-CEDYAEEVP
HBT/Cdc27B  50-  QAYSAYHLLKGTQMAQSRYLFALSCFQMDLLNEAESALCPVNEPGAE-IP
                                    SEQ ID NO 3

Cdc27A      71-  GGAAGHYLLGLIYRYSGRKNCSIQQFRMALSFDPLCWEAYGELCSLGNNK
HBT/Cdc27B  99-  NGAAGHYLLGLIY---KRKNAA-QQFKQSLTIDPLLWAAYEELCILG---
                                    SEQ ID NO 3

Cdc27A     121-  FNSLQWRSVITFSGAAEEASTVFGNVASQRLQKTCVEQRISFSEG-ATID
HBT/Cdc27B 141-  --------------AAEEATAVFGETAALSIQKQYMQQ-LSTSLGLNTYN
                                    SEQ ID NO 3

Cdc27A     170-  Q--ITDSDKAL--KDTGLSQTEHIPGENQQDLKIMQQPGDIPPNTDRQLS
HBT/Cdc27B 177-  EERNSTSTKNTSSEDYSPRQSKHTQSHGLKDISGNFESHGVNGGV----S

Cdc27A     214-  TNGWDLNTPSPVLLQVMD-ALPPLLKNMRRPAV-EG-SLMS------V
HBT/Cdc27B 223-  NMSFY-NTPSPVAAQLSGIAPPPL-FRNFQ-PAVANPNSLITDSSPKSTV

Cdc27A     264-  HG-VRVRRRNFFSE----ELSAEAQEESG-RRRSARIAA-------RKKN
HBT/Cdc27B 270-  NSTLQAPRRKFVDEGKLRKISGRLFSDSGPRR-SSRLSADSGANINSSVA

Cdc27A     300-  PMSQSFGKDSHWLHLSPSESNYAPSLSSMIGKCRIQSSK------EVIPD
HBT/Cdc27B 319-  TVSGNVNNASKYLGGSK--------LSSLALRS-VTLRKGHSWANENM-D

Cdc27A     341-  -TV--------TLNDPATTSGQSVSDIGSSVDDEEKSNPSE--SSPDRFS
HBT/Cdc27B 359-  EGVRGEPFDDSRPNTASTTGSMASND----QEDETMSIGGIAMSSQT---

Cdc27A     376-  LIS-GISEVLSLLKILGDGHRHLHMYKCQEALLAYQKLSQKQYNTHWVLM
HBT/Cdc27B 402-  -ITIGVSEILNLLRTLGEGCRLSYMYRCQEALDTYMKLPHKHYNTGWVLS

Cdc27A     423-  QVGKAYFELQDYFNADSSFTLAHQKYPYALEGMDTYSTVLYHLKEEMRLG
HBT/Cdc27  451-  QVGKAYFELIDYLEAEKAFRLARLASPYCLEGMDIYSTVLYHLKEDMKLS

Cdc27A     473-  YLAQELISVDRLSPESWCAVGNCYSLRKDHDTALKMFQRAIQLNERFTYA
HBT/Cdc27B 500-  YLAQELISTDRLAPQSWCAMGNCYSLQKDHETALKNFLRAVQLNPRFAYA

Cdc27A     523-  HTLCGHEFAALEEFEDAERCYRKALGIDTRHYNAWYGLGMTYLRQEKFEF
HBT/Cdc27B 551-  HTLCGHEYTTLEDFENGMKSYQNALRVDTRHYNAWYGLGMIYLRQEKLEF

Cdc27A     573-  AQHQFQLALQINPRSSVIMCYYGIALHESKRNDEALMMMEKAVLTDAKNP
HBT/Cdc27B 601-  SEHHFRMAFLINPSSSVIMSYLGTSLHALKRSEEALETMEQAIVADRKNP

Cdc27A     623-  LPKYYKAHILTSLGDYHKAQKVLEELKECAPQESSVHASL-GKIYNQLKQ
HBT/Cdc27B 651-  LPMYQKANILVCLERLDEALEVLEELKEYAPSESSVYA-IMGRIYKRRNM

Cdc27A     673-  YDKAVLHFGIALDLSPSPSDAVKIKVNYSFPVFASQASIMVTFCI-739
HBT/Cdc27B 700-  HDKAMLHFGLALDMKPPATDVAAIKAAMEKLHVPDEIDESP-740
```

FIGURE 8

```
ATG GAA GCT ATG CTT GTG GAC TGT GTA AAC AAC AGT CTT CGT CAT TTT GTC TAC
 M   E   A   M   L   V   D   C   V   N   N   S   L   R   H   F   V   Y  -18
AAA AAT GCT ATT TTC ATG TGC GAG CGT CTC TGC GCT GAG TTT CCT TCT GAG GTT
 K   N   A   I   F   M   C   E   R   L   C   A   E   F   P   S   E   V  -36
AAT TTG CAG CTA TTA GCC ACC AGC TAC CTG CAG AAT AAT CAA GCT TAC AGT GCA
 N   L   Q   L   L   A   T   S   Y   L   Q   N   N   Q   A   Y   S   A  -54
TAT CAT CTG CTA AAG GGA ACA CAA ATG GCT CAG TCC CGA TAC TTG TTC GCA TTA
 Y   H   L   L   K   G   T   Q   M   A   Q   S   R   Y   L   F   A   L  -72
                                     GTT
                                      V
                                     hbt5421
TCA TGC TTC CAG ATG GAC CTT CTC AAT GAA GCT GAA TCT GCA CTC TGC CCT GTT
 S   C   F   Q   M   D   L   L   N   E   A   E   S   A   L   C   P   V  -90
AAT GAA CCT GGT GCG GAG ATC CCA AAT GGT GCA GCA GGC CAT TAC CTT CTT GGA
 N   E   P   G   A   E   I   P   N   G   A   A   G   H   Y   L   L   G -108
CTT ATT TAC AAA AGG AAG AAT GCT GCT CAA CAA TTT AAA CAG TCC TTG ACA ATA
 L   I   Y   K   R   K   N   A   A   Q   Q   F   K   Q   S   L   T   I -126
GAC CCT CTA CTT TGG GCT GCA TAT GAG GAA TTA TGT ATA TTA GGT GCT GCT GAG
 D   P   L   L   W   A   A   Y   E   E   L   C   I   L   G   A   A   E -144
GAA GCA ACT GCA GTT TTT GGT GAA ACA GCT GCT CTC TCC ATT CAA AAG CAG TAT
 E   A   T   A   V   F   G   E   T   A   A   L   S   I   Q   K   Q   Y -162
ATG CAA CAA CTG TCA ACT TCC CTC GGC TTA AAC ACT TAC AAC GAG GAA CGT AAT
 M   Q   Q   L   S   T   S   L   G   L   N   T   Y   N   E   E   R   N -180
TCA ACT TCT ACT AAA AAC ACG AGT TCT GAA GAT TAT AGT CCA AGG CAG TCT AAA
 S   T   S   T   K   N   T   S   S   E   D   Y   S   P   R   Q   S   K -198
CAC ACA CAA AGC CAT GGC CTT AAA GAT ATC TCC GGA AAT TTC CAT TCT CAT GGA
 H   T   Q   S   H   G   L   K   D   I   S   G   N   F   H   S   H   G -216
GTT AAT GGA GGT GTT TCG AAC ATG TCA TTC TAT AAT ACG CCT TCG CCA GTG GCT
 V   N   G   G   V   S   N   M   S   F   Y   N   T   P   S   P   V   A -234
GCA CAG CTA TCC GGT ATA GCT CCA CCA CCA CTT TTC CGG AAT TTT CAG CCA GCT
 A   Q   L   S   G   I   A   P   P   P   L   F   R   N   F   Q   P   A -252
              AGT
               S
              hbt5422; hbt5423; hbt5859; hbt9624
GTT GCA AAC CCA AAC TCC CTT ATT ACT GAC AGT TCT CCA AAG TCC ACT GTT AAC
 V   A   N   P   N   S   L   I   T   D   S   S   P   K   S   T   V   N -270
TCT ACT CTT CAA GCA CCT AGA AGA AAG TTT GTA GAT GAA GGA AAG TTA CGT AAG
 S   T   L   Q   A   P   R   R   K   F   V   D   E   G   K   L   R   K -288
ATT TCT GGC AGA CTA TTT TCT GAT TCT GGT CCA CGA CGG AGT TCA AGA CTG TCT
 I   S   G   R   L   F   S   D   S   G   P   R   R   S   S   R   L   S -306
GCT GAT TCA GGG GCA AAC ATT AAT TCA AGT GTT GCA ACA GTA AGC GGA AAT GTG
 A   D   S   G   A   N   I   N   S   S   V   A   T   V   S   G   N   V -324
AAC AAC GCT TCC AAG TAT TTG GGA GGT TCT AAA TTG AGT TCT TTG GCA CTT CGT
 N   N   A   S   K   Y   L   G   G   S   K   L   S   S   L   A   L   R -342
TCT GTA ACA CTT CGG AAG GGA CAC TCC TGG GCA AAT GAA AAC ATG GAT GAA GGG
 S   V   T   L   R   K   G   H   S   W   A   N   E   N   M   D   E   G -360
GTC CGT GGG GAA CCT TTT GAT GAT TCA AGG CCT AAT ACT GCC TCA ACG ACT GGT
 V   R   G   E   P   F   D   D   S   R   P   N   T   A   S   T   T   G -378
TCT ATG GCT TCC AAT GAT CAA GAA GAC GAA ACA ATG TCG ATT GGT GGC ATA GCA
 S   M   A   S   N   D   Q   E   D   E   T   M   S   I   G   G   I   A -396
ATG AGT TCT CAA ACA ATC ACA ATT GGT GTT TCG GAA ATT TTA AAC CTC CTT AGG
 M   S   S   Q   T   I   T   I   G   V   S   E   I   L   N   L   L   R -414
ACA CTC GGA GAA GGG TGT AGA CTT TCA TAC ATG TAC AGG TGT CAG GAG GCA CTG
 T   L   G   E   G   C   R   L   S   Y   M   Y   R   C   Q   E   A   L -432
              AGG                                            hbt9620
               R
              hbt1611
```

FIGURE 9-1

```
GAT ACG TAT ATG AAA CTT CCA CAT AAG CAT TAT AAT ACA GGA TGG GTT CTT TCC
 D   T   Y   M   K   L   P   H   K   H   Y   N   T] [G   W   V   L   S   -450
CAG GTC GGG AAA GCA TAC TTT GAA CTA ATT GAC TAT TTA GAG GCT GAA AAG GCA
 Q   V   G   K   A   Y   F   E   L   I   D   Y   L   E   A   E   K   A   -468
hbt9620 hbt5721
TTC CGT CTT GCC CGT CTG GCT TCT CCT TAT TGC TTA GAA GGA ATG GAT ATA TAC
 F   R   L   A   R   L   A   S   P   Y   C] [L   E   G   M   D   I   Y   -486
TCT ACG GTC CTC TAT CAT TTG AAG GAA GAC ATG AAG CTG AGT TAC TTG GCT CAG
 S   T   V   L   Y   H   L   K   E   D   M   K   L   S   Y   L   A   Q   -504
        hbt5721
GAA CTA ATA TCA ACC GAT CGC TTA GCT CCT CAA TCT TGG TGT GCT ATG GGA AAT
 E   L   I   S   T   D   R   L   A] [P   Q   S   W   C   A   M   G   N   -522
                                        TAA
                                         *  hbt2311
TGC TAT AGC TTG CAA AAG GAC CAT GAG ACC GCA CTG AAG AAT TTC CTA CGA GCT
 C   Y   S   L   Q   K   D   H   E   T   A   L   K   N   F   L   R   A   -540
                                                                    GTT
                                                         hbt8052    V
GTT CAA CTG AAT CCA AGA TTT GCA TAT GCA CAT ACC TTA TGT GGC CAC GAA TAC
 V   Q   L   N   P   R   F] [A   Y   A   H   T   L   C   G   H   E   Y   -558
ACA ACT CTT GAG GAT TTT GAG AAC GGA ATG AAA AGT TAC CAA AAC GCA CTT CGT
 T   T   L   E   D   F   E   N   G   M   K   S   Y   Q   N   A   L   R   -576
GTA GAT ACA AGA CAC TAC AAC GCA TGG TAC GGG CTT GGA ATG ATA TAT CTA CGC
 V   D   T   R   H   Y   N   A   W   Y   G   L   G   M   I   Y   L   R   -594
CAA GAG AAG TTA GAG TTC TCA GAG CAT CAC TTC AGA ATG GCT TTC CTA ATA AAC
 Q   E   K   L   E   F   S   E   H   H   F   R   M   A   F   L   I   N   -612
CCG AGT TCC TCT GTT ATA ATG TCT TAT TTA GGG ACA TCT TTG CAT GCC TTG AAG
 P   S   S] [S   V   I   M   S   Y   L   G   T   S   L   H   A   L   K   -630
AGA AGT GAG GAA GCA CTA GAG ATA ATG GAG CAA GCC ATA GTA GCA GAT AGA AAA
 R   S   E   E   A   L   E   I   M   E   Q   A   I   V   A   D   R   K   -648
AAC CCT CTT CCA ATG TAC CAG AAA GCT AAC ATA CTT GTC TGC TTA GAA AGA TTA
 N] [P   L   P   M   Y   Q   K   A   N   I   L   V   C   L   E   R   L   -666
GAT GAA GCT CTA GAA GTT CTT GAG GAG CTC AAA GAG TAT GCG CCT TCA GAG AGC
 D   E   A   L   E   V   L   E   E   L   K   E   Y   A   P   S   E] [S   -684
AGC GTT TAC GCT TTA ATG GGC AGG ATC TAT AAG CGG CGA AAC ATG CAC GAT AAA
 S   V   Y   A   L   M   G   R   I   Y   K   R   R   N   M   H   D   K   -702
GCC ATG CTT CAT TTC GGT CTA GCT TTA GAT ATG AAA CCG CCT GCA ACT GAC GTT
 A   M   L   H   F   G   L   A   L   D   M   K   P   P   A]  T   D   V   -720
GCT GCA ATA AAG GCT GCA ATG GAG AAA TTG CAT GTT CCA GAT GAG ATC GAT GAG
 A   A   I   K   A   A   M   E   K   L   H   V   P   D   E   I   D   E   -738
AGC CCG TGA
 S   P   *
```

FIGURE 9-2

```
ATGGAAGCTA TGCTTGTGGA CTGTGTAAAC AACAGTCTTC GTCATTTTGT   -50
CTACAAAAAT GCTATTTTCA TGTGCGAGCG TCTCTGCGCT GAGTTTCCTT  -100
CTGAGGTAAT CACCCTCTTC TTTCACTCTC TCTCTCTGAT TTTACCTCTC  -150
TAATTCAAAT TCTGTAAATC GAAGCTCTTG GAATGGTAAA TTTGATATTT  -200
TTGGGTTTGT AATTCCTCTG GGTATCTATG AATTCGTCGA AAGTGCGTCT  -250
CTTTTTGGAT TTGGAATTCG ATAGCTTCAC TGTGTTCTTC GAGATTGATT  -300
TTGGTTTCTT ACCTTTTAGC CCTTTGTTTT CAAGATCCGT GTGTTCAATT  -350
AGGAGATGAA TTCGTGTTCT TTTCTCTCTC TTGTTGAATT TGTTTTCTCT  -400
AGTAGCTGTG CTCAATGCTC ATTACTGATT TGGTCTTTGG AAAATTTGCA  -450
TTTTGAGGGT TAATGACTTT TGTCCATATA TGTGATCTCA AGTTTAAGTA  -500
TTTATTATCC TTGGAACTTA GCTATGAGTC AACTGTTAGA GGAATGTCTC  -550
TGGGATTATC TCAAGCTTTG TTAAAATTTG GGTTAATACA GCTTCAATAG  -600
TAGTTGAGAA AGTATTCATT CATTCAGCCT TGGTCTGGA ATATTTTCAA   -650
CATTCGTAGT GGTTGTCCAG TTTCTAGCTT CAGTTAGTAG AAATCATGTC  -700
AATAAATGAT TGGCCTTTTT GTTTGATCAC TTTCTGAATT TTCCTCTTAT  -750
ATAGGTTAAT TTGCAGCTAT TAGCCACCAG CTACCTGCAG AATAATCAAG  -800
CTTACAGTGC ATATCATCTG CTAAAGGGTG CGTGGCATTG TTTCTTGACT  -850
TGTTGCTTGT TAGCCTTTTA GTCAGAATTT TGCACCTTCT TTTGTTAGGT  -900
CGTTTTGATT ATCTTTGTAT ATATATTTTT TTTTTGTTAT GTAAAGGAAC  -950
ACAAATGGCT CAGTCCCGAT ACTTGTTCGC ATTATCATGC TTCCAGATGG -1000
           ■ hbt5421
ACCTTCTCAA TGAAGCTGAA TCTGCACTCT GCCCTGTTAA TGAACCTGGT -1050
GCGGAGGTAT TTAATGTTCT CTGGTATTTT GCCTTTATTC GCTTACTGAA -1100
TGTCATTTTA CAAAAACAGT GTGTCAGTTT CTGGACCTTA TTTATTGATT -1150
TAGTTCAGTG AAGATAACAA CATGCTTCTG ATTATTGTGC AGATCCCAAA -1200
TGGTGCAGCA GGCCATTACC TTCTTGGACT TATTTACAAG TACGTTTTTT -1250
GTTCTGTCTA TGCATTTTTT CTTGATTCTG AATGGCTTAG ATGAGATGAT -1300
TCCTCATATA TAACAGTGAC CTTTTAGGTA TACTGATAGA AGGAAGAATG -1350
CTGCTCAACA ATTTAAACAG TCCTTGACAA TAGACCCTCT ACTTTGGGCT -1400
GCATATGAGG AATTATGTAT ATTAGGTGAA CATAATCCGT TTTCTGCATA -1450
CTTCACAGAT ATGTTATGGT TCTCTTACAC TTTTCTGTCT GCTCAACTTT -1500
CAGGTGCTGC TGAGGAAGCA ACTGCAGTTT TTGGTGAAAC AGCTGCTCTC -1550
TCCATTCAAA AGCAGTATAT GCAACAACTG TCAACTTCCC TCGGCTTAAA -1600
CACTTACAAC GAGGAACGTA ATTCAACTTC TACTAAAAAC ACGAGTTCTG -1650
AAGATTATAG TCCAAGGCAG TCTAAACACA CACAAAGCCA TGGCCTTAAA -1700
GATATCTCCG GAAATTTCCA TTCTCATGGA GTTAATGGAG GTGTTTCGAA -1750
CATGTCATTC TATAATACGC CTTCGCCAGT GGCTGCACAG GTAATGTCAC -1800
ACAATTGTCG TACTGCTTTT TTATGTAATA CAACTATATC TCCATCTGTT -1850
GATCACACAT TCTGTAGTAC TTAGGAGATT TGTGCATCAT GGGTGTTGAT -1900
TTCACAGCGT TTGTATCTGT TTTTTCTATA TCTGTTATGC CAAAAGAATG -1950
GGTTGTCTAT TCTTTTGACT ATTAAAAATG GGGTCTTCAT TATGTTTTAG -2000
TGTCTTTGGT TTGGCTTGTT AATTTTATCA ACCTTTTTAG TTATCTGAAT -2050
AATAACAGCT GTAAGTAAAT GCTTTTTTGT ATTTTTGAAA TTGTAGCTAT -2100
CCGGTATAGC TCCACCACCA CTTTTCCGGA ATTTTCAGCC AGCTGTTGCA -2150
  ■ hbt5422, hbt5423, hbt5859, hbt9624
AACCCAAACT CCCTTATTAC TGACAGTTCT CCAAAGTCCA CTGTTAACTC -2200
TACTCTTCAA GCACCTAGAA GAAAGTTTGT AGATGAAGGA AAGTTACGTA -2250
AGGTAGGATT CACATAATCA CATATCTCTA CTTGACATCA TCAAATCATA -2300
ATTTGAATT ATTGGTCTTT CTCTGTAATA GTCTATTTCG TACTCGGGAT  -2350
GAAATTTTCT ATACCAACTT TCTTACCGTG AGTGCATGTC TCTTATGTTT -2400
GCAGATTTCT GGCAGACTAT TTTCTGATTC TGGTCCACGA CGGAGTTCAA -2450
```

FIGURE 10-1

```
GACTGTCTGC TGATTCAGGG GCAAACATTA ATTCAAGTGT TGCAACAGTA  -2500
AGCGGAAATG TGAACAACGC TTCCAAGTAT TTGGGAGGTT CTAAATTGAG  -2550
TTCTTTGGCA CTTCGTTCTG TAACACTTCG GAAGGGACAC TCCTGGGCAA  -2600
ATGAAAACAT GGATGAAGGT TGTGACATTC CATGCACTAT ACCACTATAT  -2650
TGTTTGAAAT CTGCCCTTGT GTGACTATTG TTATCATGCC TTCTATTTTT  -2700
GGTGTCTGCA TATTTGTAAT ACCGTCATTC TGATGGGTTT AGGGGTCCGT  -2750
GGGGAACCTT TTGATGATTC AAGGCCTAAT ACTGCCTCAA CGACTGGTTC  -2800
TATGGCTTCC AATGATCAAG AAGACGAAAC AATGTCGATT GGTGGCATAG  -2850
CAATGAGTTC TCAAACAATC ACAATTGGTG TTTCGGAAAT TTTAAACCTC  -2900
CTTAGGACAC TCGGAGAAGG GTGTAGACTT TCATACATGT ACAGGTGTCA  -2950
          ⓐ hbt1611

GGTAGGCATA TTATTGTTCT CGTGAATTAT GCAAGTGAGG TGAACCTATA  -3000
TAGGCTTATC TCATTGTCTC CTTCTGCTTC TGGGTCGTTC AGGAGGCACT  -3050
                                            ⓐ hbt9620

GGATACGTAT ATGAAACTTC CACATAAGCA TTATAATACA GGATGGGTTC  -3100
TTTCCCAGGT AACTAGTGAC TCTTTCTCTT TTAGGCTGCC ATATATGGAT  -3150
ATAGCCTGAA TCAGTTTTAC TCTAGTGGCC TGTGATAGTT ATTGTTGAAA  -3200
GGTTTATATA CACATACTAT GGCTATTAAA TGTAGGTCGG GAAAGCATAC  -3250
TTTGAACTAA TTGACTATTT AGAGGCTGAA AAGGCATTCC GTCTTGCCCG  -3300
TCTGGCTTCT CCTTATTGCT TAGAAGGAAT GGATATATAC TCTACGGTCC  -3350
TCTATGTAAG TGTATTATCC TGGTTTCTAA ACATGCAATC TCGGATGAGT  -3400
      ⓐ hbt5721

GCGGAAAGAA ATCACATTTA TGTAAATTTT TCATCAGCAA GATATGATAT  -3450
TTATTTGCAG CATTTGAAGG AAGACATGAA GCTGAGTTAC TTGGCTCAGG  -3500
AACTAATATC AACCGATCGC TTAGCTCCTC AATCTTGGTA TTTTTTGTCG  -3550
              ⓣ hbt2311

AAGTTGTTTT TCTGATTAAC GTTTTCATTT ATTGTTGGTA ATAAGAGAAA  -3600
TAAGCAATCA ATTATGTAGG TGTGCTATGG GAAATTGCTA TAGCTTGCAA  -3650
AAGGACCATG AGACCGCACT GAAGAATTTC CTACGAGCTG TTCAACTGAA  -3700
                                       ⓣ hbt8052

TCCAAGATTT GCATATGCAC ATACCTTATG TGGCCACGAG TAAGAGAGCC  -3750
TCTATCCATT TGACTTTGTC TTGCACAATG TGCTTAAAAT TATCTGGTTA  -3800
TTGGTCTAAT TGACACTTTC TATCTTTACT GTCTCTGTAG ATACACAACT  -3850
CTTGAGGATT TTGAGAACGG AATGAAAAGT TACCAAAACG CACTTCGTGT  -3900
AGATACAAGA CACTACAACG CATGGTACGG GCTTGGAATG ATATATCTAC  -3950
GCCAAGAGAA GTTAGAGTTC TCAGAGCATC ACTTCAGAAT GGCTTTCCTA  -4000
ATAAACCCGA GTTCCTCTGT TATAATGTCT TATTTAGGGA CATCTTTGCA  -4050
TGCCTTGAAG GTTATCTTAT TACTTTCATC TTATCAGGTC TACAAGAAAA  -4100
ACAATCTTTG AAGAATGACT AAATGCTTCT TCTTGTTTTG TGTTAATAGA  -4150
GAAGTGAGGA AGCACTAGAG ATAATGGAGC AAGCCATAGT AGCAGATAGA  -4200
AAAAACCCTC TTCCAATGTA CCAGAAAGCT AACATACTTG TCTGCTTAGA  -4250
AAGATTAGAT GAAGCTCTAG AAGTTCTTGA GGAGCTCAAA GAGTATGCGC  -4300
CTTCAGAGAG CAGCGTTTAC GCTTAATGG GCAGGATCTA TAAGCGGCGA  -4350
AACATGCACG ATAAAGCCAT GCTTCATTTC GGTCTAGCTT TAGATATGAA  -4400
ACCGCCTGCA ACTGACGTTG CTGCAATAAA GGTTCGAGTC TTTAAAACAG  -4450
AGTCGTCCAA TGATGGTTTT TAAATCTGAA AATTCAAGGA TTCATAGCTT  -4500
AAACTGGTTA TTATTGTCTG AAACAGGCTG CAATGGAGAA ATTGCATGTT  -4550
CCAGATGAGA TCGATGAGAG CCCGTGA
```

FIGURE 10-2

FIGURE 13-1

SEQ ID Nr. 31: HBT 1F GAAGAAAGGCAACAACTATGGAAGCTATG

SEQ ID Nr. 32: HBT 1R: GAACTGTCAGTAATAAGGGAGTTTGGGTTT

SEQ ID Nr. 33: HBT 2F: ATGCAACAACTGTCAACTTCCCTCG

SEQ ID Nr. 34: HBT 2R: TATCCATTCCTTCTAAGCAATAAGGAGAAGC

SEQ ID Nr. 35: HBT 3F: AAATTTTAAACCTCCTTAGGACACTCGGA

SEQ ID Nr. 36: HBT 3R: TCACGGGCTCTCATCGATCTCATCT

SEQ ID Nr. 37: HBT 3'2F: GTTCTTGAGGAGCTCAAAGAGTATG

SEQ ID Nr. 38: HBT 3'1F: GCTTTAATGGGCAGGATCTATAAG

SEQ ID Nr. 39: HBT BF: TATTCAAATGGTCAATTATAAAGCCCAATAAG

SEQ ID Nr. 40: HBT 5'1R: ACATGAAAATAGCATTTTTGTAGAC

SEQ ID Nr. 41: HBT AF: AGAGTGACCTACTTACTACATTGGTACAAAACC

SEQ ID Nr. 42: HBT AR: CCCATTAAAGCGTAAACGCTGCTCTCTGAAG

SEQ ID Nr. 43: HBT BF: TATTCAAATGGTCAATTATAAAGCCCAATAAG

SEQ ID Nr. 44: HBT BR: TGAATGAATACTTTCTCAACTACTATTGAAGC

SEQ ID Nr. 45: HBT CF: TATGAGTCAACTGTTAGAGGAATGTCTCTG

SEQ ID Nr. 46: HBT CR: GAAGTTGACAGTTGTTGCATATACTGC

SEQ ID Nr. 47: HBT DF: TCTTACACTTTTCTGTCTGCTCAACTTTCA

SEQ ID Nr. 48: HBT DR: CAAAGAACTCAATTTAGAACCTCCCAAATAC

SEQ ID Nr. 49: HBT EF: CAGATTTCTGGCAGACTATTTTCTGATTCT

SEQ ID Nr. 50: HBT ER: AAGTAACTCAGCTTCATGTCTTCCTTCAAA

SEQ ID Nr. 51: HBT FF: GATATTTATTTGCAGCATTTGAAGGAAGAC

SEQ ID Nr. 52: HBT FR: GAATTTTCAGATTTAAAAACCATCATTGGA

SEQ ID Nr. 53: HBT GF: AGTCTTTAAAACAGAGTCGTCCAATGATG

SEQ ID Nr. 54: HBT GR: ATATTGCGATTAGGTAGTGTTACGGACAAC

SEQ ID Nr. 55: YC F: GAAGTCGACACAAACTATGGAAGCT

SEQ ID Nr. 56: YC R: AATCATACCCAAGGATCCTGGAG

FIGURE 13-2

SEQ ID Nr. 57: HBT NF: GCAACAACTGTCAACTTCCCTCGGCTT

SEQ ID Nr. 58: HBT NR: AGAACCAGTCGTTGAGGCAGTATTAGGCC

SEQ ID Nr. 59: CDC27 1F: ATGATGGAGAATCTACTGGCGAATTG

SEQ ID Nr. 60: CDC27 1R: CATCGAGGAAAGAGAAGGTGCATAG

SEQ ID Nr. 61: CDC27 2F: ATCCTAGTGAATCTTCCCCGGATCG

SEQ ID Nr. 62: CDC27 2R: AGCCAGTTGAAATTGATGCTGCG

SEQ ID Nr. 63: CDC27 3F: GATGCAGAGAGATGCTACCGGAAGGC

SEQ ID Nr. 64: CDC27 3R: CTAAATGCAAAATGTGACCATGATTG

SEQ ID Nr. 65: AXR3-F: TCT TCC CGG TGG AGA TAC AG

SEQ ID Nr. 66: AXR3-R: GCC CAT GGT AAA AGA GCT GA

A
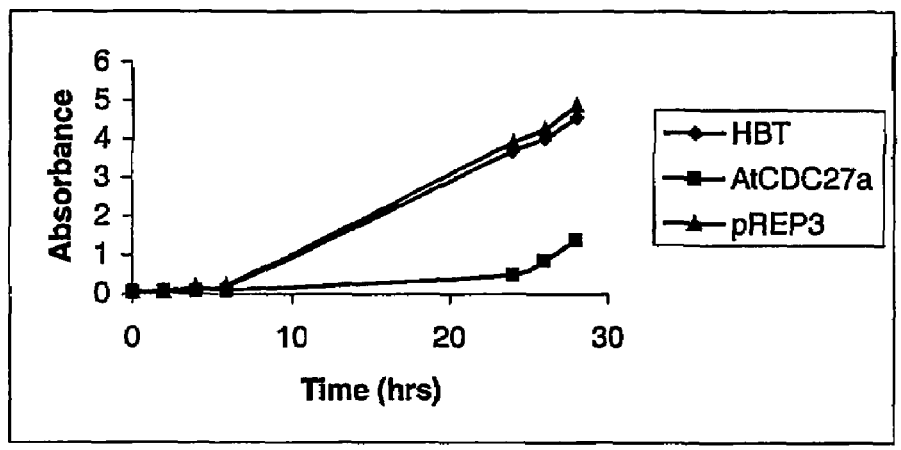
B
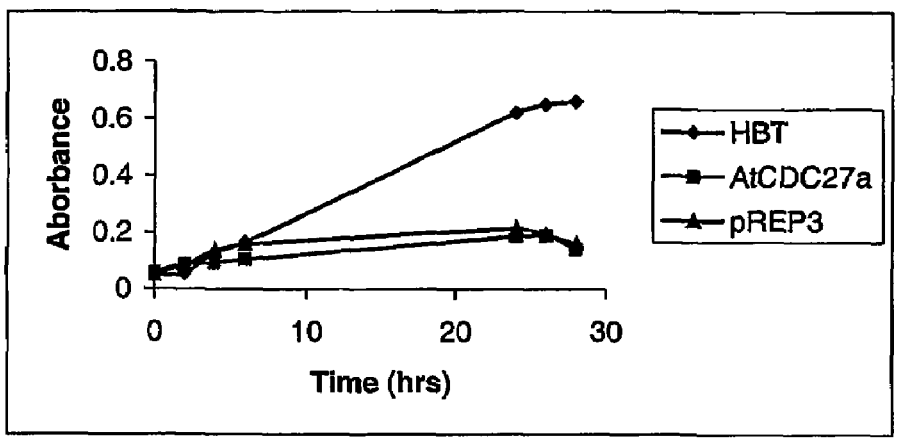
FIGURE 15

A
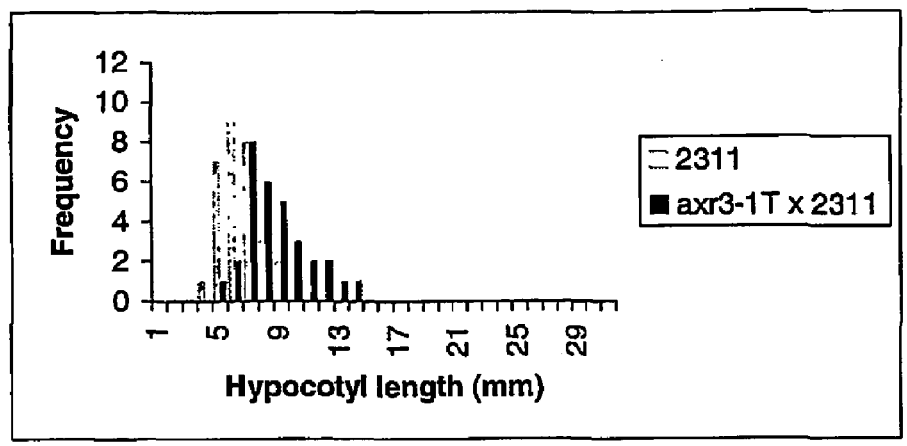
B
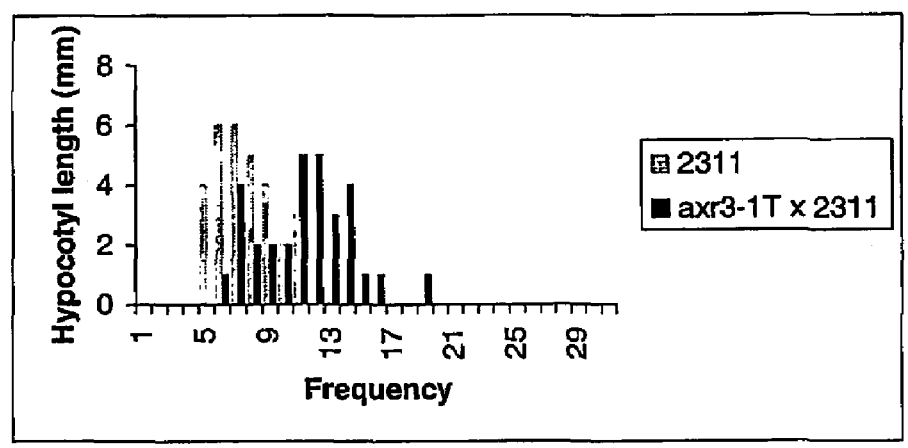
C
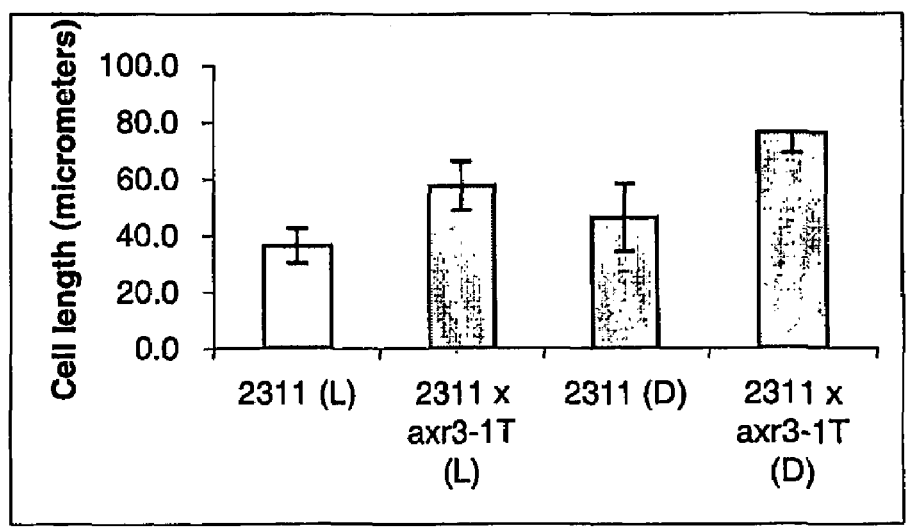
FIGURE 18

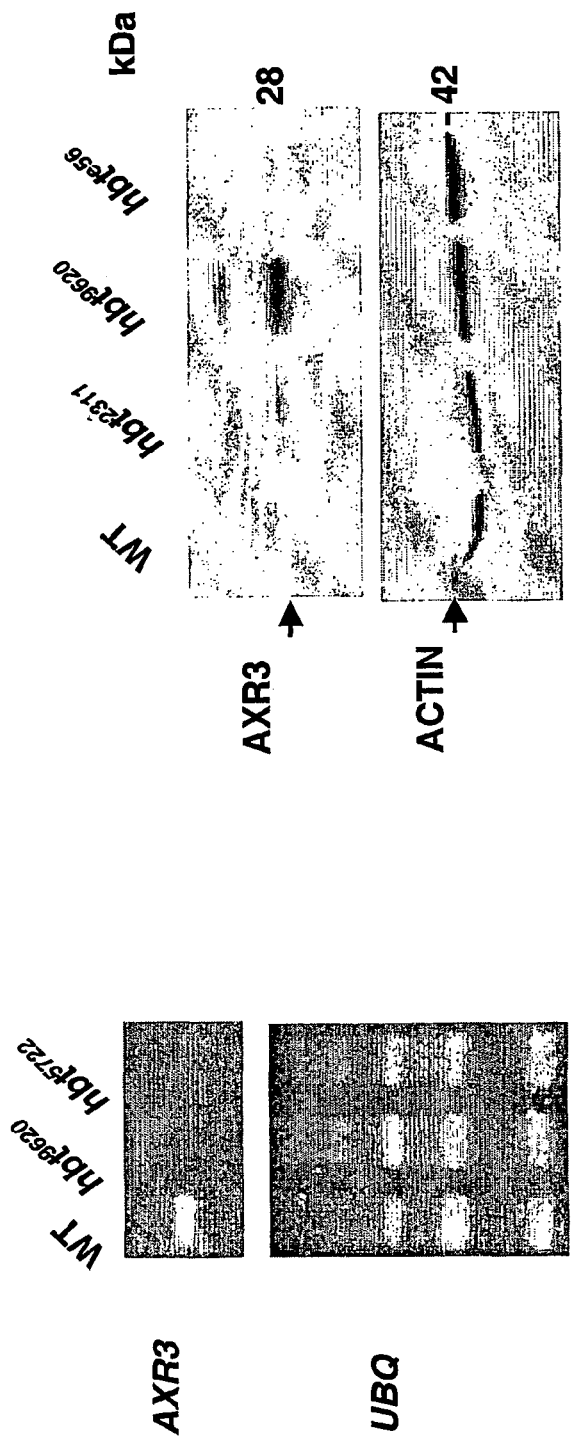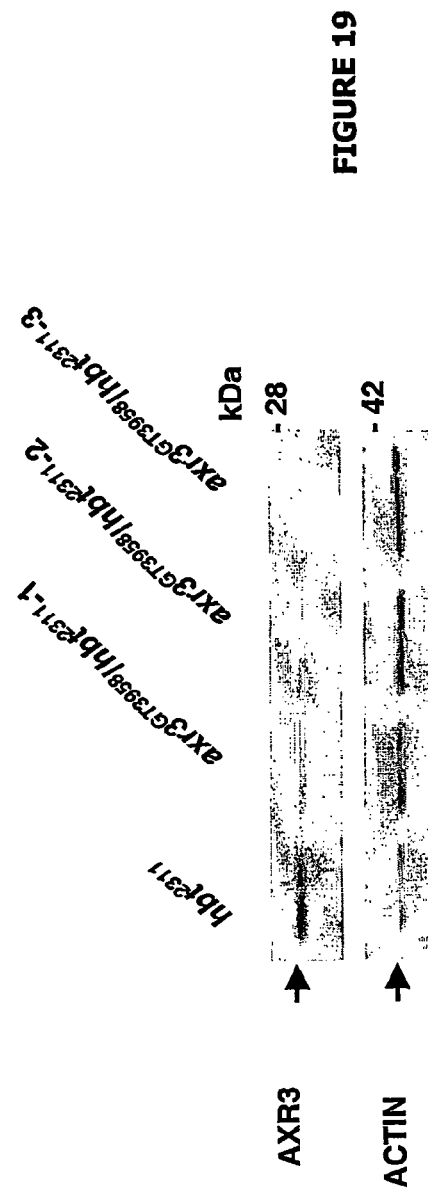
FIGURE 19

SEQUENCE LISTING

<160> NUMBER OF SEQ ID NOS: 66

<210> SEQ ID NO 1
<211> LENGTH: 4577
<212> TYPE: DNA
<213> ORGANISM: Arabidopsis thaliana

<400> SEQUENCE: 1

```
atggaagcta tgcttgtgga ctgtgtaaac aacagtcttc gtcatttgt ctacaaaaat      60 gctattttca tgtgcgagcg tctctgcgct gagtttcctt ctgaggtaat caccctcttc     120
tttcactctc tctctctgat tttacctctc taattcaaat tctgtaaatc gaagctcttg    180
gaatggtaaa tttgatattt ttgggtttgt aattcctctg ggtatctatg aattcgtcga    240
aagtgcgtct cttttggat ttggaattcg atagcttcac tgtgttcttc gagattgatt     300
ttggtttctt accttttagc cctttgtttt caagatccgt gtgttcaatt aggagatgaa    360
ttcgtgttct tttctctctc ttgttgaatt tgttttctct agtagctgtg ctcaatgctc    420
attactgatt tggtctttgg aaaatttgca ttttgagggt taatgacttt tgtccatata    480
tgtgatctca agtttaagta tttattatcc ttggaactta gctatgagtc aactgttaga    540
ggaatgtctc tgggattatc tcaagctttg ttaaaatttg ggttaataca gcttcaatag    600
tagttgagaa agtattcatt cattcagcct ttggtctgga atattttcaa cattcgtagt    660
ggttgtccag tttctagctt cagttagtag aaatcatgtc aataaatgat tggccttttt    720
gtttgatcac tttctgaatt ttcctcttat ataggttaat ttgcagctat tagccaccag    780
ctacctgcag aataatcaag cttacagtgc atatcatctg ctaaagggtg cgtggcattg    840
tttcttgact tgttgcttgt tagccttta gtcagaattt tgcaccttct tttgttaggt    900
cgttttgatt atctttgtat atatatttt tttttgttat gtaaaggaac acaaatggct     960
cagtcccgat acttgttcgc attatcatgc ttccagatgg accttctcaa tgaagctgaa   1020
tctgcactct gccctgttaa tgaacctggt gcggaggtat ttaatgttct ctggtatttt    1080
gcctttattc gcttactgaa tgtcatttta caaaaacagt gtgtcagttt ctggaccta    1140 tttattgatt tagttcagtg aagataacaa catgcttctg attattgtgc agatcccaaa   1200
tggtgcagca ggccattacc ttcttggact tatttacaag tacgttttt gttctgtcta    1260 tgcatttttt cttgattctg aatggcttag atgagatgat tcctcatata taacagtgac    1320 ctttaggta tactgataga aggaagaatg ctgctcaaca atttaaacag tccttgacaa    1380
tagaccctct actttgggct gcatatgagg aattatgtat attaggtgaa cataatccgt    1440
tttctgcata cttcacagat atgttatggt tctcttacac ttttctgtct gctcaacttt    1500
caggtgctgc tgaggaagca actgcagttt ttggtgaaac agctgctctc tccattcaaa    1560
agcagtatat gcaacaactg tcaacttccc tcggcttaaa cacttacaac gaggaacgta    1620
attcaacttc tactaaaaac acgagttctg aagattatag tccaaggcag tctaaacaca    1680
cacaaagcca tggccttaaa gatatctccg gaaatttcca ttctcatgga gttaatggag   1740
```

-continued

```
gtgtttcgaa catgtcattc tataatacgc cttcgccagt ggctgcacag gtaatgtcac    1800
acaattgtcg tactgctttt ttatgtaata caactatatc tccatctgtt gatcacacat    1860
tctgtagtac ttaggagatt tgtgcatcat gggtgttgat ttcacagcgt ttgtatctgt    1920
tttttctata tctgttatgc caaaagaatg ggttgtctat tcttttgact attaaaaatg    1980
gggtcttcat tatgttttag tgtctttggt ttggcttgtt aattttatca acctttttag    2040
ttatctgaat aataacagct gtaagtaaat gcttttttgt attttgaaa ttgtagctat     2100 ccggtatagc tccaccacca cttttccgga attttcagcc agctgttgca aacccaaact    2160
cccttattac tgacagttct ccaaagtcca ctgttaactc tactcttcaa gcacctagaa    2220
gaaagtttgt agatgaagga aagttacgta aggtaggatt cacataatca catatctcta    2280
cttgacatca tcaaatcata attttgaatt attggtcttt ctctgtaata gtctatttcg    2340
tactcgggat gaaattttct ataccaactt tcttaccgtg agtgcatgtc tcttatgttt    2400
gcagatttct ggcagactat tttctgattc tggtccacga cggagttcaa gactgtctgc    2460
tgattcaggg gcaaacatta attcaagtgt tgcaacagta agcggaaatg tgaacaacgc    2520
ttccaagtat ttgggaggtt ctaaattgag ttctttggca cttcgttctg taacacttcg    2580
gaagggacac tcctgggcaa atgaaaacat ggatgaaggt tgtgacattc catgcactat    2640
accactatat tgtttgaaat ctgcccttgt gtgactattg ttatcatgcc ttctattttt    2700
ggtgtctgca tatttgtaat accgtcattc tgatgggttt aggggtccgt ggggaacctt    2760
ttgatgattc aaggcctaat actgcctcaa cgactggttc tatggcttcc aatgatcaag    2820
aagacgaaac aatgtcgatt ggtggcatag caatgagttc tcaaacaatc acaattggtg    2880
tttcggaaat tttaaacctc cttaggacac tcggagaagg tgtagacttt catacatgt     2940 acaggtgtca ggtaggcata ttattgttct cgtgaattat gcaagtgagg tgaacctata    3000
taggcttatc tcattgtctc cttctgcttc tgggtcgttc aggaggcact ggatacgtat    3060
atgaaacttc cacataagca ttataataca ggatgggttc tttcccaggt aactagtgac    3120
tctttctctt ttaggctgcc atatatggat atagcctgaa tcagttttac tctagtggcc    3180
tgtgatagtt attgttgaaa ggtttatata cacatactat ggctattaaa tgtaggtcgg    3240
gaaagcatac tttgaactaa ttgactattt agaggctgaa aaggcattcc gtcttgcccg    3300
tctggcttct ccttattgct tagaaggaat ggatatatac tctacggtcc tctatgtaag    3360
tgtattatcc tggtttctaa acatgcaatc tcggatgagt gcggaaagaa atcacattta    3420
tgtaaatttt tcatcagcaa gatatgatat ttatttgcag catttgaagg aagacatgaa    3480
gctgagttac ttggctcagg aactaatatc aaccgatcgc ttagctcctc aatcttggta    3540
ttttttgtcg aagttgtttt tctgattaac gttttcattt attgttggta ataagagaaa    3600
taagcaatca attatgtagg tgtgctatgg gaaattgcta tagcttgcaa aaggaccatg    3660
agaccgcact gaagaatttc ctacgagctg ttcaactgaa tccaagattt gcatatgcac    3720
ataccttatg tggccacgag taagagagcc tctatccatt tgactttgtc ttgcacaatg    3780
tgcttaaaat tatctggtta ttggtctaat tgacactttc tatctttact gtctctgtag    3840
atacacaact cttgaggatt ttgagaacgg aatgaaaagt taccaaaacg cacttcgtgt    3900
agatacaaga cactacaacg catggtacgg gcttggaatg atatatctac gccaagagaa    3960
gttagagttc tcagagcatc acttcagaat ggctttccta ataaacccga gttcctctgt    4020
tataatgtct tatttaggga catctttgca tgccttgaag gttatcttat tactttcatc    4080
```

```
ttatcaggtc tacaagaaaa acaatctttg aagaatgact aaatgcttct tcttgttttg    4140
tgttaataga gaagtgagga agcactagag ataatggagc aagccatagt agcagataga    4200
aaaaaccctc ttccaatgta ccagaaagct aacatacttg tctgcttaga aagattagat    4260
gaagctctag aagttcttga ggagctcaaa gagtatgcgc cttcagagag cagcgtttac    4320
gctttaatgg gcaggatcta taagcggcga aacatgcacg ataaagccat gcttcatttc    4380
ggtctagctt tagatatgaa accgcctgca actgacgttg ctgcaataaa ggttcgagtc    4440
tttaaaacag agtcgtccaa tgatggtttt taaatctgaa aattcaagga ttcatagctt    4500
aaactggtta ttattgtctg aaacaggctg caatggagaa attgcatgtt ccagatgaga    4560
tcgatgagag cccgtga                                                   4577

<210> SEQ ID NO 2
<211> LENGTH: 2480
<212> TYPE: DNA
<213> ORGANISM: Arabidopsis thaliana

<400> SEQUENCE: 2
gaagaggcaa caactatgga agctatgctt gtggactgtg taaacaacag tcttcgtcat      60
tttgtctaca aaaatgctat tttcatgtgc gagcgtctct gcgctgagtt tccttctgag     120
gttaatttgc agctattagc caccagctac ctgcagaata tcaagctta cagtgcatat      180 catctgctaa agggaacaca aatggctcag tcccgatact tgttcgcatt atcatgcttc     240
cagatggacc ttctcaatga agctgaatct gcactctgcc ctgttaatga acctggtgcg     300
gagatcccaa atggtgcagc aggccattac cttcttggac ttatttacaa aaggaagaat     360
gctgctcaac aatttaaaca gtccttgaca atagaccctc tactttgggc tgcatatgag     420
gaattatgta tattaggtgc tgctgaggaa gcaactgcag ttttttggtga aacagctgct     480 ctctccattc aaaagcagta tatgcaacaa ctgtcaactt ccctcggctt aaacacttac     540
aacgaggaac gtaattcaac ttctactaaa aacacgagtt ctgaagatta tagtccaagg     600
cagtctaaac acacacaaag ccatggcctt aaagatatct ccggaaattt ccattctcat     660
ggagttaatg gaggtgtttc gaacatgtca ttctataata cgccttcgcc agtggctgca     720
cagctatccg gtatagctcc accaccactt ttccggaatt ttcagccagc tgttgcaaac     780
ccaaactccc ttattactga cagttctcca aagtccactg ttaactctac tcttcaagca     840
cctagaagaa gtttgtagatg tgaaggaaag ttacgtaaga tttctggcag actattttct     900
gattctggtc cacgacggag ttcaagactg tctgctgatt caggggcaaa cattaattca     960
agtgttgcaa cagtaagcgg aaatgtgaac aacgcttcca agtatttggg aggttctaaa    1020
ttgagttctt tggcacttcg ttctgtaaca cttcggaagg acactcctg gcaaatgaa      1080 aacatggatg aaggggtccg tggggaacct tttgatgatt caaggcctaa tactgcctca    1140
acgactggtt ctatggcttc caatgatcaa gaagacgaaa caatgtcgat tggtggcata    1200
gcaatgagtt ctcaaacaat cacaattggt gtttcggaaa ttttaaacct ccttaggaca    1260
ctcggagaag ggtgtagact ttcatacatg tacaggtgtc aggaggcact ggatacgtat    1320
atgaaacttc cacataagca ttataataca ggatgggttc tttcccaggt cgggaaagca    1380
tactttgaac taattgacta tttagaggct gaaaaggcat tccgtcttgc ccgtctggct    1440
tctccttatt gcttagaagg aatggatata tactctacgg tcctctatca tttgaaggaa    1500
gacatgaagc tgagttactt ggctcaggaa ctaaatatcaa ccgatcgctt agctcctcaa    1560
tcttggtgtg ctatgggaaa ttgctatagc ttgcaaaagg accatgagac cgcactgaag    1620
```

-continued

| | |
|---|---|
| aatttcctac gagctgttca actgaatcca agatttgcat atgcacatac cttatgtggc | 1680 |
| cacgaataca caactcttga ggattttgag aacggaatga aaagttacca aaacgcactt | 1740 |
| cgtgtagata caagacacta caacgcatgg tacgggcttg gaatgatata tctacgccaa | 1800 |
| gagaagttag agttctcaga gcatcacttc agaatggctt tcctaataaa cccgagttcc | 1860 |
| tctgttataa tgtcttattt agggacatct ttgcatgcct tgaagagaag tgaggaagca | 1920 |
| ctagagataa tggagcaagc catagtagca gatagaaaaa accctcttcc aatgtaccag | 1980 |
| aaagctaaca tacttgtctg cttagaaaga ttagatgaag ctctagaagt tcttgaggag | 2040 |
| ctcaaagagt atgcgccttc agagagcagc gtttacgctt taatgggcag gatctataag | 2100 |
| cggcgaaaca tgcacgataa agccatgctt catttcggtc tagctttaga tatgaaaccg | 2160 |
| cctgcaactg acgttgctgc aataaaggct gcaatggaga aattgcatgt tccagatgag | 2220 |
| atcgatgaga gcccgtgaaa ccatagctac tccaagaacc ttgggtatga attaatgtga | 2280 |
| gaccgttgct gctccacgaa ccatgggtat gaattattta gtgcaaagcc tacctctttt | 2340 |
| agggaactag ttgggtttga atgtagtttt gttaccaaac cgtaacacag ccacaagagc | 2400 |
| ccacatgact tgagtatgta tcatgagttg atctgtatgt tgtccgtaac actacctaat | 2460 |
| cgcaatatat gattttccca | 2480 |

<210> SEQ ID NO 3
<211> LENGTH: 2235
<212> TYPE: DNA
<213> ORGANISM: Arabidopsis thaliana

<400> SEQUENCE: 3

| | |
|---|---|
| atggaagcta tgcttgtgga ctgtgtaaac aacagtcttc gtcattttgt ctacaaaaat | 60 |
| gctattttca tgtgcgagcg tctctgcgct gagtttcctt ctgaggttaa tttgcagcta | 120 |
| ttagccacca gctacctgca gaataatcaa gcttacagtg catatcatct gctaaaggga | 180 |
| acacaaatgg ctcagtcccg atacttgttc gcattatcat gcttccagat ggaccttctc | 240 |
| aatgaagctg aatctgcact ctgccctgtt aatgaacctg gtgcggagat cccaaatggt | 300 |
| gcagcaggcc attccttct tggacttatt tacaagtata ctgatagaag gaagaatgct | 360 |
| gctcaacaat ttaaacagtc cttgacaata gaccctctac tttgggctgc atatgaggaa | 420 |
| ttatgtatat taggtgctgc tgaggaagca actgcagttt tggtgaaac agctgctctc | 480 |
| tccattcaaa agcagtatat gcaacaactg tcaacttccc tcggcttaaa cacttacaac | 540 |
| gaggaacgta attcaacttc tactaaaaac acgagttctg aagattatag tccaaggcag | 600 |
| tctaaacaca cacaaagcca tggccttaaa gatatctccg gaaatttcca ttctcatgga | 660 |
| gttaatggag gtgtttcgaa catgtcattc tataatacgc cttcgccagt ggctgcacag | 720 |
| ctatccggta tagctccacc accacttttc cggaattttc agccagctgt tgcaaaccca | 780 |
| aactccctta ttactgacag ttctccaaag tccactgtta actctactct tcaagcacct | 840 |
| agaagaaagt ttgtagatga aggaaagtta cgtaagattt ctggcagact attttctgat | 900 |
| tctggtccac gacggagttc aagactgtct gctgattcag gggcaaacat taattcaagt | 960 |
| gttgcaacag taagcggaaa tgtgaacaac gcttccaagt atttgggagg ttctaaattg | 1020 |
| agttcttttgg cacttcgttc tgtaacactt cggaagggac actcctgggc aaatgaaaac | 1080 |
| atggatgaag gggtccgtgg ggaaccttt gatgattcaa ggcctaatac tgcctcaacg | 1140 |
| actggttcta tggcttccaa tgatcaagaa gacgaaacaa tgtcgattgg tggcatagca | 1200 |

```
atgagttctc aaacaatcac aattggtgtt tcggaaattt taaacctcct taggacactc    1260
ggagaagggt gtagactttc atacatgtac aggtgtcagg aggcactgga tacgtatatg    1320
aaacttccac ataagcatta taatacagga tgggttcttt cccaggtcgg gaaagcatac    1380
tttgaactaa ttgactattt agaggctgaa aaggcattcc gtcttgcccg tctggcttct    1440
ccttattgct tagaaggaat ggatatatac tctacggtcc tctatcattt gaaggaagac    1500
atgaagctga gttacttggc tcaggaacta atatcaaccg atcgcttagc tcctcaatct    1560
tggtgtgcta tgggaaattg ctatagcttg caaaaggacc atgagaccgc actgaagaat    1620
ttcctacgag ctgttcaact gaatccaaga tttgcatatg cacatacctt atgtggccac    1680
gaatacacaa ctcttgagga ttttgagaac ggaatgaaaa gttaccaaaa cgcacttcgt    1740
gtagatacaa gacactacaa cgcatggtac gggcttggaa tgatatatct acgcaagag    1800 aagttagagt tctcagagca tcacttcaga atggctttcc taataaaccc gagttcctct    1860
gttataatgt cttatttagg gacatctttg catgccttga agagaagtga ggaagcacta    1920
gagataatgg agcaagccat agtagcagat agaaaaaacc ctcttccaat gtaccagaaa    1980
gctaacatac ttgtctgctt agaaagatta gatgaagctc tagaagttct tgaggagctc    2040
aaagagtatg cgccttcaga gagcagcgtt tacgctttaa tgggcaggat ctataagcgg    2100
cgaaacatgc acgataaagc catgcttcat ttcggtctag ctttagatat gaaaccgcct    2160
gcaactgacg ttgctgcaat aaaggctgca atggagaaat tgcatgttcc agatgagatc    2220
gatgagagcc cgtga                                                     2235

<210> SEQ ID NO 4
<211> LENGTH: 486
<212> TYPE: DNA
<213> ORGANISM: Arabidopsis thaliana

<400> SEQUENCE: 4
atggaagcta tgcttgtgga ctgtgtaaac aacagtcttc gtcattttgt ctacaaaaat      60
gctattttca tgtgcgagcg tctctgcgct gagtttcctt ctgaggttaa tttgcagcta     120
ttagccacca gctacctgca gaataatcaa gcttacagtg catatcatct gctaaaggga     180
acacaaatgg ctcagtcccg atacttgttc gcattatcat gcttccagat ggaccttctc     240
aatgaagctg aatctgcact ctgccctgtt aatgaacctg gtgcggagat cccaaatggt     300
gcagcaggcc attaccttct tggacttatt tacaaaagga agaatgctgc tcaacaattt     360
aaacagtcct tgacaataga ccctctactt tgggctgcat atgaggaatt atgtatatta     420
ggtgctgctg aggaagcaac tgcagttttt ggtgaaacag ctgctctctc cattcaaaag     480
cagtat                                                                486

<210> SEQ ID NO 5
<211> LENGTH: 498
<212> TYPE: DNA
<213> ORGANISM: Arabidopsis thaliana

<400> SEQUENCE: 5
atggaagcta tgcttgtgga ctgtgtaaac aacagtcttc gtcattttgt ctacaaaaat      60
gctattttca tgtgcgagcg tctctgcgct gagtttcctt ctgaggttaa tttgcagcta     120
ttagccacca gctacctgca gaataatcaa gcttacagtg catatcatct gctaaaggga     180
acacaaatgg ctcagtcccg atacttgttc gcattatcat gcttccagat ggaccttctc     240
aatgaagctg aatctgcact ctgccctgtt aatgaacctg gtgcggagat cccaaatggt     300
```

```
gcagcaggcc attaccttct tggacttatt tacaagtata ctgatagaag gaagaatgct    360
gctcaacaat ttaaacagtc cttgacaata gaccctctac tttgggctgc atatgaggaa    420
ttatgtatat taggtgctgc tgaggaagca actgcagttt ttggtgaaac agctgctctc    480
tccattcaaa agcagtat                                                  498

<210> SEQ ID NO 6
<211> LENGTH: 162
<212> TYPE: PRT
<213> ORGANISM: Arabidopsis thaliana

<400> SEQUENCE: 6

Met Glu Ala Met Leu Val Asp Cys Val Asn Asn Ser Leu Arg His Phe
1               5                   10                  15

Val Tyr Lys Asn Ala Ile Phe Met Cys Glu Arg Leu Cys Ala Glu Phe
            20                  25                  30

Pro Ser Glu Val Asn Leu Gln Leu Leu Ala Thr Ser Tyr Leu Gln Asn
        35                  40                  45

Asn Gln Ala Tyr Ser Ala Tyr His Leu Leu Lys Gly Thr Gln Met Ala
    50                  55                  60

Gln Ser Arg Tyr Leu Phe Ala Leu Ser Cys Phe Gln Met Asp Leu Leu
65                  70                  75                  80

Asn Glu Ala Glu Ser Ala Leu Cys Pro Val Asn Glu Pro Gly Ala Glu
                85                  90                  95

Ile Pro Asn Gly Ala Ala Gly His Tyr Leu Leu Gly Leu Ile Tyr Lys
            100                 105                 110

Arg Lys Asn Ala Ala Gln Gln Phe Lys Gln Ser Leu Thr Ile Asp Pro
        115                 120                 125

Leu Leu Trp Ala Ala Tyr Glu Glu Leu Cys Ile Leu Gly Ala Ala Glu
    130                 135                 140

Glu Ala Thr Ala Val Phe Gly Glu Thr Ala Ala Leu Ser Ile Gln Lys
145                 150                 155                 160

Gln Tyr

<210> SEQ ID NO 7
<211> LENGTH: 166
<212> TYPE: PRT
<213> ORGANISM: Arabidopsis thaliana

<400> SEQUENCE: 7

Met Glu Ala Met Leu Val Asp Cys Val Asn Asn Ser Leu Arg His Phe
1               5                   10                  15

Val Tyr Lys Asn Ala Ile Phe Met Cys Glu Arg Leu Cys Ala Glu Phe
            20                  25                  30

Pro Ser Glu Val Asn Leu Gln Leu Leu Ala Thr Ser Tyr Leu Gln Asn
        35                  40                  45

Asn Gln Ala Tyr Ser Ala Tyr His Leu Leu Lys Gly Thr Gln Met Ala
    50                  55                  60

Gln Ser Arg Tyr Leu Phe Ala Leu Ser Cys Phe Gln Met Asp Leu Leu
65                  70                  75                  80

Asn Glu Ala Glu Ser Ala Leu Cys Pro Val Asn Glu Pro Gly Ala Glu
                85                  90                  95

Ile Pro Asn Gly Ala Ala Gly His Tyr Leu Leu Gly Leu Ile Tyr Lys
            100                 105                 110

Tyr Thr Asp Arg Arg Lys Asn Ala Ala Gln Gln Phe Lys Gln Ser Leu
```

```
              115                 120                 125
Thr Ile Asp Pro Leu Leu Trp Ala Ala Tyr Glu Glu Leu Cys Ile Leu
    130                 135                 140

Gly Ala Ala Glu Glu Ala Thr Ala Val Phe Gly Glu Thr Ala Ala Leu
145                 150                 155                 160

Ser Ile Gln Lys Gln Tyr
                165

<210> SEQ ID NO 8
<211> LENGTH: 740
<212> TYPE: PRT
<213> ORGANISM: Arabidopsis thaliana

<400> SEQUENCE: 8

Met Glu Ala Met Leu Val Asp Cys Val Asn Asn Ser Leu Arg His Phe
1               5                   10                  15

Val Tyr Lys Asn Ala Ile Phe Met Cys Glu Arg Leu Cys Ala Glu Phe
            20                  25                  30

Pro Ser Glu Val Asn Leu Gln Leu Leu Ala Thr Ser Tyr Leu Gln Asn
        35                  40                  45

Asn Gln Ala Tyr Ser Ala Tyr His Leu Leu Lys Gly Thr Gln Met Ala
    50                  55                  60

Gln Ser Arg Tyr Leu Phe Ala Leu Ser Cys Phe Gln Met Asp Leu Leu
65                  70                  75                  80

Asn Glu Ala Glu Ser Ala Leu Cys Pro Val Asn Glu Pro Gly Ala Glu
                85                  90                  95

Ile Pro Asn Gly Ala Ala Gly His Tyr Leu Leu Gly Leu Ile Tyr Lys
            100                 105                 110

Arg Lys Asn Ala Ala Gln Gln Phe Lys Gln Ser Leu Thr Ile Asp Pro
        115                 120                 125

Leu Leu Trp Ala Ala Tyr Glu Glu Leu Cys Ile Leu Gly Ala Ala Glu
    130                 135                 140

Glu Ala Thr Ala Val Phe Gly Glu Thr Ala Ala Leu Ser Ile Gln Lys
145                 150                 155                 160

Gln Tyr Met Gln Gln Leu Ser Thr Ser Leu Gly Leu Asn Thr Tyr Asn
                165                 170                 175

Glu Glu Arg Asn Ser Thr Ser Thr Lys Asn Thr Ser Ser Glu Asp Tyr
            180                 185                 190

Ser Pro Arg Gln Ser Lys His Thr Gln Ser His Gly Leu Lys Asp Ile
        195                 200                 205

Ser Gly Asn Phe His Ser His Gly Val Asn Gly Val Ser Asn Met
    210                 215                 220

Ser Phe Tyr Asn Thr Pro Ser Pro Val Ala Ala Gln Leu Ser Gly Ile
225                 230                 235                 240

Ala Pro Pro Leu Phe Arg Asn Phe Gln Pro Ala Val Ala Asn Pro
                245                 250                 255

Asn Ser Leu Ile Thr Asp Ser Ser Pro Lys Ser Thr Val Asn Ser Thr
            260                 265                 270

Leu Gln Ala Pro Arg Arg Lys Phe Val Asp Glu Gly Lys Leu Arg Lys
        275                 280                 285

Ile Ser Gly Arg Leu Phe Ser Asp Ser Gly Pro Arg Arg Ser Ser Arg
    290                 295                 300

Leu Ser Ala Asp Ser Gly Ala Asn Ile Asn Ser Ser Val Ala Thr Val
305                 310                 315                 320
```

```
Ser Gly Asn Val Asn Ala Ser Lys Tyr Leu Gly Ser Lys Leu
            325                 330                 335

Ser Ser Leu Ala Leu Arg Ser Val Thr Leu Arg Lys Gly His Ser Trp
            340                 345                 350

Ala Asn Glu Asn Met Asp Glu Gly Val Arg Gly Glu Pro Phe Asp Asp
            355                 360                 365

Ser Arg Pro Asn Thr Ala Ser Thr Thr Gly Ser Met Ala Ser Asn Asp
370                 375                 380

Gln Glu Asp Glu Thr Met Ser Ile Gly Gly Ile Ala Met Ser Ser Gln
385                 390                 395                 400

Thr Ile Thr Ile Gly Val Ser Glu Ile Leu Asn Leu Leu Arg Thr Leu
                    405                 410                 415

Gly Glu Gly Cys Arg Leu Ser Tyr Met Tyr Arg Cys Gln Glu Ala Leu
                420                 425                 430

Asp Thr Tyr Met Lys Leu Pro His Lys His Tyr Asn Thr Gly Trp Val
                435                 440                 445

Leu Ser Gln Val Gly Lys Ala Tyr Phe Glu Leu Ile Asp Tyr Leu Glu
    450                 455                 460

Ala Glu Lys Ala Phe Arg Leu Ala Arg Leu Ala Ser Pro Tyr Cys Leu
465                 470                 475                 480

Glu Gly Met Asp Ile Tyr Ser Thr Val Leu Tyr His Leu Lys Glu Asp
                485                 490                 495

Met Lys Leu Ser Tyr Leu Ala Gln Glu Leu Ile Ser Thr Asp Arg Leu
                500                 505                 510

Ala Pro Gln Ser Trp Cys Ala Met Gly Asn Cys Tyr Ser Leu Gln Lys
                515                 520                 525

Asp His Glu Thr Ala Leu Lys Asn Phe Leu Arg Ala Val Gln Leu Asn
            530                 535                 540

Pro Arg Phe Ala Tyr Ala His Thr Leu Cys Gly His Glu Tyr Thr Thr
545                 550                 555                 560

Leu Glu Asp Phe Glu Asn Gly Met Lys Ser Tyr Gln Asn Ala Leu Arg
                565                 570                 575

Val Asp Thr Arg His Tyr Asn Ala Trp Tyr Gly Leu Gly Met Ile Tyr
                580                 585                 590

Leu Arg Gln Glu Lys Leu Glu Phe Ser Glu His His Phe Arg Met Ala
            595                 600                 605

Phe Leu Ile Asn Pro Ser Ser Ser Val Ile Met Ser Tyr Leu Gly Thr
610                 615                 620

Ser Leu His Ala Leu Lys Arg Ser Glu Glu Ala Leu Glu Ile Met Glu
625                 630                 635                 640

Gln Ala Ile Val Ala Asp Arg Lys Asn Pro Leu Pro Met Tyr Gln Lys
                645                 650                 655

Ala Asn Ile Leu Val Cys Leu Glu Arg Leu Asp Glu Ala Leu Glu Val
                660                 665                 670

Leu Glu Glu Leu Lys Glu Tyr Ala Pro Ser Glu Ser Ser Val Tyr Ala
            675                 680                 685

Leu Met Gly Arg Ile Tyr Lys Arg Arg Asn Met His Asp Lys Ala Met
            690                 695                 700

Leu His Phe Gly Leu Ala Leu Asp Met Lys Pro Pro Ala Thr Asp Val
705                 710                 715                 720

Ala Ala Ile Lys Ala Ala Met Glu Lys Leu His Val Pro Asp Glu Ile
                725                 730                 735

Asp Glu Ser Pro
```

-continued

740

<210> SEQ ID NO 9
<211> LENGTH: 744
<212> TYPE: PRT
<213> ORGANISM: Arabidopsis thaliana

<400> SEQUENCE: 9

Met Glu Ala Met Leu Val Asp Cys Val Asn Asn Ser Leu Arg His Phe
1               5                   10                  15

Val Tyr Lys Asn Ala Ile Phe Met Cys Glu Arg Leu Cys Ala Glu Phe
            20                  25                  30

Pro Ser Glu Val Asn Leu Gln Leu Leu Ala Thr Ser Tyr Leu Gln Asn
        35                  40                  45

Asn Gln Ala Tyr Ser Ala Tyr His Leu Leu Lys Gly Thr Gln Met Ala
    50                  55                  60

Gln Ser Arg Tyr Leu Phe Ala Leu Ser Cys Phe Gln Met Asp Leu Leu
65                  70                  75                  80

Asn Glu Ala Glu Ser Ala Leu Cys Pro Val Asn Glu Pro Gly Ala Glu
                85                  90                  95

Ile Pro Asn Gly Ala Ala Gly His Tyr Leu Leu Gly Leu Ile Tyr Lys
            100                 105                 110

Tyr Thr Asp Arg Arg Lys Asn Ala Ala Gln Gln Phe Lys Gln Ser Leu
        115                 120                 125

Thr Ile Asp Pro Leu Leu Trp Ala Ala Tyr Glu Glu Leu Cys Ile Leu
    130                 135                 140

Gly Ala Ala Glu Glu Ala Thr Ala Val Phe Gly Glu Thr Ala Ala Leu
145                 150                 155                 160

Ser Ile Gln Lys Gln Tyr Met Gln Gln Leu Ser Thr Ser Leu Gly Leu
                165                 170                 175

Asn Thr Tyr Asn Glu Glu Arg Asn Ser Thr Ser Thr Lys Asn Thr Ser
            180                 185                 190

Ser Glu Asp Tyr Ser Pro Arg Gln Ser Lys His Thr Gln Ser His Gly
        195                 200                 205

Leu Lys Asp Ile Ser Gly Asn Phe His Ser His Gly Val Asn Gly Gly
    210                 215                 220

Val Ser Asn Met Ser Phe Tyr Asn Thr Pro Ser Pro Val Ala Ala Gln
225                 230                 235                 240

Leu Ser Gly Ile Ala Pro Pro Leu Phe Arg Asn Phe Gln Pro Ala
                245                 250                 255

Val Ala Asn Pro Asn Ser Leu Ile Thr Asp Ser Ser Pro Lys Ser Thr
            260                 265                 270

Val Asn Ser Thr Leu Gln Ala Pro Arg Arg Lys Phe Val Asp Glu Gly
        275                 280                 285

Lys Leu Arg Lys Ile Ser Gly Arg Leu Phe Ser Asp Ser Gly Pro Arg
    290                 295                 300

Arg Ser Ser Arg Leu Ser Ala Asp Ser Gly Ala Asn Ile Asn Ser Ser
305                 310                 315                 320

Val Ala Thr Val Ser Gly Asn Val Asn Asn Ala Ser Lys Tyr Leu Gly
                325                 330                 335

Gly Ser Lys Leu Ser Ser Leu Ala Leu Arg Ser Val Thr Leu Arg Lys
            340                 345                 350

Gly His Ser Trp Ala Asn Glu Asn Met Asp Glu Gly Val Arg Gly Glu
        355                 360                 365

```
Pro Phe Asp Asp Ser Arg Pro Asn Thr Ala Ser Thr Thr Gly Ser Met
    370                 375                 380

Ala Ser Asn Asp Gln Glu Asp Glu Thr Met Ser Ile Gly Gly Ile Ala
385                 390                 395                 400

Met Ser Ser Gln Thr Ile Thr Ile Gly Val Ser Glu Ile Leu Asn Leu
                405                 410                 415

Leu Arg Thr Leu Gly Glu Gly Cys Arg Leu Ser Tyr Met Tyr Arg Cys
            420                 425                 430

Gln Glu Ala Leu Asp Thr Tyr Met Lys Leu Pro His Lys His Tyr Asn
        435                 440                 445

Thr Gly Trp Val Leu Ser Gln Val Gly Lys Ala Tyr Phe Glu Leu Ile
    450                 455                 460

Asp Tyr Leu Glu Ala Glu Lys Ala Phe Arg Leu Ala Arg Leu Ala Ser
465                 470                 475                 480

Pro Tyr Cys Leu Glu Gly Met Asp Ile Tyr Ser Thr Val Leu Tyr His
                485                 490                 495

Leu Lys Glu Asp Met Lys Leu Ser Tyr Leu Ala Gln Glu Leu Ile Ser
            500                 505                 510

Thr Asp Arg Leu Ala Pro Gln Ser Trp Cys Ala Met Gly Asn Cys Tyr
        515                 520                 525

Ser Leu Gln Lys Asp His Glu Thr Ala Leu Lys Asn Phe Leu Arg Ala
    530                 535                 540

Val Gln Leu Asn Pro Arg Phe Ala Tyr Ala His Thr Leu Cys Gly His
545                 550                 555                 560

Glu Tyr Thr Thr Leu Glu Asp Phe Glu Asn Gly Met Lys Ser Tyr Gln
                565                 570                 575

Asn Ala Leu Arg Val Asp Thr Arg His Tyr Asn Ala Trp Tyr Gly Leu
            580                 585                 590

Gly Met Ile Tyr Leu Arg Gln Glu Lys Leu Glu Phe Ser Glu His His
        595                 600                 605

Phe Arg Met Ala Phe Leu Ile Asn Pro Ser Ser Val Ile Met Ser
    610                 615                 620

Tyr Leu Gly Thr Ser Leu His Ala Leu Lys Arg Ser Glu Glu Ala Leu
625                 630                 635                 640

Glu Ile Met Glu Gln Ala Ile Val Ala Asp Arg Lys Asn Pro Leu Pro
                645                 650                 655

Met Tyr Gln Lys Ala Asn Ile Leu Val Cys Leu Glu Arg Leu Asp Glu
            660                 665                 670

Ala Leu Glu Val Leu Glu Glu Leu Lys Glu Tyr Ala Pro Ser Glu Ser
        675                 680                 685

Ser Val Tyr Ala Leu Met Gly Arg Ile Tyr Lys Arg Arg Asn Met His
    690                 695                 700

Asp Lys Ala Met Leu His Phe Gly Leu Ala Leu Asp Met Lys Pro Pro
705                 710                 715                 720

Ala Thr Asp Val Ala Ala Ile Lys Ala Ala Met Glu Lys Leu His Val
                725                 730                 735

Pro Asp Glu Ile Asp Glu Ser Pro
            740

<210> SEQ ID NO 10
<211> LENGTH: 4577
<212> TYPE: DNA
<213> ORGANISM: Arabidopsis thaliana

<400> SEQUENCE: 10
```

```
atggaagcta tgcttgtgga ctgtgtaaac aacagtcttc gtcatttgt ctacaaaaat      60
gttattttca tgtgcgagcg tctctgcgct gagtttcctt ctgaggtaat caccctcttc     120
tttcactctc tctctctgat tttacctctc taattcaaat tctgtaaatc gaagctcttg    180
gaatggtaaa tttgatattt tgggtttgt aattcctctg ggtatctatg aattcgtcga    240
aagtgcgtct cttttggat ttggaattcg atagcttcac tgtgttcttc gagattgatt     300
ttggtttctt accttttagc cctttgtttt caagatccgt gtgttcaatt aggagatgaa    360
ttcgtgttct tttctctctc ttgttgaatt tgttttctct agtagctgtg ctcaatgctc    420
attactgatt tggtctttgg aaaatttgca ttttgagggt taatgacttt tgtccatata    480
tgtgatctca agtttaagta tttattatcc ttggaactta gctatgagtc aactgttaga    540
ggaatgtctc tgggattatc tcaagctttg ttaaaatttg ggttaataca gcttcaatag    600
tagttgagaa agtattcatt cattcagcct tggtctgga atattttcaa cattcgtagt     660
ggttgtccag tttctagctt cagttagtag aaatcatgtc aataaatgat tggcttttt     720
gtttgatcac tttctgaatt ttcctcttat ataggttaat ttgcagctat tagccaccag    780
ctacctgcag aataatcaag cttacagtgc atatcatctg ctaaagggtg cgtggcattg    840
tttcttgact tgttgcttgt tagccttta gtcagaattt tgcaccttct tttgttaggt    900
cgttttgatt atctttgtat atatatttt tttttgttat gtaaaggaac acaaatggct    960
cagtcccgat acttgttcgc attatcatgc ttccagatgg accttctcaa tgaagctgaa   1020
tctgcactct gccctgttaa tgaacctggt gcggaggtat ttaatgttct ctggtatttt   1080
gcctttattc gcttactgaa tgtcatttta caaaaacagt gtgtcagttt ctggacctta   1140
tttattgatt tagttcagtg aagataacaa catgcttctg attattgtgc agatcccaaa   1200
tggtgcagca ggccattacc ttcttggact tatttacaag tacgtttttt gttctgtcta   1260
tgcattttt cttgattctg aatggcttag atgagatgat tcctcatata taacagtgac   1320
cttttaggta tactgataga aggaagaatg ctgctcaaca atttaaacag tccttgacaa   1380
tagaccctct actttgggct gcatatgagg aattatgtat attaggtgaa cataatccgt   1440
tttctgcata cttcacagat atgttatggt tctcttacac ttttctgtct gctcaacttt   1500
caggtgctgc tgaggaagca actgcagttt tggtgaaac agctgctctc tccattcaaa   1560
agcagtatat gcaacaactg tcaacttccc tcggcttaaa cacttacaac gaggaacgta   1620
attcaacttc tactaaaaac acgagttctg aagattatag tccaaggcag tctaaacaca   1680
cacaaagcca tggccttaaa gatatctccg gaaatttcca ttctcatgga gttaatggag   1740
gtgtttcgaa catgtcattc tataatacgc cttcgccagt ggctgcacag gtaatgtcac   1800
acaattgtcg tactgctttt ttatgtaata caactatatc tccatctgtt gatcacacat   1860
tctgtagtac ttaggagatt tgtgcatcat gggtgttgat ttcacagcgt ttgtatctgt   1920
ttttctata tctgttatgc caaagaatg ggttgtctat tcttttgact attaaaaatg    1980
gggtcttcat tatgtttag tgtctttggt ttggcttgtt aatttatca acctttttag   2040
ttatctgaat aataacagct gtaagtaaat gctttttgt attttgaaa ttgtagctat   2100
ccggtatagc tccaccacca cttttccgga attttcagcc agctgttgca aacccaaact   2160
cccttattac tgacagttct ccaaagtcca ctgttaactc tactcttcaa gcacctagaa   2220
gaaagtttgt agatgaagga aagttacgta aggtaggatt cacataatca catatctcta   2280
cttgacatca tcaaatcata attttgaatt attggtcttt ctctgtaata gtctatttcg   2340
```

```
tactcgggat gaaattttct ataccaactt tcttaccgtg agtgcatgtc tcttatgttt    2400
gcagatttct ggcagactat tttctgattc tggtccacga cggagttcaa gactgtctgc    2460
tgattcaggg gcaaacatta attcaagtgt tgcaacagta agcggaaatg tgaacaacgc    2520
ttccaagtat ttgggaggtt ctaaattgag ttctttggca cttcgttctg taacacttcg    2580
gaagggacac tcctgggcaa atgaaaacat ggatgaaggt tgtgacattc catgcactat    2640
accactatat tgtttgaaat ctgcccttgt gtgactattg ttatcatgcc ttctatttt     2700 ggtgtctgca tatttgtaat accgtcattc tgatgggttt aggggtccgt ggggaacctt    2760
ttgatgattc aaggcctaat actgcctcaa cgactggttc tatggcttcc aatgatcaag    2820
aagacgaaac aatgtcgatt ggtggcatag caatgagttc tcaaacaatc acaattggtg    2880
tttcggaaat tttaaacctc cttaggacac tcggagaagg tgtagacttc tcatacatgt    2940
acaggtgtca ggtaggcata ttattgttct cgtgaattat gcaagtgagg tgaacctata    3000
taggcttatc tcattgtctc cttctgcttc tgggtcgttc aggaggcact ggatacgtat    3060
atgaaacttc cacataagca ttataataca ggatgggttc tttcccaggt aactagtgac    3120
tctttctctt ttaggctgcc atatatggat atagcctgaa tcagttttac tctagtggcc    3180
tgtgatagtt attgttgaaa ggtttatata cacatactat ggctattaaa tgtaggtcgg    3240
gaaagcatac tttgaactaa ttgactattt agaggctgaa aaggcattcc gtcttgcccg    3300
tctggcttct ccttattgct tagaaggaat ggatatatac tctacggtcc tctatgtaag    3360
tgtattatcc tggtttctaa acatgcaatc tcggatgagt gcggaaagaa atcacattta    3420
tgtaaatttt tcatcagcaa gatatgatat ttatttgcag catttgaagg aagacatgaa    3480
gctgagttac ttggctcagg aactaatatc aaccgatcgc ttagctcctc aatcttggta    3540 tttttgtcg aagttgtttt tctgattaac gttttcattt attgttggta ataagagaaa     3600
taagcaatca attatgtagg tgtgctatgg gaaattgcta tagcttgcaa aaggaccatg    3660
agaccgcact gaagaatttc ctacgagctg ttcaactgaa tccaagattt gcatatgcac    3720 atacctatg tggccacgag taagagagcc tctatccatt tgactttgtc ttgcacaatg     3780
tgcttaaaat tatctggtta ttggtctaat tgacactttc tatctttact gtctctgtag    3840
atacacaact cttgaggatt ttgagaacgg aatgaaaagt taccaaaacg cacttcgtgt    3900
agatacaaga cactacaacg catggtacgg gcttggaatg atatatctac gccaagagaa    3960
gttagagttc tcagagcatc acttcagaat ggctttccta ataaacccga gttcctctgt    4020
tataatgtct tatttaggga catctttgca tgccttgaag gttatcttat tactttcatc    4080
ttatcaggtc tacaagaaaa acaatctttg aagaatgact aaatgcttct tcttgttttg    4140
tgttaataga gaagtgagga agcactagag ataatggagc aagccatagt agcagataga    4200
aaaaaccctc ttccaatgta ccagaaagct aacatacttg tctgcttaga aagattagat    4260
gaagctctag aagttcttga ggagctcaaa gagtatgcgc cttcagagag cagcgtttac    4320
gctttaatgg gcaggatcta taagcggcga acatgcacg ataaagccat gcttcatttc     4380
ggtctagctt tagatatgaa accgcctgca actgacgttg ctgcaataaa ggttcgagtc    4440
tttaaaacag agtcgtccaa tgatggtttt taaatctgaa aattcaagga ttcatagctt    4500
aaactggtta ttattgtctg aaacaggctg caatggagaa attgcatgtt ccagatgaga    4560
tcgatgagag cccgtga                                                   4577
```

<210> SEQ ID NO 11
<211> LENGTH: 4577

<212> TYPE: DNA
<213> ORGANISM: Arabidopsis thaliana

<400> SEQUENCE: 11

| | | | | |
|---|---|---|---|---|
| atggaagcta | tgcttgtgga | ctgtgtaaac | aacagtcttc | gtcatttgt ctacaaaaat | 60 |
| gctattttca | tgtgcgagcg | tctctgcgct | gagtttcctt | ctgaggtaat caccctcttc | 120 |
| tttcactctc | tctctctgat | tttacctctc | taattcaaat | tctgtaaatc gaagctcttg | 180 |
| gaatggtaaa | tttgatattt | tgggtttgt | aattcctctg | ggtatctatg aattcgtcga | 240 |
| aagtgcgtct | cttttggat | ttggaattcg | atagcttcac | tgtgttcttc gagattgatt | 300 |
| ttggtttctt | accttttagc | cctttgtttt | caagatccgt | gtgttcaatt aggagatgaa | 360 |
| ttcgtgttct | tttctctctc | ttgttgaatt | tgttttctct | agtagctgtg ctcaatgctc | 420 |
| attactgatt | tggtctttgg | aaaatttgca | ttttgagggt | taatgacttt tgtccatata | 480 |
| tgtgatctca | agtttaagta | tttattatcc | ttggaactta | gctatgagtc aactgttaga | 540 |
| ggaatgtctc | tgggattatc | tcaagctttg | ttaaaatttg | gttaataca gcttcaatag | 600 |
| tagttgagaa | agtattcatt | cattcagcct | tggtctgga | atattttcaa cattcgtagt | 660 |
| ggttgtccag | tttctagctt | cagttagtag | aaatcatgtc | aataaatgat tggccttttt | 720 |
| gtttgatcac | tttctgaatt | ttcctcttat | ataggttaat | ttgcagctat tagccaccag | 780 |
| ctacctgcag | aataatcaag | cttacagtgc | atatcatctg | ctaaagggtg cgtggcattg | 840 |
| tttcttgact | tgttgcttgt | tagccttta | gtcagaattt | tgcaccttct tttgttaggt | 900 |
| cgttttgatt | atctttgtat | atatatttt | ttttgttat | gtaaaggaac acaaatggct | 960 |
| cagtcccgat | acttgttcgc | attatcatgc | ttccagatgg | accttctcaa tgaagctgaa | 1020 |
| tctgcactct | gccctgttaa | tgaacctggt | gcggaggtat | ttaatgttct ctggtatttt | 1080 |
| gcctttattc | gcttactgaa | tgtcatttta | caaaacagt | gtgtcagttt ctggaccttt a | 1140 |
| tttattgatt | tagttcagtg | aagataacaa | catgcttctg | attattgtgc agatcccaaa | 1200 |
| tggtgcagca | ggccatttacc | ttcttggact | tatttacaag | tacgtttttt gttctgtcta | 1260 |
| tgcatttttt | cttgattctg | aatggcttag | atgagatgat | tcctcatata taacagtgac | 1320 |
| cttttaggta | tactgataga | aggaagaatg | ctgctcaaca | atttaaacag tccttgacaa | 1380 |
| tagaccctct | actttgggct | gcatatgagg | aattatgtat | attaggtgaa cataatccgt | 1440 |
| tttctgcata | cttcacagat | atgttatggt | tctcttacac | ttttctgtct gctcaacttt | 1500 |
| caagtgctgc | tgaggaagca | actgcagttt | tggtgaaac | agctgctctc tccattcaaa | 1560 |
| agcagtatat | gcaacaactg | tcaacttccc | tcggcttaaa | cacttacaac gaggaacgta | 1620 |
| attcaacttc | tactaaaaac | acgagttctg | aagattatag | tccaaggcag tctaaacaca | 1680 |
| cacaaagcca | tggccttaaa | gatatctccg | gaaatttcca | ttctcatgga gttaatggag | 1740 |
| gtgtttcgaa | catgtcattc | tataatacgc | cttcgccagt | ggctgcacag gtaatgtcac | 1800 |
| acaattgtcg | tactgctttt | ttatgtaata | caactatatc | tccatctgtt gatcacacat | 1860 |
| tctgtagtac | ttaggagatt | tgtgcatcat | gggtgttgat | ttcacagcgt ttgtatctgt | 1920 |
| ttttctata | tctgttatgc | caaaagaatg | ggttgtctat | tcttttgact attaaaaatg | 1980 |
| gggtcttcat | tatgttttag | tgtctttggt | ttggcttgtt | aatttatca acctttttag | 2040 |
| ttatctgaat | aataacagct | gtaagtaaat | gcttttttgt | attttgaaa ttgtagctat | 2100 |
| ccggtatagc | tccaccacca | cttttccgga | attttcagcc | agctgttgca aacccaaact | 2160 |
| cccttattac | tgacagttct | ccaaagtcca | ctgttaactc | tactcttcaa gcacctagaa | 2220 |

```
gaaagtttgt agatgaagga aagttacgta aggtaggatt cacataatca catatctcta      2280
cttgacatca tcaaatcata attttgaatt attggtcttt ctctgtaata gtctatttcg      2340
tactcgggat gaaattttct ataccaactt tcttaccgtg agtgcatgtc tcttatgttt      2400
gcagatttct ggcagactat tttctgattc tggtccacga cggagttcaa gactgtctgc      2460
tgattcaggg gcaaacatta attcaagtgt tgcaacagta agcggaaatg tgaacaacgc      2520
ttccaagtat ttgggaggtt ctaaattgag ttctttggca cttcgttctg taacacttcg      2580
gaagggacac tcctgggcaa atgaaaacat ggatgaaggt tgtgacattc catgcactat      2640
accactatat tgtttgaaat ctgcccttgt gtgactattg ttatcatgcc ttctattttt      2700
ggtgtctgca tatttgtaat accgtcattc tgatgggttt aggggtccgt ggggaacctt      2760
ttgatgattc aaggcctaat actgcctcaa cgactggttc tatggcttcc aatgatcaag      2820
aagacgaaac aatgtcgatt ggtggcatag caatgagttc tcaaacaatc acaattggtg      2880
tttcggaaat tttaaacctc cttaggacac tcggagaagg gtgtagactt tcatacatgt      2940
acaggtgtca ggtaggcata ttattgttct cgtgaattat gcaagtgagg tgaacctata      3000
taggcttatc tcattgtctc cttctgcttc tgggtcgttc aggaggcact ggatacgtat      3060
atgaaacttc cacataagca ttataataca ggatgggttc tttcccaggt aactagtgac      3120
tctttctctt ttaggctgcc atatatggat atagcctgaa tcagttttac tctagtggcc      3180
tgtgatagtt attgttgaaa ggtttatata cacatactat ggctattaaa tgtaggtcgg      3240
gaaagcatac tttgaactaa ttgactattt agaggctgaa aaggcattcc gtcttgcccg      3300
tctggcttct ccttattgct tagaaggaat ggatatatac tctacggtcc tctatgtaag      3360
tgtattatcc tggtttctaa acatgcaatc tcggatgagt gcggaaagaa atcacattta      3420
tgtaaatttt tcatcagcaa gatatgatat ttatttgcag catttgaagg aagacatgaa      3480
gctgagttac ttggctcagg aactaatatc aaccgatcgc ttagctcctc aatcttggta      3540
ttttttgtcg aagttgtttt tctgattaac gttttcattt attgttggta ataagagaaa      3600
taagcaatca attatgtagg tgtgctatgg gaaattgcta tagcttgcaa aaggaccatg      3660
agaccgcact gaagaatttc ctacgagctg ttcaactgaa tccaagattt gcatatgcac      3720 atacctatg tggccacgag taagagagcc tctatccatt tgactttgtc ttgcacaatg      3780
tgcttaaaat tatctggtta ttggtctaat tgacactttc tatctttact gtctctgtag      3840
atacacaact cttgaggatt ttgagaacgg aatgaaaagt taccaaaacg cacttcgtgt      3900
agatacaaga cactacaacg catggtacgg gcttggaatg atatatctac gccaagagaa      3960
gttagagttc tcagagcatc acttcagaat ggctttccta ataaacccga gttcctctgt      4020
tataatgtct tatttaggga catctttgca tgccttgaag gttatcttat tactttcatc      4080
ttatcaggtc tacaagaaaa acaatctttg aagaatgact aaatgcttct tcttgttttg      4140
tgttaataga gaagtgagga agcactagag ataatggagc aagccatagt agcagataga      4200
aaaaaccctc ttccaatgta ccagaaagct aacatacttg tctgcttaga aagattagat      4260
gaagctctag aagttcttga ggagctcaaa gagtatgcgc cttcagagag cagcgtttac      4320
gctttaatgg gcaggatcta aagcggcga aacatgcacg ataaagccat gcttcatttc      4380
ggtctagctt tagatatgaa accgcctgca actgacgttg ctgcaataaa ggttcgagtc      4440
tttaaaacag agtcgtccaa tgatggtttt taaatctgaa aattcaagga ttcatagctt      4500
aaactggtta ttattgtctg aaacaggctg caatggagaa attgcatgtt ccagatgaga      4560
tcgatgagag cccgtga                                                    4577
```

<210> SEQ ID NO 12
<211> LENGTH: 4577
<212> TYPE: DNA
<213> ORGANISM: Arabidopsis thaliana

<400> SEQUENCE: 12

| | | | | | |
|---|---|---|---|---|---|
| atggaagcta | tgcttgtgga | ctgtgtaaac | aacagtcttc | gtcattttgt | ctacaaaaat | 60 |
| gctattttca | tgtgcgagcg | tctctgcgct | gagtttcctt | ctgaggtaat | caccctcttc | 120 |
| tttcactctc | tctctctgat | tttacctctc | taattcaaat | tctgtaaatc | gaagctcttg | 180 |
| gaatggtaaa | tttgatattt | tgggtttgt | aattcctctg | ggtatctatg | aattcgtcga | 240 |
| aagtgcgtct | cttttggat | ttggaattcg | atagcttcac | tgtgttcttc | gagattgatt | 300 |
| ttggtttctt | acctttttagc | cctttgtttt | caagatccgt | gtgttcaatt | aggagatgaa | 360 |
| ttcgtgttct | tttctctctc | ttgttgaatt | tgttttctct | agtagctgtg | ctcaatgctc | 420 |
| attactgatt | tggtctttgg | aaaatttgca | ttttgagggt | taatgacttt | tgtccatata | 480 |
| tgtgatctca | agtttaagta | tttattatcc | ttggaactta | gctatgagtc | aactgttaga | 540 |
| ggaatgtctc | tgggattatc | tcaagctttg | ttaaaatttg | ggttaataca | gcttcaatag | 600 |
| tagttgagaa | agtattcatt | cattcagcct | tggtctgga | atattttcaa | cattcgtagt | 660 |
| ggttgtccag | tttctagctt | cagttagtag | aaatcatgtc | aataaatgat | tggccttttt | 720 |
| gtttgatcac | tttctgaatt | ttcctcttat | ataggttaat | ttgcagctat | tagccaccag | 780 |
| ctacctgcag | aataatcaag | cttacagtgc | atatcatctg | ctaaagggtg | cgtggcattg | 840 |
| tttcttgact | tgttgcttgt | tagcctttta | gtcagaattt | tgcaccttct | tttgttaggt | 900 |
| cgttttgatt | atctttgtat | atatattttt | tttttgttat | gtaaaggaac | acaaatggct | 960 |
| cagtcccgat | acttgttcgc | attatcatgc | ttccagatgg | accttctcaa | tgaagctgaa | 1020 |
| tctgcactct | gccctgttaa | tgaacctggt | gcggaggtat | ttaatgttct | ctggtatttt | 1080 |
| gcctttattc | gcttactgaa | tgtcatttta | caaaaacagt | gtgtcagttt | ctggaccta | 1140 |
| tttattgatt | tagttcagtg | aagataacaa | catgcttctg | attattgtgc | agatcccaaa | 1200 |
| tggtgcagca | ggccattacc | ttcttggact | tatttacaag | tacgtttttt | gttctgtcta | 1260 |
| tgcattttt | cttgattctg | aatggcttag | atgagatgat | tcctcatata | taacagtgac | 1320 |
| cttttaggta | tactgataga | aggaagaatg | ctgctcaaca | atttaaacag | tccttgacaa | 1380 |
| tagaccctct | actttgggct | gcatatgagg | aattatgtat | attaggtgaa | cataatccgt | 1440 |
| tttctgcata | cttcacagat | atgttatggt | tctcttacac | ttttctgtct | gctcaacttt | 1500 |
| caggtgctgc | tgaggaagca | actgcagttt | tggtgaaac | agctgctctc | tccattcaaa | 1560 |
| agcagtatat | gcaacaactg | tcaacttccc | tcggcttaaa | cacttacaac | gaggaacgta | 1620 |
| attcaacttc | tactaaaaac | acgagttctg | aagattatag | tccaaggcag | tctaaacaca | 1680 |
| cacaaagcca | tggccttaaa | gatatctccg | gaaatttcca | ttctcatgga | gttaatggag | 1740 |
| gtgtttcgaa | catgtcattc | tataatacgc | cttcgccagt | ggctgcacag | gtaatgtcac | 1800 |
| acaattgtcg | tactgctttt | ttatgtaata | caactatatc | tccatctgtt | gatcacacat | 1860 |
| tctgtagtac | ttaggagatt | tgtgcatcat | gggtgttgat | ttcacagcgt | ttgtatctgt | 1920 |
| tttttctata | tctgttatgc | caaaagaatg | ggttgtctat | tcttttgact | attaaaaatg | 1980 |
| gggtcttcat | tatgttttag | tgtctttggt | ttggcttgtt | aattttatca | accttttag | 2040 |
| ttatctgaat | aataacagct | gtaagtaaat | gcttttttgt | attttgaaa | ttgtagctat | 2100 |

```
ccggtatagc tccaccacca cttttccgga attttcagcc agctgttgca aacccaaact   2160
cccttattac tgacagttct ccaaagtcca ctgttaactc tactcttcaa gcacctagaa   2220
gaaagtttgt agatgaagga aagttacgta aggtaggatt cacataatca catatctcta   2280
cttgacatca tcaaatcata attttgaatt attggtcttt ctctgtaata gtctatttcg   2340
tactcgggat gaaattttct ataccaactt tcttaccgtg agtgcatgtc tcttatgttt   2400
gcagatttct ggcagactat tttctgattc tggtccacga cggagttcaa gactgtctgc   2460
tgattcaggg gcaaacatta attcaagtgt tgcaacagta agcggaaatg tgaacaacgc   2520
ttccaagtat ttgggaggtt ctaaattgag ttctttggca cttcgttctg taacacttcg   2580
gaagggacac tcctgggcaa atgaaaacat ggatgaaggt tgtgacattc catgcactat   2640
accactatat tgtttgaaat ctgcccttgt gtgactattg ttatcatgcc ttctattttt   2700
ggtgtctgca tatttgtaat accgtcattc tgatgggttt aggggtccgt ggggaacctt   2760
ttgatgattc aaggcctaat actgcctcaa cgactggttc tatggcttcc aatgatcaag   2820
aagacgaaac aatgtcgatt ggtggcatag caatgagttc tcaaacaatc acaattggtg   2880
tttcggaaat tttaaacctc cttaggacac tcagagaagg gtgtagactt tcatacatgt   2940
acaggtgtca ggtaggcata ttattgttct cgtgaattat gcaagtgagg tgaacctata   3000
taggcttatc tcattgtctc cttctgcttc tgggtcgttc aggaggcact ggatacgtat   3060
atgaaacttc cacataagca ttataataca ggatgggttc tttcccaggt aactagtgac   3120
tctttctctt ttaggctgcc atatatggat atagcctgaa tcagttttac tctagtggcc   3180
tgtgatagtt attgttgaaa ggtttatata cacatactat ggctattaaa tgtaggtcgg   3240
gaaagcatac tttgaactaa ttgactattt agaggctgaa aaggcattcc gtcttgcccg   3300
tctggcttct ccttattgct tagaaggaat ggatatatac tctacggtcc tctatgtaag   3360
tgtattatcc tggtttctaa acatgcaatc tcggatgagt gcggaaagaa atcacattta   3420
tgtaaatttt tcatcagcaa gatatgatat ttatttgcag catttgaagg aagacatgaa   3480
gctgagttac ttggctcagg aactaatatc aaccgatcgc ttagctcctc aatcttggta   3540
ttttttgtcg aagttgtttt tctgattaac gttttcattt attgttggta ataagagaaa   3600
taagcaatca attatgtagg tgtgctatgg gaaattgcta tagcttgcaa aaggaccatg   3660
agaccgcact gaagaatttc ctacgagctg ttcaactgaa tccaagattt gcatatgcac   3720
ataccttatg tggccacgag taagagagcc tctatccatt tgactttgtc ttgcacaatg   3780
tgcttaaaat tatctggtta ttggtctaat tgacactttc tatctttact gtctctgtag   3840
atacacaact cttgaggatt ttgagaacgg aatgaaaagt taccaaaacg cacttcgtgt   3900
agatacaaga cactacaacg catggtacgg gcttggaata atatatctac gccaagagaa   3960
gttagagttc tcagagcatc acttcagaat ggctttccta ataaacccga gttcctctgt   4020
tataatgtct tatttaggga catctttgca tgccttgaag gttatcttat tactttcatc   4080
ttatcaggtc tacaagaaaa acaatctttg aagaatgact aaatgcttct tcttgttttg   4140
tgttaataga gaagtgagga agcactagag ataatggagc aagccatagt agcagataga   4200
aaaaaccctc ttccaatgta ccagaaagct aacatacttg tctgcttaga aagattagat   4260
gaagctctag aagttcttga ggagctcaaa gagtatgcgc cttcagagag cagcgtttac   4320
gctttaatgg gcaggatcta taagcggcga acatgcacg ataaagccat gcttcatttc   4380
ggtctagctt tagatatgaa accgcctgca actgacgttg ctgcaataaa ggttcgagtc   4440
tttaaaacag agtcgtccaa tgatggtttt taaatctgaa aattcaagga ttcatagctt   4500
```

```
aaactggtta ttattgtctg aaacaggctg caatggagaa attgcatgtt ccagatgaga    4560
tcgatgagag cccgtga                                                   4577

<210> SEQ ID NO 13
<211> LENGTH: 4577
<212> TYPE: DNA
<213> ORGANISM: Arabidopsis thaliana

<400> SEQUENCE: 13
atggaagcta tgcttgtgga ctgtgtaaac aacagtcttc gtcattttgt ctacaaaaat      60
gctattttca tgtgcgagcg tctctgcgct gagtttcctt ctgaggtaat caccctcttc     120
tttcactctc tctctctgat tttacctctc taattcaaat tctgtaaatc gaagctcttg     180
gaatggtaaa tttgatattt tgggtttgt  aattcctctg ggtatctatg aattcgtcga     240
aagtgcgtct cttttggat  ttggaattcg atagcttcac tgtgttcttc gagattgatt     300
ttggtttctt accttttagc cctttgtttt caagatccgt gtgttcaatt aggagatgaa     360
ttcgtgttct tttctctctc ttgttgaatt tgttttctct agtagctgtg ctcaatgctc     420
attactgatt tggtctttgg aaaatttgca ttttgagggt taatgacttt tgtccatata     480
tgtgatctca gtttaagta  tttattatcc ttggaactta gctatgagtc aactgttaga     540
ggaatgtctc tgggattatc tcaagctttg ttaaaatttg ggttaataca gcttcaatag     600
tagttgagaa agtattcatt cattcagcct ttggtctgga atattttcaa cattcgtagt     660
ggttgtccag tttctagctt cagttagtag aaatcatgtc aataaatgat tggccttttt     720
gtttgatcac tttctgaatt ttcctcttat ataggttaat ttgcagctat tagccaccag     780
ctacctgcag aataatcaag cttacagtgc atatcatctg ctaaagggtg cgtggcattg     840
tttcttgact tgttgcttgt tagccttta  gtcagaattt tgcaccttct tttgttaggt     900
cgttttgatt atctttgtat atatatttt  ttttgttat  gtaaaggaac acaaatggct     960
cagtcccgat acttgttcgc attatcatgc ttccagatgg accttctcaa tgaagctgaa    1020
tctgcactct gccctgttaa tgaacctggt gcggaggtat ttaatgttct ctggtatttt    1080
gcctttattc gcttactgaa tgtcattta  caaaaacagt gtgtcagttt ctggacctta    1140
tttattgatt tagttcagtg aagataacaa catgcttctg attattgtgc agatcccaaa    1200
tggtgcagca ggccattacc ttcttggact tatttacaag tacgttttt  gttctgtcta    1260 tgcattttt  cttgattctg aatggcttag atgagatgat tcctcatata taacagtgac    1320 ctttaggta  tactgataga aggaagaatg ctgctcaaca atttaaacag tccttgacaa    1380
tagaccctct actttgggct gcatatgagg aattatgtat attaggtgaa cataatccgt    1440
tttctgcata cttcacagat atgttatggt tctcttacac ttttctgtct gctcaacttt    1500
caggtgctgc tgaggaagca actgcagttt ttggtgaaac agctgctctc tccattcaaa    1560
agcagtatat gcaacaactg tcaacttccc tcggcttaaa cacttacaac gaggaacgta    1620
attcaacttc tactaaaaac acgagttctg aagattatag tccaaggcag tctaaacaca    1680
cacaaagcca tggccttaaa gatatctccg gaaatttcca ttctcatgga gttaatggag    1740
gtgtttcgaa catgtcattc tataatacgc cttcgccagt ggctgcacag gtaatgtcac    1800
acaattgtcg tactgctttt ttatgtaata caactatatc tccatctgtt gatcacacat    1860
tctgtagtac ttaggagatt tgtgcatcat gggtgttgat ttcacagcgt ttgtatctgt    1920 ttttctata  tctgttatgc caaagaatg  ggttgtctat tcttttgact attaaaaatg    1980
```

```
gggtcttcat tatgttttag tgtctttggt ttggcttgtt aattttatca acctttttag    2040
ttatctgaat aataacagct gtaagtaaat gcttttttgt attttttgaaa ttgtagctat    2100 ccggtatagc tccaccacca cttttccgga attttcagcc agctgttgca aacccaaact    2160
cccttattac tgacagttct ccaaagtcca ctgttaactc tactcttcaa gcacctagaa    2220
gaaagtttgt agatgaagga aagttacgta aggtaggatt cacataatca catatctcta    2280
cttgacatca tcaaatcata attttgaatt attggtcttt ctctgtaata gtctatttcg    2340
tactcgggat gaaattttct ataccaactt tcttaccgtg agtgcatgtc tcttatgttt    2400
gcagatttct ggcagactat tttctgattc tggtccacga cggagttcaa gactgtctgc    2460
tgattcaggg gcaaacatta attcaagtgt tgcaacagta agcggaaatg tgaacaacgc    2520
ttccaagtat ttgggaggtt ctaaattgag ttctttggca cttcgttctg taacacttcg    2580
gaagggacac tcctgggcaa atgaaaacat ggatgaaggt tgtgacattc catgcactat    2640
accactatat tgtttgaaat ctgcccttgt gtgactattg ttatcatgcc ttctattttt    2700
ggtgtctgca tatttgtaat accgtcattc tgatgggttt aggggtccgt ggggaacctt    2760
ttgatgattc aaggcctaat actgcctcaa cgactggttc tatggcttcc aatgatcaag    2820
aagacgaaac aatgtcgatt ggtggcatag caatgagttc tcaaacaatc acaattggtg    2880
tttcggaaat tttaaacctc cttaggacac tcggagaagg gtgtagactt tcatacatgt    2940
acaggtgtca ggtaggcata ttattgttct cgtgaattat gcaagtgagg tgaacctata    3000
taggcttatc tcattgtctc cttctgcttc tgggtcgttc aagaggcact ggatacgtat    3060
atgaaacttc cacataagca ttataataca ggatgggttc tttcccaggt aactagtgac    3120
tctttctctt ttaggctgcc atatatggat atagcctgaa tcagttttac tctagtggcc    3180
tgtgatagtt attgttgaaa ggtttatata cacatactat ggctattaaa tgtaggtcgg    3240
gaaagcatac tttgaactaa ttgactattt agaggctgaa aaggcattcc gtcttgcccg    3300
tctggcttct ccttattgct tagaaggaat ggatatatac tctacggtcc tctatgtaag    3360
tgtattatcc tggtttctaa acatgcaatc tcggatgagt gcggaaagaa atcacatttta   3420 tgtaaatttt tcatcagcaa gatatgatat ttatttgcag catttgaagg aagacatgaa    3480
gctgagttac ttggctcagg aactaatatc aaccgatcgc ttagctcctc aatcttggta    3540 tttttttgtcg aagttgtttt tctgattaac gttttcattt attgttggta ataagagaaa   3600
taagcaatca attatgtagg tgtgctatgg gaaattgcta tagcttgcaa aaggaccatg    3660
agaccgcact gaagaatttc ctacgagctg ttcaactgaa tccaagattt gcatatgcac    3720
ataccttatg tggccacgag taagagagcc tctatccatt tgactttgtc ttgcacaatg    3780
tgcttaaaat tatctggtta ttggtctaat tgacactttc tatctttact gtctctgtag    3840
atacacaact cttgaggatt ttgagaacgg aatgaaaagt taccaaaacg cacttcgtgt    3900
agatacaaga cactacaacg catggtacgg gcttggaatg atatatctac gccaagagaa    3960
gttagagttc tcagagcatc acttcagaat ggctttccta ataaacccga gttcctctgt    4020
tataatgtct tatttaggga catctttgca tgccttgaag gttatcttat tactttcatc    4080
ttatcaggtc tacaagaaaa acaatctttg aagaatgact aaatgcttct tcttgttttg    4140
tgttaataga gaagtgagga agcactagag ataatggagc aagccatagt agcagataga    4200
aaaaaccctc ttccaatgta ccagaaagct aacatacttg tctgcttaga aagattagat    4260
gaagctctag aagttcttga ggagctcaaa gagtatgcgc cttcagagag cagcgtttac    4320
gctttaatgg gcaggatcta taagcggcga aacatgcacg ataaagccat gcttcatttc    4380
```

| | |
|---|---:|
| ggtctagctt tagatatgaa accgcctgca actgacgttg ctgcaataaa ggttcgagtc | 4440 |
| tttaaaacag agtcgtccaa tgatggtttt taaatctgaa aattcaagga ttcatagctt | 4500 |
| aaactggtta ttattgtctg aaacaggctg caatggagaa attgcatgtt ccagatgaga | 4560 |
| tcgatgagag cccgtga | 4577 |

```
<210> SEQ ID NO 14
<211> LENGTH: 4577
<212> TYPE: DNA
<213> ORGANISM: Arabidopsis thaliana

<400> SEQUENCE: 14
```

| | |
|---|---:|
| atggaagcta tgcttgtgga ctgtgtaaac aacagtcttc gtcattttgt ctacaaaaat | 60 |
| gctattttca tgtgcgagcg tctctgcgct gagtttcctt ctgaggtaat caccctcttc | 120 |
| tttcactctc tctctctgat tttacctctc taattcaaat tctgtaaatc gaagctcttg | 180 |
| gaatggtaaa tttgatattt tgggtttgt aattcctctg gtatctatg aattcgtcga | 240 |
| aagtgcgtct cttttggat ttggaattcg atagcttcac tgtgttcttc gagattgatt | 300 |
| ttggtttctt acctttagc cctttgtttt caagatccgt gtgttcaatt aggagatgaa | 360 |
| ttcgtgttct tttctctctc ttgttgaatt tgttttctct agtagctgtg ctcaatgctc | 420 |
| attactgatt tggtctttgg aaaatttgca ttttgagggt taatgacttt tgtccatata | 480 |
| tgtgatctca agtttaagta tttattatcc ttggaactta gctatgagtc aactgttaga | 540 |
| ggaatgtctc tgggattatc tcaagctttg ttaaaatttg ggttaataca gcttcaatag | 600 |
| tagttgagaa agtattcatt cattcagcct ttggtctgga atattttcaa cattcgtagt | 660 |
| ggttgtccag tttctagctt cagttagtag aaatcatgtc aataaatgat tggcctttt | 720 |
| gtttgatcac tttctgaatt ttcctcttat ataggttaat ttgcagctat tagccaccag | 780 |
| ctacctgcag aataatcaag cttacagtgc atatcatctg ctaaagggtg cgtggcattg | 840 |
| ttcttgact tgttgcttgt tagcctttta gtcagaattt tgcaccttct tttgttaggt | 900 |
| cgttttgatt atctttgtat atatattttt tttttgttat gtaaaggaac acaaatggct | 960 |
| cagtcccgat acttgttcgc attatcatgc ttccagatgg accttctcaa tgaagctgaa | 1020 |
| tctgcactct gccctgttaa tgaacctggt gcggaggtat ttaatgttct ctggtatttt | 1080 |
| gcctttattc gcttactgaa tgtcatttta caaaaacagt gtgtcagttt ctggacctta | 1140 |
| tttattgatt tagttcagtg aagataacaa catgcttctg attattgtgc agatcccaaa | 1200 |
| tggtgcagca ggccattacc ttcttggact tatttacaag tacgttttt gttctgtcta | 1260 |
| tgcatttttt cttgattctg aatggcttag atgagatgat tcctcatata taacagtgac | 1320 |
| cttttaggta tactgataga aggaagaatg ctgctcaaca atttaaacag tccttgacaa | 1380 |
| tagaccctct actttgggct gcatatgagg aattatgtat attaggtgaa cataatccgt | 1440 |
| tttctgcata cttcacagat atgttatggt tctcttacac ttttctgtct gctcaacttt | 1500 |
| caggtgctgc tgaggaagca actgcagttt tggtgaaac agctgctctc tccattcaaa | 1560 |
| agcagtatat gcaacaactg tcaacttccc tcggcttaaa cacttacaac gaggaacgta | 1620 |
| attcaacttc tactaaaaac acgagttctg aagattatag tccaaggcag tctaaacaca | 1680 |
| cacaaagcca tggccttaaa gatatctccg gaaatttcca ttctcatgga gttaatggag | 1740 |
| gtgtttcgaa catgtcattc tataatacg cttcgccagt ggctgcacag gtaatgtcac | 1800 |
| acaattgtcg tactgctttt ttatgtaata caactatatc tccatctgtt gatcacacat | 1860 |

```
tctgtagtac ttaggagatt tgtgcatcat gggtgttgat ttcacagcgt ttgtatctgt    1920 ttttctata tctgttatgc caaaagaatg ggttgtctat tcttttgact attaaaaatg     1980
gggtcttcat tatgttttag tgtctttggt ttggcttgtt aattttatca acctttttag    2040
ttatctgaat aataacagct gtaagtaaat gcttttttgt attttgaaa ttgtagctat     2100 ccggtatagc tccaccacca cttttccgga attttcagcc agctgttgca aacccaaact    2160
cccttattac tgacagttct ccaaagtcca ctgttaactc tactcttcaa gcacctagaa    2220
gaaagtttgt agatgaagga aagttacgta aggtaggatt cacataatca catatctcta    2280
cttgacatca tcaaatcata attttgaatt attggtcttt ctctgtaata gtctatttcg    2340
tactcgggat gaaattttct ataccaactt tcttaccgtg agtgcatgtc tcttatgttt    2400
gcagatttct ggcagactat tttctgattc tggtccacga cggagttcaa gactgtctgc    2460
tgattcaggg gcaaacatta attcaagtgt tgcaacagta agcggaaatg tgaacaacgc    2520
ttccaagtat ttgggaggtt ctaaattgag ttctttggca cttcgttctg taacacttcg    2580
gaagggacac tcctgggcaa atgaaaacat ggatgaaggt tgtgacattc catgcactat    2640
accactatat tgtttgaaat ctgcccttgt gtgactattg ttatcatgcc ttctattttt    2700
ggtgtctgca tatttgtaat accgtcattc tgatgggttt aggggtccgt ggggaacctt    2760
ttgatgattc aaggcctaat actgcctcaa cgactggttc tatggcttcc aatgatcaag    2820
aagacgaaac aatgtcgatt ggtggcatag caatgagttc tcaaacaatc acaattggtg    2880
tttcggaaat tttaaacctc cttaggacac tcggagaagg gtgtagactt tcatacatgt    2940
acaggtgtca ggtaggcata ttattgttct cgtgaattat gcaagtgagg tgaacctata    3000
taggcttatc tcattgtctc cttctgcttc tgggtcgttc aggaggcact ggatacgtat    3060
atgaaacttc cacataagca ttataataca ggatgggttc tttcccaggt aactagtgac    3120
tctttctctt ttaggctgcc atatatggat atagcctgaa tcagttttac tctagtggcc    3180
tgtgatagtt attgttgaaa ggtttatata cacatactat ggctattaaa tgtaggtcgg    3240
gaaagcatac tttgaactaa ttgactattt agaggctgaa aaggcattcc gtcttgcccg    3300
tctggcttct ccttattgct tagaaggaat ggatatatac tctacggtcc tctatgtaaa    3360
tgtattatcc tggtttctaa acatgcaatc tcggatgagt gcggaaagaa atcacattta    3420
tgtaaatttt tcatcagcaa gatatgatat ttatttgcag catttgaagg aagacatgaa    3480
gctgagttac ttggctcagg aactaatatc aaccgatcgc ttagctcctc aatcttggta    3540
ttttttgtcg aagttgtttt tctgattaac gttttcattt attgttggta ataagagaaa    3600
taagcaatca attatgtagg tgtgctatgg gaaattgcta tagcttgcaa aaggaccatg    3660
agaccgcact gaagaatttc ctacgagctg ttcaactgaa tccaagattt gcatatgcac    3720
ataccttatg tggccacgag taagagagcc tctatccatt tgactttgtc ttgcacaatg    3780
tgcttaaaat tatctggtta ttggtctaat tgacactttc tatctttact gtctctgtag    3840
atacacaact cttgaggatt ttgagaacgg aatgaaaagt taccaaaacg cacttcgtgt    3900
agatacaaga cactacaacg catggtacgg gcttggaatg atatatctac gccaagagaa    3960
gttagagttc tcagagcatc acttcagaat ggctttccta ataaacccga gttcctctgt    4020
tataatgtct tatttaggga catctttgca tgccttgaag gttatcttat tactttcatc    4080
ttatcaggtc tacaagaaaa acaatctttg aagaatgact aaatgcttct tcttgttttg    4140
tgttaataga gaagtgagga agcactagag ataatggagc aagccatagt agcagataga    4200
aaaaaccctc ttccaatgta ccagaaagct aacatacttg tctgcttaga aagattagat    4260
```

```
gaagctctag aagttcttga ggagctcaaa gagtatgcgc cttcagagag cagcgtttac    4320
gctttaatgg gcaggatcta aagcggcga aacatgcacg ataaagccat gcttcatttc    4380
ggtctagctt tagatatgaa accgcctgca actgacgttg ctgcaataaa ggttcgagtc    4440
tttaaaacag agtcgtccaa tgatggtttt taaatctgaa aattcaagga ttcatagctt    4500
aaactggtta ttattgtctg aaacaggctg caatggagaa attgcatgtt ccagatgaga    4560
tcgatgagag cccgtga                                                  4577

<210> SEQ ID NO 15
<211> LENGTH: 4577
<212> TYPE: DNA
<213> ORGANISM: Arabidopsis thaliana

<400> SEQUENCE: 15
atggaagcta tgcttgtgga ctgtgtaaac aacagtcttc gtcattttgt ctacaaaaat      60
gctattttca tgtgcgagcg tctctgcgct gagtttcctt ctgaggtaat caccctcttc     120
tttcactctc tctctctgat tttacctctc taattcaaat tctgtaaatc gaagctcttg     180
gaatggtaaa tttgatattt tgggtttgt aattcctctg ggtatctatg aattcgtcga     240
aagtgcgtct cttttggat ttggaattcg atagcttcac tgtgttcttc gagattgatt      300
ttggtttctt accttttagc cctttgtttt caagatccgt gtgttcaatt aggagatgaa     360
ttcgtgttct tttctctctc ttgttgaatt tgttttctct agtagctgtg ctcaatgctc     420
attactgatt tggtctttgg aaaatttgca ttttgagggt taatgacttt tgtccatata     480
tgtgatctca agtttaagta tttattatcc ttggaactta gctatgagtc aactgttaga     540
ggaatgtctc tgggattatc tcaagctttg ttaaaatttg ggttaataca gcttcaatag     600
tagttgagaa agtattcatt cattcagcct ttggtctgga atattttcaa cattcgtagt     660
ggttgtccag tttctagctt cagttagtag aaatcatgtc aataaatgat tggcctttt      720 gtttgatcac tttctgaatt ttcctcttat ataggttaat ttgcagctat agccaccag     780 ctacctgcag aataatcaag cttacagtgc atatcatctg ctaaagggtg cgtggcattg     840
tttcttgact tgttgcttgt tagccttta gtcagaattt tgcaccttct tttgttaggt      900
cgttttgatt atctttgtat atatatttt ttttgttat gtaaaggaac acaaatggct     960
cagtcccgat acttgttcgc attatcatgc ttccagatgg accttctcaa tgaagctgaa    1020
tctgcactct gccctgttaa tgaacctggt gcggaggtat ttaatgttct ctggtatttt    1080
gcctttattc gcttactgaa tgtcatttta caaaaacagt gtgtcagttt ctggacctta    1140
tttattgatt tagttcagtg aagataacaa catgcttctg attattgtgc agatcccaaa    1200
tggtgcagca ggccattacc ttcttggact tatttacaag tacgtttttt gttctgtcta    1260 tgcattttt cttgattctg aatggcttag atgagatgat tcctcatata taacagtgac    1320
cttttaggta tactgataga aggaagaatg ctgctcaaca atttaaacag tccttgacaa    1380
tagaccctct actttgggct gcatatgagg aattatgtat attaggtgaa cataatccgt    1440
tttctgcata cttcacagat atgttatggt tctcttacac ttttctgtct gctcaacttt    1500
caggtgctgc tgaggaagca actgcagttt tggtgaaac agctgctctc tccattcaaa    1560
agcagtatat gcaacaactg tcaacttccc tcggcttaaa cacttacaac gaggaacgta    1620
attcaacttc tactaaaaac acgagttctg aagattatag tccaaggcag tctaaacaca    1680
cacaaagcca tggccttaaa gatatctccg gaaatttcca ttctcatgga gttaatggag    1740
```

-continued

```
gtgtttcgaa catgtcattc tataatacgc cttcgccagt ggctgcacag gtaatgtcac    1800
acaattgtcg tactgctttt ttatgtaata caactatatc tccatctgtt gatcacacat    1860
tctgtagtac ttaggagatt tgtgcatcat gggtgttgat ttcacagcgt ttgtatctgt    1920
tttttctata tctgttatgc caaaagaatg ggttgtctat tcttttgact attaaaaatg    1980
gggtcttcat tatgtttag tgtctttggt ttggcttgtt aattttatca accttttag     2040 ttatctgaat aataacagct gtaagtaaat gcttttttgt attttgaaa ttgtagctat    2100 ccggtatagc tccaccacca cttttccgga attttcagcc agctgttgca aacccaaact    2160
cccttattac tgacagttct ccaaagtcca ctgttaactc tactcttcaa gcacctagaa    2220
gaaagtttgt agatgaagga aagttacgta aggtaggatt cacataatca catatctcta    2280
cttgacatca tcaaatcata attttgaatt attggtcttt ctctgtaata gtctatttcg    2340
tactcgggat gaaattttct ataccaactt tcttaccgtg agtgcatgtc tcttatgttt    2400
gcagatttct ggcagactat tttctgattc tggtccacga cggagttcaa gactgtctgc    2460
tgattcaggg gcaaacatta attcaagtgt tgcaacagta agcggaaatg tgaacaacgc    2520
ttccaagtat ttgggaggtt ctaaattgag ttctttggca cttcgttctg taacacttcg    2580
gaagggacac tcctgggcaa atgaaaacat ggatgaaggt tgtgacattc catgcactat    2640
accactatat tgtttgaaat ctgcccttgt gtgactattg ttatcatgcc ttctattttt    2700
ggtgtctgca tatttgtaat accgtcattc tgatggtttt aggggtccgt ggggaacctt    2760
ttgatgattc aaggcctaat actgcctcaa cgactggttc tatggcttcc aatgatcaag    2820
aagacgaaac aatgtcgatt ggtggcatag caatgagttc tcaaacaatc acaattggtg    2880
tttcggaaat tttaaacctc cttaggacac tcggagaagg gtgtagactt tcatacatgt    2940
acaggtgtca ggtaggcata ttattgttct cgtgaattat gcaagtgagg tgaacctata    3000
taggcttatc tcattgtctc cttctgcttc tgggtcgttc aggaggcact ggatacgtat    3060
atgaaacttc cacataagca ttataataca ggatgggttc tttcccaggt aactagtgac    3120
tctttctctt ttaggctgcc atatatggat atagcctgaa tcagttttac tctagtggcc    3180
tgtgatagtt attgttgaaa ggtttatata cacatactat ggctattaaa tgtaggtcgg    3240
gaaagcatac tttgaactaa ttgactattt agaggctgaa aaggcattcc gtcttgcccg    3300
tctggcttct ccttattgct tagaaggaat ggatatatac tctacggtcc tctatgtaag    3360
tgtattatcc tggtttctaa acatgcaatc tcggatgagt gcggaaagaa atcacatttta   3420 tgtaaattt tcatcagcaa gatatgatat ttatttgcag catttgaagg aagacatgaa    3480
gctgagttac ttggctcagg aactaatatc aaccgatcgc ttagctcctt aatcttggta    3540 tttttgtcg aagttgtttt tctgattaac gttttcattt attgttggta ataagagaaa    3600
taagcaatca attatgtagg tgtgctatgg gaaattgcta tagcttgcaa aaggaccatg    3660
agaccgcact gaagaatttc ctacgagctg ttcaactgaa tccaagattt gcatatgcac    3720
ataccttatg tggccacgag taagagagcc tctatccatt tgactttgtc ttgcacaatg    3780
tgcttaaaat tatctggtta ttggtctaat tgacactttc tatctttact gtctctgtag    3840
atacacaact cttgaggatt ttgagaacgg aatgaaaagt taccaaaacg cacttcgtgt    3900
agatacaaga cactacaacg catggtacgg gcttggaatg atatatctac gccaagagaa    3960
gttagagttc tcagagcatc acttcagaat ggctttccta ataaacccga gttcctctgt    4020
tataatgtct tatttaggga catctttgca tgccttgaag gttatcttat tactttcatc    4080
ttatcaggtc tacaagaaaa acaatctttg aagaatgact aaatgcttct tcttgttttg    4140
```

```
tgttaataga gaagtgagga agcactagag ataatggagc aagccatagt agcagataga      4200
aaaaaccctc ttccaatgta ccagaaagct aacatacttg tctgcttaga aagattagat      4260
gaagctctag aagttcttga ggagctcaaa gagtatgcgc cttcagagag cagcgtttac      4320
gctttaatgg gcaggatcta taagcggcga acatgcacg ataaagccat gcttcatttc       4380
ggtctagctt tagatatgaa accgcctgca actgacgttg ctgcaataaa ggttcgagtc      4440
tttaaaacag agtcgtccaa tgatggtttt taaatctgaa aattcaagga ttcatagctt      4500
aaactggtta ttattgtctg aaacaggctg caatggagaa attgcatgtt ccagatgaga      4560
tcgatgagag cccgtga                                                     4577

<210> SEQ ID NO 16
<211> LENGTH: 4577
<212> TYPE: DNA
<213> ORGANISM: Arabidopsis thaliana

<400> SEQUENCE: 16
atggaagcta tgcttgtgga ctgtgtaaac aacagtcttc gtcattttgt ctacaaaaat        60
gctattttca tgtgcgagcg tctctgcgct gagtttcctt ctgaggtaat caccctcttc       120
tttcactctc tctctctgat tttacctctc taattcaaat tctgtaaatc gaagctcttg       180
gaatggtaaa tttgatattt tgggtttgt aattcctctg ggtatctatg aattcgtcga        240
aagtgcgtct cttttggat ttggaattcg atagcttcac tgtgttcttc gagattgatt        300
ttggtttctt accttttagc cctttgtttt caagatccgt gtgttcaatt aggagatgaa       360
ttcgtgttct tttctctctc ttgttgaatt tgttttctct agtagctgtg ctcaatgctc       420
attactgatt tggtctttgg aaaatttgca ttttgagggt taatgacttt tgtccatata       480
tgtgatctca gtttaagta tttattatcc ttggaactta gctatgagtc aactgttaga        540
ggaatgtctc tgggattatc tcaagctttg ttaaaatttg ggttaataca gcttcaatag       600
tagttgagaa agtattcatt cattcagcct tggtctgga atattttcaa cattcgtagt        660
ggttgtccag tttctagctt cagttagtag aaatcatgtc aataaatgat tggcctttt        720 gtttgatcac tttctgaatt ttcctcttat ataggttaat ttgcagctat tagccaccag       780
ctacctgcag aataatcaag cttacagtgc atatcatctg ctaaagggtg cgtggcattg       840
tttcttgact tgttgcttgt tagccttta gtcagaattt tgcaccttct tttgttaggt       900
cgttttgatt atctttgtat atatatttttt ttttgttat gtaaaggaac acaaatggct       960
cagtcccgat acttgttcgc attatcatgc ttccagatgg accttctcaa tgaagctgaa      1020
tctgcactct gccctgttaa tgaacctggt gcggaggtat ttaatgttct ctggtatttt      1080
gcctttattc gcttactgaa tgtcatttta caaaaacagt gtgtcagttt ctggacctta      1140
tttattgatt tagttcagtg aagataacaa catgcttctg attattgtgc agatcccaaa      1200
tggtgcagca ggccattacc ttcttggact tatttacaag tacgttttt gttctgtcta       1260 tgcattttt cttgattctg aatggcttag atgagatgat tcctcatata taacagtgac       1320
cttttaggta tactgataga aggaagaatg ctgctcaaca atttaaacag tccttgacaa      1380
tagaccctct actttgggct gcatatgagg aattatgtat attaggtgaa cataatccgt       1440
tttctgcata cttcacagat atgttatggt tctcttacac ttttctgtct gctcaacttt      1500
caggtgctgc tgaggaagca actgcagttt ttggtgaaac agctgctctc tccattcaaa      1560
agcagtatat gcaacaactg tcaacttccc tcggcttaaa cacttacaac gaggaacgta      1620
```

```
attcaacttc tactaaaaac acgagttctg aagattatag tccaaggcag tctaaacaca    1680
cacaaagcca tggccttaaa gatatctccg gaaatttcca ttctcatgga gttaatggag    1740
gtgtttcgaa catgtcattc tataatacgc cttcgccagt ggctgcacag gtaatgtcac    1800
acaattgtcg tactgctttt ttatgtaata caactatatc tccatctgtt gatcacacat    1860
tctgtagtac ttaggagatt tgtgcatcat gggtgttgat ttcacagcgt ttgtatctgt    1920
tttttctata tctgttatgc caaaagaatg ggttgtctat tcttttgact attaaaaatg    1980
gggtcttcat tatgttttag tgtctttggt ttggcttgtt aattttatca acctttttag    2040
ttatctgaat aataacagct gtaagtaaat gcttttttgt atttttgaaa ttgtagctat    2100
ccggtatagc tccaccacca cttttccgga attttcagcc agctgttgca aacccaaact    2160
cccttattac tgacagttct ccaaagtcca ctgttaactc tactcttcaa gcacctagaa    2220
gaaagtttgt agatgaagga aagttacgta aggtaggatt cacataatca catatctcta    2280
cttgacatca tcaaatcata attttgaatt attggtcttt tctgtaata gtctatttcg    2340 tactcgggat gaaattttct ataccaactt tcttaccgtg agtgcatgtc tcttatgttt    2400
gcagatttct ggcagactat tttctgattc tggtccacga cggagttcaa gactgtctgc    2460
tgattcaggg gcaaacatta attcaagtgt tgcaacagta agcggaaatg tgaacaacgc    2520
ttccaagtat ttgggaggtt ctaaattgag ttctttggca cttcgttctg taacacttcg    2580
gaagggacac tcctgggcaa atgaaaacat ggatgaaggt tgtgacattc catgcactat    2640
accactatat tgtttgaaat ctgcccttgt gtgactattg ttatcatgcc ttctattttt    2700
ggtgtctgca tatttgtaat accgtcattc tgatgggttt aggggtccgt ggggaacctt    2760
ttgatgattc aaggcctaat actgcctcaa cgactggttc tatggcttcc aatgatcaag    2820
aagacgaaac aatgtcgatt ggtggcatag caatgagttc tcaaacaatc acaattggtg    2880
tttcggaaat tttaaacctc cttaggacac tcggagaagg tgtgtagactt tcatacatgt    2940 acaggtgtca ggtaggcata ttattgttct cgtgaattat gcaagtgagg tgaacctata    3000
taggcttatc tcattgtctc cttctgcttc tgggtcgttc aggaggcact ggatacgtat    3060
atgaaacttc cacataagca ttataataca ggatgggttc tttcccaggt aactagtgac    3120
tctttctctt ttaggctgcc atatatggat atagcctgaa tcagttttac tctagtggcc    3180
tgtgatagtt attgttgaaa ggtttatata cacatactat ggctattaaa tgtaggtcgg    3240
gaaagcatac tttgaactaa ttgactattt agaggctgaa aaggcattcc gtcttgcccg    3300
tctggcttct ccttattgct tagaaggaat ggatatatac tctacggtcc tctatgtaag    3360
tgtattatcc tggtttctaa acatgcaatc tcggatgagt gcggaaagaa atcacatttta    3420 tgtaaatttt tcatcagcaa gatatgatat ttatttgcag catttgaagg aagacatgaa    3480
gctgagttac ttggctcagg aactaatatc aaccgatcgc ttagctcctc aatcttggta    3540
ttttttgtcg aagttgtttt tctgattaac gttttcattt attgttggta ataagagaaa    3600
taagcaatca attatgtagg tgtgctatgg gaaattgcta tagcttgcaa aaggaccatg    3660
agaccgtact gaagaatttc ctacgagctg ttcaactgaa tccaagattt gcatatgcac    3720
ataccttatg tggccacgag taagagagcc tctatccatt tgactttgtc ttgcacaatg    3780
tgcttaaaat tatctggtta ttggtctaat tgacactttc tatctttact gtctctgtag    3840
atacacaact cttgaggatt ttgagaacgg aatgaaaagt taccaaaacg cacttcgtgt    3900
agatacaaga cactacaacg catggtacgg gcttggaatg atatatctac gccaagagaa    3960
gttagagttc tcagagcatc acttcagaat ggctttccta ataaacccga gttcctctgt    4020
```

-continued

```
tataatgtct tatttaggga catctttgca tgccttgaag gttatcttat tactttcatc    4080
ttatcaggtc tacaagaaaa acaatctttg aagaatgact aaatgcttct tcttgttttg    4140
tgttaataga gaagtgagga agcactagag ataatggagc aagccatagt agcagataga    4200
aaaaaccctc ttccaatgta ccagaaagct aacatacttg tctgcttaga aagattagat    4260
gaagctctag aagttcttga ggagctcaaa gagtatgcgc cttcagagag cagcgtttac    4320
gctttaatgg gcaggatcta taagcggcga acatgcacg ataaagccat gcttcatttc    4380
ggtctagctt tagatatgaa accgcctgca actgacgttg ctgcaataaa ggttcgagtc    4440
tttaaaacag agtcgtccaa tgatggtttt taaatctgaa aattcaagga ttcatagctt    4500
aaactggtta ttattgtctg aaacaggctg caatggagaa attgcatgtt ccagatgaga    4560
tcgatgagag cccgtga                                                  4577
```

<210> SEQ ID NO 17
<211> LENGTH: 2235
<212> TYPE: DNA
<213> ORGANISM: Arabidopsis thaliana

<400> SEQUENCE: 17

```
atggaagcta tgcttgtgga ctgtgtaaac aacagtcttc gtcattttgt ctacaaaaat      60
gttattttca tgtgcgagcg tctctgcgct gagtttcctt ctgaggttaa tttgcagcta     120
ttagccacca gctacctgca gaataatcaa gcttacagtg catatcatct gctaaaggga     180
acacaaatgg ctcagtcccg atacttgttc gcattatcat gcttccagat ggaccttctc     240
aatgaagctg aatctgcact ctgccctgtt aatgaacctg gtgcggagat cccaaatggt     300
gcagcaggcc attccttct tggacttatt tacaagtata ctgatagaag gagaatgct     360 gctcaacaat ttaaacagtc cttgacaata gaccctctac tttgggctgc atatgaggaa     420
ttatgtatat taggtgctgc tgaggaagca actgcagttt tggtgaaac agctgctctc     480 tccattcaaa agcagtatat gcaacaactg tcaacttccc tcggcttaaa cacttacaac     540
gaggaacgta attcaacttc tactaaaaac acgagttctg aagattatag tccaaggcag     600
tctaaacaca cacaaagcca tggccttaaa gatatctccg gaaatttcca ttctcatgga     660
gttaatggag tgtttcgaa catgtcattc tataatacgc cttcgccagt ggctgcacag     720
ctatccggta tagctccacc accacttttc cggaattttc agccagctgt tgcaaaccca     780 aactcccta ttactgacag ttctccaaag tccactgtta actctactct tcaagcacct     840
agaagaaagt ttgtagatga aggaaagtta cgtaagattt ctggcagact attttctgat     900
tctggtccac gacggagttc aagactgtct gctgattcag gggcaaacat taattcaagt     960
gttgcaacag taagcggaaa tgtgaacaac gcttccaagt atttgggagg ttctaaattg    1020
agttctttgg cacttcgttc tgtaacactt cggaagggac actcctgggc aaatgaaaac    1080
atggatgaag gggtccgtgg ggaaccttt gatgattcaa ggcctaatac tgcctcaacg    1140
actggttcta tggcttccaa tgatcaagaa gacgaaacaa tgtcgattgg tggcatagca    1200
atgagttctc aaacaatcac aattggtgtt tcggaaattt taaacctcct taggacactc    1260
ggagaagggt gtagacttc atacatgtac aggtgtcagg aggcactgga tacgtatatg    1320
aaacttccac ataagcatta taatacagga tgggttctt cccaggtcgg gaaagcatac    1380
tttgaactaa ttgactattt agaggctgaa aaggcattcc gtcttgcccg tctggcttct    1440
ccttattgct tagaaggaat ggatatatac tctacggtcc tctatcattt gaaggaagac    1500
```

```
atgaagctga gttacttggc tcaggaacta atatcaaccg atcgcttagc tcctcaatct    1560
tggtgtgcta tgggaaattg ctatagcttg caaaaggacc atgagaccgc actgaagaat    1620
ttcctacgag ctgttcaact gaatccaaga tttgcatatg cacataccct atgtggccac    1680
gaatacacaa ctcttgagga ttttgagaac ggaatgaaaa gttaccaaaa cgcacttcgt    1740
gtagatacaa gacactacaa cgcatggtac gggcttggaa tgatatatct acgccaagag    1800
aagttagagt tctcagagca tcacttcaga atggctttcc taataaaccc gagttcctct    1860
gttataatgt cttatttagg gacatctttg catgccttga agagaagtga ggaagcacta    1920
gagataatgg agcaagccat agtagcagat agaaaaaacc ctcttccaat gtaccagaaa    1980
gctaacatac ttgtctgctt agaaagatta gatgaagctc tagaagttct tgaggagctc    2040
aaagagtatg cgccttcaga gagcagcgtt tacgctttaa tgggcaggat ctataagcgg    2100
cgaaacatgc acgataaagc catgcttcat ttcggtctag ctttagatat gaaaccgcct    2160
gcaactgacg ttgctgcaat aaaggctgca atggagaaat tgcatgttcc agatgagatc    2220
gatgagagcc cgtga                                                     2235

<210> SEQ ID NO 18
<211> LENGTH: 2313
<212> TYPE: DNA
<213> ORGANISM: Arabidopsis thaliana

<400> SEQUENCE: 18
atggaagcta tgcttgtgga ctgtgtaaac aacagtcttc gtcattttgt ctacaaaaat      60
gctattttca tgtgcgagcg tctctgcgct gagtttcctt ctgaggttaa tttgcagcta     120
ttagccacca gctacctgca gaataatcaa gcttacagtg catatcatct gctaaaggga     180
acacaaatgg ctcagtcccg atacttgttc gcattatcat gcttccagat ggaccttctc     240
aatgaagctg aatctgcact ctgccctgtt aatgaacctg gtgcggagat cccaaatggt     300
gcagcaggcc attaccttct tggacttatt tacaagtata ctgatagaag gagaatgct       360 gctcaacaat ttaaacagtc cttgacaata gaccctctac tttgggctgc atatgaggaa     420
ttatgtatat taggtgaaca taatccgttt tctgcatact tcacagatat gttatggttc     480
tcttacactt ttctgtctgc tcaactttca agtgctgctg aggaagcaac tgcagttttt     540
ggtgaaacag ctgctctctc cattcaaaag cagtatatgc aacaactgtc aacttccctc     600
ggcttaaaca cttacaacga ggaacgtaat tcaacttcta ctaaaaacac gagttctgaa     660
gattatagtc caaggcagtc taaacacaca caaagccatg gccttaaaga tatctccgga     720
aatttccatt ctcatggagt taatggaggt gtttcgaaca tgtcattcta taatacgcct     780
tcgccagtgg ctgcacagct atccggtata gctccaccac cacttttccg gaattttcag     840
ccagctgttg caaacccaaa ctcccttatt actgacagtt ctccaaagtc cactgttaac     900
tctactcttc aagcacctag aagaaagttt gtagatgaag aaagttacg taagatttct     960 ggcagactat tttctgattc tggtccacga cggagttcaa gactgtctgc tgattcaggg    1020
gcaaacatta ttcaagtgt tgcaacagta agcggaaatg tgaacaacgc ttccaagtat    1080
ttgggaggtt ctaaattgag ttcttttggca cttcgttctg taacacttcg gaagggacac    1140
tcctgggcaa atgaaaacat ggatgaaggg tccgtgggg aaccttttga tgattcaagg     1200
cctaatactg cctcaacgac tggttctatg gcttccaatg atcaagaaga cgaaacaatg    1260
tcgattggtg gcatagcaat gagttctcaa acaatcacaa ttggtgtttc ggaaatttta    1320
aacctcctta ggacactcgg agaagggtgt agactttcat acatgtacag gtgtcaggag    1380
```

```
gcactggata cgtatatgaa acttccacat aagcattata atacaggatg ggttctttcc    1440
caggtcggga agcatactt tgaactaatt gactatttag aggctgaaaa ggcattccgt    1500
cttgcccgtc tggcttctcc ttattgctta aaggaatgg atatatactc tacggtcctc    1560
tatcatttga aggaagacat gaagctgagt tacttggctc aggaactaat atcaaccgat    1620
cgcttagctc ctcaatcttg gtgtgctatg ggaaattgct atagcttgca aaaggaccat    1680
gagaccgcac tgaagaattt cctacgagct gttcaactga atccaagatt tgcatatgca    1740
cataccttat gtggccacga atacacaact cttgaggatt ttgagaacgg aatgaaaagt    1800
taccaaaacg cacttcgtgt agatacaaga cactacaacg catggtacgg cttggaatg     1860 atatatctac gccaagagaa gttagagttc tcagagcatc acttcagaat ggctttccta    1920
ataaacccga gttcctctgt tataatgtct tatttaggga catctttgca tgccttgaag    1980
agaagtgagg aagcactaga gataatggag caagccatag tagcagatag aaaaaacccct    2040 cttccaatgt accagaaagc taacatactt gtctgcttag aaagattaga tgaagctcta    2100
gaagttcttg aggagctcaa agagtatgcg ccttcagaga gcagcgttta cgctttaatg    2160
ggcaggatct ataagcggcg aaacatgcac gataaagcca tgcttcattt cggtctagct    2220
ttagatatga aaccgcctgc aactgacgtt gctgcaataa aggctgcaat ggagaaattg    2280
catgttccag atgagatcga tgagagcccg tga                                 2313

<210> SEQ ID NO 19
<211> LENGTH: 2235
<212> TYPE: DNA
<213> ORGANISM: Arabidopsis thaliana

<400> SEQUENCE: 19
atggaagcta tgcttgtgga ctgtgtaaac aacagtcttc gtcattttgt ctacaaaaat      60
gctattttca tgtgcgagcg tctctgcgct gagtttcctt ctgaggttaa tttgcagcta    120
ttagccacca gctacctgca gaataatcaa gcttacagtg catatcatct gctaaaggga    180
acacaaatgg ctcagtcccg atacttgttc gcattatcat gcttccagat ggaccttctc    240
aatgaagctg aatctgcact ctgccctgtt aatgaacctg gtgcggagat cccaaatggt    300
gcagcaggcc attccttct tggacttatt tacaagtata ctgatagaag gaagaatgct    360
gctcaacaat ttaaacagtc cttgacaata gaccctctac tttgggctgc atatgaggaa    420
ttatgtatat taggtgctgc tgaggaagca actgcagttt ttggtgaaac agctgctctc    480
tccattcaaa agcagtatat gcaacaactg tcaacttccc tcggcttaaa cacttacaac    540
gaggaacgta ttcaacttc tactaaaaac acgagttctg aagattatag tccaaggcag    600
tctaaacaca cacaaagcca tggccttaaa gatatctccg gaaatttcca ttctcatgga    660
gttaatggag tgtttcgaa catgtcattc tataatacgc cttcgccagt ggctgcacag    720
ctatccggta tagctccacc accacttttc cggaattttc agccagctgt tgcaaaccca    780
aactccctta ttactgacag ttctccaaag tccactgtta actctactct tcaagcacct    840
agaagaaagt ttgtagatga aggaaagtta cgtaagattt ctggcagact attttctgat    900
tctggtccac gacggagttc aagactgtct gctgattcag gggcaaacat taattcaagt    960
gttgcaacag taagcggaaa tgtgaacaac gcttccaagt atttgggagg ttctaaattg   1020
agttctttgg cacttcgttc tgtaacactt cggaagggac actcctgggc aaatgaaaac   1080
atggatgaag gggtccgtgg ggaaccttt gatgattcaa ggcctaatac tgcctcaacg   1140
```

```
actggttcta tggcttccaa tgatcaagaa gacgaaacaa tgtcgattgg tggcatagca   1200
atgagttctc aaacaatcac aattggtgtt tcggaaattt taaacctcct taggacactc   1260
agagaagggt gtagactttc atacatgtac aggtgtcagg aggcactgga tacgtatatg   1320
aaacttccac ataagcatta taatacagga tgggttcttt cccaggtcgg gaaagcatac   1380
tttgaactaa ttgactattt agaggctgaa aaggcattcc gtcttgcccg tctggcttct   1440
ccttattgct tagaaggaat ggatatatac tctacggtcc tctatcattt gaaggaagac   1500
atgaagctga gttacttggc tcaggaacta atatcaaccg atcgcttagc tcctcaatct   1560
tggtgtgcta tgggaaattg ctatagcttg caaaaggacc atgagaccgc actgaagaat   1620
ttcctacgag ctgttcaact gaatccaaga tttgcatatg cacataccct atgtggccac   1680
gaatacacaa ctcttgagga ttttgagaac ggaatgaaaa gttaccaaaa cgcacttcgt   1740
gtagatacaa gacactacaa cgcatggtac gggcttggaa tgatatatct acgccaagag   1800
aagttagagt tctcagagca tcacttcaga atggctttcc taataaaccc gagttcctct   1860
gttataatgt cttatttagg gacatctttg catgccttga agagaagtga ggaagcacta   1920
gagataatgg agcaagccat agtagcagat agaaaaaaacc ctcttccaat gtaccagaaa   1980
gctaacatac ttgtctgctt agaaagatta gatgaagctc tagaagttct tgaggagctc   2040
aaagagtatg cgccttcaga gagcagcgtt tacgctttaa tgggcaggat ctataagcgg   2100
cgaaacatgc acgataaagc catgcttcat ttcggtctag ctttagatat gaaaccgcct   2160
gcaactgacg ttgctgcaat aaaggctgca atggagaaat tgcatgttcc agatgagatc   2220
gatgagagcc cgtga                                                    2235
```

<210> SEQ ID NO 20
<211> LENGTH: 2169
<212> TYPE: DNA
<213> ORGANISM: Arabidopsis thaliana

<400> SEQUENCE: 20

```
atggaagcta tgcttgtgga ctgtgtaaac aacagtcttc gtcatttgt ctacaaaaat     60 gctattttca tgtgcgagcg tctctgcgct gagtttcctt ctgaggttaa tttgcagcta    120
ttagccacca gctacctgca gaataatcaa gcttacagtg catatcatct gctaaaggga    180
acacaaatgg ctcagtcccg atacttgttc gcattatcat gcttccagat ggaccttctc    240
aatgaagctg aatctgcact ctgccctgtt aatgaacctg gtgcggagat cccaaatggt    300
gcagcaggcc attccttct ggacttatt tacaagtata ctgatagaag gaagaatgct    360
gctcaacaat ttaaacagtc cttgacaata gaccctctac tttgggctgc atatgaggaa    420
ttatgtatat taggtgctgc tgaggaagca actgcagttt tggtgaaac agctgctctc    480 tccattcaaa agcagtatat gcaacaactg tcaacttccc tcggcttaaa cacttacaac    540
gaggaacgta attcaacttc tactaaaaac acgagttctg aagattatag tccaaggcag    600
tctaaacaca cacaaagcca tggccttaaa gatatctccg gaaattttcca ttctcatgga    660 gttaatggag tgtttcgaa catgtcattc tataatacgc cttcgccagt ggctgcacag    720
ctatccggta tagctccacc accactttc cggaattttc agccagctgt tgcaaaccca    780
aactccctta ttactgacag ttctccaaag tccactgtta actctactct tcaagcacct    840
agaagaaagt ttgtagatga aggaaagtta cgtaagattt ctggcagact attttctgat    900
tctggtccac gacggagttc aagactgtct gctgattcag gggcaaacat taattcaagt    960
gttgcaacag taagcggaaa tgtgaacaac gcttccaagt atttgggagg ttctaaattg   1020
```

-continued

```
agttctttgg cacttcgttc tgtaacactt cggaagggac actcctgggc aaatgaaaac    1080
atggatgaag gggtccgtgg ggaaccttttt gatgattcaa ggcctaatac tgcctcaacg   1140
actggttcta tggcttccaa tgatcaagaa gacgaaacaa tgtcgattgg tggcatagca    1200
atgagttctc aaacaatcac aattggtgtt tcggaaattt taaacctcct taggacactc    1260
ggagaagggt gtagactttc atacatgtac aggtgtcagg tcgggaaagc atactttgaa    1320
ctaattgact atttagaggc tgaaaaggca ttccgtcttg cccgtctggc ttctccttat    1380
tgcttagaag gaatggatat atactctacg gtcctctatc atttgaagga agacatgaag    1440
ctgagttact tggctcagga actaatatca accgatcgct tagctcctca atcttggtgt    1500
gctatgggaa attgctatag cttgcaaaag gaccatgaga ccgcactgaa gaatttccta    1560
cgagctgttc aactgaatcc aagatttgca tatgcacata ccttatgtgg ccacgaatac    1620
acaactcttg aggattttga aacggaatg aaaagttacc aaaacgcact tcgtgtagat     1680
acaagacact acaacgcatg gtacgggctt ggaatgatat atctacgcca agagaagtta    1740
gagttctcag agcatcactt cagaatggct ttcctaataa acccgagttc ctctgttata    1800
atgtcttatt tagggacatc tttgcatgcc ttgaagagaa gtgaggaagc actagagata    1860
atggagcaag ccatagtagc agatagaaaa aaccctcttc caatgtacca gaaagctaac    1920
atacttgtct gcttagaaag attagatgaa gctctagaag ttcttgagga gctcaaagag    1980
tatgcgcctt cagagagcag cgtttacgct ttaatgggca ggatctataa gcggcgaaac    2040
atgcacgata aagccatgct tcatttcggt ctagctttag atatgaaacc gcctgcaact    2100
gacgttgctg caataaaggc tgcaatggag aaattgcatg ttccagatga gatcgatgag    2160
agcccgtga                                                            2169
```

<210> SEQ ID NO 21
<211> LENGTH: 2115
<212> TYPE: DNA
<213> ORGANISM: Arabidopsis thaliana

<400> SEQUENCE: 21

```
atggaagcta tgcttgtgga ctgtgtaaac aacagtcttc gtcattttgt ctacaaaaat     60
gctattttca tgtgcgagcg tctctgcgct gagtttcctt ctgaggttaa tttgcagcta    120
ttagccacca gctacctgca gaataatcaa gcttacagtg catatcatct gctaaaggga    180
acacaaatgg ctcagtcccg atacttgttc gcattatcat gcttccagat ggaccttctc    240
aatgaagctg aatctgcact ctgccctgtt aatgaacctg gtgcggagat cccaaatggt    300
gcagcaggcc attccttcct tggacttatt tacaagtata ctgatagaag gaagaatgct    360
gctcaacaat ttaaacagtc cttgacaata gaccctctac tttgggctgc atatgaggaa    420
ttatgtatat aggtgctgc tgaggaagca actgcagttt tggtgaaaac agctgctctc    480
tccattcaaa agcagtatat gcaacaactg tcaacttccc tcggcttaaa cacttacaac    540
gaggaacgta attcaacttc tactaaaaac acgagttctg aagattatag tccaaggcag    600
tctaaacaca cacaaagcca tggccttaaa gatatctccg gaaatttcca ttctcatgga    660
gttaatggag tgtttcgaa catgtcattc tataatacgc cttcgccagt ggctgcacag    720
ctatccggta tagctccacc accacttttc cggaattttc agccagctgt tgcaaaccca    780
aactccctta ttactgacag ttctccaaag tccactgtta actctactct tcaagcacct    840
agaagaaagt ttgtagatga aggaaagtta cgtaagattt ctggcagact attttctgat    900
```

| | |
|---|---|
| tctggtccac gacggagttc aagactgtct gctgattcag gggcaaacat taattcaagt | 960 |
| gttgcaacag taagcggaaa tgtgaacaac gcttccaagt atttgggagg ttctaaattg | 1020 |
| agttctttgg cacttcgttc tgtaacactt cggaagggac actcctgggc aaatgaaaac | 1080 |
| atggatgaag gggtccgtgg ggaaccttt gatgattcaa ggcctaatac tgcctcaacg | 1140 |
| actggttcta tggcttccaa tgatcaagaa gacgaaacaa tgtcgattgg tggcatagca | 1200 |
| atgagttctc aaacaatcac aattggtgtt tcggaaattt taaacctcct taggacactc | 1260 |
| ggagaagggt gtagactttc atacatgtac aggtgtcagg aggcactgga tacgtatatg | 1320 |
| aaacttccac ataagcatta taatacagga tgggttcttt cccagcattt gaaggaagac | 1380 |
| atgaagctga gttacttggc tcaggaacta atatcaaccg atcgcttagc tcctcaatct | 1440 |
| tggtgtgcta tgggaaattg ctatagcttg caaaaggacc atgagaccgc actgaagaat | 1500 |
| ttcctacgag ctgttcaact gaatccaaga tttgcatatg cacatacctt atgtggccac | 1560 |
| gaatacacaa ctcttgagga ttttgagaac ggaatgaaaa gttaccaaaa cgcacttcgt | 1620 |
| gtagatacaa gacactacaa cgcatggtac gggcttggaa tgatatatct acgccaagag | 1680 |
| aagttagagt tctcagagca tcacttcaga atggctttcc taataaaccc gagttcctct | 1740 |
| gttataatgt cttatttagg gacatctttg catgccttga agagaagtga ggaagcacta | 1800 |
| gagataatgg agcaagccat agtagcagat agaaaaaacc ctcttccaat gtaccagaaa | 1860 |
| gctaacatac ttgtctgctt agaaagatta gatgaagctc tagaagttct tgaggagctc | 1920 |
| aaagagtatg cgccttcaga gagcagcgtt tacgctttaa tgggcaggat ctataagcgg | 1980 |
| cgaaacatgc acgataaagc catgcttcat ttcggtctag ctttagatat gaaaccgcct | 2040 |
| gcaactgacg ttgctgcaat aaaggctgca atggagaaat tgcatgttcc agatgagatc | 2100 |
| gatgagagcc cgtga | 2115 |

<210> SEQ ID NO 22
<211> LENGTH: 1557
<212> TYPE: DNA
<213> ORGANISM: Arabidopsis thaliana

<400> SEQUENCE: 22

| | |
|---|---|
| atggaagcta tgcttgtgga ctgtgtaaac aacagtcttc gtcattttgt ctacaaaaat | 60 |
| gctatttca tgtgcgagcg tctctgcgct gagtttcctt ctgaggttaa tttgcagcta | 120 |
| ttagccacca gctacctgca gaataatcaa gcttacagtg catatcatct gctaaaggga | 180 |
| acacaaatgg ctcagtcccg atacttgttc gcattatcat gcttccagat ggaccttctc | 240 |
| aatgaagctg aatctgcact ctgccctgtt aatgaacctg gtgcggagat cccaaatggt | 300 |
| gcagcaggcc attccttct tggacttatt tacaagtata ctgatagaag gagaatgct | 360 |
| gctcaacaat ttaaacagtc cttgacaata gaccctctac tttgggctgc atatgaggaa | 420 |
| ttatgtatat taggtgctgc tgaggaagca actgcagttt ttggtgaaac agctgctctc | 480 |
| tccattcaaa agcagtatat gcaacaactg tcaacttccc tcggcttaaa cacttacaac | 540 |
| gaggaacgta attcaacttc tactaaaaac acgagttctg aagattatag tccaaggcag | 600 |
| tctaaacaca cacaaagcca tggccttaaa gatatctccg gaaatttcca ttctcatgga | 660 |
| gttaatggag gtgtttcgaa catgtcattc tataatacgc cttcgccagt ggctgcacag | 720 |
| ctatccggta tagctccacc accactttc cggaattttc agccagctgt tgcaaaccca | 780 |
| aactccctta ttactgacag ttctccaaag tccactgtta actctactct tcaagcacct | 840 |
| agaagaaagt ttgtagatga aggaaagtta cgtaagattt ctggcagact atttctgat | 900 |

```
tctggtccac gacggagttc aagactgtct gctgattcag gggcaaacat taattcaagt    960
gttgcaacag taagcggaaa tgtgaacaac gcttccaagt atttgggagg ttctaaattg   1020
agttctttgg cacttcgttc tgtaacactt cggaagggac actcctgggc aaatgaaaac   1080
atggatgaag gggtccgtgg ggaaccttt gatgattcaa ggcctaatac tgcctcaacg   1140
actggttcta tggcttccaa tgatcaagaa gacgaaacaa tgtcgattgg tggcatagca   1200
atgagttctc aaacaatcac aattggtgtt tcggaaattt taaacctcct taggacactc   1260
ggagaagggt gtagactttc atacatgtac aggtgtcagg aggcactgga tacgtatatg   1320
aaacttccac ataagcatta taatacagga tgggttcttt cccaggtcgg gaaagcatac   1380
tttgaactaa ttgactattt agaggctgaa aaggcattcc gtcttgcccg tctggcttct   1440
ccttattgct tagaaggaat ggatatatac tctacggtcc tctatcattt gaaggaagac   1500
atgaagctga gttacttggc tcaggaacta atatcaaccg atcgcttagc tccttaa      1557
```

<210> SEQ ID NO 23
<211> LENGTH: 2235
<212> TYPE: DNA
<213> ORGANISM: Arabidopsis thaliana

<400> SEQUENCE: 23

```
atggaagcta tgcttgtgga ctgtgtaaac aacagtcttc gtcattttgt ctacaaaaat     60
gctattttca tgtgcgagcg tctctgcgct gagtttcctt ctgaggttaa tttgcagcta    120
ttagccacca gctacctgca gaataatcaa gcttacagtg catatcatct gctaaaggga    180
acacaaatgg ctcagtcccg atacttgttc gcattatcat gcttccagat ggaccttctc    240
aatgaagctg aatctgcact ctgccctgtt aatgaacctg gtgcggagat cccaaatggt    300
gcagcaggcc attccttct tggacttatt tacaagtata ctgatagaag gaagaatgct    360
gctcaacaat ttaaacagtc cttgacaata gaccctctac tttgggctgc atatgaggaa    420
ttatgtatat taggtgctgc tgaggaagca actgcagttt tggtgaaaac agctgctctc    480
tccattcaaa agcagtatat gcaacaactg tcaacttccc tcggcttaaa cacttacaac    540
gaggaacgta attcaacttc tactaaaaac acgagttctg aagattatag tccaaggcag    600
tctaaacaca cacaaagcca tggccttaaa gatatctccg gaaatttcca ttctcatgga    660
gttaatggag tgtttcgaa catgtcattc tataatacgc cttcgccagt ggctgcacag    720
ctatccggta tagctccacc accacttttc cggaattttc agccagctgt tgcaaaccca    780
aactccctta ttactgacag ttctccaaag tccactgtta actctactct tcaagcacct    840
agaagaaagt ttgtagatga aggaaagtta cgtaagattt ctggcagact attttctgat    900
tctggtccac gacggagttc aagactgtct gctgattcag gggcaaacat taattcaagt    960
gttgcaacag taagcggaaa tgtgaacaac gcttccaagt atttgggagg ttctaaattg   1020
agttctttgg cacttcgttc tgtaacactt cggaagggac actcctgggc aaatgaaaac   1080
atggatgaag gggtccgtgg ggaaccttt gatgattcaa ggcctaatac tgcctcaacg   1140
actggttcta tggcttccaa tgatcaagaa gacgaaacaa tgtcgattgg tggcatagca   1200
atgagttctc aaacaatcac aattggtgtt tcggaaattt taaacctcct taggacactc   1260
ggagaagggt gtagactttc atacatgtac aggtgtcagg aggcactgga tacgtatatg   1320
aaacttccac ataagcatta taatacagga tgggttcttt cccaggtcgg gaaagcatac   1380
tttgaactaa ttgactattt agaggctgaa aaggcattcc gtcttgcccg tctggcttct   1440
```

```
cctattgct tagaaggaat ggatatatac tctacggtcc tctatcattt gaaggaagac    1500
atgaagctga gttacttggc tcaggaacta atatcaaccg atcgcttagc tcctcaatct    1560
tggtgtgcta tgggaaattg ctatagcttg caaaaggacc atgagaccgt actgaagaat    1620
ttcctacgag ctgttcaact gaatccaaga tttgcatatg cataccctt atgtggccac     1680 gaatacacaa ctcttgagga ttttgagaac ggaatgaaaa gttaccaaaa cgcacttcgt    1740 gtagataca gacactacaa cgcatggtac gggcttggaa tgatatatct acgccaagag     1800
aagttagagt tctcagagca tcacttcaga atggcttttcc taataaaccc gagttcctct    1860
gttataatgt cttatttagg gacatctttg catgccttga agagaagtga ggaagcacta    1920
gagataatgg agcaagccat agtagcagat agaaaaaacc ctcttccaat gtaccagaaa    1980
gctaacatac ttgtctgctt agaaagatta gatgaagctc tagaagttct tgaggagctc    2040
aaagagtatg cgccttcaga gagcagcgtt tacgctttaa tgggcaggat ctataagcgg    2100
cgaaacatgc acgataaagc catgcttcat ttcggtctag ctttagatat gaaaccgcct    2160
gcaactgacg ttgctgcaat aaaggctgca atggagaaat tgcatgttcc agatgagatc    2220
gatgagagcc cgtga                                                    2235

<210> SEQ ID NO 24
<211> LENGTH: 743
<212> TYPE: PRT
<213> ORGANISM: Arabidopsis thaliana

<400> SEQUENCE: 24

Met Glu Ala Met Leu Val Asp Cys Val Asn Asn Ser Leu Arg His Phe
1               5                   10                  15

Val Tyr Lys Asn Val Ile Phe Met Cys Glu Arg Leu Cys Ala Glu Phe
            20                  25                  30

Pro Ser Glu Val Asn Leu Gln Leu Leu Ala Thr Ser Tyr Leu Gln Asn
        35                  40                  45

Asn Gln Ala Tyr Ser Ala Tyr His Leu Leu Lys Gly Thr Gln Met Ala
    50                  55                  60

Gln Ser Arg Tyr Leu Phe Ala Leu Ser Cys Phe Gln Met Asp Leu Leu
65                  70                  75                  80

Asn Glu Ala Glu Ser Ala Leu Cys Pro Val Asn Glu Pro Gly Ala Glu
                85                  90                  95

Ile Pro Asn Gly Ala Ala Gly His Tyr Leu Leu Gly Leu Ile Tyr Lys
            100                 105                 110

Tyr Thr Asp Arg Arg Lys Asn Ala Ala Gln Gln Phe Lys Gln Ser Leu
        115                 120                 125

Thr Ile Asp Pro Leu Leu Trp Ala Ala Tyr Glu Glu Leu Cys Ile Leu
    130                 135                 140

Gly Ala Ala Glu Glu Ala Thr Ala Val Phe Gly Glu Thr Ala Ala Leu
145                 150                 155                 160

Ser Ile Gln Lys Gln Tyr Met Gln Gln Leu Ser Thr Ser Leu Gly Leu
                165                 170                 175

Asn Thr Tyr Asn Glu Glu Arg Asn Ser Thr Ser Thr Lys Asn Thr Ser
            180                 185                 190

Ser Glu Asp Tyr Ser Pro Arg Gln Ser Lys His Thr Gln Ser His Gly
        195                 200                 205

Leu Lys Asp Ile Ser Gly Asn Phe His Ser His Gly Val Asn Gly Gly
    210                 215                 220

Val Ser Asn Met Ser Phe Tyr Asn Thr Pro Ser Pro Val Ala Ala Gln
```

-continued

```
               225                 230                 235                 240

Leu Ser Gly Ile Ala Pro Pro Leu Phe Arg Asn Phe Gln Pro Ala
                245                 250                 255

Val Ala Asn Pro Asn Ser Leu Ile Thr Asp Ser Ser Pro Lys Ser Thr
                260                 265                 270

Val Asn Ser Thr Leu Gln Ala Pro Arg Arg Lys Phe Val Asp Glu Gly
                275                 280                 285

Lys Leu Arg Lys Ile Ser Gly Arg Leu Phe Ser Asp Ser Gly Pro Arg
                290                 295                 300

Arg Ser Ser Arg Leu Ser Ala Asp Ser Gly Ala Asn Ile Asn Ser Ser
305                 310                 315                 320

Val Ala Thr Val Ser Gly Asn Val Asn Asn Ala Ser Lys Tyr Leu Gly
                325                 330                 335

Gly Ser Lys Leu Ser Ser Leu Ala Leu Arg Ser Val Thr Leu Arg Lys
                340                 345                 350

Gly His Ser Trp Ala Asn Glu Asn Met Asp Glu Gly Val Arg Gly Glu
                355                 360                 365

Pro Phe Asp Asp Ser Arg Pro Asn Thr Ala Ser Thr Thr Gly Ser Met
                370                 375                 380

Ala Ser Asn Asp Gln Glu Asp Glu Thr Met Ser Ile Gly Gly Ile Ala
385                 390                 395                 400

Met Ser Ser Gln Thr Ile Thr Ile Gly Val Ser Glu Ile Leu Asn Leu
                405                 410                 415

Leu Arg Thr Leu Gly Glu Gly Cys Arg Leu Ser Tyr Met Tyr Arg Cys
                420                 425                 430

Gln Glu Ala Leu Asp Thr Tyr Met Lys Leu Pro His Lys His Tyr Asn
                435                 440                 445

Thr Gly Trp Val Leu Ser Gln Val Gly Lys Ala Tyr Phe Glu Leu Ile
                450                 455                 460

Asp Tyr Leu Glu Ala Glu Lys Ala Phe Arg Leu Ala Arg Leu Ala Ser
465                 470                 475                 480

Pro Tyr Cys Leu Glu Gly Met Asp Ile Tyr Ser Thr Val Leu Tyr His
                485                 490                 495

Leu Lys Glu Asp Met Lys Leu Ser Tyr Leu Ala Gln Glu Leu Ile Ser
                500                 505                 510

Thr Asp Arg Leu Ala Pro Gln Ser Trp Cys Ala Met Gly Asn Cys Tyr
                515                 520                 525

Ser Leu Gln Lys Asp His Glu Thr Ala Leu Lys Asn Phe Leu Arg Ala
                530                 535                 540

Val Gln Leu Asn Pro Arg Phe Ala Tyr Ala His Thr Leu Cys Gly His
545                 550                 555                 560

Glu Tyr Thr Thr Leu Glu Asp Phe Glu Asn Gly Met Lys Ser Tyr Gln
                565                 570                 575

Asn Ala Leu Arg Val Asp Thr Arg His Tyr Asn Ala Trp Tyr Gly Leu
                580                 585                 590

Gly Met Ile Tyr Leu Arg Gln Glu Lys Leu Glu Phe Ser Glu His His
                595                 600                 605

Phe Arg Met Ala Phe Leu Ile Asn Pro Ser Ser Ser Val Ile Met Ser
                610                 615                 620

Tyr Leu Gly Thr Ser Leu His Ala Leu Lys Arg Ser Glu Glu Ala Leu
625                 630                 635                 640

Glu Ile Met Glu Gln Ala Ile Val Ala Asp Arg Lys Asn Pro Leu Pro
                645                 650                 655
```

```
Met Tyr Gln Lys Ala Asn Ile Leu Val Cys Leu Glu Arg Leu Asp Glu
            660                 665                 670

Ala Leu Glu Val Leu Glu Glu Leu Lys Glu Tyr Ala Pro Ser Glu Ser
            675                 680                 685

Ser Val Tyr Ala Leu Met Gly Arg Ile Tyr Lys Arg Arg Asn Met His
            690                 695                 700

Asp Lys Ala Met Leu His Phe Gly Leu Ala Leu Asp Met Lys Pro Pro
705                 710                 715                 720

Ala Thr Asp Val Ala Ala Ile Lys Ala Ala Met Glu Lys Leu His Val
            725                 730                 735

Pro Asp Glu Ile Asp Glu Ser
            740

<210> SEQ ID NO 25
<211> LENGTH: 770
<212> TYPE: PRT
<213> ORGANISM: Arabidopsis thaliana

<400> SEQUENCE: 25

Met Glu Ala Met Leu Val Asp Cys Val Asn Asn Ser Leu Arg His Phe
1               5                   10                  15

Val Tyr Lys Asn Ala Ile Phe Met Cys Glu Arg Leu Cys Ala Glu Phe
            20                  25                  30

Pro Ser Glu Val Asn Leu Gln Leu Leu Ala Thr Ser Tyr Leu Gln Asn
            35                  40                  45

Asn Gln Ala Tyr Ser Ala Tyr His Leu Leu Lys Gly Thr Gln Met Ala
            50                  55                  60

Gln Ser Arg Tyr Leu Phe Ala Leu Ser Cys Phe Gln Met Asp Leu Leu
65                  70                  75                  80

Asn Glu Ala Glu Ser Ala Leu Cys Pro Val Asn Glu Pro Gly Ala Glu
            85                  90                  95

Ile Pro Asn Gly Ala Ala Gly His Tyr Leu Leu Gly Leu Ile Tyr Lys
            100                 105                 110

Tyr Thr Asp Arg Arg Lys Asn Ala Ala Gln Gln Phe Lys Gln Ser Leu
            115                 120                 125

Thr Ile Asp Pro Leu Leu Trp Ala Ala Tyr Glu Glu Leu Cys Ile Leu
            130                 135                 140

Gly Glu His Asn Pro Phe Ser Ala Tyr Phe Thr Asp Met Leu Trp Phe
145                 150                 155                 160

Ser Tyr Thr Phe Leu Ser Ala Gln Leu Ser Ser Ala Ala Glu Glu Ala
            165                 170                 175

Thr Ala Val Phe Gly Glu Thr Ala Ala Leu Ser Ile Gln Lys Gln Tyr
            180                 185                 190

Met Gln Gln Leu Ser Thr Ser Leu Gly Leu Asn Thr Tyr Asn Glu Glu
            195                 200                 205

Arg Asn Ser Thr Ser Thr Lys Asn Thr Ser Ser Glu Asp Tyr Ser Pro
            210                 215                 220

Arg Gln Ser Lys His Thr Gln Ser His Gly Leu Lys Asp Ile Ser Gly
225                 230                 235                 240

Asn Phe His Ser His Gly Val Asn Gly Gly Val Ser Asn Met Ser Phe
            245                 250                 255

Tyr Asn Thr Pro Ser Pro Val Ala Ala Gln Leu Ser Gly Ile Ala Pro
            260                 265                 270

Pro Pro Leu Phe Arg Asn Phe Gln Pro Ala Val Ala Asn Pro Asn Ser
```

-continued

```
                275                 280                 285
Leu Ile Thr Asp Ser Ser Pro Lys Ser Thr Val Asn Ser Thr Leu Gln
290                 295                 300
Ala Pro Arg Arg Lys Phe Val Asp Glu Gly Lys Leu Arg Lys Ile Ser
305                 310                 315                 320
Gly Arg Leu Phe Ser Asp Ser Gly Pro Arg Arg Ser Ser Arg Leu Ser
                325                 330                 335
Ala Asp Ser Gly Ala Asn Ile Asn Ser Ser Val Ala Thr Val Ser Gly
                340                 345                 350
Asn Val Asn Asn Ala Ser Lys Tyr Leu Gly Gly Ser Lys Leu Ser Ser
                355                 360                 365
Leu Ala Leu Arg Ser Val Thr Leu Arg Lys Gly His Ser Trp Ala Asn
370                 375                 380
Glu Asn Met Asp Glu Gly Val Arg Gly Glu Pro Phe Asp Asp Ser Arg
385                 390                 395                 400
Pro Asn Thr Ala Ser Thr Thr Gly Ser Met Ala Ser Asn Asp Gln Glu
                405                 410                 415
Asp Glu Thr Met Ser Ile Gly Gly Ile Ala Met Ser Ser Gln Thr Ile
                420                 425                 430
Thr Ile Gly Val Ser Glu Ile Leu Asn Leu Leu Arg Thr Leu Gly Glu
                435                 440                 445
Gly Cys Arg Leu Ser Tyr Met Tyr Arg Cys Gln Glu Ala Leu Asp Thr
                450                 455                 460
Tyr Met Lys Leu Pro His Lys His Tyr Asn Thr Gly Trp Val Leu Ser
465                 470                 475                 480
Gln Val Gly Lys Ala Tyr Phe Glu Leu Ile Asp Tyr Leu Glu Ala Glu
                485                 490                 495
Lys Ala Phe Arg Leu Ala Arg Leu Ala Ser Pro Tyr Cys Leu Glu Gly
                500                 505                 510
Met Asp Ile Tyr Ser Thr Val Leu Tyr His Leu Lys Glu Asp Met Lys
                515                 520                 525
Leu Ser Tyr Leu Ala Gln Glu Leu Ile Ser Thr Asp Arg Leu Ala Pro
530                 535                 540
Gln Ser Trp Cys Ala Met Gly Asn Cys Tyr Ser Leu Gln Lys Asp His
545                 550                 555                 560
Glu Thr Ala Leu Lys Asn Phe Leu Arg Ala Val Gln Leu Asn Pro Arg
                565                 570                 575
Phe Ala Tyr Ala His Thr Leu Cys Gly His Glu Tyr Thr Thr Leu Glu
                580                 585                 590
Asp Phe Glu Asn Gly Met Lys Ser Tyr Gln Asn Ala Leu Arg Val Asp
                595                 600                 605
Thr Arg His Tyr Asn Ala Trp Tyr Gly Leu Gly Met Ile Tyr Leu Arg
                610                 615                 620
Gln Glu Lys Leu Glu Phe Ser Glu His His Phe Arg Met Ala Phe Leu
625                 630                 635                 640
Ile Asn Pro Ser Ser Ser Val Ile Met Ser Tyr Leu Gly Thr Ser Leu
                645                 650                 655
His Ala Leu Lys Arg Ser Glu Glu Ala Leu Glu Ile Met Glu Gln Ala
                660                 665                 670
Ile Val Ala Asp Arg Lys Asn Pro Leu Pro Met Tyr Gln Lys Ala Asn
                675                 680                 685
Ile Leu Val Cys Leu Glu Arg Leu Asp Glu Ala Leu Glu Val Leu Glu
                690                 695                 700
```

```
Glu Leu Lys Glu Tyr Ala Pro Ser Glu Ser Val Tyr Ala Leu Met
705                 710                 715                 720

Gly Arg Ile Tyr Lys Arg Arg Asn Met His Asp Lys Ala Met Leu His
            725                 730                 735

Phe Gly Leu Ala Leu Asp Met Lys Pro Pro Ala Thr Asp Val Ala Ala
            740                 745                 750

Ile Lys Ala Ala Met Glu Lys Leu His Val Pro Asp Glu Ile Asp Glu
            755                 760                 765

Ser Pro
    770

<210> SEQ ID NO 26
<211> LENGTH: 744
<212> TYPE: PRT
<213> ORGANISM: Arabidopsis thaliana

<400> SEQUENCE: 26

Met Glu Ala Met Leu Val Asp Cys Val Asn Asn Ser Leu Arg His Phe
1               5                   10                  15

Val Tyr Lys Asn Ala Ile Phe Met Cys Glu Arg Leu Cys Ala Glu Phe
            20                  25                  30

Pro Ser Glu Val Asn Leu Gln Leu Leu Ala Thr Ser Tyr Leu Gln Asn
        35                  40                  45

Asn Gln Ala Tyr Ser Ala Tyr His Leu Leu Lys Gly Thr Gln Met Ala
    50                  55                  60

Gln Ser Arg Tyr Leu Phe Ala Leu Ser Cys Phe Gln Met Asp Leu Leu
65              70                  75                  80

Asn Glu Ala Glu Ser Ala Leu Cys Pro Val Asn Glu Pro Gly Ala Glu
                85                  90                  95

Ile Pro Asn Gly Ala Ala Gly His Tyr Leu Leu Gly Leu Ile Tyr Lys
            100                 105                 110

Tyr Thr Asp Arg Arg Lys Asn Ala Ala Gln Gln Phe Lys Gln Ser Leu
        115                 120                 125

Thr Ile Asp Pro Leu Leu Trp Ala Ala Tyr Glu Leu Cys Ile Leu
    130                 135                 140

Gly Ala Ala Glu Glu Ala Thr Ala Val Phe Gly Glu Thr Ala Ala Leu
145                 150                 155                 160

Ser Ile Gln Lys Gln Tyr Met Gln Gln Leu Ser Thr Ser Leu Gly Leu
                165                 170                 175

Asn Thr Tyr Asn Glu Glu Arg Asn Ser Thr Ser Thr Lys Asn Thr Ser
            180                 185                 190

Ser Glu Asp Tyr Ser Pro Arg Gln Ser Lys His Thr Gln Ser His Gly
        195                 200                 205

Leu Lys Asp Ile Ser Gly Asn Phe His Ser His Gly Val Asn Gly Gly
    210                 215                 220

Val Ser Asn Met Ser Phe Tyr Asn Thr Pro Ser Pro Val Ala Ala Gln
225                 230                 235                 240

Leu Ser Gly Ile Ala Pro Pro Leu Phe Arg Asn Phe Gln Pro Ala
                245                 250                 255

Val Ala Asn Pro Asn Ser Leu Ile Thr Asp Ser Ser Pro Lys Ser Thr
            260                 265                 270

Val Asn Ser Thr Leu Gln Ala Pro Arg Arg Lys Phe Val Asp Glu Gly
        275                 280                 285

Lys Leu Arg Lys Ile Ser Gly Arg Leu Phe Ser Asp Ser Gly Pro Arg
```

-continued

```
               290                 295                 300
Arg Ser Ser Arg Leu Ser Ala Asp Ser Gly Ala Asn Ile Asn Ser Ser
305                 310                 315                 320

Val Ala Thr Val Ser Gly Asn Val Asn Asn Ala Ser Lys Tyr Leu Gly
                325                 330                 335

Gly Ser Lys Leu Ser Ser Leu Ala Leu Arg Ser Val Thr Leu Arg Lys
                340                 345                 350

Gly His Ser Trp Ala Asn Glu Asn Met Asp Glu Gly Val Arg Gly Glu
                355                 360                 365

Pro Phe Asp Asp Ser Arg Pro Asn Thr Ala Ser Thr Thr Gly Ser Met
370                 375                 380

Ala Ser Asn Asp Gln Glu Asp Glu Thr Met Ser Ile Gly Gly Ile Ala
385                 390                 395                 400

Met Ser Ser Gln Thr Ile Thr Ile Gly Val Ser Glu Ile Leu Asn Leu
                405                 410                 415

Leu Arg Thr Leu Arg Glu Gly Cys Arg Leu Ser Tyr Met Tyr Arg Cys
                420                 425                 430

Gln Glu Ala Leu Asp Thr Tyr Met Lys Leu Pro His Lys His Tyr Asn
                435                 440                 445

Thr Gly Trp Val Leu Ser Gln Val Gly Lys Ala Tyr Phe Glu Leu Ile
                450                 455                 460

Asp Tyr Leu Glu Ala Glu Lys Ala Phe Arg Leu Ala Arg Leu Ala Ser
465                 470                 475                 480

Pro Tyr Cys Leu Glu Gly Met Asp Ile Tyr Ser Thr Val Leu Tyr His
                485                 490                 495

Leu Lys Glu Asp Met Lys Leu Ser Tyr Leu Ala Gln Glu Leu Ile Ser
                500                 505                 510

Thr Asp Arg Leu Ala Pro Gln Ser Trp Cys Ala Met Gly Asn Cys Tyr
                515                 520                 525

Ser Leu Gln Lys Asp His Glu Thr Ala Leu Lys Asn Phe Leu Arg Ala
                530                 535                 540

Val Gln Leu Asn Pro Arg Phe Ala Tyr Ala His Thr Leu Cys Gly His
545                 550                 555                 560

Glu Tyr Thr Thr Leu Glu Asp Phe Glu Asn Gly Met Lys Ser Tyr Gln
                565                 570                 575

Asn Ala Leu Arg Val Asp Thr Arg His Tyr Asn Ala Trp Tyr Gly Leu
                580                 585                 590

Gly Met Ile Tyr Leu Arg Gln Glu Lys Leu Glu Phe Ser Glu His His
                595                 600                 605

Phe Arg Met Ala Phe Leu Ile Asn Pro Ser Ser Ser Val Ile Met Ser
610                 615                 620

Tyr Leu Gly Thr Ser Leu His Ala Leu Lys Arg Ser Glu Glu Ala Leu
625                 630                 635                 640

Glu Ile Met Glu Gln Ala Ile Val Ala Asp Arg Lys Asn Pro Leu Pro
                645                 650                 655

Met Tyr Gln Lys Ala Asn Ile Leu Val Cys Leu Glu Arg Leu Asp Glu
                660                 665                 670

Ala Leu Glu Val Leu Glu Glu Leu Lys Glu Tyr Ala Pro Ser Glu Ser
                675                 680                 685

Ser Val Tyr Ala Leu Met Gly Arg Ile Tyr Lys Arg Arg Asn Met His
                690                 695                 700

Asp Lys Ala Met Leu His Phe Gly Leu Ala Leu Asp Met Lys Pro Pro
705                 710                 715                 720
```

```
Ala Thr Asp Val Ala Ala Ile Lys Ala Ala Met Glu Lys Leu His Val
                725                 730                 735

Pro Asp Glu Ile Asp Glu Ser Pro
            740
```

<210> SEQ ID NO 27
<211> LENGTH: 722
<212> TYPE: PRT
<213> ORGANISM: Arabidopsis thaliana

<400> SEQUENCE: 27

```
Met Glu Ala Met Leu Val Asp Cys Val Asn Asn Ser Leu Arg His Phe
1               5                   10                  15

Val Tyr Lys Asn Ala Ile Phe Met Cys Glu Arg Leu Cys Ala Glu Phe
            20                  25                  30

Pro Ser Glu Val Asn Leu Gln Leu Leu Ala Thr Ser Tyr Leu Gln Asn
        35                  40                  45

Asn Gln Ala Tyr Ser Ala Tyr His Leu Leu Lys Gly Thr Gln Met Ala
    50                  55                  60

Gln Ser Arg Tyr Leu Phe Ala Leu Ser Cys Phe Gln Met Asp Leu Leu
65                  70                  75                  80

Asn Glu Ala Glu Ser Ala Leu Cys Pro Val Asn Glu Pro Gly Ala Glu
                85                  90                  95

Ile Pro Asn Gly Ala Ala Gly His Tyr Leu Leu Gly Leu Ile Tyr Lys
            100                 105                 110

Tyr Thr Asp Arg Arg Lys Asn Ala Ala Gln Gln Phe Lys Gln Ser Leu
        115                 120                 125

Thr Ile Asp Pro Leu Leu Trp Ala Ala Tyr Glu Glu Leu Cys Ile Leu
    130                 135                 140

Gly Ala Ala Glu Glu Ala Thr Ala Val Phe Gly Glu Thr Ala Ala Leu
145                 150                 155                 160

Ser Ile Gln Lys Gln Tyr Met Gln Gln Leu Ser Thr Ser Leu Gly Leu
                165                 170                 175

Asn Thr Tyr Asn Glu Glu Arg Asn Ser Thr Ser Thr Lys Asn Thr Ser
            180                 185                 190

Ser Glu Asp Tyr Ser Pro Arg Gln Ser Lys His Thr Gln Ser His Gly
        195                 200                 205

Leu Lys Asp Ile Ser Gly Asn Phe His Ser His Gly Val Asn Gly Gly
    210                 215                 220

Val Ser Asn Met Ser Phe Tyr Asn Thr Pro Ser Pro Val Ala Ala Gln
225                 230                 235                 240

Leu Ser Gly Ile Ala Pro Pro Leu Phe Arg Asn Phe Gln Pro Ala
                245                 250                 255

Val Ala Asn Pro Asn Ser Leu Ile Thr Asp Ser Ser Pro Lys Ser Thr
            260                 265                 270

Val Asn Ser Thr Leu Gln Ala Pro Arg Arg Lys Phe Val Asp Glu Gly
        275                 280                 285

Lys Leu Arg Lys Ile Ser Gly Arg Leu Phe Ser Asp Ser Gly Pro Arg
    290                 295                 300

Arg Ser Ser Arg Leu Ser Ala Asp Ser Gly Ala Asn Ile Asn Ser Ser
305                 310                 315                 320

Val Ala Thr Val Ser Gly Asn Val Asn Asn Ala Ser Lys Tyr Leu Gly
                325                 330                 335

Gly Ser Lys Leu Ser Ser Leu Ala Leu Arg Ser Val Thr Leu Arg Lys
```

-continued

```
                340                 345                 350
Gly His Ser Trp Ala Asn Glu Asn Met Asp Glu Gly Val Arg Gly Glu
            355                 360                 365
Pro Phe Asp Asp Ser Arg Pro Asn Thr Ala Ser Thr Thr Gly Ser Met
370                 375                 380
Ala Ser Asn Asp Gln Glu Asp Glu Thr Met Ser Ile Gly Gly Ile Ala
385                 390                 395                 400
Met Ser Ser Gln Thr Ile Thr Ile Gly Val Ser Glu Ile Leu Asn Leu
                405                 410                 415
Leu Arg Thr Leu Gly Glu Gly Cys Arg Leu Ser Tyr Met Tyr Arg Cys
            420                 425                 430
Gln Val Gly Lys Ala Tyr Phe Glu Leu Ile Asp Tyr Leu Glu Ala Glu
        435                 440                 445
Lys Ala Phe Arg Leu Ala Arg Leu Ala Ser Pro Tyr Cys Leu Glu Gly
450                 455                 460
Met Asp Ile Tyr Ser Thr Val Leu Tyr His Leu Lys Glu Asp Met Lys
465                 470                 475                 480
Leu Ser Tyr Leu Ala Gln Glu Leu Ile Ser Thr Asp Arg Leu Ala Pro
                485                 490                 495
Gln Ser Trp Cys Ala Met Gly Asn Cys Tyr Ser Leu Gln Lys Asp His
            500                 505                 510
Glu Thr Ala Leu Lys Asn Phe Leu Arg Ala Val Gln Leu Asn Pro Arg
        515                 520                 525
Phe Ala Tyr Ala His Thr Leu Cys Gly His Glu Tyr Thr Thr Leu Glu
530                 535                 540
Asp Phe Glu Asn Gly Met Lys Ser Tyr Gln Asn Ala Leu Arg Val Asp
545                 550                 555                 560
Thr Arg His Tyr Asn Ala Trp Tyr Gly Leu Gly Met Ile Tyr Leu Arg
                565                 570                 575
Gln Glu Lys Leu Glu Phe Ser Glu His His Phe Arg Met Ala Phe Leu
            580                 585                 590
Ile Asn Pro Ser Ser Ser Val Ile Met Ser Tyr Leu Gly Thr Ser Leu
        595                 600                 605
His Ala Leu Lys Arg Ser Glu Glu Ala Leu Glu Ile Met Glu Gln Ala
610                 615                 620
Ile Val Ala Asp Arg Lys Asn Pro Leu Pro Met Tyr Gln Lys Ala Asn
625                 630                 635                 640
Ile Leu Val Cys Leu Glu Arg Leu Asp Glu Ala Leu Glu Val Leu Glu
                645                 650                 655
Glu Leu Lys Glu Tyr Ala Pro Ser Glu Ser Ser Val Tyr Ala Leu Met
            660                 665                 670
Gly Arg Ile Tyr Lys Arg Arg Asn Met His Asp Lys Ala Met Leu His
        675                 680                 685
Phe Gly Leu Ala Leu Asp Met Lys Pro Pro Ala Thr Asp Val Ala Ala
690                 695                 700
Ile Lys Ala Ala Met Glu Lys Leu His Val Pro Asp Glu Ile Asp Glu
705                 710                 715                 720
Ser Pro
```

<210> SEQ ID NO 28
<211> LENGTH: 704
<212> TYPE: PRT
<213> ORGANISM: Arabidopsis thaliana

<400> SEQUENCE: 28

```
Met Glu Ala Met Leu Val Asp Cys Val Asn Asn Ser Leu Arg His Phe
1               5                  10                 15
Val Tyr Lys Asn Ala Ile Phe Met Cys Glu Arg Leu Cys Ala Glu Phe
            20                  25                  30
Pro Ser Glu Val Asn Leu Gln Leu Leu Ala Thr Ser Tyr Leu Gln Asn
        35                  40                  45
Asn Gln Ala Tyr Ser Ala Tyr His Leu Leu Lys Gly Thr Gln Met Ala
    50                  55                  60
Gln Ser Arg Tyr Leu Phe Ala Leu Ser Cys Phe Gln Met Asp Leu Leu
65                  70                  75                  80
Asn Glu Ala Glu Ser Ala Leu Cys Pro Val Asn Glu Pro Gly Ala Glu
                85                  90                  95
Ile Pro Asn Gly Ala Ala Gly His Tyr Leu Leu Gly Leu Ile Tyr Lys
            100                 105                 110
Tyr Thr Asp Arg Arg Lys Asn Ala Ala Gln Gln Phe Lys Gln Ser Leu
        115                 120                 125
Thr Ile Asp Pro Leu Leu Trp Ala Ala Tyr Glu Glu Leu Cys Ile Leu
    130                 135                 140
Gly Ala Ala Glu Glu Ala Thr Ala Val Phe Gly Glu Thr Ala Ala Leu
145                 150                 155                 160
Ser Ile Gln Lys Gln Tyr Met Gln Gln Leu Ser Thr Ser Leu Gly Leu
                165                 170                 175
Asn Thr Tyr Asn Glu Glu Arg Asn Ser Thr Ser Thr Lys Asn Thr Ser
            180                 185                 190
Ser Glu Asp Tyr Ser Pro Arg Gln Ser Lys His Thr Gln Ser His Gly
        195                 200                 205
Leu Lys Asp Ile Ser Gly Asn Phe His Ser His Gly Val Asn Gly Gly
    210                 215                 220
Val Ser Asn Met Ser Phe Tyr Asn Thr Pro Ser Pro Val Ala Ala Gln
225                 230                 235                 240
Leu Ser Gly Ile Ala Pro Pro Leu Phe Arg Asn Phe Gln Pro Ala
                245                 250                 255
Val Ala Asn Pro Asn Ser Leu Ile Thr Asp Ser Ser Pro Lys Ser Thr
            260                 265                 270
Val Asn Ser Thr Leu Gln Ala Pro Arg Arg Lys Phe Val Asp Glu Gly
        275                 280                 285
Lys Leu Arg Lys Ile Ser Gly Arg Leu Phe Ser Asp Ser Gly Pro Arg
    290                 295                 300
Arg Ser Ser Arg Leu Ser Ala Asp Ser Gly Ala Asn Ile Asn Ser Ser
305                 310                 315                 320
Val Ala Thr Val Ser Gly Asn Val Asn Asn Ala Ser Lys Tyr Leu Gly
                325                 330                 335
Gly Ser Lys Leu Ser Ser Leu Ala Leu Arg Ser Val Thr Leu Arg Lys
            340                 345                 350
Gly His Ser Trp Ala Asn Glu Asn Met Asp Glu Gly Val Arg Gly Glu
        355                 360                 365
Pro Phe Asp Asp Ser Arg Pro Asn Thr Ala Ser Thr Thr Gly Ser Met
    370                 375                 380
Ala Ser Asn Asp Gln Glu Asp Glu Thr Met Ser Ile Gly Gly Ile Ala
385                 390                 395                 400
Met Ser Ser Gln Thr Ile Thr Ile Gly Val Ser Glu Ile Leu Asn Leu
                405                 410                 415
```

```
Leu Arg Thr Leu Gly Glu Gly Cys Arg Leu Ser Tyr Met Tyr Arg Cys
            420                 425                 430

Gln Glu Ala Leu Asp Thr Tyr Met Lys Leu Pro His Lys His Tyr Asn
            435                 440                 445

Thr Gly Trp Val Leu Ser Gln His Leu Lys Glu Asp Met Lys Leu Ser
            450                 455                 460

Tyr Leu Ala Gln Glu Leu Ile Ser Thr Asp Arg Leu Ala Pro Gln Ser
465                 470                 475                 480

Trp Cys Ala Met Gly Asn Cys Tyr Ser Leu Gln Lys Asp His Glu Thr
                485                 490                 495

Ala Leu Lys Asn Phe Leu Arg Ala Val Gln Leu Asn Pro Arg Phe Ala
            500                 505                 510

Tyr Ala His Thr Leu Cys Gly His Glu Tyr Thr Thr Leu Glu Asp Phe
            515                 520                 525

Glu Asn Gly Met Lys Ser Tyr Gln Asn Ala Leu Arg Val Asp Thr Arg
            530                 535                 540

His Tyr Asn Ala Trp Tyr Gly Leu Gly Met Ile Tyr Leu Arg Gln Glu
545                 550                 555                 560

Lys Leu Glu Phe Ser Glu His His Phe Arg Met Ala Phe Leu Ile Asn
                565                 570                 575

Pro Ser Ser Ser Val Ile Met Ser Tyr Leu Gly Thr Ser Leu His Ala
            580                 585                 590

Leu Lys Arg Ser Glu Glu Ala Leu Glu Ile Met Glu Gln Ala Ile Val
            595                 600                 605

Ala Asp Arg Lys Asn Pro Leu Pro Met Tyr Gln Lys Ala Asn Ile Leu
            610                 615                 620

Val Cys Leu Glu Arg Leu Asp Glu Ala Leu Glu Val Leu Glu Glu Leu
625                 630                 635                 640

Lys Glu Tyr Ala Pro Ser Glu Ser Ser Val Tyr Ala Leu Met Gly Arg
                645                 650                 655

Ile Tyr Lys Arg Arg Asn Met His Asp Lys Ala Met Leu His Phe Gly
            660                 665                 670

Leu Ala Leu Asp Met Lys Pro Pro Ala Thr Asp Val Ala Ala Ile Lys
            675                 680                 685

Ala Ala Met Glu Lys Leu His Val Pro Asp Glu Ile Asp Glu Ser Pro
            690                 695                 700

<210> SEQ ID NO 29
<211> LENGTH: 518
<212> TYPE: PRT
<213> ORGANISM: Arabidopsis thaliana

<400> SEQUENCE: 29

Met Glu Ala Met Leu Val Asp Cys Val Asn Asn Ser Leu Arg His Phe
1               5                   10                  15

Val Tyr Lys Asn Ala Ile Phe Met Cys Glu Arg Leu Cys Ala Glu Phe
                20                  25                  30

Pro Ser Glu Val Asn Leu Gln Leu Ala Thr Ser Tyr Leu Gln Asn
            35                  40                  45

Asn Gln Ala Tyr Ser Ala Tyr His Leu Leu Lys Gly Thr Gln Met Ala
            50                  55                  60

Gln Ser Arg Tyr Leu Phe Ala Leu Ser Cys Phe Gln Met Asp Leu Leu
65                  70                  75                  80

Asn Glu Ala Glu Ser Ala Leu Cys Pro Val Asn Glu Pro Gly Ala Glu
```

-continued

```
                85                  90                  95
Ile Pro Asn Gly Ala Ala Gly His Tyr Leu Leu Gly Leu Ile Tyr Lys
            100                 105                 110
Tyr Thr Asp Arg Arg Lys Asn Ala Ala Gln Gln Phe Lys Gln Ser Leu
        115                 120                 125
Thr Ile Asp Pro Leu Leu Trp Ala Ala Tyr Glu Glu Leu Cys Ile Leu
    130                 135                 140
Gly Ala Ala Glu Glu Ala Thr Ala Val Phe Gly Glu Thr Ala Ala Leu
145                 150                 155                 160
Ser Ile Gln Lys Gln Tyr Met Gln Gln Leu Ser Thr Ser Leu Gly Leu
                165                 170                 175
Asn Thr Tyr Asn Glu Glu Arg Asn Ser Thr Ser Thr Lys Asn Thr Ser
            180                 185                 190
Ser Glu Asp Tyr Ser Pro Arg Gln Ser Lys His Thr Gln Ser His Gly
        195                 200                 205
Leu Lys Asp Ile Ser Gly Asn Phe His Ser His Gly Val Asn Gly Gly
    210                 215                 220
Val Ser Asn Met Ser Phe Tyr Asn Thr Pro Ser Pro Val Ala Ala Gln
225                 230                 235                 240
Leu Ser Gly Ile Ala Pro Pro Leu Phe Arg Asn Phe Gln Pro Ala
                245                 250                 255
Val Ala Asn Pro Asn Ser Leu Ile Thr Asp Ser Ser Pro Lys Ser Thr
            260                 265                 270
Val Asn Ser Thr Leu Gln Ala Pro Arg Arg Lys Phe Val Asp Glu Gly
        275                 280                 285
Lys Leu Arg Lys Ile Ser Gly Arg Leu Phe Ser Asp Ser Gly Pro Arg
    290                 295                 300
Arg Ser Ser Arg Leu Ser Ala Asp Ser Gly Ala Asn Ile Asn Ser Ser
305                 310                 315                 320
Val Ala Thr Val Ser Gly Asn Val Asn Asn Ala Ser Lys Tyr Leu Gly
                325                 330                 335
Gly Ser Lys Leu Ser Ser Leu Ala Leu Arg Ser Val Thr Leu Arg Lys
            340                 345                 350
Gly His Ser Trp Ala Asn Glu Asn Met Asp Glu Gly Val Arg Gly Glu
        355                 360                 365
Pro Phe Asp Asp Ser Arg Pro Asn Thr Ala Ser Thr Thr Gly Ser Met
    370                 375                 380
Ala Ser Asn Asp Gln Glu Asp Glu Thr Met Ser Ile Gly Gly Ile Ala
385                 390                 395                 400
Met Ser Ser Gln Thr Ile Thr Ile Gly Val Ser Glu Ile Leu Asn Leu
                405                 410                 415
Leu Arg Thr Leu Gly Glu Gly Cys Arg Leu Ser Tyr Met Tyr Arg Cys
            420                 425                 430
Gln Glu Ala Leu Asp Thr Tyr Met Lys Leu Pro His Lys His Tyr Asn
        435                 440                 445
Thr Gly Trp Val Leu Ser Gln Val Gly Lys Ala Tyr Phe Glu Leu Ile
    450                 455                 460
Asp Tyr Leu Glu Ala Glu Lys Ala Phe Arg Leu Ala Arg Leu Ala Ser
465                 470                 475                 480
Pro Tyr Cys Leu Glu Gly Met Asp Ile Tyr Ser Thr Val Leu Tyr His
                485                 490                 495
Leu Lys Glu Asp Met Lys Leu Ser Tyr Leu Ala Gln Glu Leu Ile Ser
            500                 505                 510
```

Thr Asp Arg Leu Ala Pro
        515

<210> SEQ ID NO 30
<211> LENGTH: 744
<212> TYPE: PRT
<213> ORGANISM: Arabidopsis thaliana

<400> SEQUENCE: 30

Met Glu Ala Met Leu Val Asp Cys Val Asn Asn Ser Leu Arg His Phe
1               5                   10                  15

Val Tyr Lys Asn Ala Ile Phe Met Cys Glu Arg Leu Cys Ala Glu Phe
            20                  25                  30

Pro Ser Glu Val Asn Leu Gln Leu Leu Ala Thr Ser Tyr Leu Gln Asn
        35                  40                  45

Asn Gln Ala Tyr Ser Ala Tyr His Leu Leu Lys Gly Thr Gln Met Ala
    50                  55                  60

Gln Ser Arg Tyr Leu Phe Ala Leu Ser Cys Phe Gln Met Asp Leu Leu
65                  70                  75                  80

Asn Glu Ala Glu Ser Ala Leu Cys Pro Val Asn Glu Pro Gly Ala Glu
                85                  90                  95

Ile Pro Asn Gly Ala Ala His Tyr Leu Leu Gly Leu Ile Tyr Lys
            100                 105                 110

Tyr Thr Asp Arg Arg Lys Asn Ala Ala Gln Gln Phe Lys Gln Ser Leu
        115                 120                 125

Thr Ile Asp Pro Leu Leu Trp Ala Ala Tyr Glu Glu Leu Cys Ile Leu
    130                 135                 140

Gly Ala Ala Glu Glu Ala Thr Ala Val Phe Gly Glu Thr Ala Ala Leu
145                 150                 155                 160

Ser Ile Gln Lys Gln Tyr Met Gln Gln Leu Ser Thr Ser Leu Gly Leu
                165                 170                 175

Asn Thr Tyr Asn Glu Glu Arg Asn Ser Thr Ser Thr Lys Asn Thr Ser
            180                 185                 190

Ser Glu Asp Tyr Ser Pro Arg Gln Ser Lys His Thr Gln Ser His Gly
        195                 200                 205

Leu Lys Asp Ile Ser Gly Asn Phe His Ser His Gly Val Asn Gly Gly
    210                 215                 220

Val Ser Asn Met Ser Phe Tyr Asn Thr Pro Ser Pro Val Ala Ala Gln
225                 230                 235                 240

Leu Ser Gly Ile Ala Pro Pro Leu Phe Arg Asn Phe Gln Pro Ala
                245                 250                 255

Val Ala Asn Pro Asn Ser Leu Ile Thr Asp Ser Ser Pro Lys Ser Thr
            260                 265                 270

Val Asn Ser Thr Leu Gln Ala Pro Arg Arg Lys Phe Val Asp Glu Gly
        275                 280                 285

Lys Leu Arg Lys Ile Ser Gly Arg Leu Phe Ser Asp Ser Gly Pro Arg
    290                 295                 300

Arg Ser Ser Arg Leu Ser Ala Asp Ser Gly Asn Ile Asn Ser Ser
305                 310                 315                 320

Val Ala Thr Val Ser Gly Asn Val Asn Ala Ser Lys Tyr Leu Gly
                325                 330                 335

Gly Ser Lys Leu Ser Ser Leu Ala Leu Arg Ser Val Thr Leu Arg Lys
            340                 345                 350

Gly His Ser Trp Ala Asn Glu Asn Met Asp Glu Gly Val Arg Gly Glu

-continued

```
                355                 360                 365
Pro Phe Asp Asp Ser Arg Pro Asn Thr Ala Ser Thr Gly Ser Met
370                 375                 380

Ala Ser Asn Asp Gln Glu Asp Glu Thr Met Ser Ile Gly Gly Ile Ala
385                 390                 395                 400

Met Ser Ser Gln Thr Ile Thr Ile Gly Val Ser Glu Ile Leu Asn Leu
                405                 410                 415

Leu Arg Thr Leu Gly Glu Gly Cys Arg Leu Ser Tyr Met Tyr Arg Cys
                420                 425                 430

Gln Glu Ala Leu Asp Thr Tyr Met Lys Leu Pro His Lys His Tyr Asn
                435                 440                 445

Thr Gly Trp Val Leu Ser Gln Val Gly Lys Ala Tyr Phe Glu Leu Ile
                450                 455                 460

Asp Tyr Leu Glu Ala Glu Lys Ala Phe Arg Leu Ala Arg Leu Ala Ser
465                 470                 475                 480

Pro Tyr Cys Leu Glu Gly Met Asp Ile Tyr Ser Thr Val Leu Tyr His
                485                 490                 495

Leu Lys Glu Asp Met Lys Leu Ser Tyr Leu Ala Gln Glu Leu Ile Ser
                500                 505                 510

Thr Asp Arg Leu Ala Pro Gln Ser Trp Cys Ala Met Gly Asn Cys Tyr
                515                 520                 525

Ser Leu Gln Lys Asp His Glu Thr Val Leu Lys Asn Phe Leu Arg Ala
                530                 535                 540

Val Gln Leu Asn Pro Arg Phe Ala Tyr Ala His Thr Leu Cys Gly His
545                 550                 555                 560

Glu Tyr Thr Thr Leu Glu Asp Phe Glu Asn Gly Met Lys Ser Tyr Gln
                565                 570                 575

Asn Ala Leu Arg Val Asp Thr Arg His Tyr Asn Ala Trp Tyr Gly Leu
                580                 585                 590

Gly Met Ile Tyr Leu Arg Gln Glu Lys Leu Glu Phe Ser Glu His His
                595                 600                 605

Phe Arg Met Ala Phe Leu Ile Asn Pro Ser Ser Val Ile Met Ser
610                 615                 620

Tyr Leu Gly Thr Ser Leu His Ala Leu Lys Arg Ser Glu Ala Leu
625                 630                 635                 640

Glu Ile Met Glu Gln Ala Ile Val Ala Asp Arg Lys Asn Pro Leu Pro
                645                 650                 655

Met Tyr Gln Lys Ala Asn Ile Leu Val Cys Leu Glu Arg Leu Asp Glu
                660                 665                 670

Ala Leu Glu Val Leu Glu Glu Leu Lys Glu Tyr Ala Pro Ser Glu Ser
                675                 680                 685

Ser Val Tyr Ala Leu Met Gly Arg Ile Tyr Lys Arg Arg Asn Met His
                690                 695                 700

Asp Lys Ala Met Leu His Phe Gly Leu Ala Leu Asp Met Lys Pro Pro
705                 710                 715                 720

Ala Thr Asp Val Ala Ala Ile Lys Ala Ala Met Glu Lys Leu His Val
                725                 730                 735

Pro Asp Glu Ile Asp Glu Ser Pro
                740

<210> SEQ ID NO 31
<211> LENGTH: 29
<212> TYPE: DNA
<213> ORGANISM: Artificial Sequence
```

```
<220> FEATURE:
<223> OTHER INFORMATION: primer

<400> SEQUENCE: 31
gaagaaaggc aacaactatg gaagctatg                                    29

<210> SEQ ID NO 32
<211> LENGTH: 30
<212> TYPE: DNA
<213> ORGANISM: Artificial Sequence
<220> FEATURE:
<223> OTHER INFORMATION: primer

<400> SEQUENCE: 32
gaactgtcag taataaggga gtttgggttt                                   30

<210> SEQ ID NO 33
<211> LENGTH: 25
<212> TYPE: DNA
<213> ORGANISM: Artificial Sequence
<220> FEATURE:
<223> OTHER INFORMATION: primer

<400> SEQUENCE: 33
atgcaacaac tgtcaacttc cctcg                                        25

<210> SEQ ID NO 34
<211> LENGTH: 31
<212> TYPE: DNA
<213> ORGANISM: Artificial Sequence
<220> FEATURE:
<223> OTHER INFORMATION: primer

<400> SEQUENCE: 34
tatccattcc ttctaagcaa taaggagaag c                                 31

<210> SEQ ID NO 35
<211> LENGTH: 29
<212> TYPE: DNA
<213> ORGANISM: Artificial Sequence
<220> FEATURE:
<223> OTHER INFORMATION: primer

<400> SEQUENCE: 35
aaattttaaa cctccttagg acactcgga                                    29

<210> SEQ ID NO 36
<211> LENGTH: 25
<212> TYPE: DNA
<213> ORGANISM: Artificial Sequence
<220> FEATURE:
<223> OTHER INFORMATION: primer

<400> SEQUENCE: 36
tcacgggctc tcatcgatct catct                                        25

<210> SEQ ID NO 37
<211> LENGTH: 25
<212> TYPE: DNA
<213> ORGANISM: Artificial Sequence
<220> FEATURE:
<223> OTHER INFORMATION: primer

<400> SEQUENCE: 37
gttcttgagg agctcaaaga gtatg                                        25
```

<210> SEQ ID NO 38
<211> LENGTH: 24
<212> TYPE: DNA
<213> ORGANISM: Artificial Sequence
<220> FEATURE:
<223> OTHER INFORMATION: primer

<400> SEQUENCE: 38
gctttaatgg gcaggatcta taag                                    24

<210> SEQ ID NO 39
<211> LENGTH: 32
<212> TYPE: DNA
<213> ORGANISM: Artificial Sequence
<220> FEATURE:
<223> OTHER INFORMATION: primer

<400> SEQUENCE: 39
tattcaaatg gtcaattata aagcccaata ag                            32

<210> SEQ ID NO 40
<211> LENGTH: 25
<212> TYPE: DNA
<213> ORGANISM: Artificial Sequence
<220> FEATURE:
<223> OTHER INFORMATION: primer

<400> SEQUENCE: 40
acatgaaaat agcatttttg tagac                                   25

<210> SEQ ID NO 41
<211> LENGTH: 33
<212> TYPE: DNA
<213> ORGANISM: Artificial Sequence
<220> FEATURE:
<223> OTHER INFORMATION: primer

<400> SEQUENCE: 41
agagtgacct acttactaca ttggtacaaa acc                           33

<210> SEQ ID NO 42
<211> LENGTH: 31
<212> TYPE: DNA
<213> ORGANISM: Artificial Sequence
<220> FEATURE:
<223> OTHER INFORMATION: primer

<400> SEQUENCE: 42
cccattaaag cgtaaacgct gctctctgaa g                             31

<210> SEQ ID NO 43
<211> LENGTH: 32
<212> TYPE: DNA
<213> ORGANISM: Artificial Sequence
<220> FEATURE:
<223> OTHER INFORMATION: primer

<400> SEQUENCE: 43
tattcaaatg gtcaattata aagcccaata ag                            32

<210> SEQ ID NO 44
<211> LENGTH: 32
<212> TYPE: DNA
<213> ORGANISM: Artificial Sequence
<220> FEATURE:
<223> OTHER INFORMATION: primer -continued

<400> SEQUENCE: 44
tgaatgaata ctttctcaac tactattgaa gc                32

<210> SEQ ID NO 45
<211> LENGTH: 30
<212> TYPE: DNA
<213> ORGANISM: Artificial Sequence
<220> FEATURE:
<223> OTHER INFORMATION: primer

<400> SEQUENCE: 45
tatgagtcaa ctgttagagg aatgtctctg                30

<210> SEQ ID NO 46
<211> LENGTH: 27
<212> TYPE: DNA
<213> ORGANISM: Artificial Sequence
<220> FEATURE:
<223> OTHER INFORMATION: primer

<400> SEQUENCE: 46
gaagttgaca gttgttgcat atactgc                27

<210> SEQ ID NO 47
<211> LENGTH: 30
<212> TYPE: DNA
<213> ORGANISM: Artificial Sequence
<220> FEATURE:
<223> OTHER INFORMATION: primer

<400> SEQUENCE: 47
tcttacactt ttctgtctgc tcaactttca                30

<210> SEQ ID NO 48
<211> LENGTH: 31
<212> TYPE: DNA
<213> ORGANISM: Artificial Sequence
<220> FEATURE:
<223> OTHER INFORMATION: primer

<400> SEQUENCE: 48
caaagaactc aatttagaac ctcccaaata c                31

<210> SEQ ID NO 49
<211> LENGTH: 30
<212> TYPE: DNA
<213> ORGANISM: Artificial Sequence
<220> FEATURE:
<223> OTHER INFORMATION: primer

<400> SEQUENCE: 49
cagatttctg gcagactatt ttctgattct                30

<210> SEQ ID NO 50
<211> LENGTH: 30
<212> TYPE: DNA
<213> ORGANISM: Artificial Sequence
<220> FEATURE:
<223> OTHER INFORMATION: primer

<400> SEQUENCE: 50
aagtaactca gcttcatgtc ttccttcaaa                30

<210> SEQ ID NO 51

```
<211> LENGTH: 30
<212> TYPE: DNA
<213> ORGANISM: Artificial Sequence
<220> FEATURE:
<223> OTHER INFORMATION: primer

<400> SEQUENCE: 51
gatatttatt tgcagcattt gaaggaagac                                    30

<210> SEQ ID NO 52
<211> LENGTH: 30
<212> TYPE: DNA
<213> ORGANISM: Artificial Sequence
<220> FEATURE:
<223> OTHER INFORMATION: primer

<400> SEQUENCE: 52
gaattttcag atttaaaaac catcattgga                                    30

<210> SEQ ID NO 53
<211> LENGTH: 29
<212> TYPE: DNA
<213> ORGANISM: Artificial Sequence
<220> FEATURE:
<223> OTHER INFORMATION: primer

<400> SEQUENCE: 53
agtctttaaa acagagtcgt ccaatgatg                                     29

<210> SEQ ID NO 54
<211> LENGTH: 30
<212> TYPE: DNA
<213> ORGANISM: Artificial Sequence
<220> FEATURE:
<223> OTHER INFORMATION: primer

<400> SEQUENCE: 54
atattgcgat taggtagtgt tacggacaac                                    30

<210> SEQ ID NO 55
<211> LENGTH: 25
<212> TYPE: DNA
<213> ORGANISM: Artificial Sequence
<220> FEATURE:
<223> OTHER INFORMATION: primer

<400> SEQUENCE: 55
gaagtcgaca caaactatgg aagct                                         25

<210> SEQ ID NO 56
<211> LENGTH: 23
<212> TYPE: DNA
<213> ORGANISM: Artificial Sequence
<220> FEATURE:
<223> OTHER INFORMATION: primer

<400> SEQUENCE: 56
aatcataccc aaggatcctg gag                                           23

<210> SEQ ID NO 57
<211> LENGTH: 27
<212> TYPE: DNA
<213> ORGANISM: Artificial Sequence
<220> FEATURE:
<223> OTHER INFORMATION: primer

<400> SEQUENCE: 57
```

```
gcaacaactg tcaacttccc tcggctt                                        27

<210> SEQ ID NO 58
<211> LENGTH: 29
<212> TYPE: DNA
<213> ORGANISM: Artificial Sequence
<220> FEATURE:
<223> OTHER INFORMATION: primer

<400> SEQUENCE: 58
agaaccagtc gttgaggcag tattaggcc                                      29

<210> SEQ ID NO 59
<211> LENGTH: 26
<212> TYPE: DNA
<213> ORGANISM: Artificial Sequence
<220> FEATURE:
<223> OTHER INFORMATION: primer

<400> SEQUENCE: 59
atgatggaga atctactggc gaattg                                         26

<210> SEQ ID NO 60
<211> LENGTH: 25
<212> TYPE: DNA
<213> ORGANISM: Artificial Sequence
<220> FEATURE:
<223> OTHER INFORMATION: primer

<400> SEQUENCE: 60
catcgaggaa agagaaggtg catag                                          25

<210> SEQ ID NO 61
<211> LENGTH: 25
<212> TYPE: DNA
<213> ORGANISM: Artificial Sequence
<220> FEATURE:
<223> OTHER INFORMATION: primer

<400> SEQUENCE: 61
atcctagtga atcttccccg gatcg                                          25

<210> SEQ ID NO 62
<211> LENGTH: 23
<212> TYPE: DNA
<213> ORGANISM: Artificial Sequence
<220> FEATURE:
<223> OTHER INFORMATION: primer

<400> SEQUENCE: 62
agccagttga aattgatgct gcg                                            23

<210> SEQ ID NO 63
<211> LENGTH: 26
<212> TYPE: DNA
<213> ORGANISM: Artificial Sequence
<220> FEATURE:
<223> OTHER INFORMATION: primer

<400> SEQUENCE: 63
gatgcagaga gatgctaccg gaaggc                                         26

<210> SEQ ID NO 64
<211> LENGTH: 26
<212> TYPE: DNA
```

```
<213> ORGANISM: Artificial Sequence
<220> FEATURE:
<223> OTHER INFORMATION: primer

<400> SEQUENCE: 64
gatgcagaga gatgctaccg gaaggc                                              26

<210> SEQ ID NO 65
<211> LENGTH: 20
<212> TYPE: DNA
<213> ORGANISM: Artificial Sequence
<220> FEATURE:
<223> OTHER INFORMATION: primer

<400> SEQUENCE: 65
tcttcccggt ggagatacag                                                     20

<210> SEQ ID NO 66
<211> LENGTH: 20
<212> TYPE: DNA
<213> ORGANISM: Artificial Sequence
<220> FEATURE:
<223> OTHER INFORMATION: primer

<400> SEQUENCE: 66
gcccatggta aaagagctga                                                     20
```

PLANT DEVELOPMENT REGULATING GENE AND ITS USES

CROSS REFERENCE TO RELATED APPLICATIONS

This application is a section 371 application of PCT/EP01/13116, filed Nov. 13, 2001, which claims the benefit under 35 U.S.C. §119(e) of U.S. Provisional Application No. 60/250,402, filed Nov. 30, 2000.

FIELD OF THE INVENTION

The current invention is situated in the field of plant development. More specifically reference is made to an isolated and characterized gene required for correct plant development as well as to mutants thereof and to the use of said wild-type or mutant genes to modify plant development. Said genes can furthermore be utilized for mimicking or modifying auxin-related effects.

BACKGROUND TO THE INVENTION

In recent years a great number of genes has been characterized that are involved in different aspects of plant development and/or in the establishment of cell patterns underlying the different plant tissues and organs. Identification of such genes is usually based on isolation of mutagenized *Arabidopsis thaliana* plants exhibiting extreme or less extreme phenotypic aberrations in organs such as flowers, leaves or roots or exhibiting earlier defects, e.g. during embyro development. Without being exhaustive, genes involved in early establishment of flower meristem and organ identity include LEAFY (LFY), APETALA1 (AP1) and APETALA2 (AP2). Genes involved in later steps of flower organ identity patterning include APETALA3 (AP3), PISTILLATA (PI) and AGAMOUS (AG). Genes controlling the number of flower organs include CLAVATA1 (CLV1), CLAVATA3 (CLV3), ETTIN (ETT), PERIANTH (PAN) and TOUSLED (TSL). TOUSLED also regulates flower organ size. Flower meristem and organ identification further relies on the UNUSUAL FLOWER ORGAN (UFO) gene and flowering time is regulated by e.g. the CONSTANS (CO) and the LUMINIDEPENDENS (LD) genes. The inflorescence meristem can be held in an indeterminate state by e.g. the TERMINAL FLOWER 1 (TFL) gene. Many of the cited flower development genes encode transcription factors of e.g. the MADS-box class (e.g. AG), the ARF-class (e.g. ETT); or leucine-rich repeat-type receptor protein kinases (e.g. CLV1 and CLV2); or protein kinases (e.g. TSL) (Nemhauser et al. 1998, Sessions et al. 1997 and references cited in both; Aukerman et al. 1999, Pnueli et al. 1998). A naked, pin-formed inflorescence is formed in *A. thaliana* plants mutated in the PIN-FORMED1 (PIN1) gene (Palme and Gälweiler 1999).

Development of the shoot apical meristem (which is the source of leaf and flower primordia) relies on e.g. WUSCHEL (WUS) whereas its maintenance depends on e.g. the KNOTTED-like homeobox transcription factor gene SHOOT MERISTEMLESS (STM) and, during embryonic development, on the ZWILLE (ZLL) gene. Meristem size is regulated in early development by e.g. the PRIMORDIA TIMING (PT) gene and in later stages by e.g. CLV1. The rate of leaf formation is increased in clavata mutants. separation of organs emanating from the shoot apical meristem and separation of organs from each other relies on at least the CUP-SHAPED COTYLEDON (CUC1 and CUC2) genes and on AINTEGUMENTA (ANT). Initiation of lateral organ formation from the shoot apical meristem requires the MGOUN (MGO) genes. Leaf development is controlled by a number of genes including ARGONAUTE1 (AGO1), PHABULOSA (PHB) and PHANTASTICA (PHAN). Trichome formation from leaf epidermal cells involves e.g. GLABROUS1 (GL1), GLABRA2 (GL2), TRANSPARENT TESTA GLABRA (TTG), TRIPTYCHON (TRY) and ZWICHEL (ZWI) genes. Stomata patterning relies on e.g. GL2 and TTG (Benfey et al. 1999, Bowman and Eshed 2000, Doerner 1999, Langdale 1998, Lenhard and Laux 1999, McSteen and Hake 1998 and references cited in all).

The fate of root epidermal cells is controlled by genes such as GL2, TTG and CAPRICE (CPC). GL2 and TTG repress root hair formation whereas CPC, a MYB-type transcription factor, is a positive regulator of the root hair cell fate.

Establishment of the root cortex and root endodermis from the ground tissue involves the genes SCARECROW (SCR) encoding a putative transcriptional regulator and the related SHORT-ROOT (SHR). Both SCR and SHR might also stabilize endodermal cell identity. The MONOPTEROS (MP) gene is required for root and hypocotyl initiation. Depending on the strength of the mp mutant allele either the root or the root and the hypocotyl are lacking. (Benfey 1999, Helariutta et al. 2000, Scheres and Berleth 1998 and references cited therein).

A gene locus identified as HOBBIT (HBT), was shown to be involved in root meristem formation (Willemsen et al. 1998). Strong hbt mutant alleles result in impaired root meristem activity. Other defects in hbt mutant seedling roots are linked to lack of establishment of columella and lateral root cap cell identities. The hbt mutant phenotypes can be traced back to early defects in the development of the embryonal hypophyseal cell region. The ectopic formation of lateral root primordia and lateral roots in hbt mutant seedlings has also been described (Willemsen et al. 1998). According to the latter article it is described that the auxin production or the auxin perception are not generally defective in hbt mutants, however, the HBT gene function remains to be elucidated.

One of the problems thus underlying the present invention is to provide the isolated HBT gene and its functions together with particularly useful applications of said gene in agriculture, horticulture, and plant cell and tissue culture. A solution is achieved by providing the embodiments characterized in the claims.

SUMMARY OF THE INVENTION

Plant development is characterized by the integrated control of cell division and cell identity specification processes. The *Arabidopsis* HOBBIT (HBT) gene appears to have have a function in both cell cycle control and cell fate specification of specific cell types. This is the first time that it has been demonstrated at the molecular level that a plant gene connects the cell cycle progression and the perception of patterning cues.

The present invention provides the sequence of the Hobbit gene and its function in the cell cycle and in auxin related effects. The present invention also provides nucleic acids, proteins, vectors, host cells, plants, and methods to use the present invention for altering the cell cycle or to mimick and/or modulate auxin-related effects.

Phenotypes of the hbt Mutant

Before the identity and the function of the HOBBIT gene was revealed, the phenotypes of hobbit mutant *Arabidopsis* seedlings was described by Willemsen et al. 1998. Both embryonic and post-embryonic features of the hbt phenotype can be subdivided into two classes, one related to cell division and one related to cell fate. Post-embryonically, the HBT gene is required for meristematic activity of both the shoot and the root meristems. This necessity extends to the formation of lateral and adventitious roots and roots regenerated from callus tissue. The progeny of the hypophyseal cell (the quiescent centre and the columella) together with the adjacent initials and lateral root cap show defects beyond disturbed divisions. Post-embryonically they show cell differentiation defects, such as the absence of the gravity response mediating starch granules in the columella of the strong hbt alleles.

The overall phenotypic characteristics of hbt mutant *A. thaliana* seedlings are a 'stout' appearance, with cotyledons and hypocotyls present though stunted and a severely reduces root system (FIG. 1).

Figure 2:
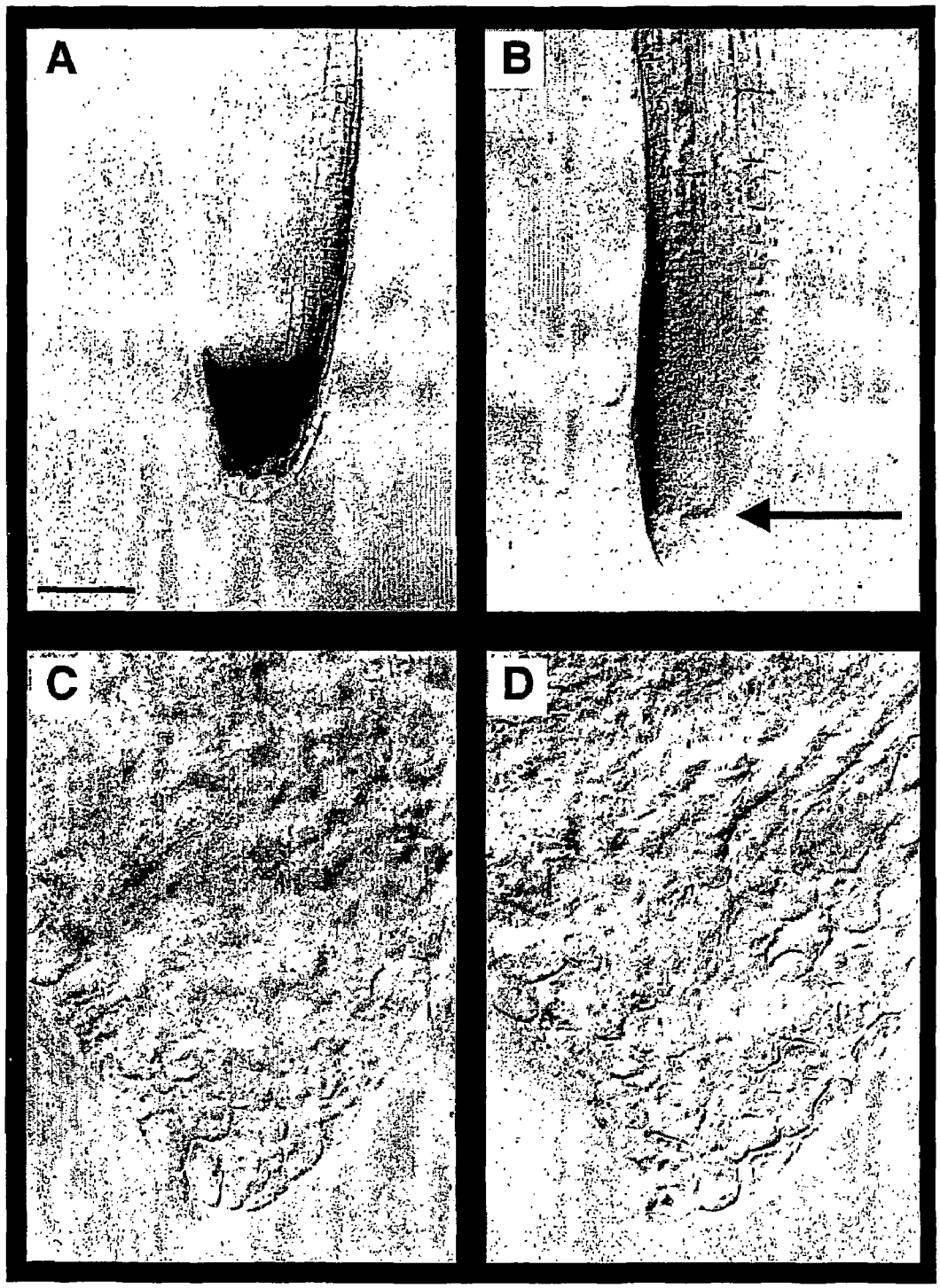

In the present invention, said hbt mutant seedlings were further characterized (example 1 and 2) and the HBT gene was isolated (example 8) and its functions characterized. In roots, it was shown that the region specific columella root cap marker 35S::B2 is much less expressed and that the lateral root cap marker LRC244 is not expressed in the strong hbt[2311] allele (FIG. 2). This demonstrates that HBT gene activity is required for cell fate specification in distal root tips.

Figure 3:
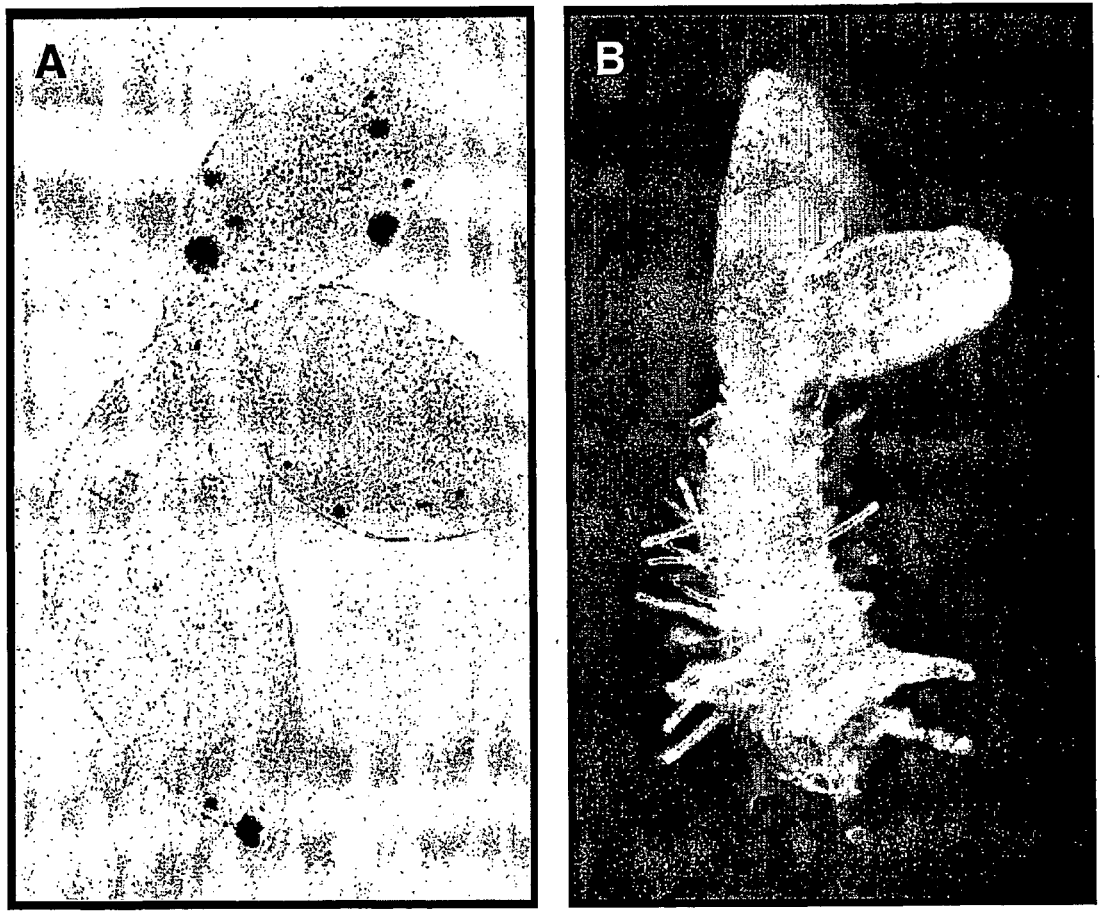

Additionally, in non-root cells of hbt mutants, the inventors surprisingly found expression the root-specific marker (FIG. 3). As hbt mutant *A. thaliana* seedlings display ectopic expression of the root cap specific marker 35S::B2 operably linked to GUS in the hypocotyls and in the cotyledons, the inventors conclude that stable determination of cell fate in non-root cells also requires functional HBT activity. Also the ectopic formation of root hairs on aerial plant parts of the hbt mutant supports this new finding (FIG. 3).

Figure 4:
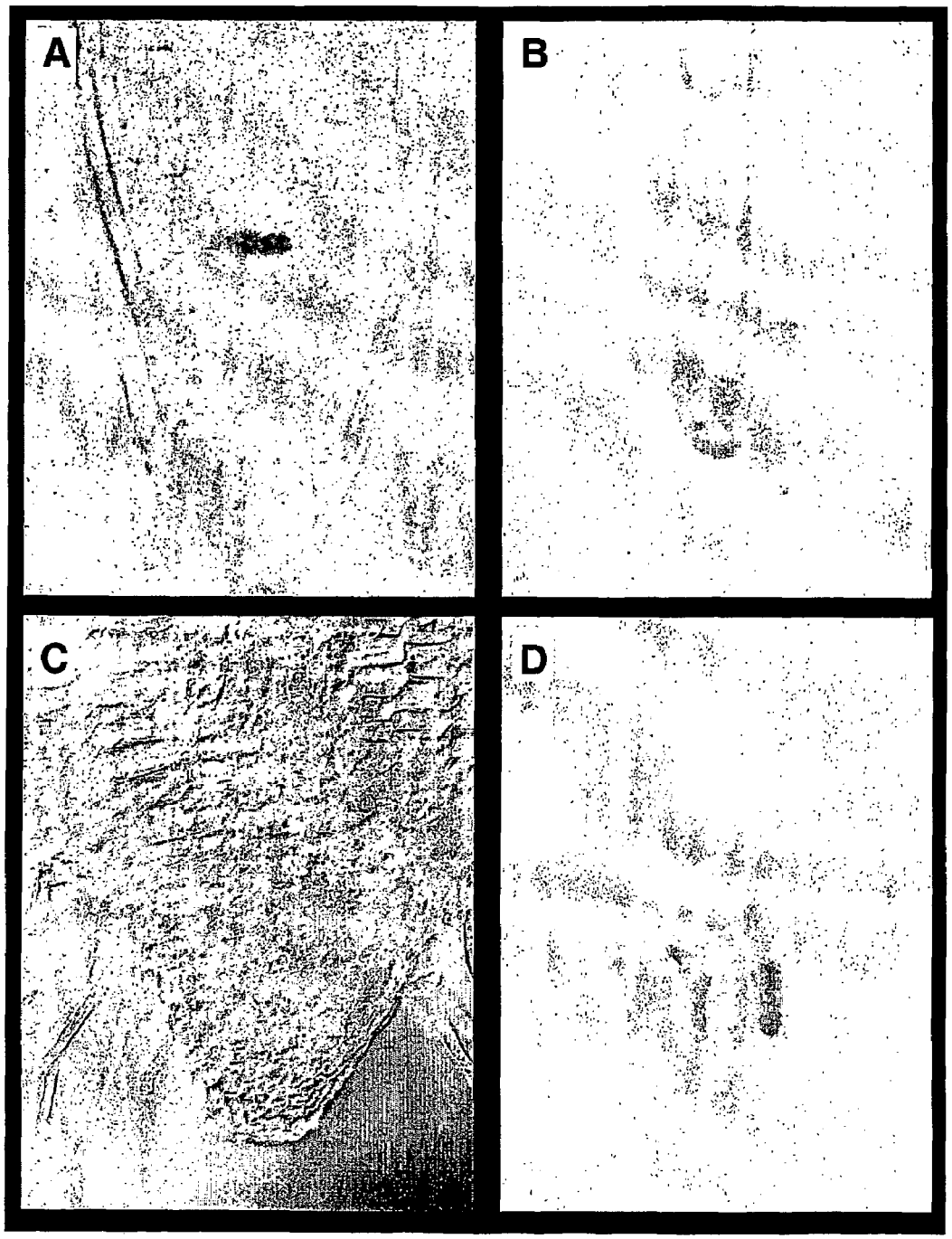

FIG. 4 shows further that identity establishment of the cells forming the root tip quiescent center is lost in hbt mutant *A. thaliana* seedlings. The expression pattern of the QC46 promoter fused to GUS (pQC46::GUS), which is a region specific marker for the quiescent center has totally disappeared in the hbt mutant compared to the wilt-type quiescent center. The SCARECROW (SCR) promoter linked to GUS (pSCR::GUS), which is a marker specific for the root endodermis is limited to the distal part of the root. Because only the quiescent center of hbt mutant *A. thaliana* seedlings is altered (FIG. 4), there is a basal specificity of the hbt specification defect. These results enforce the role of the HBT gene in establishing the distal root meristem region as discussed in Willemsen et al. (1998).

Figure 5:
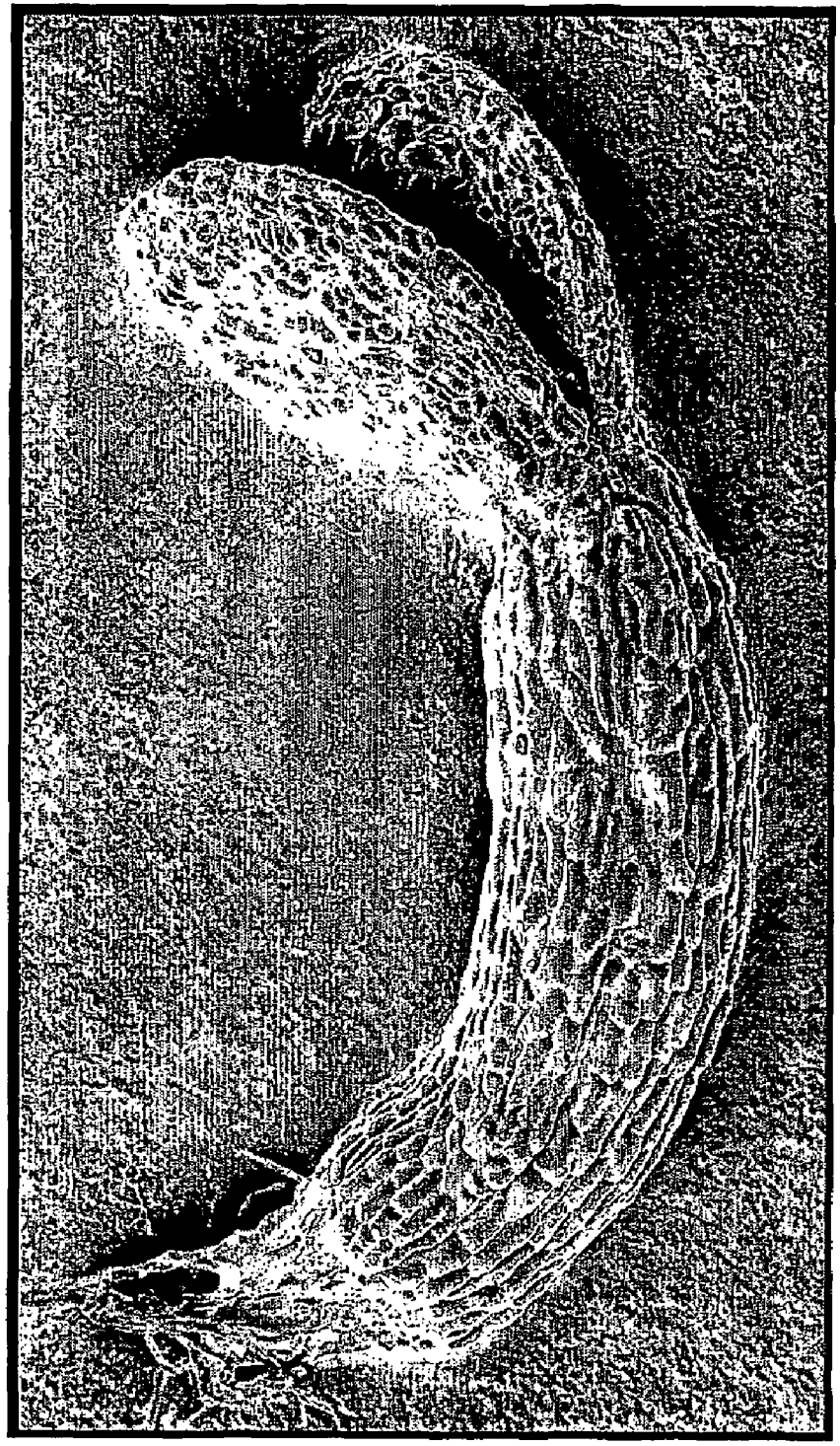

Another defect linked to mutations in the HBT gene relates to cell morphology. Elongation of newly formed epidermal cells seems to be impaired in hbt mutant *A. thaliana* seedlings and growth of said cells results in their swelling. This bloated phenotype is illustrated in FIG. 5.

Function of HOBBIT

In the present invention it was shown for the first time that HOBBIT is involved in cell cycle regulation and also in auxin-related effects. These two functional features of the HOBBIT gene are very unique, because no other biological factor was identified until now that was involved in both processes and that forms a link between both processes. Therefor, the gene of the present invention is to be considered as a key molecule in biological processes in the cell.

The early embryonic phenotype of hbt mutant shows striking similarities with three mutants involved in auxin responses; monopteros (Hardtke and Berleth, 1998), auxin resistant6 (axr6) (Bobbie et al. 2000) and bodenlos (Hamann et al. 1999). In all these mutants division planes in the hypophyseal cell deviate from normal, resulting in a failure to produce the derivatives of this cell, the quiescent centre, the root cap and root meristem. The inventors launched the idea that also in the hbt mutant auxin responses could be disturbed. Early investigations showed that addition of exogenous auxin did not rescue the mutant phenotype and that the perception of auxin was still intact in hbt mutants (Willemsen et al. 1998). Thus, no relationship between auxin and HOBBIT could be established.

Now, in the present invent, the inventors showed for the firs time that HOBBIT participates in auxin-mediated processes.

When determining the function of the HOBBIT gene, the inventors made very surprising observations when the stability of the CYCB1-GUS and the AXR3-GUS fusion proteins was analyzed. Unexpectedly, both proteins are, relative to wild-type *A. thaliana* seedlings, stabilized in hbt mutant seedlings. This is illustrated for CYCB1-GUS in FIG. 6 and for AXR3-GUS in FIG. 7. With these experiments, the inventors showed for the first time a direct link between the HOBBIT gene and its regulatory effects on cell cycle and its involvement in auxin signaling, respectively.

Therefore according to one embodiment the invention relates tho the use of a plant cdc17B for regulating the cell cycle of a cell. According to another embodiment, the invention relates to the use of a plant cdc27B for modulating or mimicking auxin-related effects in a plant or plant cell.

CYCB1, i.e. cyclin B1, is a mitotic cyclin which is required for activation of M-phase-specific cyclin-dependent kinases (CDKs; see Mironov et al. 1999 and Reed 1996 for reviews). Proteolytic turnover of cyclin B1 is a prerequisite for exit from mitosis and for resetting the cell cycle to the G1-phase. Degradation of cyclin B1 depends on the so-called "mitotic destruction box motif" in the mitotic cyclin B1 proteins and is executed by a specialized E3 ubiquitin ligase complex, the anaphase-promoting complex/cyclosome (APC/C). The APC/C is only active during late M-phase and during G1-phase (Brandeis and Hunt 1996, King et al. 1995, Sudakin et al. 1995, Tyers and Jorgensen 2000).

AXR3 was found to be identical to IAA17, a member of the auxin-inducible Aux/IAA gene family. The Aux/IAA genes display varied tissue-specific expression, kinetics of auxin induction and auxin dose-response relations (Abel et al. 1995, Ainley et al. 1988, Conner et al. 1990, Rouse et al. 1998, Theologis et al. 1985, Yamamoto et al. 1992). The short-lived Aux/IAA nuclear proteins comprise up to 4 highly conserved domains. Homo- or heterodimerization between Aux/IAA proteins or between Aux/IAA proteins and auxin response factors (ARFs, which are transcriptional activators) is effected through the domains III and IV (Abel et al. 1994; 1995, Kim et al. 1997, Ulmasov et al. 1997). Degradation of the Aux/IAA proteins depends on domain II and is essential for normal auxin signaling (Worley et al. 2000).

Thus, with the stabilization of CYCB1-GUS as well as of the AXR3-GUS fusion protein, direct links are made between the HOBBIT gene and its regulatory effects on cell cycle and on auxin signaling, respectively.

Interestingly, at least four other plant development regulation genes have been linked to auxin signaling. These are PIN1 involved in the polar transport of auxin and its polar localization being controlled by another plant development regulation gene, GNOM (Palm and Gälweiler 1999; Steinmann et al. 1999); ETT which is also known as ARF3 and which binds to auxin-responsive elements in promoters of auxin-inducible genes (Nemhauser et al. 1998, Walker and Estelle 1998, and references cited in both); and MP, also known as IAA24, a member of the AUX/IAA genes (Nemhauser et al. 1998, Walker and Estelle 1998, and references cited in both).

In the present invention, the inventors showed for the first time that the plant developmental gene HOBBIT is linked to auxin signaling.

Other components which are known to be linked to auxin signaling are part of an E3 ubiquitination ligase complex known as $SCF^{Tir1}$ (del Pozo and Estelle 1999, Gray and Estelle 2000). SCF complexes belong to a different family of E3 ubiquitin ligases than the earlier described APC/C and are constitutively active throughout the cell cycle (see Tyers and Jorgensen 2000 for review). *A. thaliana* tir1 mutants are deficient in the auxin response. TIR1 is the F-box protein component of $SCF^{Tir1}$. F-box proteins are responsible for recruiting specific substrate for proteolytic degradation. Another *A. thaliana* gene, AUXIN-RESISTANT 1 (AXR1) is an E1-type ubiquitin activating enzyme which, in concert with ECR1, activates the ubiquitin-related protein RUB1. RUB1-modification of an *A. thaliana* cullin/Cdc53, also an SCF component, has been observed (del Pozo et al. 1999, Gray and Estelle 2000, Tyers and Jorgensen 2000).

The HOBBIT gene, that was identified via a map based cloning approach, encodes an *Arabidopsis* homologue of an APC component that seems to connect important biological processes involved in plant development by coupling the competence to respond to auxin to cell cycle progression. This is particularly important since the Hobbit, as a competence factor through the auxin hormone, is restricting the pattern formation only to dividing cells. This invention is supported by the following experimental data.

The multisubunit anaphase promoting complex (APC) regulates cell cycle progression in yeasts and in animals, by mediating the stability of cell cycle regulators. In the present invention it is shown that the *Arabidopsis* HOBBIT gene encodes a homologue of one of the components of the APC, CDC27/NUC2 (FIG. 8). The HBT gene can also function as an APC component, as it can partially complement the division arrest phenotype in *Schizosaccharomyces pombe* mutant nuc2ts (example 6, FIG. 15). Several other components of the APC have *Arabidopsis* homologues and these are expressed continiously in all dividing cells. HBT transcripts however, accumulate only at the G2/M boundary (example 7, FIG. 16). These results demonstrate that although there is evidence that HBT takes part of an APC-like complex, there is a clear distinction between the novel identified HOBBIT and other components of the APC (like cdc27A and cdc26) already known in the art.

Three distal root cell types are dependent on auxin signaling for their correct differentiation and it is the response to auxin that is disturbed in hbt seedlings. We provide evidence that this defect depends on the accumulation of the AXR3/IAA17 protein, an unstable repressor of auxin responses (example 3, example 9, example 10, example 11). These data suggest that HBT gene activity acts as a cell-cycle regulated competence factor for auxin-mediated patterning responses, thus linking at the molecular level cell cycle progression and the perception of patterning cues.

The inventors elucidated a mechanism by which the competence to respond to differentiation cues is dependent on HBT-mediated stability of the Aux/IAA class of transcriptional regulators of auxin responses. This model may explain the observed correlation between cell division and the capacity of cells to respond to patterning signals in plants. Furthermore, it suggests that the plant APC has evolved to acquire new functions in multicellular development, which differ from the hitherto described roles in cell cycle control.

Figure 17:
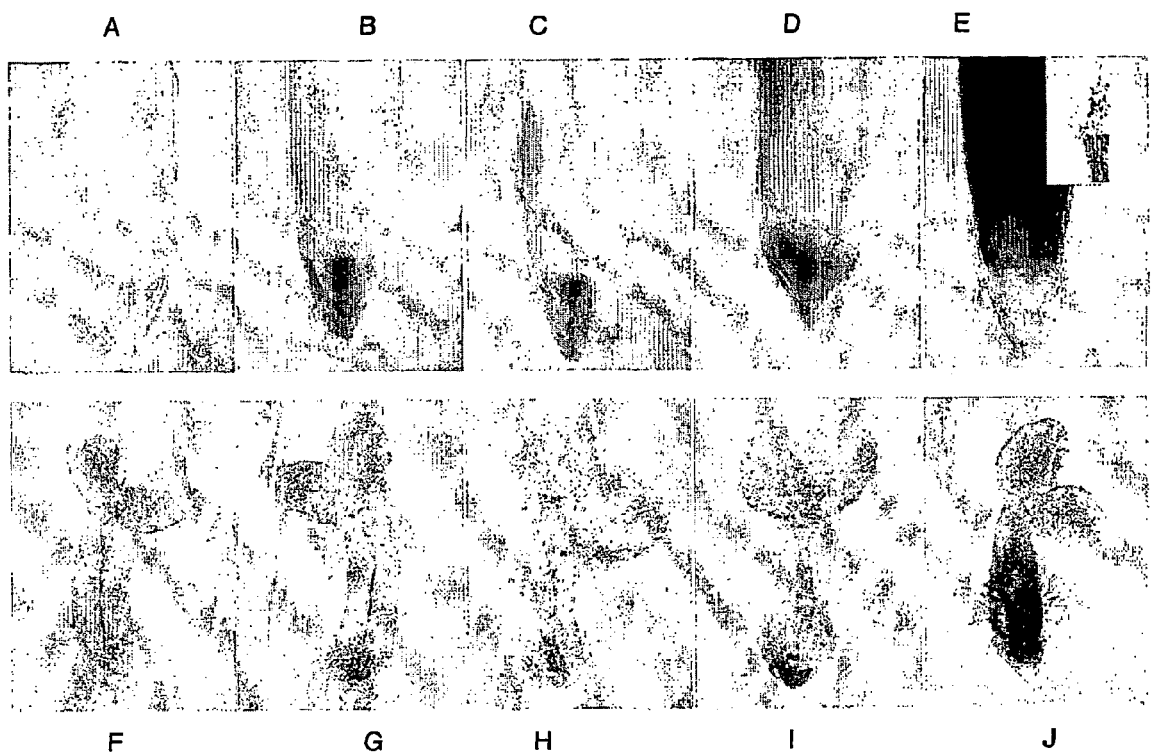

In the columella root cap of wildtype roots there is an accumulation of auxin, as can be visualised by the DR5::GUS staining in these cells (example 9, FIG. 17). In hbt seedlings this DR5 peak is absent, and they display an altered auxin sensitivity with regard to the induction of DR5::GUS activity. This suggested that HBT action could involve proteolysis of proteins that regulate auxin responses. The stability of Aux/IAA proteins, thought to mediate auxin responses, is thought to be regulated by the ubiquitin pathway, so they were likely candidates (Guilfoyle et al., 1998; Ulmasov et al., 1999b). In the present invention it is shown that hbt genetically interacts with a null allele of a member of the Aux/IAA family, axr3-1T (example 10, FIG. 18), suggesting that HBT has a function in tuning auxin responses. Auxin has an important role in patterning the root meristem and this is likely to depend on the correct distribution of the members of the fine-tuned network of positive and negative regulators of auxin responses. If the destruction of auxin response factors is mediated by the cell cycle regulated availability of the HBT protein, the competence of cells to respond to the patterning molecule auxin is restricted to the site where cells are produced, the meristems. In this scenario, the HBT gene is crucial for the interaction between pattern formation and cell division in the meristems of the developing plant. To our knowledge this is the first time that it has been reported that a plant gene connects cell cycle progression and the perception of patterning cues at the molecular level. In animals systems however, some examples of similar connections have been described, such as the coupling of the capacity of *C. elegans* vulval precursor cells to respond to signals that mediate selection between vulval cell fates to different phases of the cell cycle. The here described function for the HBT gen is also unique as it extends CDC27 function as a component of the APC.

Isolation of the HOBBIT Gene

An efficient way with which new genes can be identified and subsequently studied is by introducing point mutations with chemical mutagenising agents, such as ethyl methane sulphonate (EMS). The most straightforward and reliable method to then isolate the gene involved is via a map bases cloning approach. This approach was used to isolate the HOBBIT gene (example 1 and 2).

The HBT gene was mapped on the *A. thaliana* chromosome 2 in the interval between the markers m246 and GPA1 which was confirmed by RFLP fine mapping. In the present invention, a laborious map-based cloning approach was followed to isolate the HBT gene. The open reading frame containing nucleotide substitution mutations was Identified and the corresponding cDNA was isolated (examples 1 and 2).

The wild type HBT cDNA was identified by RT-PCR and identified herein as SEQ ID No. 2 (example 8). A clone containing this cDNA was deposited at the "Belgian Coordinated Collections of Microorganisms", BCCM-LMBP collection, on Oct. 11, 2000 and given the accession number LMBP4265 by the International Depositary Authority. Sequence analysis revealed that the HBT gene unexpectedly encodes a CDC27 homologue. It is present in the GenBank database as part of the sequence under accession number AC006081, more specific with the inverse complement of nucleotides 16314-20890 (FIG. 14). The relevant part of that genomic sequence is defined in SEQ ID NO 1. The HBT cDNA is identified in the current invention as SEQ ID NO 2 and another splice variant of the HBT genes was characterized and identified herein as SEQ ID NO 3 (both from *A. thaliana* ecotype Col-0, Columbia). Both HBT splice variants encode, however, CDC27 homologues which are extended by 162 and 166 amino-terminal amino acids, respectively, (defined as SEQ ID NO 6 and as SEQ ID NO 7 respectively) relative to the predicted protein sequence annotated in Gen- Bank (AC006081; protein ID AAD24396.1). The nucleotide sequences corresponding to SEQ ID NOs 6 and 7 are defined in SEQ ID NOs 4 and 5, respectively. The full-length HBT proteins are given by SEQ ID NO 8 and SEQ ID NO 9 respectively. The HBT proteins are ~47% identical to another *A. thaliana* CDC27 homologue with GenBank accession number AC001645 (protein ID AAB63645.1). For matters of clarity, the terms HOBBIT, HBT and AtCDC27B refer to the same proteins as defined by SEQ ID NO 8 (also referred to as CDC27B1) and by SEQ ID NO 9 (also referred to as CDC27B2). Said other *A. thaliana* CDC27 homologue (GenBank AC001645; protein ID AAB63645.1) is referred to as AtCDC27A. An alignment of AtCDC27A and HBT/AtCDC27B2 is given in FIG. 8.

CDC27 proteins are known in the art as being part of a large protein complex called the APC/C (cfr. supra). In yeast, the APC/C consists of at least 8 proteins of which three, CDC16, CDC23 and CDC27 contain tetratricopeptide repeats (TPRs; Peters et al. 1996, Small and Peeters 2000).

The experimental data presented in the present application are the first demonstration that cdc27B in yeast can be part of the APC (FIG. 15) and that plants lacking functional HOBBIT activity have an abnormal DNA content in the S-phase of the cell cycle (i. e. between the G1 and the G2 phase).

In the process of elucidating the function of the HBT gene, several hbt mutants were generated. These hbt mutants were identified and characterized by the inventors at the genomic and at the cDNA level, an overview thereof is given in FIGS. 9 and 10:

1. $hbt^{5421}$: a point mutation of the adenosine nucleotide at position 62 (resulting cDNA: SEQ ID NO 17; FIG. 9) or position 62 (resulting genomic clone: SEQ ID NO 10; FIG. 10) into a thymidine, resulting in a substitution of the natural alanine into the mutant valine at position 21 (resulting in SEQ ID NO 24; FIG. 9).
2. $hbt^{5422}/hbt^{5423}/hbt^{5859}/hbt^{9624}$: four independently isolated mutants carrying the same point mutation of the guanosine nucleotide at position 1503 (resulting genomic clone: SEQ ID NO 11; FIG. 10) into an adenosine, resulting in insertion of nucleotides 434-511 of the cDNA (resulting in SEQ ID NO 18) and the corresponding amino acids 145-171 of the protein (resulting in SEQ ID NO 25).
3. $hbt^{1611}$: a point mutation of the guanosine nucleotide at position 1261 (resulting cDNA: SEQ ID NO 19; FIG. 9) or at position 2913 (resulting genomic clone: SEQ ID NO 12; FIG. 10) into an adenosine, resulting in a substitution of the natural glycine into the mutant arginine at position 421 (resulting in SEQ ID NO 26; FIG. 9).
4. $hbt^{9620}$: a point mutation of the guanosine nucleotide at position 3042 (resulting genomic clone: SEQ ID NO 13; FIG. 10) into an adenosine, resulting in a deletion of nucleotides 1300 to 1365 (resulting cDNA: SEQ ID NO 20; FIG. 9) and the corresponding amino acids 434-455 (resulting in SEQ ID NO 27; FIG. 9).
5. $hbt^{5721}$: a point mutation of the guanosine nucleotide at position 3360 (resulting genomic clone: SEQ ID NO 14; FIG. 10) into an adenosine, resulting in a deletion of nucleotides 1366 to 1485 (resulting cDNA: SEQ ID NO 21; FIG. 9) and the corresponding amino acids 456-495 (resulting in SEQ ID NO 28; FIG. 9).
6. $hbt^{2311}$: a point mutation of the cytosine nucleotide at position 1555 (resulting cDNA: SEQ ID NO 22; FIG. 9) or position 3530 (resulting genomic clone: SEQ ID NO 15; FIG. 10) into a thymidine, resulting in the formation of a stop codon at the position of the natural glutamine at position 519 (FIG. 9) and, thus, deletion of the amino acids 520 to 744 (resulting in SEQ ID NO 29; FIG. 9).
7. $hbt^{8052}$: a point mutation of the cytosine nucleotide at position 1610 (resulting cDNA: SEQ ID NO 23; FIG. 9) or at position 3667 (resulting genomic clone: SEQ ID NO 16; FIG. 10) into a thymidine, resulting in a substitution of the natural alanine into the mutant valine at position 537 (resulting in SEQ ID NO 30; FIG. 9).

As two functional inactive mutations, $hbt^{5421}$ and $hbt^{5422}/hbt^{5423}/hbt^{5859}/hbt^{9624}$ occur in the novel CDC27B amino-terminal domain of the current invention (SEQ ID NO 7), it is believed that this domain is essential for the activity of the cdc27B protein and therefore it is strongly believed that the protein annotated with GenBank accession number AC006081 (protein ID AAD24396.1) is non-active and non-functional.

Figure 11:
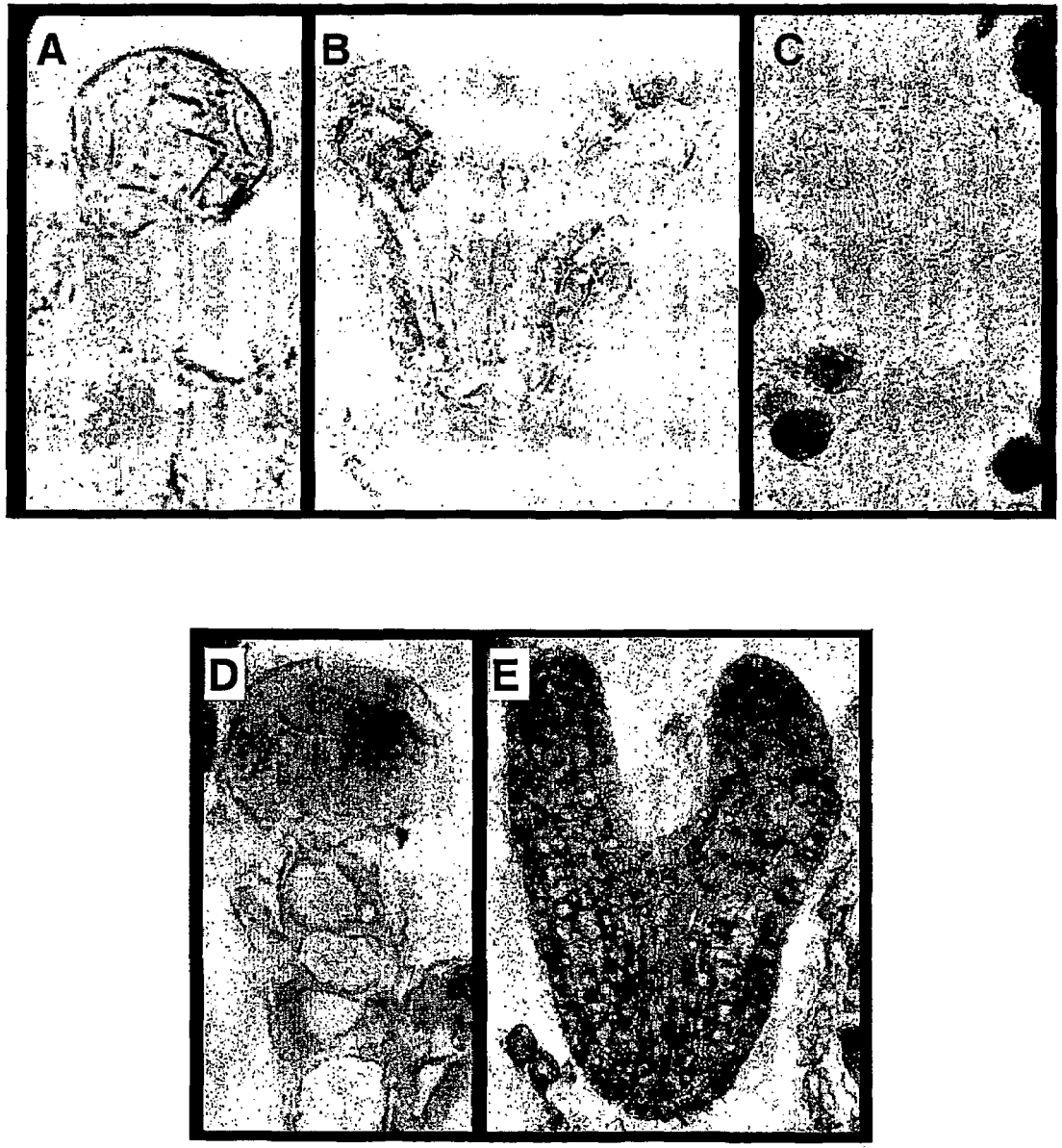
Figure 12:
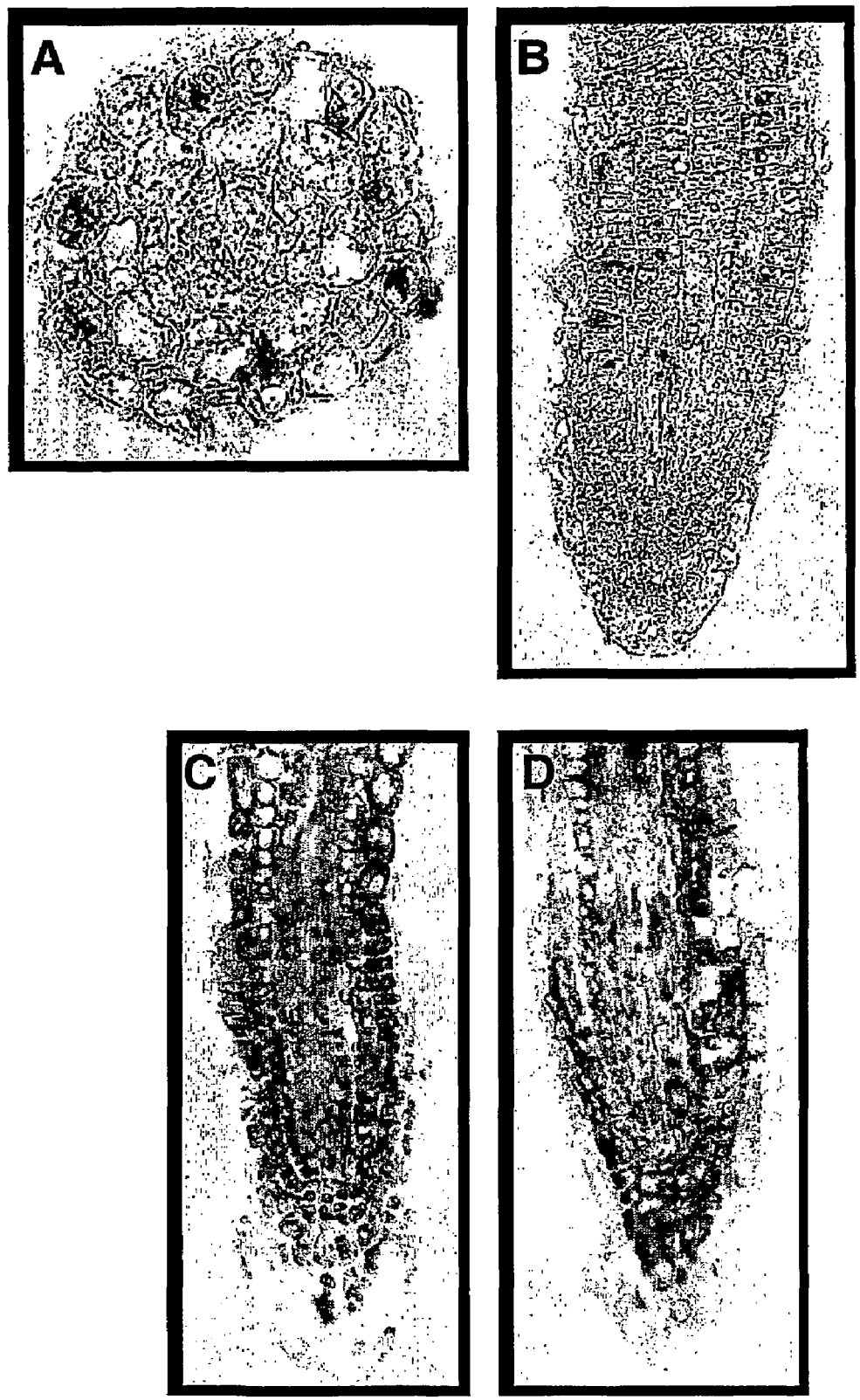

In order to demonstrate the functional distinction between the novel identified gene of the present invention and other genes that show homology, transcription of the HOBBIT, AtCDC16 (GenBank AC005679; protein ID AAC83033.1) and AtCDC27A genes was analyzed in *A. thaliana* embryos (FIG. 11) and *A. thaliana* seedling roots (FIG. 12). AtCDC16 transcripts are homogeneously dispersed in all but suspensor cells of developing *A. thaliana* embryos as well as in all but root cap cells in *A. thaliana* seedling roots. AtCDC27A transcripts are also found in many cells of the *A. thaliana* seedling root. HBT gene expression, however, displays an unexpected patchy expression pattern in developing embryos as well as in seedling root tissues. Such patchy expression patterns are indicative of a cell cycle stage-specific gene transcription. Thus, although homologues on the amino acid level, the biological functions of AtCDC27A and HBT are almost certainly very different as based on their expression patterns.

In summary, the inventors showed for the first time that cdc27B/HOBBIT is involved in auxin-related responses, that the HOBBIT expression is coupled to the cells cycle and that it has a possible role in the APC. The inventors found that HOBBIT is a competence factor through the auxin hormone. The inventors also found that HOBBIT restricts the pattern formation to only dividing cells.

Said aspects of the invention lead to the formulation of the following preferred embodiments of the current invention.

DETAILED DESCRIPTION OF THE INVENTION

Isolation of cdc27B cDNA and Encoded Protein Sequences

The HBT gene encodes a CDC27/NUC2 homologue.

The HBT gene is located on chromosome 2 close to the molecular marker mi148. The identification of ORF T2G17.20 as the HBT gene was determined by sequencing the mutant alleles and was verified by complementation of $hbt^{2311}$ homozygotes using a 9 kb genomic fragment spanning the HBT locus (examples 1 and 2).

To confirm the predicted splicing of the HBT cDNA, two clones were isolated from a Col-0 cDNA library (Giraudat et al., 1992). In addition, RNA was isolated from Col-0 roots and a RT-PCR was performed. Sequencing of the cDNAs confirmed the deviations in annotation that we observed between these three cDNAs and the published ORF (protein ID AC006081). Furthermore these sequence experiments revealed at least two splicing variants. A small fraction of the cDNAs lacks 12 base pairs, resulting in a first TPR domain with 30 rather than the generic 34 amino acids. The majority of the cDNAs represent the long version. The functional significance of the alternative splice versions of HBT mRNA is not clear. The size of the transcript, 2.5 kb, was confirmed by Northern blot analysis. RNase Protection analysis revealed two potential transcriptional starts, with putative upstream TATA and CAAT boxes (example 8).

Comparison of the genomic and cDNA sequences revealed that the HBT gene contains 15 exons and 14 introns, resulting in a predicted protein of 745 residues. The most conspicuous feature of the HBT protein is the presence of 10 domains with the consensus residues of Tetratrico Peptide Repeats (TPRs), one in the amino terminal half of the protein and a stretch of nine domains in the carboxyl terminal half. These TPR domains are thought to be involved in protein-protein interactions. Comparison of the HBT protein sequence with others revealed that the HBT protein shares the highest homology with CDC27/BIMA/NUC2 proteins of evolutionary distant organisms such as yeast, mammals and Drosophila. In addition, the distribution of the TPR domains in the HBT protein, the conserved repeat in domain 5 and 7, and the aberrant TPR repeat in domain 4 are typical for CDC27 orthologues. CDC27 proteins have been shown to be a component of the Anaphase Promoting Complex (APC) or Cycleosome, involved in cell cycle progression by ubiquitinating protein targets (Lamb et al., 1994; King et al., 1995). A HBT-related sequence is present in the *Arabidopsis* genome. The deduced AtCDC27a protein (ACC no.: BAB01271) shares an overall homology of 41% with HBT. The homology in the region containing the TPR domains is 65% (see FIG. 8). Based on the protein sequence and the homology with CDC27 proteins, we hypothesize that the HBT protein could regulate the stability of target proteins via the ubiquination pathway.

Accordingly the invention embodies an isolated DNA sequence with nucleotide sequence as given in SEQ ID NOs 1 to 3, encoding a plant development regulating protein with amino acid sequence as given in SEQ ID NOs 8 or 9, which comprises a novel amino acid sequence required for protein function as given in SEQ ID NOs 6 and 7, respectively. More specifically, said isolated DNA sequences encodes wild-type HOBBIT proteins that are CDC27-homologues.

The term "plant development regulating protein" as used below refers to a plant CDC27 protein. Specific examples of plant CDC27 proteins are the cdc27b proteins identified and described herein.

Further embodied in the current invention are the isolated DNA sequences with nucleotide sequences as given in SEQ ID NOs 10 to 23 encoding functionally inactive mutants of said plant development regulating protein with amino acid sequences as given in SEQ ID NOs 24 to 30.

A related preferred embodiment of the current invention comprises an isolated nucleic acid encoding at least part of a novel plant development regulating protein or encoding an immunologically and/or functional fragment of such a protein or encoding functionally inactive mutants of said plant development regulating protein, selected from the group consisting of:
(a) a nucleic acid comprising at least part of the DNA sequence as given in any of SEQ ID NOs 1 to 5, 10-23, or the complement thereof,
(b) a nucleic acid consisting of the DNA sequence as given in any of SEQ ID NOs 1 to 5, 10 to 23, or the complement thereof,
(c) a nucleic acid comprising the RNA sequences corresponding to any of SEQ ID NOs 1-5, 10-23, or the complement thereof,
(d) a nucleic acid hybridizing, preferably specially hybridizing, with the nucleotide sequence as defined in (a) (b) or (c),
(e) a nucleic acid encoding a protein with an amino acid sequence which is at least 50% identical, preferably 55%, 60%, 65%, 70% or 75% identical, more preferable 80%, 85% or 90% identical, most preferable 95% identical to the amino acid sequence as given in any of SEQ ID NOs 8, 9 or 24 to 30,
(f) a nucleic acid encoding a protein comprising the amino acid sequence as given in any of SEQ ID NOs 6, 7, 8, 9, or 24 to 30,
(g) a nucleic acid which is degenerated as a results of the genetic code relative to a nucleotide sequence encoding a protein as given in any of SEQ ID NOs 8, 9 or 24 to 30, or relative to a nucleic acid sequence as defined in (a) to (f),
(h) a nucleic acid which is diverging due to the differences in codon usage between the organisms relative to a nucleotide sequence encoding a protein as given in any of SEQ ID NOs 8, 9 or 24 to 30. or relative to a nucleic acid sequence as defined in (a) to (f),
(i) a nucleic acid which is diverging due to the differences between alleles relative to a nucleotide sequence encoding a protein as given in any of SEQ ID NOs 8, 9 or 24 to 30 or relative to a nucleic acid sequence as defined in (a) to (f),
(j) a nucleic acid encoding a fragment or a functional fragment and/or an immunologically active fragment of a protein encoded by a DNA sequence as given in SEQ ID NOs 1 to 5 or 10 to 23 or as defined in any one of (a) to (i),
(k) a nucleic acid specifically hybridizing to a nucleotide sequence encoding a peptide as given in SEQ ID NO 6 or 7, and,
(l) a nucleic acid encoding a protein as defined in any of SEQ ID NOs 6 to 9 or 24 to 30 or as defined in any one of (a) to (k) interrupted by intervening DNA sequences, provided that said nucleic acid is not the nucleic acid as deposited under the GenBank accession number AC006081.

The present invention also relates to nucleic acid sequences hybridizing with unique sequences of the nucleic acids coding for the plant development regulating protein of the invention. It should be clear that the person skilled in the art can easily identify and select the stretches of sequences which are unique to the protein of the invention when comparing for instance in FIG. 8 the amino acid sequences of Cdc27A and HBT/Cdc27B. The nucleic acid sequences coding for these unique parts can easily be deduced therefrom.

The present invention also relates to isolated nucleic acids as mentioned above under (a) to (l) which are DNA, cDNA, genomic DNA or synthetic DNA, or RNA wherein T is replaced by U.

Also part of the invention are nucleic acid molecules of at least 15 nucleotides in length hybridizing specifically with at least one of the nucleic acid molecules of the invention as defined above or specifically amplifying the above defined nucleic acid molecules.

According to another embodiment, the invention relates to a vector comprising a nucleic acid sequence of the invention. This vector can be an expression vector wherein said nucleic acid sequence is operably linked to one or more control sequences allowing the expression in prokaryotic and/or eukaryotic host cells.

Also the host cells containing a nucleic acid molecule of the invention are part of the present invention. Preferred host cells according to the invention are bacterial, insect, fungal, plant or animal cells.

The present invention further relates to an isolated plant development regulating protein comprising one of the polypeptides selected from the group consisting of:
(a) a polypeptide as given in any of SEQ ID NOs 6 to 9,
(b) a polypeptide with an amino acid sequence which is at least 50% Identical, preferably 55%, 60%, 65%, 70% or 75% identical, more preferable 80%, 85% or 90% identical, most preferable 95% identical to the amino acid sequence as given in any of SEQ ID NOs 6 to 9, and (c) a polypeptide encoded by a nucleic acid as given in any of SEQ ID NOs 1 to 3.

The present invention further relates to an isolated plant development regulating protein consisting of an amino acid sequence as given in SEQ ID NO 8 or 9. According to another embodiment, the proteins according to the invention are CDC27 proteins, such as plant CDC27B proteins, or functional homologues thereof. According to another embodiment, the invention relates to plant cc27B proteins from *A. thaliana*, such as the AtCDC27B protein.

The invention further relates to proteins with an amino acid sequence which is at least 50% identical, preferably 55%, 60%, 65%, 70% or 75% identical, more preferable 80%, 85% or 90% identical, most preferable 95% identical to the amino acid sequence as given in SEQ ID NO 8 or 9.

A further embodiment of the invention comprises homologues, derivatives and/or immunologically active fragments of the plant development regulating proteins according to the invention, fragments thereof and proteins comprising said homologues, derivatives and/or immunologically active fragments of said plant development regulating protein or fragments thereof.

As such, the present invention also relates to an isolated polypeptide encodable by a nucleic acid molecule of the invention as defined above Analysis of Mutant Alleles Genomic DNA from homozygous hbt mutants (example 1) was amplified at the HBT locus and sequenced. This led to the identification of single base pair changes in ten mutant alleles. For the weak allele e56, which does not complement other hbt alleles (Willemsen et al., 1998), no mutation could be identified in the genomic region including 1070 bp of the upstream promoter region and 230 bp downstream of the polyadenylation signal (data not shown). Although the molecular lesion in hbt$^{e56}$ remains unidentified, RT-PCR analysis showed that e56 mutants have strongly reduced HBT transcript levels, suggesting epigenetic effects on HBT transcription.

In the Col-0 allele, 2311, a stop codon was introduced at position 519. The resulting truncated proteins lack a major part of the TPR domains, which may indicate that these alleles are nulls; in the temperature sensitive *S. pombe* mutant nuc2-663, an amino acid change in one of the TPR domains results in spore lethality in tetrads as does a null mutant and constructs caring versions of the NUC2 protein with truncations in the TPR domains could not complement nuc2-663 (Hirano et al., 1988, 1990). Despite the absence of many TPR domains in these three hbt alleles, gametophytic lethality and metaphase arrest are not observed. Furthermore, all Col alleles (except the weak allele e56) cause similar phenotypes despite different molecular defects, consistent with the notion that they are all nulls.

Accordingly, in another embodiment, the invention relates to functionally inactive mutants of the plant development regulating proteins of the invention, consisting of an amino acid sequence as given in any of SEQ ID NOs 24 to 30, or encoded by a nucleic acid as given in any of SEQ ID NOs 10 to 23, or a functional fragment thereof. In this context, the expression "functional fragment" relates to a fragment of the mutant protein comprising the mutation.

The invention further relates to the polypeptides as defined above which have the ability to regulate plant development.

Any of said proteins could be produced in a biological system, e.g. a cell culture. Alternatively any of said proteins is chemically manufactured e.g. by solid phase peptide synthesis. Said proteins or fragments thereof can be part of a fusion protein as is the case in e.g. a two-hybrid assay which enables e.g. the identification of proteins interacting with the plant development regulating protein according to the invention.

Therefore, according to another embodiment, the invention also relates to a method for producing a polypeptide of the invention comprising culturing a host cell further specified above under conditions allowing the expression of the polypeptide and recovering the produced polypeptide from the culture.

The proteins or fragments thereof obtained by a method of the invention are furthermore useful e.g. to modulate the interaction between a plant development regulating protein as defined in the invention and interacting protein partners identified according to the invention. Chemically synthesized peptides are particularly useful e.g. as a source of antigens for the production of antisera and/or antibodies.

The current invention thus furthermore encompasses antisera and/or antibodies specifically recognizing the plant development regulating protein according to the invention or immunologically active parts or epitopes thereof. Said antisera and/or antibodies are useful in many areas related to the invention including: (i) identification in any organism, preferably plants, of other plant development regulating proteins and their genes according to the invention; (ii) quantification of synthesis in organisms and/or recombinant organisms of the plant development regulating protein according to the invention; (iii) purification of the plant development regulating protein according to the invention; (iv) immunoprecipitation of the plant development regulating protein according to the invention e.g. as a way to identify other protein partners complexing with said plant development regulating protein; (v) immunolocalization of the plant development regulating protein according to the invention which is expressed in an organism or a recombinant organism.

Use of cdc27B in Plants

During the different stages of plant development it is the integrated action of pattern formation and morphogenesis that positions organs, tissues and individual cell types at appropriate positions. In contrast to animal systems where movement of cells contributes to development, plants are surrounded by a rigid cell wall that allows little movement. For these reasons, pattern formation and morphogenesis in the plant take place at the sites of cell production, the meristems. In these meristems, patterning cues must provide the information necessary to create the differences in division rates and planes and the directed enlargement of cells as they leave the meristem. The differentiation of cells starts as cells are leaving the meristem. With all these different processes occurring in the same place and at the same time it is important to connect cell division and pattern formation. Interestingly, pattern formation and cell division share common regulatory mechanisms. An important mechanism to control cell cycle progression is the destruction of regulatory proteins via the ubiquitin pathway. In this pathway, ubiquitin molecules are attached to target proteins by ubiquitin ligases like the SKP1, CDC53/CULLIN and F-box protein complex (SCF) and the Anaphase Promoting Complex (APC). Afterwards the now 'labeled' proteins are destroyed by the 26S Proteasome. This ubiquitin pathway also serves a crucial role in balancing positive and negative response molecules of an important molecule for plant development, auxin. In the present invention, *Arabidopsis* homologues of components of the ubiquitin mediated proteolytic pathway in cell cycle progression and auxin response have been identified and mutations in the corresponding genes confer a broad range of growth defects, showing the central role of these processes in plant development.

A Role for the HBT Gene in Tuning Auxin Responses?

The basic idea that HBT is involved in auxin responses originates from three different observations. First, cell types defective in Hobbit are also dependent on auxin and are also defective in responsiveness to auxin (see FIG. 17(*i*): the auxin-responsive machinery of the cell is intact, but the response to auxin is altered and FIG. 17(*j*): the hypocotyls in hbt mutants has gained sensitivity, where it normally is not responsive to auxin. Second, the ARX3 "gain of function" mutant plants, show the same phenotypic characteristics as the hbt mutants and third, auxin responsiveness involves ubiquitination or auxin regulating proteins.

When a synthetic auxin response element was assayed, hbt seedlings showed an altered auxin sensitivity for both the synthetic auxin, 2,4 D, and for the endogenous auxin, IAA (example 9, FIG. 17). Although they can sense auxin, a much higher concentration is necessary to induce a transcriptional response. We also observed a partial restoration of the hbt mutant phenotype in hbt axr3-1T double mutants. The AXR3/IAA17 gene is thought to be a regulator of auxin perception and semi-dominant mutations in this gene confer pleiotropic growth defects, all related to an elevated auxin response (Ouellet et al., 2001). The involvement of auxin in various growth processes and organs implies that in each tissue there must be a specific balance of the positive and negative regulators of auxin responses. Several observations suggest that HBT might have a role in controlling this balance in the meristem. First, auxin sensitivity is altered in hbt seedlings (example 9, FIG. 17). Second, there is a genetic interaction with the axr3-1T allele (example 10, FIG. 18). And third, expression of the HBT gene is confined to the population of dividing cells in the meristems and is therefore dependent on cell cycle progression (examples 4 and 7, FIGS. 11, 12 and 16). Thus, the presence of the HBT protein only at the G2/M phase in the cell cycle, could provide an unique regulatory mechanism in plants, such that it mediates the removal of regulators of auxin, at a specific phase of the cell cycle. To our knowledge this is the first example in plants where a cell cycle-regulated component confines the competence to respond to a patterning signal to meristem. In animals there are a few examples of a direct link between cell cycle progression and the ability of cells to respond to signal transduction pathways. For example, the capacity of *C. elegans* vulval precursor cells to respond to signals that mediate selection between vulval cell fates is coupled to different phases of the cell cycle (Wang and Sternberg, 1999).

Thus, regulation of protein stability may be used in widely different developmental systems to regulate competence.

The invention thus relates to the use of a plant cdc27B characterized in that the modification or mimicking auxin-related effects is based on the modulation of the stability of regulator proteins of patterning signals.

In another embodiment the invention also relates to the use of a plant cdc27B wherein said modulation or mimicking of auxin-related effects results in altered cell fate of a cell and/or altered pattern formation in a plant or plant cell, for instance an increase in the number of plant meristems or an increase in the size of naturally occurring plant meristems Combined with the post-embryonic cell division arrest this may be taken to suggest a role of the HBT gene in cell cycle regulation. Nonetheless, we favor the hypothesis that the HBT gene has a more specialised function that has diverged from the role that the APC components CDC27 proteins serve in cell cycle progression. This preference is based on several observations. First, hbt embryos can go through numerous rounds of cell divisions without severe problems, suggesting that the *Arabidopsis* APC can mediate cell cycle progression in the absence of HBT gene activity. Second, cell division arrests only when there were also several cell differentiation problems, resulting amongst others in the loss of identity in certain cell types. Third, the nuc2 mutations in *S. pombe* result in a metaphase arrest. Although post embryonically cell division ceases in hbt seedlings this was not accompanied by a metaphase arrest (Hirano et al., 1988,1990). And finally, other APC components with a similar protein structure in *Arabidopsis*, AtCDC16, AtCDC23 and AtCDC27a all showed similar expression patterns. Their transcripts were present at a high level in all dividing cells. In contrast, the HBT gene was expressed at a low level and accumulated only at the G2/M transition. Thus we considered whether the defects caused by mutations in the HBT gene could be due to the stabilisation of APC targets not related to cell division.

In the present invention, *Arabidopsis* homologues of components of the ubiquitin mediated proteolytic pathway in cell cycle progression and auxin response have been identified and mutations in the corresponding genes confer a broad range of growth defects, showing the central role of these processes in plant development.

The HOBBIT gene encodes a homologue of an APC component that seems to connect these processes by coupling the competence to respond to auxin to cell cycle progression. This is particularly important since Hobbit, as a competence factor through the auxin hormone, is restricting the pattern formation only to dividing cells.

This invention is supported by the following experimental data.

Experimental Results hbt Mutants Display Diverse Cell Differentiation Defects at the Post-Embryonic Stage In a previous study, the first detected morphological defect in hbt mutant embryos was shown to be a disruption of the invariant orientation of cell division planes in a founder cell for the root meristem, the hypophyseal cell (Willemsen et al., 1998). This leads to morphological defects in the cell types that arise from this founder cell; the quiescent center and the columella. These morphological defects are accompanied by differentiation defects, since several markers that are normally expressed in these cell types, are not expressed in hbt seedlings (Willemsen et al, 1998).

In the present invention it is determined whether cell differentiation defects are confined to these distal cell types, or whether other regions of the root also had differentiation defects. Therefore, we analyzed the activity of the SCARECROW (SCR) gene promoter, visualized by a construct carrying the b-glucuronidase (GUS) gene fused to the SCR promoter, in the hbt mutant background (example 3). The SCR gene is normally expressed in the ground tissue layer of more proximal regions of the root and in the endodermis (FIG. 4B). As illustrated in FIG. 4D, there is SCR::GUS expression in the hbt seedling root, but only in the distal part. At the position where in wildtype roots the quiescent center would be (demonstrated by the QC46::GUS construct in FIG. 4A), there is no GUS staining in the hbt mutant background (FIG. 4C). We therefore conclude that the post-embryonic distal cell differentiation defect is region-specific, consistent with a specific requirement for HBT gene function in cell differentiation within the distal domain of the root meristem. Whereas the distal root defects in hbt mutant occur in the region with early embryonic defects, other regions of the seedling develop cell differentiation defects post-embryonically. The reduced stature of hbt seedlings suggests that cell expansion defects occur in the mutants. Closer inspection of cell sizes and cell shapes in hbt mutants indeed reveals dramatic differences with the wildtype as can be seen for example FIG. 5, where scanning EMs show the irregular surface of the hypocotyl of hbt seedlings compared to a wildtype seedling. Mutant cells are reduced in size and bloated. The shoot apical meristem (SAM) in hbt mutants contains a dome of irregularly shaped cells which initially divide to give rise to a significant amount of progeny cells. While a single central zone gives rise to organ primordia at its flanks in wildtype SAMs, organ primordia are initiated at variable positions in hbt mutants and these primordia frequently fail to grow out to give rise to leaves. After repeated initiation of aberrant organ primordia, SAM activity ceases. In earlier experiments it was tested whether the hbt mutant phenotype could be rescued by treatment with several plant hormones. No such rescue was detected (Willemsen et al., 1998), however a dramatic re-specification of epidermal cells on the hypocotyl of hbt seedlings that were treated with ethylene was observed. On the hypocotyls of these hbt seedlings a large number of ectopic outgrowths was induced, that strongly resembled root hairs. With seedlings germinated in the dark, similar results were obtained.

Defects in epidermal cell fate regulation are not only observed after induction (eg. with ethylene), but the separation of trichoblast and atrichoblast fates in files of cells in the root epidermis is also disturbed in hbt mutants. A construct carrying the promoter of the GLABRA2 (GL2) gene, involved in atrichoblast specification, fused to the GUS gene (Masucci et al., 1996) was crossed to the hbt$^{2311}$ allele and in the progeny of this cross showed ectopic activity in the epidermis of hbt seedlings. GL2 encodes a homeodomain protein required for atrichoblast differentiation, and expression is restricted to those files of cells containing atrichoblasts in the wildtype root. However, even though the expression pattern roughly resembles the wildtype pattern, root hair cells in hbt mutants also show high activity of the GL2 promoter. Our data suggest that the HBT gene is required for the maintenance of cell differentiation choices in epidermal cells.

Whereas hbt defects during embryogenesis are regionally confined, the post-embryonic phenotypes in hbt mutants are more diverse, suggesting that HBT is required for diverse developmental processes.

The HBT Gene Partially Complements Yeast nuc2 Mutants

To investigate whether the HBT and AtCDC27a can function as a component of the APC, the full-size cDNAs were cloned in a yeast vector with a thiamine-repressible promoter and transformed into a *S. pombe* nuc2ts strain. The HBT cDNA partially rescued the nuc2 phenotype at restrictive temperature, reproducibly restoring growth to approx. 4-fold higher density compared to the empty vector control (FIG. 15). Complementation was not complete as growth rates and final density were respectively 5 and 10-fold less compared to the permissive temperature (compare FIGS. 15A and 15B). We concluded that HBT protein has the capacity to interact with and can replace the *S.pombe* nuc2 in the yeast APC, consistent with its proposed interaction with the homologous plant complex. In contrast, at the permissive temperature induction of AtCDC27a gene expression appears to be toxic in *S.pombe* (FIG. 15A).

This result is an indirect proof that HBT can be part of an APC complex in yeast.

The HOBBIT is Part of the APC Complex in Plants

Evidence that cdc27B/HBT is part of the APC complex in plants or that it is part of a similar complex which is not yet characterized, is generated by immunoprecipitation and coimmunolocalization experiments. These experiments are performed with standard protocols (Sambrook and Russel, 2001) and with antibodies specifically recognizing the Hobbit protein and proteins of the APC complex. In order to improve the detection of the HBT protein in the coimmunoprecipitation, an epitope-tagged HBT protein is used and accordingly, an antibody specifically recognizing that epitope.

Hbt Mutants Have Disturbed S-phase

Figure 20:
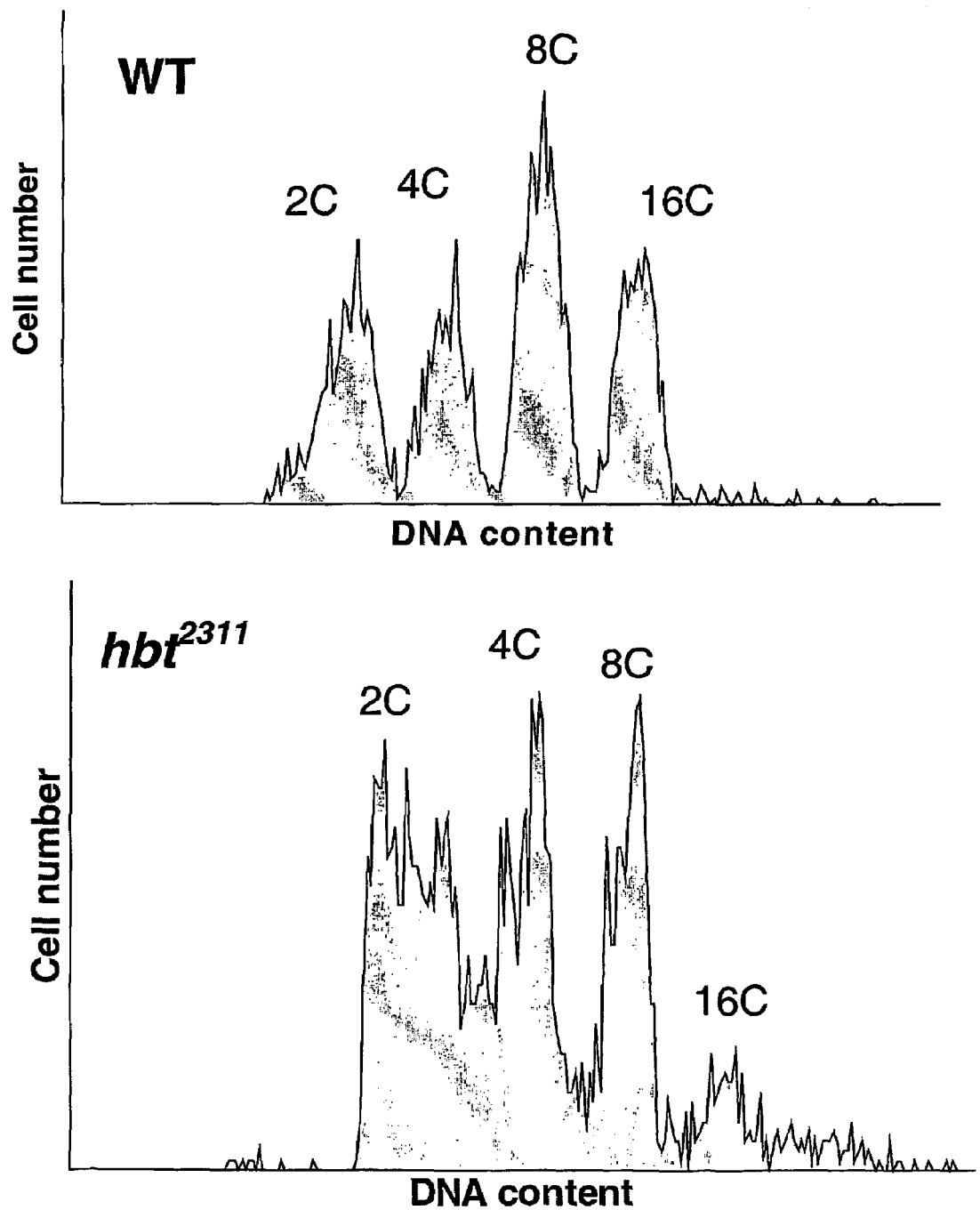

As demonstrated in the experiments of example 12 and in the FIG. 20, the inventors surprisingly found that hbt mutants have a defect in the S-phase of the cell cycle. The hypocotyls cells of the hbt mutant have a higher nuclear content in the 2C and 4C peaks. (generally corresponding to the the G1 and the G2 phase respectively) than the wild-type cells and the there is no clear separation between the 2C stage and the 4C stage as in the WT cells. At that transition the cells seem to have a variety of amount of DNA. These results clearly demonstrate that the hbt mutants have trouble with the correct progression of the S-phase. Therefor the inventors concluded that the hbt is needed for a successful completion of the S-phase, possibly through its function in the APC or an APC-like complex. Apparently the HOBBIT protein plays a role as a modulator of S-phase progression. This is the first time that it was demonstrated that cdc27B/HOBBIT is involved in the DNA replication. It was surprising, that the inventors were able to demonstrate a first link between the cdc27B/HOBBIT protein and the APC.

It is well known by the person skilled in the art that an augmented DNA content in plants cells can be an indication for endoreduplication. This happens when there is DNA replication without a successive mitosis and cytokinasis step. Endoreduplication in seeds is particularly interesting for agrobiotech industry, since it is a way to improve seed content and therefor seed quality.

HBT Gene Expression Analysis

To assess whether the distribution of HBT transcript provided clues on its diverse roles in development, we analyzed the distribution of HBT mRNA by in situ hybridization (examples 4 and 7). HBT transcripts were detected at similar levels in all organs of the plant, also in the shoot meristem, but in a spotted matters.

In the in situ hybridization experiments, probes synthesized from differents region of the cDNA (see example 7) all gave similar results. The data shown in FIG. 16 were obtained from probes corresponding to the 5' region, which contains unique sequence. Sense probes were taken along as a control and these detected no signal above background.

The distribution of HBT transcript varies during different stages of embryogenesis and also among cells within one embryo (FIGS. 16A-D). Up to the triangular stage, only a low signal is detectable in most of the embryonic cells. From early heart stage onwards the expression level is higher in particular cells. The stochastic and punctate distribution of these cells with higher HBT mRNA levels suggests that expression is elevated in a specific phase of the cell cycle. Co-localization of HBT and AtCYCB2 transcripts on single sections of late stage embryos revealed that peak HBT transcript accumulation occurs in the same cells that accumulate AtCYCB2 message (FIGS. 16J-L), suggesting that HBT transcription reaches maximum levels at G2/M phase.

Since HBT sequence shows high homology with the AtCDC27, we compared the expression patterns of both genes. AtCDC27 mRNA abundance is ubiquitously high during all the embryonic stages (FIGS. 16G-I). This expression pattern contrast with the low and punctate expression pattern of HBT. AtCDC16 displays similar high and ubiquitous transcript levels (FIG. 11).

We also localized HBT and AtCDC27 transcripts in young seedlings. Roots sections hybridized with HBT showed again a punctate expression only in the actively dividing cells (FIGS. 16M-O). In situ hybridizations with HBT probe on other parts of the plants, such as flowers and lateral root iniation sites showed similar results (data not shown). AtCDC27 (FIGS. 12D, 16P-R) and AtCDC16 (FIG. 12C) transcript levels were uniformly high in all dividing cells.

In lines segregating for the strong hbt allele 2311, no difference in the expression level or pattern between wt and the mutant embryos was observed (compare FIGS. 16D and 6E) suggesting that during embryogenesis HBT function is not required for the regulation of its own transcription.

Auxin Sensitivity of hbt Seedlings

Although earlier experiments revealed that hbt seedlings can sense auxin (IAA; Willemsen et al., 1998), standard tests at that time could not reveal changes in auxin responsiveness in hbt mutants. However, new methods to detect auxin responses have emerged, for example with synthetic auxin responsive promoter elements binding ARF transcription factors, such as DR5::GUS (Ulmasov et al., 1997). Since there is also a resemblance of the hbt early embryo phenotype to axr6, bdl and mp mutants (Hardtke and Berleth, 1998; Hamann et al., 1999; Hobbie et al 2000), we used the DR5::GUS construct to re-investigated auxin responses in hbt seedlings. In wildtype seedling roots there is a maximum of DR5::GUS staining in the upper part of the columella (FIG. 17A). This peak is absent in hbt seedlings (FIG. 17F) where no GUS staining is visible. Since the specification of the columella cells is defective in hbt seedlings, we wanted to know whether hbt mutant cells are capable of sensing auxin. Therefore, hbt seedlings were incubated for 3 days on media containing different concentrations of the synthetic auxin 2,4 D, and DR5::GUS expression was analysed. At low concentrations of applied 2,4 D ($5.10^{-9}$ M until $5.10^{-8}$ M; FIGS. 17B and 17C) there is an ectopic expression of the DR5::GUS promoter in the meristem of wildtype roots. At these concentrations there is no staining observed in hbt seedlings (FIGS. 17G and H). Only at a concentration of $5.10^{-7}$ M 2,4 D there is a DR5 peak in the root pole of hbt, when expression in the wildtype root is already quite intense and throughout the entire root (FIGS. 17D and 17I). At $5.10^{-6}$ M 2,4 D the DR5::GUS stainings showed a different situation. Although we never observed any ectopic DR5 expression in the hypocotyls of wildtype seedlings, hbt hypocotyls showed a strong DR5 expression (FIGS. 17E and 17J). Application of indole acetic acid (IAA) with the same concentrations gave similar results. The DR5::GUS expression in hbt embryos showed no differences compared to wildtype, also not after 2,4 D induction. Taken together, these data suggest that although cells in the hbt seedling can sense auxin, they do so with a different efficiency. It is therefore possible that the HBT gene has a role in the perception of auxin levels.

hbt and axr31-T Show a Genetic Interaction

Mutations that stabilize the AXR3 protein display reduced columella specification and low but correctly localized DR5::GUS activity (Sabatini et al., 1999). In hbt seedlings both columella specification and DR5::GUS activity are also strongly reduced or absent, suggesting that AXR3 might be stabilized in the hbt mutant background. To investigate whether these hbt defects require functional AXR3 protein we crossed the hbt$^{2311}$ allele to an insertion allele of axr3-1, designated, axr3-1T (example 10). Even though this allele is a presumptive null allele the transposon is inserted in the first exon—it has no mutant phenotype. In the F2 generation of this cross, the hypocotyls of the hbt$^{2311}$ axr3-1T doubles had a longer hypocotyl compared to the single hbt$^{2311}$ mutant (FIG. 18A). Epidermal cell length measurements showed that the differences in hypocotyl length between the hbt$^{2311}$ axr3-1T double mutants and the hbt$^{2311}$ single mutants are due to an increased cell elongation (FIG. 18C). Mutant axr3-1 hypocotyls show a reduced elongation only when the seedlings were germinated in the dark, caused by a reduction in cell size (Leyser et al., 1996). Both hbt$^{2311}$ single mutant seedling hypocotyles and hbt$^{2311}$ axr3-1T double mutant hypocotyls germinated in the dark, however did not show a reduction, but rather an increase in hypocotyl length (FIG. 18B). Again, this increase in the length of the hypocotyl was due to an increase in cell size (FIG. 18C). No differences in hypocotyl sizes were observed for the axr3-1T single. mutant, nor for seedlings with heterozygous genotypes (data not shown). We also observed preliminary evidence for the rescue of root growth and columella cell type specification in hbt$^{2311}$ axr3-1T double mutants (data not shown). Together, these results show that the axr3-1 mutant and the hbt mutant interact with each other at a genetic level, partially restoring the elongation defects observed for hbt hypocotyls and likely several other defects. We therefore postulate that HBT regulates the stability of the AXR3 protein.

HBT Mutants Contain Higher Levels of ARX3 Protein

The inventors showed for the first time that there is indeed a stablilization of the ARX3 protein in hbt mutants. This was shown indirectly via the GUS styaining (example 3, FIG. 7). Further studies were done with PT-PCR experiments on wild type and hbt mutant plants (example 11). In FIG. 19A it is demonstrated that in the hbt mutants the transcript is certainly not upregulated compared to the transcriptlevel of ARX3 in the WT. To the contrary, a lower level of ARX3 transcript was demonstrated in the hbt mutant background.

In a second experiment (FIG. 19B and example 11), the level of ARX3 protein in the wild-type plant and in three different hbt mutants was revealed by SDS-PAGE of plant extracts followed by Western blotting and immunostaining. Whereas in the Wild-type plant no ARX3 protein was detected, a clear ARX3 signal was present in all the extracts of the hbt mutants.

In a third experiment (FIG. 19C, example 11) it was demonstrated that the protein recognized by the anti ARX3 serum was indeed the correct ARX3 protein. This was proven by the fact that the signal of ARX3 from the hbt mutants could be abolished again by crossing the mutants with the arx3$^{GT3958}$ plant. This plant has a mutation in the ARX3 gene and has no expression of the ARX3 protein. In these crossed plants, no or lower ARX3 protein could be detected with the ARX3 antisum (FIG. 19C).

Identification of other Targets of HOBBIT

Via proteomics, comparing the protein profile of wild type *Arabidopsis* plants and hbt mutants, protein spots can be identified on 2-D gels that differ between the WT and the mutant by their presence/absence or by their intensity. These possible targets or are further characterized by spectophotometry.

Also a Two-hybrid experiment, using cdc27B/HOBBIT as a bait protein is performed in order to identify other targets or interacting proteins of HOBBIT. Furthermore, also the mutant hbt alleles are used in the Two-Hybrid screen in order to map the functional domains of the HOBBIT protein and to identify the regions in the proteins where the interacting partners of HOBBIT bind.

Without being bound to any theory or mode of action, it can easily be envisaged that the HOBBIT/HBT/AtCDC27B plant development regulating gene of the invention is involved in the modulation of cell fate and/or the regulation of cell patterning in meristematic tissues. This statement is based on the phenotypic aberrations of hbt mutant A.thaliana seedlings and combination of these data with the patchy expression pattern of the HBT gene and the stabilization of the AXR3-GUS fusion protein.

More specifically, although HBT is likely to be expressed in a cell cycle-dependent fashion, modulation of cell fate and/or patterning through HBT likely relies on modulation of non cell cycle-regulated targets or signal such as AXR3. Thus, cell fate decisions and/or formation of cell patterns are likely to be taken in dividing cells. As such, plants could restrict modulation of cell fate and/or the regulation of cell pattern formation to meristematic tissues.

Furthermore, and again without being bound to any theory or mode of action, the observation of mutations in the HOBBIT/HBT/AtCDC27B gene affecting stability of cell cycle control proteins, as exemplified by stabilization of CYCB1-GUS, is indicative of a role of HOBBIT/HBT/AtCDC27B in cell cycle regulation. The unexpected patchy pattern of HOBBIT gene expression further points to a specialized role of HOBBIT in cell cycle regulation.

Another theory or mode of action for the HOBBIT/HBT/AtCDC27B gene, again without being bound to it, concerns the stabilization of the AXR3-GUS fusion protein. This observation underscores a role of HOBBIT in mediating auxin-related effects.

Therefore in further embodiments the invention relates to the use of cdc27B for modifying cell fate and/or pattern formation and/or plant development and/or plant morphology and/or plant biochemistry and/or plant physiology comprising the modification of expression in particular cells, preferably cycling cells, in particular domains, tissues or organs of a plant, preferably comprising cycling cells, of a genetic sequence encoding a plant development regulating protein, preferably a plant development regulating protein encoded by a nucleic acid of the invention operably linked to a plant-operable promoter sequence.

When reference is made herein to "the use of cdc27B" it is meant the use of a cdc27B protein as well as the use of a gene encoding cdc27B. The term cdc27B protein herein clearly contemplates any homologue, derivative, functional fragment or immunologically active fragment of a cdc27B protein. Further in particular embodiments, cdc27b is plant cdc27B. In a further embodiment of the invention, the plant development regulating protein is a HOBBIT/HBT/CDC27B protein according to the invention, such as for instance, the A. thaliana HOBBIT/HBT/AtCDC27B protein, or a biologically active homologue or derivative thereof. The present invention clearly contemplates the use of functional homologues of plant development regulating proteins according to the present invention. Accordingly, the present invention is not limited in application to the use of nucleotide sequences encoding the A. thaliana plant development regulating protein. It can be expected that genes and proteins similar to the one here defined from A. thaliana are present in other plant species and can be isolated by means of techniques known in the art. Also deletion mutants, which lack one or more amino acids compared to the amino acid sequence as defined in the present application, are to be considered as homologues. These similar genes are also within the scope of the present invention.

Therefor the use of cdc27B as stated herein can be achieved by modification of the expression level of a cdc27B gene in a cell e.g. by ectopic expression, downregulation of the expression, controlling the endogenous sequence etc.

Alternatively the use of cdc27B as stated herein can be achieved by influencing the level of protein activity in the cell e.g. by administration of cdc27B protein, by using cdc27B blocking agents etc.

Modulation of the expression in a plant of a plant development regulating protein or a homologue or derivative thereof as defined in the current invention such as a cdc27B protein can produce a range of desirable phenotypes in plants, such as, for example, by modifying one or more developmental, morphological, biochemical, or physiological characteristics including: (i) modifying the length of the G1 and/or the S and/or the G2 and/or the M phase of the cell cycle of a plant; (ii) modifying the G1/S and/or S/G2 and/or G2/M and/or M/G1 phase transition of a plant cell; (iii) modification of the initiation, promotion, stimulation or enhancement of cell division; (iv) modification of the initiation, promotion, stimulation or enhancement of DNA replication; (v) modification of the cell size; (vi) modification of the initiation, promotion, stimulation or enhancement of seed set and/or seed size and/or seed development; (vii) modification of the initiation, promotion, stimulation or enhancement of tuber formation; (viii) modification of the tuber number; (ix) modification of the initiation, promotion, stimulation or enhancement of fruit formation; (x) modification of the fruit number; (xi) modification of the initiation, promotion, stimulation or enhancement of leaf formation; (xii) modification of the leaf number; (xiii) modification of the initiation, promotion, stimulation or enhancement of shoot initiation and/or development; (xiv) modification of the initiation, promotion, stimulation or enhancement of root initiation and/or development; (xv) modification of the initiation, promotion, stimulation or enhancement of lateral root initiation and/or development; (xvi) modification of the initiation, promotion, stimulation or enhancement of flower formation; (xvii) modification of the flowering time; (xviii) modification of the flower number; (xix) modification of the initiation, promotion, stimulation or enhancement of nodule formation and/or nodule function; (xx) modification of the initiation, promotion, stimulation or enhancement of bushiness of the plant; (xxi) modification of the initiation, promotion, stimulation or enhancement of dwarfism in the plant; (xxii) modification of the initiation, promotion, stimulation or enhancement of senescence; (xxiii) modification of stem thickness and/or strength characteristics and/or wind-resistance of the stem and/or stem length; (xxiv) modification of tolerance and/or resistance to biotic stresses such as pathogen infection; (xxv) modification of tolerance and/or resistance to abiotic stresses such as drought stress or salt stress; (xxvi) mimicking or modification of auxin-related responses; (xxvii) modulation of plant tropic responses; (xxviii) modulation of vascularization in plants, plant organs or plant tissues; (xxix) modification of the shade avoidance response.

A person skilled in the art will recognize that auxins are involved amongst others in pattern formation. Accordingly, in another embodiment of the invention, the auxin related effect is defining cell fate and/or pattern formation.

The present invention also relates to a method for the production of transgenic plants, plant cells or plant tissues comprising the introduction of a nucleic acid molecule of the invention in an expressible format or a vector as defined above in said plant, plant cell or plant tissue. Reference is made to example 5 and other parts of the description for the description of an expressible format of the gene and vector.

Methods to effect expression of a plant development regulating protein such as a plant cdc27B protein, or a homologue or derivative thereof as defined in the current invention in a plant cell, tissue or organ, include either the introduction of the protein directly into said cell, tissue or organ such as by microinjection of ballistic means or, alternatively, stable introduction of an isolated nucleic acid molecule encoding said protein in an expressible format into the genome of a plant cell. Therefore, said nucleic acid can be operably linked to one or more control sequences or can be integrated in a vector according to the invention and/or can be stably integrated into the genome of a plant cell.

Methods to effect expression of a plant development regulating protein such as a plant cdc27B protein, or a homologue or derivative thereof as defined in the current invention in whole plants include regeneration of whole plants from said transformed cells in which an isolated nucleic acid molecule encoding said protein was introduced in an expressible format.

The invention also relates to plant cells and plants comprising any of the nucleic acids or vectors of the present invention.

Further, the present invention clearly extends to any plant cell or plant produced by any of the methods described herein, and to all plant parts and propagules thereof. The present invention extends further to encompass the progeny derived from a primary transformed or transfected cell, tissue, organ or whole plant that has been produced by any of said methods, the only requirement being that said progeny exhibits the same genotypic and/or phenotypic characteristic(s) as that (those) characteristic(s) that has (have) been produced in the parent by the performance of any of said methods. The invention also extends to harvestable parts of a plant such as but not limited to seeds, leaves, fruits, stem cultures, rhizomes, tubers and bulbs.

A major embodiment of the invention comprises methods for mimicking or modulating auxin-related responses by the use of cdc27B. Within the scope of the invention is the use of cdc27b to connect cell cycle progression and patterning cues, more particularly the competence to respond to auxin. Thus this embodiment comprises the use of a cell-cycle regulated component, preferably cdc27B, to confine the competence to respond to a patterning signal to the meristem. Accordingly, the use of cdc27B is the modified expression in particular cells, preferably in cycling cells, in particular domains, tissues or organs of a plant, preferably comprising cycling cells, of a plant development regulating gene or gene product or a homologue or derivative the of as defined in the invention, linked to a cell-specific, a tissue-specific or an organ-specific plant-operable promoter. The advantage of mimicking or modulating auxin-related responses via modified expression of said plant development regulating gene or gene product comprises the fact that the mimicking or modulating of the auxin-related response can be limited to the cells, preferably cycling cells, in which said gene or gene product is expressed. This is not true in the case of topical auxin application which causes pleiotropic effects due to the subsequent auxin transport through the plant in basal direction.

Mimicking an auxin-related effect, means to accomplish an effect of which can be established by auxin. Mimicking auxin-related effects can take place in the presence or absense of auxin. Mimicking auxin-related effects can also mean modulating the competence of cells that can normally not respond to auxin, preferably it is used to increase this competence.

In another embodiment of the present invention the modulation or mimicking of an auxin-related effect is based on the modulation of the stability of regulator proteins of patterning signals. These patterning signals include plant hormones such as auxin, ethylene and others. More particularly, it is dependent on the modulation of auxin regulators or even more, the modulation of the stability of AUX/IAA class of transcriptional regulators of auxin. Furthermore, it is dependent on the stability of ARX3 regulator protein. Also it is in the scope of this embodiment of the invention is that these type of proteins are degraded in a particular phase of the cell cycle, such as the G2-M transition phase.

Auxin is a pleiotropic plant hormone and therefor the outcome of modulating or mimicking auxin related effects is exemplified, but not limited to the following examples. For other auxin related effects reference is made to the scientific literature in the field and known by the person skilled in the art. It is clear that all the auxin-related effects are in the scope of the present invention.

A series of embodiments of the current invention envisage ectopic expression of a HOBBIT plant development regulating gene, for instance a plant cdc27b gene, for instance as defined in any of SEQ ID NOs 1 to 3 or gene product as defined in SEQ ID NO 8 or 9 or a homologue or derivative thereof as defined supra in particular or specific cells, domains, tissues or organs of plant meristems which is expected to enhance the competence of said cells, domains, tissues or organs to respond to signals defining cell fate and/or pattern formation. Formation of novel tissues or organs and/or a novel arrangement (relative to plants exhibiting natural HBT gene expression patterns) thereof can be the outcome. Illustrative examples include altering floral numbers and floral arrangement as the result of incorporation of non-dividing cells in meristems and/or pattern formation; altering stem branching patterns by changing the size of the cell pool competent for local outgrowth; or altering root branching patterns by changing the distribution and size of lateral root primordia. It can furthermore be envisaged that ectopic expression of a HOBBIT gene (for instance the plant cdc27 gene) throughout the cell cycle, and thus not restricted to the natural cell cycle specific expression, will further enhance cell fate decisions and patterning responses. The requirements of the plant operable promoters to achieve the embodiments listed below can easily be determined by the skilled artisan who will also be able to select a suitable plant operable promoter. An illustrative non-exhaustive list of plant operable promoters that can possibly be used is included further in the current invention.

Thus, one embodiment of the invention comprises a method for altering, preferably increasing, of the size of naturally occurring plant meristems by ectopic expression of a plant development regulating gene or gene product, such as a cdc27B gene or gene product (or protein), or a homologue or derivative thereof as defined in the invention. In this case, suitable promoters to control expression of said plant development regulating gene or gene product include e.g. a meristem-specific promoter or a promoter active in cells peripheral to said meristem. As a result thereof, the number of organs emanating and/or the rate of organ emanation from said meristem can be modified, preferably increased. The present invention thus also comprises a method for modifying, preferably increasing, the number of organs and/or the rate of organ emanation from a plant meristem by ectopic expression of a plant development regulating gene or gene product or a homologue or derivative thereof as defined in the invention. Again, said plant development regulating gene or gene product could be operably linked to promoters such as of a meristem-specific promoter or a promoter active in cells peripheral to said meristem.

Further part of the invention is a method for increasing the number of plant meristems by ectopic expression, preferably in cycling cells, of a plant development regulating gene or gene product or a homologue or derivative thereof as defined in the invention under the control of a constitutive, cell-specific, tissue-specific, organ-specific or inducible plant-operable promoter. Ectopic organs will preferably emerge from cycling cells.

As a result thereof, ectopic organ formation can be induced starting from all plant parts in the case of a constitutive promoter, or from said cell, tissue or organ wherein said promoter is operable or in a random fashion in the case of using an inducible plant operable promoter.

Useful applications of said methods include the increase of the flower number on a plant which is a desirable trait in e.g. ornamental or horticultural plants, e.g. to increase the efficiency of cut flower production or to create abundantly flow ring varieties. A more favorable distribution of flowers along the apical-basal axis of the plant can also be effectuated. Shortening flowering time in the case of e.g. cut flower production can further enhance productivity as more harvesting rounds are enabled in a single growing season. Increasing the flower number can also find its use in agriculture as flower number and seed yield are correlated. Shortening flowering time may further increase seed yield by enabling more harvesting rounds during a single growing season.

Other useful applications of said methods include the increase in leaf number which is a particularly desired trait in the production of e.g. fodder or forage crops, crops grown to be ensilaged or of leguminous crops. Increasing leaf number of grasses is desirable for pasture lands as well as for lawns.

The invention thus more specific relates to the use of a plant cdc27 for modulating or mimicking auxin-related effects in a plant or plant cell wherein said modulation or mimicking results in a modification of, for instance an increase, in the number of organs or tissues, and/or modification of the rate of organ or tissue emantotaion from a plant meristem, and/or a modification of the the arrangement of organs and/or tissues in a plant. Yet other useful applications of said methods include the activation of meristems and/or increasing the number of meristems forming e.g. fruits, tubers or bulbs or activation of meristems forming e.g. beets, turnip, radishes etc. Thus more bulbs or tubers or bigger fruits, beets, turnips or radishes etc. can be obtained. The current invention thus clearly also embodies a method for increasing plant yield by ectopic expression, preferably in cycling cells, of the plant development regulating gene or gene product or a homologue or derivative thereof as defined in the invention, linked to a plant-operable promoter. Yield is hereby defined as the amount of produced organs including seed, leaves, bulbs, tubers, beets, turnips or radishes etc.

Therefore, the invention more specific relates to the use of a plant cdc27B for mimicking or modulating auxin-related effects resulting in an increased plant yield.

Activation of lateral root meristems and/or increasing the number of lateral root meristems under conditions of e.g. nutrient deprivation can aid a plant in actively exploring the soil for new nutrient sources. Another embodiment to the invention thus encompasses a method for enhancing the survival rate of plants under nutrient-limiting conditions by ectopic expression, preferably in cycling cells, of a plant development regulating gene or gene product or a homologue or derivative thereof as defined in the invention. Preferably a root-expressible promoter, preferably inducible by nutrient limitation, is chosen to achieve said enhanced survival rate.

Other auxin-related responses include tropic responses such as gravitropism and phototropism. Enhancing the gravitropic response can aid a plant in directing deep penetration of its roots in the soil in search of water, e.g. under conditions of drought. Enhancing the phototropic response can aid a plant in e.g. early emergence of the seedling above the soil under low light-conditions or in e.g. fast re-establishing of photosynthetic capacity by displaying leaves above the water surface of flooded fields. Clearly embodied within the current invention are thus methods for enhancing the survival rate of plants under drought conditions by ectopic expression, preferably in cycling cells, of a plant development regulating gene or gene product or a homologue or derivative thereof as defined in the invention and for enhancing seedling emergence by ectopic expression of a plant development regulating gene or gene product or a homologue or derivative thereof as defined in the invention. Drought- and light-inducible promoters, respectively, are good candidates for being operably linked to said plant development regulation gene or gene product.

Therefore, the invention also relates to the use of a plant cdc27B for mimicking or modulating auxin-related effects resulting in an increased survival rate of plants, for instance under drought conditions.

The auxin-induced root formation often used in the regeneration of transgenic plants can also be mimicked or enhanced by a timely ectopic expression, preferably in cycling cells, of a plant development regulation gene or gene product of the invention. Thus embodied is a method for mimicking or enhancing root generation in tissue culture protocols by ectopic expression, preferably in cycling cells, of a plant development regulating gene or gene product or a homologue or derivative thereof as defined in the invention in the absence or presence, respectively, of an exogenous auxin source.

The invention thus also relates to the use of a plant cdc27B for mimicking or modulating auxin-related effects resulting in the mimicking of root generation in plants.

Another auxin-related response includes the shade avoidance response. Effects of canopy shade include reduced seed set, truncated fruit development and reduced seed germinability. Auxin has been implemented in establishing the shade avoidance response (Morelli and Ruberti 2000, and references cited therein). A method, also part of the invention, can be envisaged with which the shade avoidance response is enhanced by ectopic expression, preferably in cycling cells, of a plant development regulating gene or gene product or a homologue or derivative thereof as defined in the invention. Preferably, a far red (FR) light inducible promoter is used to enable said method and even more preferably, a promoter induced by changes in the ratio of red (R) to FR light, e.g. the promoter of the *Arabidopsis* Athb-2 homeobox gene (Carabelli et al. 1996).

Therefore, the invention more specific relates to the use of a plant cdc27B for mimicking or modulating auxin-related effects resulting in an increased shade avoidance response. Yet another auxin-related response includes the establishment of continuous vascular strands basal from auxin sources (e.g. Worley et al. 2000 and references cited therein). Mimicking auxin effects in e.g. a randomized fashion or by increasing the number of branch initiating meristems in e.g. tree stems can establish a complex vascular system. Such stems are of interest to e.g. carpenters for the artisanal production of furniture containing wooden planks or shelves showing the exclusive vascular pattern. Such stems are also of interest for veneering purposes. Establishment of a new vasculature is of course also imperative for proper development of any new organ as described in several embodiments of the current invention. Thus, a corresponding embodiment comprises a method for the alteration, preferably the stimulation, of vascular strand formation and patterning by ectopic expression, preferably in cycling cells, of a plant development regulating gene or gene product such as a plant cdc27b gene or gene product, or a homologue or derivative thereof as defined in the invention.

Another auxin-related response concerns the production of parthenocarpic fruits. Tobacco, eggplant and tomato plants expressing the IAA (indole acectic acid, the principal plant auxin) biosynthetic iaaM gene of *Pseudomonas syringae* pv *savastanoi* indeed produce marketable parthenocarpic fruits (Ficcadenti et al. 1999, Rotino et al. 1997). Therefore, a method for producing parthenocarpic fruits by ectopic expression, preferably in cycling cells, using a plant development regulating gene or gene product, such as a plant cdc27b, or a homologue or derivative thereof as defined in the invention is also embodied by the present invention.

It will be clear to the skilled artisan that many, if not all, of the above described methods benefit from and are enhanced by the role of HBT in the cell cycle. Therefore another embodiment of the invention is the use of cdc27b in the regulation of the cell cycle. Since it is demonstrated by the inventors that the HOBBIT gene takes part of an APC-like complex, another embodiment of the invention is the use of cdc27B for modulating the activity of an APC-like complex. With an Apc-like complex is meant a protein complex, functional in a certain stage a at certain stages of the cell cycle (e.g. at the G1/S and/or at the G2/M transition) which is involved in the tagging of proteins (i.e. cell cycle proteins or non cell cycle proteins) for protein degradation. The APC complex is known the be active in both transitions phases and is involved in the degradation of cell cycle proteins like cyclinB. The HBT gene expression shows a peak at the G2/M transition and the protein is also involved in the stability of non-cell cycle proteins. Therefore in another embodiment of the present invention the cell cycle is regulated by cdc27B at the G2/M phase transition. From their experimental data, the inventors could conclude that HOBBIT is involved in the correct progression of the S-phase of the cell cycle and therefore another embodiment in the present invention is the use of cdc27B for modulating DNA replication. Furthermore, it was shown that is is recognized by the artisan that enhanced DNA replication without consequent mitosis and cytokinesis can result in endoreduplication. Mitosis can be blocked by the prolonging the life span of cell cycle proteins like cyclinB. Another embodiment of the present invention is the use of cdc27b for modulating endoreduplication in a plant. Finally, when DNA replication is blocked in specific tissues, for example in the gamatocytesn a parson skilled in the art can induce sterility in plants. Accordingly, another embodiment of the present invention is the use of cdc27B for modulating, for instance inducing, sterility in plants.

By negatively effecting the lifetime of e.g. mitotic cyclins such as cyclin B1, it is clear that at least the transition from the M-phase to a subsequent G1-phase is shortened. Thus, the rate of cell division is positively affected by ectopic HBT expression that contributes, as mentioned, to many of the methods described supra. Accordingly, the embodiment of the current invention based thereon discloses a method for enhancing or increasing the cell cycle or the rate of cell division by ectopic expression, preferably in cycling cells, of a plant development regulating gene or gene product, for instance a plant cdc27B gene or gene product, or a homologue or derivative thereof as defined in the invention. Enhancing or increasing the cell cycle means pushing cells into the cell cycle or increasing the population of cells that are dividing.

A number of other embodiments of the current invention rely on the downregulation or the diminished activity of cdc27B in cells. This downregulation of cdc27B activity can be established by the the downregulation of expression, preferably in cycling cells, of a HBT plant development regulating gene, such as a plant cdc27B gene as defined by any of SEQ ID NOs 1 to 3 or a gene product as defined by SEQ ID NO 8 or 9. Alternatively, downregulation of cdc27B activity can be obtained by the ectopic expression, preferably in cycling cells, of a mutant hbt plant development regulating gene as defined by any of SEQ ID NOs 10 to 23 or a gene product as defined by any of SEQ ID NOs 24 to 30. Homologues or derivatives of said plant development regulating genes or gene products, or mutants thereof, can be used as well and include e.g. the corresponding genes or gene products of *A. thaliana* Col-0.

When affecting apical meristem activity it is e.g. possible to effectuate a decrease in the number of lateral organs emanating from said meristem and/or to decrease the rate of lateral organ formation.

Therefore, the invention more specific relates to the use of a plant cdc27B for regulation of the cell cycle resulting in an activation or alteration, for instance an increase in the size, of naturally occuring plant meristems, or resulting in an increase in the number of organs or tissues, and/or modifidcation of the rate of organ or tissue emanation from a latn meristem, and/or a modification of the arrangement of organs, and/or issues in a plant. Useful applications include the creation of dwarfed plant varieties. Another application concerns the abrogation of e.g. tomato side shoot meristem fitness. As a result no adventitious side shoots are formed and manual pruning is not longer required.

Thus, according to a further embodiment of the present invention introduces a method for reducing fitness or activity of natural plant meristems by downregulation of the expression, preferably in cycling cells, of a plant development regulating gene or gene product, such as a plant cdc27B gene or gene product, or a homologue or derivative thereof as defined in the invention or by ectopic expression, preferably in cycling cells, of mutants of said plant development regulation gene or gene product. Examples of said mutants are described in the invention and their sequences are represented in SEQ ID NOs 10 to 23 (nucleic acid sequences) and SEQ ID NOs 24 to 30 (amino acid sequences).

The bloating phenotype of epidermal cells in hbt mutant *A. thaliana* seedlings can also be exploited. Plant tissues or organs consisting of fewer larger cells have the advantage of containing less cell wall material than a plant tissue or organ of the same size but consisting of more small cells. This has the potential advantage of increasing the digestibility of said plant tissues or organs consisting of said larger cells. A timely impaired expression, preferably in cycling cells, of the HBT gene or gene product or a timely ectopic expression, preferably in cycling cells, of a hbt mutant gene or gene product might thus result in e.g. leaves or fruits of normal size but with large cells with said leaves or fruits exhibiting an improved digestability. As yet another embodiment is presented a method for increasing the size of plant cells in a tissue or organ and thus for enhancing digestability of said plant tissue or organ by downregulation of the expression, preferably in cycling cells, of a plant development regulating gene or gene product, such as a plant cdc27b gene or gene product, or a homologue or derivative thereof as defined in the invention or by ectopic expression, preferably in cycling cells, of mutants of said plant development regulation gene or gene product according to the invention.

A number of plant pathogens exploit the host's cell cycle machinery resulting in pathogen-induced neoplastic growth visible as e.g. galls. The newly formed plant tissues are often required for pathogen survival and cause in many cases problems with marketability of infested plants or parts thereof such as fruits or flowers. Such pathogens include plant pathogenic bacteria including *Agrobacterium tumefaciens, Rhodococcus fascians, Pseudomonas syringae* pv *savastanol, Xanthomonas campestris* pv *citri* and *Erwinia herbicola*, plant pathogenic fungi including *Plasmodiophora brassicae, Crinipellis perniciosa, Pucciniastrum geoppertianum, Taphrina wiesneri, Ustilaga maydis, Exobasidium vaccinii, E. camelliae, Entorrhiza casparyana* and *Apiosporina morbosum* and plant pathogenic gall-inducing insects including the midge *Mayetiola poae*. The host's tolerance or resistance against attack by such pathogens can be increased by repressing the pathogen-induced neoplastic growth. Due to its role in cell cycle regulation and auxin signaling, abrogation of HBT function during pathogen attack can contribute to repression of the neoplastic plant growth and thus to the establishment of increased pathogen resistance.

Another embodiment therefore comprises a method for increasing resistance of a plant against neoplastic plant growth induced by pathogens by downregulation of the expression, preferably in cycling cells, of a plant development regulating gene or gene product, such as a plant cdc27b gene or gene product, or a homologue or derivative thereof as defined in the invention or by ectopic expression, preferably in cycling cells, of mutants of said plant development regulation gene or gene product described in the present invention.

The present invention is applicable to any plant, in particular a monocotyledonous plants and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis, Albizia amara, Alsophila tricolor, Andropogon* spp., *Arachis* spp, *Areca catechu, Astelia fragrans, Astragalus cicer, Baikiaea plurijuga, Betula* spp., *Brassica* spp., *Bruguiera gymnorrhiza, Burkea africana, Butea frondosa, Cadaba farinosa, Calliandra* spp, *Camellia sinensis, Canna indica, Capsicum* spp., *Cassia* spp., *Centroema pubescens, Chaenomeles* spp., *Cinnamomum cassia, Coffea arabica, Colophospermum mopane, Coronillia varia, Cotoneaster serotina, Crataegus* spp., *Cucumis* spp., *Cupressus* spp., *Cyathea dealbata, Cydonia oblonga, Cryptomeria japonica, Cymbopogon* spp., *Cynthea dealbata, Cydonia oblonga, Dalbergia monetaria, Davallia divancata, Desmodium* spp., *Dicksonia squarosa, Diheteropogon amplectens, Dioclea* spp, *Dolichos* spp., *Dorycnium rectum, Echinochloa pyramidalis, Ehrartia* spp., *Eleusine coracana, Eragrestis* spp., *Erythrina* spp., *Eucalyptus* spp., *Euclea schimperi, Eulalia villosa, Fagopyrum* spp., *Feijoa sellowiana, Fragaria* spp., *Flemingia* spp, *Freycinetia banksii, Geranium thunbergii, Ginkgo biloba, Glycine javanica, Gliricidia* spp, *Gossypium hirsutum, Grevillea* spp., *Guibourtia coleosperma, Hedysarum* spp., *Hemarthia altissima, Heteropogon contortus, Hordeum vulgare, Hyparrhenia rufa, Hypericum erectum, Hyperthelia dissoluta, Indigo incarnata, Iris* spp., *Leptarrhena pyrolifolia, Lespediza* spp., *Lettuca* spp., *Leucaena leucocephala, Loudetia simplex, Lotonus bainesii, Lotus* spp., *Macrotyloma axillare, Malus* spp., *Manihot esculenta, Medicago sativa, Metasequoia glyptostroboides, Musa sapientum, Nicotianum* spp., *Onobrychis* spp., *Ornithopus* spp., *Oryza* spp., *Peltophorum africanum, Pennisetum* spp., *Persea gratissima, Petunia* spp., *Phaseolus* spp., *Phoenix canariensis, Phormium cookianum, Photinia* spp., *Picea glauca, Pinus* spp., *Pisum sativum, Podocarpus totara, Pogonarthria fleckii, Pogonarthria squarrosa, Populus* spp., *Prosopis cineraria, Pseudotsuga menzaesii, Pterolobium stellatum, Pyrus communis, Quercus* spp., *Rhaphiolepis umbellata, Rhopalostylis sapida, Rhus natalensis, Ribes grossularia, Ribes* spp., *Robinia pseudoacacia, Rosa* spp., *Rubus* spp., *Salix* spp., *Schyzachyrium sanguineum, Sciadopitys verticillata, Sequoia sempervirens, Sequoiadendron giganteum, Sorghum bicolor, Spinacia* spp., *Sporobolus fimbriatus, Stiburus alopecuroides, Stylosanthos humilis, Tadehagi* spp, *Taxodium distichum, Themeda triandra, Trifolium* spp., *Triticum* spp., *Tsuga heterophylla, Vaccinium* spp., *Vicia* spp. *Vitis vinifera, Watsonia pyramidata, Zantedeschia aethiopica, Zea mays,* amaranth, artichoke, asparagus, broccoli, brussel sprout, cabbage, canola, carrot, cauliflower, celery, collard greens, flax, kale, lentil, oilseed rape, okra, onion, potato, rice, soybean, straw, sugarbeet, sugar cane, sunflower, tomato, squash, and tea, amongst others, or the seeds of any plant specifically named above or a tissue, cell or organ culture of any of the above species.

The present invention further relates to a method for identifying and obtaining agonists of a plant development regulating protein or a homologue or derivative thereof as defined in the current invention.

Preferably said agonists are chemical compounds which can find uses as e.g. plant growth regulators or herbicides. Methods to identify such compounds include addition of said compounds to a yeast two-hybrid system wherein said plant development regulating protein and a protein interacting with said plant development regulating protein as identified using a method of the current invention are expressed. Another such method comprises the use of e.g. the BIACore apparatus (Pharmacia) for real-time measurement of interaction of any of said compounds with said plant development regulating protein or with said plant development regulating protein complexed with a protein interacting with said plant development regulating protein as identified using a method of the current invention In another embodiment, said agonists are protein partners capable of interacting with said plant development regulating protein. As described supra, methods to identify such proteins include for instance a two-hybrid system and immunoprecipitation.

Therefore, the present invention relates to a method for identifying and obtaining proteins interacting with a plant development regulating protein comprising a two-hybrid screening assay wherein a polypeptide according to the invention as a bait and a plant cDNA library as prey are used.

Furthermore, the present invention relates to a method for modulating the interaction between a plant development regulating protein of the invention, such as a plant cdc27B protein, and interacting protein partners obtainable by a method as defined above.

In a preferred embodiment, the method for identifying and obtaining compounds interacting with a plant development regulating protein of the invention comprises the following steps:

a) providing a yeast two-hybrid system wherein a polypeptide of the invention and a protein interacting with said plant development regulating protein, or an interacting protein obtainable by the above described method, are expressed, b) interacting said compound with the complex formed by the expressed polypeptides as defined in a), c) detecting a second complex, wherein the presence of said second complex identifies a compound which specifically binds to one of said polypeptides or to said second second complex, and, d) identifying the compound.

In another preferred embodiment, the method for identifying and obtaining compounds interacting with a plant development regulating protein, such as a plant cdc27b of the invention comprises real-time measurement of interaction of said compound with said plant development regulating protein or the complex formed by said plant development regulating protein and a protein interacting therewith, said interacting protein optinally obtainable by the above described methods.

In another embodiment, the present invention relates to a method for identifying compounds or mixtures of compounds which specifically bind to a polypeptide of the invention as defined earlier, comprising:

a) combining a polypeptide of the invention with said compound or mixtures of compounds under conditions suitable to allow complex formation, b) detecting complex formation, wherein the presence of a complex identifies, or is indicative for a molecule which specifically binds said polypeptide, and c) identifying the compound.

As such, the invention also relates to the use of a molecule identified by means of a method as described above as a plant growth regulator or herbicide.

In further embodiments of any of the methods described above, a plant development regulating protein is a plant CDC27B protein, preferably the *A.thaliana* AtCD27B protein, or a biologically active homologue or derivative thereof.

According to another embodiment, the invention also relates to a method for production of a plant growth regulator or herbicide composition comprising the steps of the methods described above and formulating the compounds obtained from said steps in a suitable form for the application in agriculture or plant cell or tissue culture.

The invention also extends to the use of any of the nucleic acids or nucleic acid molecules, the vectors, the polypeptides or the antibodies of the invention for modifying cell fate, for modifying pattern formation, for modifying plant development and/or for modifying plant morphology and/or for modifying plant physiology and/or for modifying plant biochemistry.

The invention also extends to a diagnostic composition comprising at least a nucleic acid or nucleic acid molecule, a vector, a polypeptide or an antibody of the invention. Several other issues concerning the function of the HBT gene are also envisaged by the present invention. More elements of the hbt mutant phenotype, other than the ones described herein, are rescued by increased stability of the AXR3 protein, besides the partial hypocotyl elongation rescue. The cells of hbt seedlings are irregular in shape and many are bloated. By crossing the plant with altered hbt activity with other plants, one can become a plant with the desired characteristics and the desired cell shape. For example the hypocotyls of the axr3-1T hbt double mutants have a more regular shape. The partial rescue of the root growth is accompanied by the presence of starch granules and an auxin peak in the columella cells of the root tip. Also the HBT has auxin related functions in the mature plant. In hbt mutants it is difficult to determine these functions because of the development arrests at the seedling stage in hbt mutants. It is known from mutant studies, that auxin has important but as yet poorly defined roles in, for example, flower development. Mutations in genes involved in the polar auxin transport, such as PIN1, result amongst others in the development of naked, pin-shaped inflorescences (Galweiler et al., 1998). The hbt mutant displays several cell cycle and cell differentiation defects. The effects that decide why the divisions planes are altered in the future root pole of the embryo are also envisaged by the present invention. The effect that makes cell division arrest in the hbt seedling is also envisaged by the present invention. The effect that decides the cell cycle regulated expression of HBT and that relates that expression to the above mentioned processes, is also envisaged by the present invention. The effects that decide why the cell differentiation defects are restricted to specific areas in the hbt seedling are also envisaged by the present invention.

Definitions and Elaborations to the Embodiments

The terms "protein(s)", "peptide(s)" or "oligopeptide(s)", when used herein refer to amino acids in a polymeric form of any length. Said terms also include known amino acid modifications such as disulphide bond formation, cysteinylation, oxidation, glutathionylation, methylation, acetylation, farnesylation, biotinylation, stearoylation, formylation, lipoic acid addition, phosphorylation, sulphation, ubiquitination, myristoylation, palmitoylation, geranylgeranylation, cyclization (e.g. pyroglutamic acid formation), oxidation, deamidation, dehydration, glycosylation (e.g. pentoses, hexosamines, N-acetylhexosamines, deoxyhexoses, hexoses, sialic acid etc.), acylation and radiolabels (e.g. $^{125}$I, $^{131}$I, $^{35}$S, $^{14}$C, $^{32}$P, $^{33}$P, $^{3}$H) as well as non-naturally occurring amino acid residues, L-amino acid residues and D-amino acid residues.

"Homologues" of a protein of the invention are those peptides, oligopeptides, polypeptides, proteins and enzymes which contain amino acid substitutions, deletions and/or additions relative to the said protein with respect to which they are a homologue, without altering one or more of its functional properties, in particular without reducing the activity of the resulting. For example, a homologue of said protein will consist of a bioactive amino acid sequence variant of said protein. To produce such homologues, amino acids present in the said protein can be replaced by other amino acids having similar properties, for example hydrophobicity, hydrophilicity, hydrophobic moment, antigenicity, propensity to form or break α-helical structures or β-sheet structures, and so on. An overview of physical and chemical properties of amino acids is given in Table 1.

TABLE 1

Properties of naturally occurring amino acids.

| Charg properties/ hydrophobicity | Side group | Amino Acid |
|---|---|---|
| nonpolar hydrophobic | aliphatic | ala, ile, leu, val |
| | aliphatic, S-containing | met |
| | aromatic | phe, trp |
| | imino | pro |
| polar uncharged | aliphatic | gly |
| | amide | asn, gln |
| | aromatic | tyr |
| | hydroxyl | ser, thr |
| | sulfhydryl | cys |
| positively charged | basic | arg, his, lys |
| negatively charged | acidic | asp, gly |

Substitutional variants of a protein of the invention are those in which at least one residue in said protein amino acid sequence has been removed and a different residue inserted in its place. Amino acid substitutions are typically of single residues, but may be clustered depending upon functional constraints placed upon the polypeptide; insertions will usually be of the order of about 1-10 amino acid residues and deletions will range from about 1-20 residues. Preferably, amino acid substitutions will comprise conservative amino acid substitutions, such as those described supra.

Insertional amino acid sequence variants of a protein of the invention are those in which one or more amino acid residues are introduced into a predetermined site in said protein. Insertions can comprise amino-terminal and/or carboxy-terminal fusions as well as intra-sequence insertions of single or multiple amino acids. Generally, insertions within the amino acid sequence will be smaller than amino or carboxyl terminal fusions, of the order of about 1 to 10 residues. Examples of amino- or carboxy-terminal fusion proteins or peptides include the binding domain or activation domain of a transcriptional activator as used in the yeast two-hybrid system, phage coat proteins, (histidine)$_6$-tag, glutathione S-transferase, protein A, maltose-binding protein, dihydrofolate reductase, Tag•100 epitope (EETARFQPGYRS), c-myc epitope (EQKLISEEDL), FLAG®-epitope (DYKDDDK), lacZ, CMP (calmodulin-binding peptide), HA epitope (YPYDVPDYA), protein C epitope (EDQVDPRLIDGK) and VSV epitope (YTDIEMNRLGK).

Deletional variants of a protein of the invention are characterised by the removal of one or more amino acids from the amino acid sequence of said protein.

Amino acid variants of a protein of the invention may be readily made using peptide synthetic techniques well known in the art, such as solid phase peptide synthesis and the like, or by recombinant DNA manipulations. The manipulation of DNA sequences to produce variant proteins which manifest as substitutional, insertional or deletional variants are well known in the art. For example, techniques for making substitution mutations at predetermined sites in DNA having known sequence are well known to those skilled in the art, such as by M13 mutagenesis, T7-Gen in vitro mutagenesis kit (USB, Cleveland, Ohio), QuickChange Site Directed mutagenesis kit (Stratagene, San Diego, Calif.), PCR-mediated site-directed mutagenesis or other site-directed mutagenesis protocols. Another alternative to manipulate DNA sequences to produce variant proteins, which manifest as substitutional, insertional or deletional variants comprises targeted in vivo gene modification which can be achieved by chimeric RNA/DNA oligonucleotides as described by e.g. Palmgren (1997), Trends Genet. 13, 348 and Yoon et al. (1996), Proc. Natl. Acad. Sci. USA 93, 2071-2076.

"Derivatives" of a protein of the invention are those peptides, oligopeptides, polypeptides, proteins and enzymes which comprise at least about five contiguous amino acid residues of said polypeptide but which retain the biological activity of said protein. A "derivative" may further comprise additional naturally-occurring, altered glycosylated, acylated or non-naturally occurring amino acid residues compared to the amino acid sequence of a naturally-occurring form of said polypeptide. Alternatively or in addition, a derivative may comprise one or more non-amino acid substituent compared to the amino acid sequence of a naturally-occurring form of said polypeptide, for example a reporter molecule or other ligand, covalently or non-covalently bound to the amino acid sequence such as, for example, a reporter molecule which is bound thereto to facilitate its detection.

With "immunologically active" is meant that a molecule or specific fragments thereof such as epitopes or haptens are recognized by, i.e. bind to antibodies. In the context of the current invention are embodied homologues, derivatives and/or immunologically active fragments of any of the inventive HOBBIT or mutant HOBBIT proteins as defined supra.

"Antibodies" include monoclonal, polyclonal, synthetic or heavy chain camel antibodies as well as fragments of antibodies such as Fab, Fv or scFv fragments. Monoclonal antibodies can be prepared by the techniques as described in e.g. Liddle and Cryer (1991) which comprise the fusion of mouse myeloma cells to spleen cells derived from immunized animals. Furthermore, antibodies or fragments thereof to a molecule or fragments thereof can be obtained by using methods as described in e.g. Harlow and Lane (1988). In the case of antibodies directed against small peptides such as fragments of a protein of the invention, said peptides are generally coupled to a carrier protein before immunization of animals. Such protein carriers include keyhole limpet hemocyanin (KLH), bovine serum albumin (BSA), ovalbumin and Tetanus toxoid. The carrier protein enhances the immune response of the animal and provides epitopes for T-cell receptor binding sites. The term "antibodies" furthermore includes derivatives thereof such as labelled antibodies. Antibody labels include alkaline phosphatase, PKH2, PKH26, PKH67, fluorescein (FITC), Hoecst 33258, R-phycoerythrin (PE), rhodamine (TRITC), Quantum Red, Texas Red, Cy3, biotin, agarose, peroxidase, gold spheres and radiolabels (e.g. $^{125}$I, $^{131}$I, $^{35}$S, $^{14}$C, $^{32}$P, $^{33}$P, $^3$H). Tools in molecular biology relying on antibodies against a protein include protein gel blot analysis, screening of expression libraries allowing gene identification, protein quantitative methods including ELISA and RIA, immunoaffinity purification of proteins, immunoprecipitation of proteins (e.g. Magyar et al. 1997) and immunolocalization (e.g. Terras et al. 1995). Other uses of antibodies and especially of peptide antibodies include the study of proteolytic processing (Loffler et al. 1994, Woulfe et al. 1994), determination of protein active sites (Lerner 1982), the study of precursor and post-translational processing (Baron and Baltimore 1982, Lerner et al. 1981, Semler et al. 1982), identification of protein domains involved in protein-protein interactions (Murakami et al. 1992) and the study of exon usage in gene expression (Tamura et al. 1991).

Embodied in the current invention are antibodies recognizing a HOBBIT or mutant HOBBIT protein or homologue, derivative or fragment thereof as defined supra. The terms "gene(s)", "polynucleotide(s)", "nucleic acid sequence(s)", "nucleotide sequence(s)", "DNA sequence(s)" or "nucleic acid molecule(s)", when used herein refer to nucleotides, either ribonucleotides or deoxyribonucleotides or a. combination of both, in a polymeric form of any length. Said terms furthermore include double-stranded and single-stranded DNA and RNA. Said terms also include known nucleotide modifications such as methylation, cyclization and 'caps' and substitution of one or more of the naturally occurring nucleotides with an analog such as inosine. Modifications of nucleotides include the addition of acridine, amine, biotin, cascade blue, cholesterol, Cy3®, Cy5®, Cy5.5® Dabcyl, digoxigenin, dinitrophenyl, Edans, 6-FAM, fluorescein, 3'-glyceryl, HEX, IRD-700, IRD-800, JOE, phosphate psoralen, rhodamine, ROX, thiol (SH), spacers, TAMRA, TET, AMCA-S®, SE, BODIPY®, Marina Blue®, Pacific Blue®, Oregon Green®, Rhodamine Green®, Rhodamine Red®, Rhodol Green® and Texas Red®. Polynucleotide backbone modifications include methylphosphonate, 2'-OMe-methylphosphonate RNA, phosphorothiorate, RNA, 2'-OMeRNA. Base modifications include 2-amino-dA, 2-aminopurine, 3'-(ddA), 3'dA(cordycepin), 7-deaza-dA, 8-Br-dA, 8-oxo-dA, N$^6$-Me-dA, abasic site (dSpacer), biotin dT, 2'-OMe-5Me-C, 2'-OMe-propynyl-C, 3'-(5-Me-dC), 3'-(ddC), 5-Br-dC, 5-I-dC, 5-Me-dC, 5-F-dC, carboxy-dT, convertible dA, convertible dC, convertible dG, convertible dT, convertible dU, 7-deaza-dG, 8-Br-dG, 8-oxo-dG, O$^6$-M-dG, S6-DNP-dG, 4-methyl-indole, 5-nitroindole, 2'-OMe-inosine, 2'-dI, O$^6$-phenyl-dI, 4-methyl-indole, 2'-deoxynebularine, 5-nitroindole, 2-aminopurine, dP(purine analogue), dK(pyrimidine analogue), 3-nitropyrrole, 2-thio-dT, 4-thio-dT, biotin-dT, carboxy-dT, $O^4$-Me-dT, $O^4$-triazol dT, 2'-OMe-propynyl-U, 5-Br-dU, 2'-dU, 5-F-dU, 5-I-dU, $O^4$-triazol dU and radiolabels (e.g. $^{125}I$, $^{131}I$, $^{35}S$, $^{14}C$, $^{32}P$, $^{33}P$, $^{3}H$). Said terms also encompass peptide nucleic acids (PNAs), a DNA analogue in which the backbone is a pseudopeptide consisting of N-(2-aminoethyl)-glycine units rather than a sugar. PNAs mimic the behaviour of DNA and bind complementary nucleic acid strands. The neutral backbone of PNA results in stronger binding and greater specificity than normally achieved. In addition, the unique chemical, physical and biological properties of PNA have been exploited to produce powerful biomolecular tools, antisense and antigene agents, molecular probes and biosensors.

A "coding sequence" or "open reading frame" or "ORF" is defined as a nucleotide sequence that can be transcribed into mRNA and/or translated into a polypeptide when placed under the control of appropriate regulatory sequences, i.e. when said coding sequence or ORF is present in an expressible format. Said coding sequence of ORF is bounded by a 5' translation start codon and a 3' translation stop codon. A coding sequence or ORF can include, but is not limited to RNA, mRNA, cDNA, recombinant nucleotide sequences, synthetically manufactured nucleotide sequences or genomic DNA. Said coding sequence or ORF can be interrupted by intervening nucleic acid sequences. Genes and coding sequences essentially encoding the same protein but isolated from different sources can consist of substantially divergent nucleic acid sequences. Reciprocally, substantially divergent nucleic acid sequences can be designed to effect expression of essentially the same protein. Said nucleic acid sequences are the result of e.g. the existence of different alleles of a given gene, of the degeneracy of the genetic code or of differences in codon usage. Thus, as indicated in Table 2, amino acids such as methionine and tryptophan are encoded by a single codon whereas other amino acids such as arginine, leucine and serine can each be translated from up to six different codons. Differences in preferred codon usage are illustrated below for *Agrobacterium tumefaciens* (a bacterium), *A. thaliana*, *M. sativa* (two dicotyledonous plants) and *Oryza sativa* (a monocotyledous plant). These examples were extracted from (http://.kazusa.or.jp/codon). To give one example, the codon GGC (for glycine) is the most frequently used codon in *A. tumefaciens* (36.2), is the second most frequently used codon in *O. sativa* but is used at much lower frequencies in *A. thaliana* and *M. sativa* (9% and 8.4%, respectively). Of the four possible codons encoding glycine. (see Table 6), said GGC codon is most preferably used in *A. tumefaciens* and *O. sativa*. However, in *A. thaliana* this is the GGA (and GGU) codon whereas in *M. sativa* this is the GGU (and GGA) codon.

"Hybridization" is the process wherein substantially homologous complementary nucleotide sequences anneal to each other. The hybridization process can occur entirely in solution, i.e. both complementary nucleic acids are in solution. Tools in molecular biology relying on such a process include the polymerase chain reaction (PCR; and all methods based thereon), subtractive hybridization, random primer extension, nuclease S1 mapping, primer extension, reverse transcription, cDNA synthesis, differential display of RNAs, and DNA sequence determination. The hybridization process can also occur with one of the-complementary nucleic acids immobilized to a matrix such as magnetic beads, Sepharose beads or any other resin. Tools in molecular biology relying on such a process include the isolation of poly (A+) mRNA. The hybridization process can furthermore occur with one of the complementary nucleic acids immobilized to a solid support such as a nitrocellulose or nylon membrane or immobilized by e.g. photolitography to e.g. a silicious glass support (the latter known as nucleic acid arrays or microarrays or as nucleic acid chips). Tools in molecular biology relying on such a process include RNA and DNA gel blot analysis, colony hybridization, plaque hybridization, in situ hybridization and microarray hybridization. In order to allow hybridization to occur, the nucleic acid molecules are generally thermally or chemically denatured to melt a double strand into two single strands and/or to remove hairpins or other secondary structures from single stranded nucleic acids. The stringency of hybridization is influenced by conditions such as temperature, salt concentration and hybridization buffer composition. High stringency conditions for hybridization include high temperature and/or low salt concentration (salts include NaCl and $Na_3$-citrate) and/or the inclusion of formamide in the hybridization buffer and/or lowering the concentration of compounds such as SDS (detergent) in the hybridization buffer and/or exclusion of compounds such as dextran sulfate or polyethylene glycol (promoting molecular crowding) from the hybridization buffer. Conventional hybridization conditions are described in e.g. Sambrook et al. (1989) but the skilled craftsman will appreciate that numerous different hybridization conditions can be designed in function of the known or the expected homology and/or length of the nucleic acid sequence. Sufficiently low stringency hybridization conditions are particularly preferred to isolate nucleic acids heterologous to the DNA sequences of the invention defined supra. Elements contributing to said heterology include allelism, degeneration of the genetic code and differences in preferred codon usage as discussed supra.

Clearly, the current invention embodies the use of the inventive DNA sequences encoding a HOBBIT or mutant HOBBIT protein, homologue, derivative and/or immunologically fragment thereof as defined higher in any method of hybridization. The current invention furthermore also relates to DNA sequences hybridizing to said inventive DNA sequences. DNA sequences as defined in the current invention can be interrupted by intervening sequences. With "intervening sequences" is meant any nucleic acid sequence which disrupts a coding sequence comprising said inventive DNA sequence or which disrupts the expressible format of a DNA sequence comprising said inventive DNA sequence. Removal of the intervening sequence restores said coding sequence or said expressible format. Examples of intervening sequences include introns, mobilizable DNA sequences such as transposons and DNA tags such as e.g. a T-DNA. With "mobilizable DNA. sequence" is meant any DNA sequence that can be mobilized as the result of a recombination event.

TABLE 2

Degeneracy of the genetic code.

| Amino Acid | Three-letter code | One-letter code | Possible codons | | | | | |
|---|---|---|---|---|---|---|---|---|
| Alanine | Ala | A | GCA | GCC | GCG | GCU | | |
| Arginine | Arg | R | AGA | AGG | CGA | CGC | CGG | CGU |
| Asparagine | Asn | N | AAC | AAU | | | | |
| Aspartic Acid | Asp | D | GAC | GAU | | | | |
| Cysteine | Cys | C | UGC | UGU | | | | |
| Glutamic Acid | Glu | E | GAA | GAG | | | | |
| Glutamine | Gln | Q | CAA | CAG | | | | |
| Glycine | Gly | G | GGA | GGC | GGG | GGU | | |

TABLE 2-continued

Degeneracy of the genetic code.

| Amino Acid | Three-letter code | One-letter code | Possible codons | | | | | |
|---|---|---|---|---|---|---|---|---|
| Histidine | His | H | CAC | CAU | | | | |
| Isoleucine | Ile | I | AUA | AUC | AUU | | | |
| Leucine | Leu | L | UUA | UUG | CUA | CUC | CUG | CUU |
| Lysine | Lys | K | AAA | AAG | | | | |
| Methionine | Met | M | AUG | | | | | |
| Phenylalanine | Phe | F | UUC | UUU | | | | |
| Proline | Pro | P | CCA | CCC | CCG | CCU | | |
| Serine | Ser | S | AGC | AGU | UCA | UCC | UCG | UCU |
| Threonine | Thr | T | ACA | ACC | ACG | ACU | | |
| Tryptophan | Trp | W | UGG | | | | | |
| Tyrosine | Tyr | Y | UAC | UAU | | | | |
| Valine | Val | V | GUA | GUC | GUG | GUU | | |
| Possible "STOP" codons | | | | | | | | |
| | | | UAA | UAG | UGA | | | |

To effect expression of a protein in a cell, tissue or organ, preferably of plant origin, either the protein may be introduced directly to said cell, such as by microinjection or ballistic means or alternatively, an isolated nucleic acid molecule encoding said protein may be introduced into said cell, tissue or organ in an expressible format.

Preferably, the DNA sequence of the invention comprises a coding sequence or open reading frame (ORF) encoding a HOBBIT or mutant HOBBIT protein or a homologue or derivative thereof or an immunologically active thereof as defined supra. The preferred protein of the invention comprises the amino acid sequence of said HOBBIT or mutant HOBBIT protein.

With "vector" or "vector sequence" is meant a DNA sequence which can be introduced in an organism by transformation and can be stably maintained in said organism. Vector maintenance is possible in e.g. cultures of Escherichia coli, A. tumefaciens, Saccharomyces cerevisiae or Schizosaccharomyces pombe. Other vectors such as phagemids and cosmid vectors can be maintained and multiplied in bacteria and/or viruses. Vector sequences generally comprise a set of unique sites recognized by restriction enzymes, the multiple cloning site (MCS), wherein one or more non-vector sequence(s) can be inserted.

With "non-vector sequence" is accordingly meant a DNA sequence which is integrated in one or more of the sites of the MCS comprised within a vector.

"Expression vectors" form a subset of vectors which, by virtue of comprising the appropriate regulatory sequences enabling the creation of an expressible format for the inserted non-vector sequence(s), thus allowing expression of the protein encoded by said non-vector sequence(s). Expression vectors are known in the art enabling protein expression in organisms including bacteria (e.g. E. coli), fungi (e.g. S. cerevisiae, S. pombe, Pichia pastoris), insect cells (e.g. baculoviral expression vectors), animal cells (e.g. COS or CHO cells) and plant cells (e.g. potato virus X-based expression vectors, see e.g. Vance et al. 1998—WO9844097).

The current invention clearly includes any vector or expression vector comprising a non-vector DNA sequence encoding a HOBBIT or mutant HOBBIT protein, homologue, derivative and/or immunologically active fragment thereof as defined supra.

As an alternative to expression vector-mediated protein production in biological systems, chemical protein synthesis can be applied. Synthetic peptides can be manufactured in solution phase or in solid phase. Solid phase peptide synthesis (Merrifield 1963) is, however, the most common way and involves the sequential addition of amino acids to create a linear peptide chain. Solid phase peptide synthesis includes cycles consisting of three steps: (i) immobilization of the carboxy-terminal amino acid of the growing peptide chain to a solid support or resin; (ii) chain assembly, a process consisting of activation, coupling and deprotection of the amino acid to be added to the growing peptide chain; and (iii) cleavage involving removal of the completed peptide chain from the resin and removal of the protecting groups from the amino acid side chains. Common approaches in solid phase peptide synthesis include Fmoc/tBu (9-fluorenylmethyloxycarbonyl/t-butyl) and Boc (t-butyloxycarbonyl) as the amino-terminal protecting groups of amino acids. Amino acid side chain protecting groups include methyl (Me), formyl (CHO), ethyl (Et), acetyl (Ac), t-butyl (t-Bu), anisyl, benzyl (Bzl), trifluoroacetyl (Tfa), N-hydroxysuccinimide (ONSu, OSu), benzoyl (Bz), 4-methylbenzyl (Meb), thioanizyl, thiocresyl, benzyloxymethyl (Bom), 4-nitrophenyl (ONp), benzyloxycarbonyl (Z), 2-nitrobenzoyl (NBz), 2-nitrophenylsulphenyl (Nps), 4-toluenesulphonyl (Tosyl, Tos), pentafluorophenyl (Pfp), diphenylmethyl (Dpm), 2-chlorobenzyloxycarbonyl (Cl—Z), 2,4,5-trichlorophenyl, 2-bromobenzyloxycarbonyl (Br—Z), tripheylmethyl (Trityl, Trt), and 2,5,7,8-pentamethyl-chroman-6-sulphonyl (Pmc). During chain assembly, Fmoc or Boc are removed resulting in an activated amino-terminus of the amino acid residue bound to the growing chain. The carboxy-terminus of the incoming amino acid is activated by conversion into a highly reactive ester, e.g. by HBTU. With current technologies (e.g. PerSeptive Biosystems 9050 synthesizer, Applied Biosystems Model 431A Peptide Synthesizer), linear peptides of up to 50 residues can be manufactured. A number of guidelines is available to produce peptides that are suitable for use in biological systems including (i) limiting the use of difficult amino acids such as cys, met, trp (easily oxidized and/or degraded during peptide synthesis) or arg; (ii) minimize hydrophobic amino acids (can impair peptide solubility); and (iii) prevent an amino-terminal glutamic acid (can cyclize to pyroglutamate).

By "expressible format" is meant that the isolated nucleic acid molecule is in a form suitable for being transcribed into mRNA and/or translated to produce a protein, either constitutively or following induction by an intracellular or extracellular signal, such as an environmental stimulus or stress (mitogens, anoxia, hypoxia, temperature, salt, light, dehydration, etc) or a chemical compound such as IPTG (isopropyl-β-D-thiogalactopyranoside) or such as an antibiotic (tetracycline, ampicillin, rifampicin, kanamycin), hormone (e.g. gibberellin, auxin, cytokinin, glucocorticoids, brassinosteroid, ethylene, abscisic acid etc), hormone analogue (iodoacetic acid (IAA), 2,4-D, etc), metal (zinc, copper, iron, etc), or dexamethasone, amongst others. As will be known to those skilled in the art, expression of a functional protein may also require one or more posts-translational modifications, such as glycosylation, phosphorylation, dephosphorylation, or one or more protein-protein interactions, amongst others. All such processes are included within the scope of the term "expressible format".

Preferably, expression of a protein in a specific cell, tissue, or organ, preferably of plant origin, is effected by introducing and expressing an isolated nucleic acid molecule encoding said protein, such as a cDNA molecule, genomic gene, synthetic oligonucleotide molecule, mRNA molecule or open reading frame, to said cell, tissue or organ, wherein said nucleic acid molecule is placed operably in connection with suitable regulatory sequences including a promoter, preferably a plant-expressible promoter, and a terminator sequence.

Reference herein to a "promoter" is to be taken in its broadest context and includes the transcriptional regulatory sequences derived from a classical eukaryotic genomic gene, including the TATA box which is required for accurate transcription initiation, with or without a CCAAT box sequence and additional regulatory elements (i.e. upstream activating sequences, enhancers and silencers) which alter gene expression in response to developmental and/or external stimuli, or in a tissue-specific manner.

The term "promoter" also includes the transcriptional regulatory sequences of a classical prokaryotic gene, in which case it may include a −35 box sequence and/or a −10 box transcriptional regulatory sequences.

The term "promoter" is also used to describe a synthetic or fusion molecule, or derivative which confers, activates or enhances expression of a nucleic acid molecule in a cell, tissue or organ.

Promoters may contain additional copies of one or more specific regulatory elements, to further enhance expression and/or to alter the spatial expression and/or temporal expression of a nucleic acid molecule to which it is operably connected. Such regulatory elements may be placed adjacent to a heterologous promoter sequence to drive expression of a nucleic acid molecule in response to e.g. copper, glucocorticoids, dexamethasone, tetracycline, gibberellin, cAMP, abscisic acid, auxin, wounding, ethylene, jasmonate or salicylic acid or to confer expression of a nucleic acid molecule to specific cells, tissues or organs such as meristems, leaves, roots, embryo, flowers, seeds or fruits. In the context of the present invention, the promoter preferably is a plant-expressible promoter sequence. Promoters, however, that also function or solely function in non-plant cells such as bacteria, yeast cells, insect cells and animal cells are not excluded from the invention. By "plant-expressible" is meant that the promoter sequence, including any additional regulatory elements added thereto or contained therein, is at least capable of inducing, conferring, activating or enhancing expression in a plant cell, tissue or organ, preferably a monocotyledonous or dicotyledonous plant cell, tissue, or organ.

The terms "plant-operable" and "operable in a plant" when used herein, in respect of a promoter sequence, shall be taken to be equivalent to a plant-expressible promoter sequence.

In the present context, a "regulatable promoter sequence" is a promoter that is capable of conferring expression on a structural gene in a particular cell, tissue, or organ or group of cells, tissues or organs of a plant, optionally under specific conditions, however does generally not confer expression throughout the plant under all conditions. Accordingly, a regulatable promoter sequence may be a promoter sequence that confers expression on a gene to which it is operably connected in a particular location within the plant or alternatively, throughout the plant under a specific set of conditions, such as following induction of gene expression by a chemical compound or other elicitor.

Preferably, the regulatable promoter used in the performance of the present invention confers expression in a specific location within the plant, either constitutively or following induction, however not in the whole plant under any circumstances. Included within the scope of such promoters are cell-specific promoter sequences, tissue-specific promoter sequences, organ-specific promoter sequences, cell cycle specific gene promoter sequences, inducible promoter sequences and constitutive promoter sequences that have been modified to confer expression in a particular part of the plant at any one time, such as by integration of said constitutive promoter within a transposable genetic element (Ac, Ds, Spm, En, or other transposon).

The term "cell-specific" shall be taken to indicate that expression is predominantly in a particular cell or cell-type, preferably of plant origin, albeit not necessarily exclusively in said cell or cell-type.

Similarly, the term "tissue-specific" shall be taken to indicate that expression is predominantly in a particular tissue or tissue-type, preferably of plant origin, albeit not necessarily exclusively in said tissue or tissue-type.

Similarly, the term "organ-specific" shall be taken to indicate what expression is predominantly in a particular organ, preferably of plant origin, albeit not necessarily exclusively in said organ.

Similarly, the term "cell cycle specific" shall be taken to indicate that expression is predominantly cyclic and occurring in one or more, not necessarily consecutive phases of the cell cycle albeit not necessarily exclusively in cycling cells, preferably of plant origin. Those skilled in the art will be aware that an "inducible promoter" is a promoter the transcriptional activity of which is increased or induced in response to a developmental, chemical, environmental, or physical stimulus. Similarly, the skilled craftsman will understand that a "constitutive promoter" is a promoter that is transcriptionally active throughout most, but not necessarily all parts of an organism, preferably a plant, during most, but not necessarily all phases of its growth and development.

Those skilled in the art will readily be capable of selecting appropriate promoter sequences for use in regulating appropriate expression of the HOBBIT or mutant HOBBIT protein as described supra from publicly-available or readily-available sources, without undue experimentation.

Placing a nucleic acid molecule under the regulatory control of a promoter sequence, or in operable connection with a promoter sequence, means positioning said nucleic acid molecule such that expression is controlled by the promoter sequence. A promoter is usually, but not necessarily, positioned upstream, or at the 5'-end, and within 2 kb of the start site of transcription, of the nucleic acid molecule which it regulates. In the construction of heterologous promoter/structural gene combinations it is generally preferred to position the promoter at a distance from the gene transcription start site that is approximately the same as the distance between that promoter and the gene it controls in its natural setting (i.e., the gene from which the promoter is derived). As is known in the art, some variation in this distance can be accommodated without loss of promoter function. Similarly, the preferred positioning of a regulatory sequence element with respect to a heterologous gene to be placed under its control is defined by the positioning of the element in its natural setting (i.e., the gene from which it is derived). Again, as is known in the art, some variation in this distance can also occur.

Examples of promoters suitable for use in gene constructs of the present invention include those listed in Table 3, amongst others. The promoters listed in Table 3 are provided for the purposes of exemplification only and the present invention is not to be limited by the list provided therein. Those skilled in the art will readily be in a position to provide additional promoters that are useful in performing the present invention.

In the case of constitutive promoters or promoters that induce expression throughout the entire plant, it is preferred that such sequences are modified by the addition of nucleotide sequences derived from one or more of the tissue-specific promoters listed in Table 8, or alternatively, nucleotide sequences derived from one or more of the above-mentioned tissue-specific inducible promoters, to confer tissue-specificity thereon. For example, the CaMV 35S promoter may be modified by the addition of maize Adh1 promoter sequence, to confer anaerobically-regulated root-specific expression thereon, as described previously (Ellis et al., 1987). Another example describes conferring root specific or root abundant gene expression by fusing the CaMV35S promoter to elements of the maize glycine-rich protein GRP3 gene (Feix and Wulff 2000—WO0015662). Such modifications can be achieved by routine experimentation by those skilled in the art.

The term "terminator" refers to a DNA sequence at the end of a transcriptional unit which signals termination of transcription. Terminators are 3'-non-translated DNA sequences containing a polyadenylation signal, which facilitates the addition of polyadenylate sequences to the 3'-end of a primary transcript. Terminators active in cells derived from viruses, yeasts, moulds, bacteria, insects, birds, mammals and plants are known and described in the literature. They may be isolated from bacteria, fungi, viruses, animals and/or plants.

Examples of terminators particularly suitable for use in the gene constructs of the present invention include the *Agrobacterium tumefaciens* nopaline synthase (NOS) gene terminator, the *Agrobacterium tumefaciens* octopine synthase (OCS) gene terminator sequence, the Cauliflower mosaic virus (CaMV) 35S gene terminator sequence, the *Oryza sativa* ADP-glucose pyrophosphorylase terminator sequence (t3'Bt2), the *Zea mays* zein gene terminator sequence, the rbcs-1A gene terminator, and the rbcs-3A gene terminator sequences, amongst others.

TABLE 3

Exemplary plant-operable promoters for use in the performance of the present Invention

I: CELL-SPECIFIC, TISSUE-SPECIFIC, AND ORGAN-SPECIFIC PROMOTERS

| GENE SOURCE | EXPRESSION PATTERN | REFERENCE |
| --- | --- | --- |
| α-amylase (Amy32b) | aleurone | Lanahan et al, Plant Cell 4: 203-211, 1992; Skriver et al, Proc Natl Acad Sci U.S.A. 88: 7266-7270, 1991 |
| cathepsin β-like gene | aleurone | Cejudo et al, Plant Mol Biol 20: 849-856, 1992 |
| *Agrobacterium rhizogenes* rolB | cambium | Nilsson et al, Physiol Plant 100: 456-462, 1997 |
| AtPRP4 | flowers | http://salus.medium.edu/mmg/tierney/html |
| chalcone synthase (chsA) | flowers | Van der Meer et al, Plant Mol Biol 15: 95-109, 1990 |
| LAT52 | anther | Twell et al, Mol Gen Genet 217: 240-245, 1989 |
| apetala-3 | flowers | |
| chitinase | fruit (berries, grapes, etc) | Thomas et al. CSIRO Plant Industry, Urrbrae, South Australia, Australia; http://winetitles.com.au/gwrdc/csh95-1.html |
| rbcs-3A | green tissue (eg leaf) | Lam et al, Plant Cell 2: 857-866, 1990; Tucker et al., Plant Physiol 113: 1303-1308, 1992 |
| leaf-specific genes | leaf | Baszczynski et al, Nucl Acid Res 16: 4732, 1988 |
| AtPRP4 | leaf | http://salus.medium.edu/mmg/tierney/html |
| chlorella virus adenine methyltransferase gene promoter | leaf | Mitra and Higgins, Plant Mol Biol 26: 85-93, 1994 |
| aldP gene promoter from rice | leaf | Kagaya et al, Mol Gen Genet 248: 668-674, 1995 |
| rbcs promoter from rice or tomato | leaf | Kyozuka et al, Plant Physiol 102: 991-1000, 1993 |
| Pinus cab-6 | leaf | Yamamoto et al, Plant Cell Physiol 35: 773-778, 1994 |
| rubisco promoter | leaf | |
| cab (chlorophyll a/b/binding protein | leaf | |
| pea Blec4 gene | vegetative and floral epidermal tissues | Mandaci and Dobres, Plant Mol Biol 34: 961-965 |
| SAM22 | senescent leaf | Crowell et al, Plant Mol Biol 18: 459-466, 1992 |
| ltp gene (lipid transfer gene) | | Fleming et al, Plant J 2: 855-862, 1992 |
| *R. japonicum* nif gene | nodule | U.S. Pat. No. 4 803165 |
| *B. japonicum* nifH gene | nodule | U.S. Pat. No. 5008194 |
| GmENOD40 | nodule | Yang et al, Plant J 3: 573-585, 1993 |
| PEP carboxylase (PEPC) | nodule | Pathirana et al, Plant Mol Biol 20: 437-450, 1992 |

TABLE 3-continued

Exemplary plant-operable promoters for use
in the performance of the present Invention

| | | |
|---|---|---|
| leghaemoglobin (Lb) | nodule | Gordon et al, J Exp Bot 44: 1453-1465, 1993 |
| Tungro bacilliform virus gene | phloem | Bhattacharyya-Pakrasi et al, Plant J 4: 71-79, 1992 |
| pollen-specific genes | pollen; microspore | Albani et al, Plant Mol Biol 15: 605, 1990; Albani et al, Plant Mol Biol 16: 501, 1991 |
| Zm13 | pollen | Guerrero et al, Mol Gen Genet 224: 161-168, 1993 |
| apg gene | microspore | Twell et al, Sex Plant Reprod 6: 217-224, 1993 |
| maize pollen-specific gene | pollen | Hamilton et al, Plant Mol Biol 18: 211-218, 1992 |
| sunflower pollen-expressed gene | pollen | Baltz et al, Plant J 2: 713-721, 1992 |
| *B. napus* pollen-specific gene | pollen; anther; tapetum | Arnoldo et al, J Cell Biochem, Abstract No. Y101, 204, 1992 |
| root-expressible genes | roots | Tingey et al, EMBO J 6: 1, 1987 |
| tobacco auxin-inducible gene | root tip | Van der Zaal et al, Plant Mol Biol 16: 983, 1991 |
| β-tubulin | root | Oppenheimer et al, Gene 63: 87, 1988 |
| tobacco root-specific genes | root | Conkling et al, Plant Physiol 93: 1203, 1990 |
| *B. napus* G1-3b gene | root | U.S. Pat. No. 5401836 |
| SbPRP1 | roots | Suzuki et al, Plant Mol Biol 21: 109-119, 1993 |
| AtPRP1; AtPRP3 | roots; root hairs | http://salus.medium.edu/mmg/tierney/html |
| RD2 gene | root cortex | http://2.cnsu.edu/ncsu/research |
| TobRB7 gene | root vasculature | http://2.cnsu.edu//ncsu/research |
| AtPRP4 | leaves; flowers; lateral root primordia | http://salus.medium.edu/mmg/tierney/html |
| seed-specific genes | seed | Simon et al, Plant Mol Biol 5: 191, 1985; Scofield et al, J Biol Chem 262: 12202, 1987; Baszczynski et al, Plant Mol Biol 14: 633, 1990 |
| Brazil Nut albumin | seed | Pearson et al, Plant Mol Biol 18: 235-245, 1992 |
| legumin | seed | Ellis et al, Plant Mol Biol 10: 203-214, 1988 |
| glutelin (rice) | seed | Takaiwa et al, Mol Gen Genet 208: 15-22, 1986; Takaiwa et al, FEBS Lett 221: 43-47, 1987 |
| zein | seed | Matzke et al, Plant Mol Biol 14: 323-32 1990 |
| napA | seed | Stalberg et al, Planta 199: 515-519, 1996 |
| wheat LMW and HMW glutenin-1 | endosperm | Mol Gen Genet 216: 81-90, 1989; Nucl Acids Res 17: 461-462, 1989 |
| wheat SPA | seed | Albani et al, Plant Cell 9: 171-184, 1997 |
| cZ19B1, maize 19 kDa zein | seed | WO0011177 |
| mi1ps, maize myoinositol-1-Pi synthase | seed | WO0011177 |
| wheat α, β, γ-gliadins | endosperm | EMBO J 3: 1409-1415, 1984 |
| barley ltr1 promoter | endosperm | |
| barley B1, C, D, hordein | endosperm | Theor Appl Gen 98: 1253-1262, 1999; Plant J 4: 343-355, 1993; Mol Gen Genet 250: 750-60, 1996 |
| barley DOF | endosperm | Mena et al, Plant J 116: 53-62, 1998 |
| blz2 | endosperm | EP99106056.7 |
| synthetic promoter | endosperm | Vicente-Carbajosa et al, Plant J 13: 629-640, 1998 |
| rice prolamin NRP33 | endosperm | Wu et al, Plant Cell Physiol 39: 885-889, 1998 |
| rice α-globulin Glb-1 | endosperm | Wu et al, Plant Cell Physiol 39: 885-889, 1998 |
| maize END genes | endosperm | WO0012733 |
| barley END1 | endosperm | WO9808961 |
| barley NUC1 | nucellus | WO9808961 |
| rice OSH1 | embryo | Sato et al, Proc Natl Acad Sci U.S.A. 93: 8117-8122, 1996 |
| rice α-globulin REB/OHP-1 | endosperm | Nakase et al, Plant Mol Biol 33: 513-522, 1997 |
| rice ADP-glucose PP | endosperm | Trans Res 6: 157-168, 1997 |

TABLE 3-continued

Exemplary plant-operable promoters for use
in the performance of the present Invention

| | | |
|---|---|---|
| maize ESR gene family | endosperm | Plant J 12: 235-246, 1997 |
| sorgum γ-kafirin | endosperm | Plant Mol Biol 32: 1029-1035, 1996 |
| KNOX | embryo | Postma-Haarsma et al, Plant Mol Biol 39: 257-271, 1999 |
| rice oleosin | embryo and aleuron | Wu et al, J Biochem 123: 386, 1998 |
| sunflower oleosin | seed (embryo and dry seed) | Cummins et al, Plant Mol Biol 19: 873-876; 1992 |
| LEAFY | shoot meristem | Weigel et al, Cell 69: 843-859, 1992 |
| *Arabidopsis thaliana* knat1 | shoot meristem | Accession number AJ131822 |
| *Malus domestica* kn1 | shoot meristem | Accession number Z71981 |
| CLAVATA1 | shoot meristem | Accession number AF049870 |
| stigma-specific genes | stigma | Nasrallah et al, Proc Natl Acad Sci U.S.A. 85: 5551, 1988; Trick et al, Plant Mol Biol 15: 203, 1990 |
| class I patatin gene | tuber | Liu et al, Plant Mol Biol 153: 386-395, 1991 |
| PCNA rice | meristem | Kosugi et al, Nucl Acids Res 19: 1571-1576, 1991; Kosugi and Ohashi, Plant Cell 9: 1607-1619, 1997 |
| Pea TubA1 tubulin | Dividing cells | Stotz and Long, Plant Mol Biol 41: 601-614, 1999 |
| Arabidopsis cdc2a | cycling cells | Chung and Parish, FEBS Lett 362: 215-219, 1995 |
| Arabidopsis Rop1A | Anthers; mature pollen + pollen tubes | Li et al, Plant Physiol 118: 407-417, 1998 |
| Arabidopsis AtDMC1 | Meiosis-associated | Klimyuk and Jones, Plant J 11: 1-14, 1997 |
| Pea PS-IAA4/5 and PS-IAA6 | Auxin-inducible | Wong et al, Plant J 9: 587-599, 1996 |
| Pea farnesyltransferase | Meristematic tissues; phloem near growing tissues; light- and sugar-repressed | Zhou et al, Plant J 12: 921-930, 1997 |
| Tobacco (*N. sylvestris*) cyclin B1; 1 | Dividing cells/ meristematic tissue | Trehin et al, Plant Mol.Biol. 35: 667-672, 1997 |
| *Catharanthus roseus* Mitotic cyclins CYS (A-type) and CYM (B-type) | Dividing cells/ meristematic tissue | Ito et al, Plant J 11: 983-992, 1997 |
| Arabidopsis cyc1At (=cyc B1; 1) and cyc3aAt (A-type) | Dividing cells/ meristematic tissue | Shaul et al, Proc Natl Acad Sci U.S.A. 93: 4868-4872, 1996 |
| Arabidopsis tef1 promoter box | Dividing cells/ meristematic tissue | Regad et al, Mol Gen Genet 248: 703-711, 1995 |
| *Catharanthus roseus* cyc07 | Dividing cells/ meristematic tissue | Ito et al, Plant Mol Biol 24: 863-878, 1994 |
| II: EXEMPLARY CONSTITUTIVE PROMOTERS | | |
| Actin | constitutive | McElroy et al, Plant Cell 2: 163-171, 1990 |
| CAMV 35S | constitutive | Odell et al, Nature 313: 810-812, 1985 |
| CaMV 19S | constitutive | Nilsson et al, Physiol Plant 100: 456-462, 1997 |
| GOS2 | constitutive | de Pater et al, Plant J 2: 837-844, 1992 |
| ubiquitin | constitutive | Christensen et al, Plant Mol Biol 18: 675-689, 1992 |
| rice cyclophilin | constitutive | Buchholz et al, Plant Mol Biol 25: 837-843, 1994 |
| maize histone H3 | constitutive | Lepetit et al, Mol Gen Genet 231: 276-285, 1992 |
| alfalfa histone H3 | constitutive | Wu et al, Nucleic Acids Res 17: 3057-3063, 1989; Wu et al, Plant Mol Biol 11: 641-649, 1988 |
| actin 2 | constitutive | An et al, Plant J 10: 107-121, 1996 |
| III: EXEMPLARY STRESS-INDUCIBLE PROMOTERS | | |
| NAME | STRESS | REFERENCE |
| P5CS (delta(1)-pyrroline-5-carboxylate syntase) | salt, water | Zhang et al, Plant Sci 129: 81-89, 1997 |
| cor15a | cold | Hajela et al, Plant Physiol 93: 1246-1252, 1990 |

TABLE 3-continued

Exemplary plant-operable promoters for use in the performance of the present Invention

| Name | Condition | Reference |
|---|---|---|
| cor15b | cold | Wlihelm et al, Plant Mol Biol 23: 1073-1077, 1993 |
| cor15a (−305 to +78 nt) | cold, drought | Baker et al, Plant Mol Biol 24: 01-713, 1994 |
| rd29 | salt, drought, cold | Kasuga et al, Nature Biotechnol 18: 287-291, 1999 |
| heat shock proteins, including artificial promoters containing the heat shock element (HSE) | heat | Barros et al, Plant Mol Biol 19 665-75, 1992. Marrs et al, Dev Genet 14: 27-41, 1993. Schoffl et al, Mol Gen Genet 217: 246-53, 1989. |
| smHSP (small heat shock proteins) | heat | Waters et al, J Exp Bot 47: 325-338, 1996 |
| wcs120 | cold | Ouellete et al, FEBS Lett 423: 324-328, 1998 |
| ci7 | cold | Kirch et al, Plant Mol Biol 33: 897-909, 1997 |
| Adh | cold, drought, hypoxia | Dolferus et al, Plant Physiol 105: 1075-87, 1994 |
| pwsi18 | salt and drought | Joshee et al, Plant Cell Physiol 39: 64-72, 1998 |
| ci21A | Cold | Schneider et al, Plant Physiol 113: 335-45, 1997 |
| Trg-31 | Drought | Chaudhary et al, Plant Mol Biol 30: 1247-57, 1996 |
| osmotin | Osmotic | Raghothama et al, Plant Mol Biol 23: 1117-28, 1993 |
| lapA | wounding, enviromental | WO99/03977 University of California/INRA |

IV: EXEMPLARY PATHOGEN-INDUCIBLE PROMOTERS

| NAME | PATHOGEN | REFERENCE |
|---|---|---|
| RB7 | Root-knot nematodes (Meloidogyne spp.) | US5760386 - North Carolina State University; Opperman et al, Science 263: 221-23, 1994 |
| PR-1, 2, 3, 4, 5, 8, 11 | fungal, viral, bacterial | Ward et al, Plant Cell 3: 1085-1094, 1991; Reiss et al 1996; Lebel et al, Plant J 16: 223-233, 1998; Melchers et al, Plant J 5: 469-480, 1994; Lawton et al, Plant Mol Biol, 19: 735-743, 1992 |
| HMG2 | nematodes | WO9503690 - Virginia Tech Intellectual Properties Inc. |
| Abi3 | Cyst nematodes (Heterodera spp.) | Unpublished |
| ARM1 | nematodes | Barthels et al, Plant Cell 9: 2119-2134, 1997<br>WO 98/31822 - Plant Genetic Systems |
| Att0728 | nematodes | Barthels et al, Plant Cell 9: 2119-2134, 1997<br>PCT/EP98/07761 |
| Att1712 | nematodes | Barthels et al, Plant Cell 9, 2119-2134, 1997<br>PCT/EP98/07761 |
| Gst1 | Different types of pathogens | Strittmatter et al, Mol Plant-Microbe Interact 9: 68-73, 1996 |
| LEMMI | nematodes | WO 92/21757 - Plant Genetic Systems |
| CLE | Geminivirus | PCT/EP99/03445 - CINESTAV |
| PDF1.2 | Fungal including *Alternaria brassicicola* and *Botrytis cinerea* | Manners et al, Plant Mol Biol, 38: 1071-1080, 1998 |
| Thi2.1 | Fungal - *Fusarium oxysporum* f sp. matthiolae | Vignutelli et al, Plant J 14: 285-295, 1998 |
| DB#226 | nematodes | Bird and Wilson, Mol Plant-Microbe Interact 7: 419-442, 1994<br>WO 95.322888 |
| DB#280 | nematodes | Bird and Wilson, Mol Plant-Microbe Interact 7: 419-442, 1994<br>WO 95.322888 |
| Cat2 | nematodes | Niebel et al; Mol Plant-Microbe Interact 8: 371-378, 1995 |
| ☐Tub | nematodes | Aristizabal et al (1996), 8th International Congress on Plant-Microbe Interaction, Knoxville U.S. B-29 |

TABLE 3-continued

Exemplary plant-operable promoters for use
in the performance of the present Invention

| | | |
|---|---|---|
| sHSP | nematodes | Fenoll et al (1997) In: Cellular and molecular aspects of plant-nematode interactions. Kluwer Academic, C. Fenoll, F. M. W. Grundler and S. A. Ohl (Eds.), |
| Tsw12 | nematodes | Fenoll et al (1997) In: Cellular and molecular aspects of plant-nematode interactions. Kluwer Academic, C. Fenoll, F. M. W. Grundler and S. A. Ohl (Eds.) |
| Hs1 (pro1) | nematodes | WO 98/122335 - Jung |
| nsLTP | viral, fungal, bacterial | Molina and Garcia-Olmedo FEBS Lett, 316: 119-122, 1993 |
| RIP | viral, fungal | Turner et al, Proc Natl Acad Sci U.S.A. 94: 3866-3871, 1997 |

V: EXEMPLARY LIGHT-INDUCIBLE PROMOTERS

| NAME | EXPRESSION PATERN | REFERENCE |
|---|---|---|
| Arabidopsis Athb-2 | by changes red/far-red light ratios | Carabelli et al, Proc Natl Acad Sci U.S.A. 93: 3530-3535 |
| Arabidopsis Athb-4 | far-red light | Carabelli et al, Plant J 4: 469-479 |
| rice rbcS | light | Kyozuka et al 1993, Plant Physiol 102: 991-1000 |
| rice CAB | light | Tada et al 1991, EMBO J 10: 1803-1808 |
| Lemna SSU5B (rbcS) | red light | Rolfe and Tobin 1991, Proc Natl Acad Sci U.S.A. 88: 2683-2686 |
| pea rbcS-3A promoter fragment | red light | Gilmartin and Chua 1990, Mol Cell Biol 10: 5565-5568 |
| pea glutamine synthetase GS2 | photorespiration and light | Tjaden et al 1995, Plant Physiol 108: 1109-1117 |
| bean nitrite reductase | nitrate and light | Sander et al. 1995, Plant Mol Biol 27: 165-177 |
| barley psbD-psdC | blue light/UV-A | Christopher and Mullet 1994, Plant Physiol 104: 1119-1129 |
| Arabidopsis PHYB | far-red light | Wester et al 1994, Plant J 5: 261-272 |
| mung bean AR2 | light | Mizutani and Ohta 1998, Plant Physiol 116: 357-367 |
| maize CAB-M1 | light/Ca2+ | Shiina et al 1997, Plant Physiol 115: 477-483 |
| Arabidopsis photolyase | visible light/UV-light | Sakamoto et al 1998, DNA Seq 9: 335-340 |
| Arabidopsis CHS | UV-B/UV-A/blue light | Hartmann et al 1998, Plant Mol Biol 36: 741-754 |
| Arabidopsis Lhcb1*3 | blue light | Tilghman et al 1997, Plant Mol Biol 35: 293-302 |
| pea Lhcb1*4 | blue light | Tilghman et al 1997, Plant Mol Biol 35: 293-302 |

Those skilled in the art will be aware of additional promoter sequences and terminator sequences which may be suitable for use in performing the invention. Such sequences may readily be used without any undue experimentation.

In the context of the current invention, "ectopic expression" or "ectopic overexpression" of a gene or a protein are conferring to expression patterns and/or expression levels of said gene or protein normally not occurring under natural conditions. Ectopic expression can be achieved in a number of ways including operably linking of a coding sequence encoding said protein to an isolated homologous or heterologous promoter in order to create a chimeric gene and/or operably linking said coding sequence to its own isolated promoter (i.e. the unisolated promoter naturally driving expression of said protein) in order to create a recombinant gene duplication or gene multiplication effect.

Preferably, the promoter sequence used in the context of the present invention is operably linked to a coding sequence or open reading frame (ORF) encoding a HOBBIT or mutant HOBBIT protein or a homologue, derivative and/or an immunologically active fragment thereof as defined supra.

"Downregulation of expression" as used herein means lowering levels of gene expression and/or levels of active gene product and/or levels of gene product activity. Decreases in expression may be accomplished by e.g. the addition of coding sequences or parts thereof in a sense orientation (if resulting in co-suppression) or in an antisense orientation relative to a promoter sequence and furthermore by e.g. insertion mutagenesis (e.g. T-DNA insertion or transposon insertion) or by gene silencing strategies as described by e.g. Angell and Baulcombe (1998—WO9836083), Lowe et al. (1989—WO9853083), Lederer et al. (1999—WO9915682) or Wang et al. (1999—WO9953050). Genetic constructs aimed at silencing gene expression may have the nucleotide sequence of said gene (or one or more parts thereof) contained therein in a sense and/or antisense orientation relative to the promoter sequence. Another method to downregulate gene expression comprises the use of ribozymes, e.g. as described in Atkins et al. 1994 (WO9400012), Lenee et al. 1995 (WO9503404), Lutziger et al. 2000 (WO0000619), Prinsen et al. 1997 (WO9713865) and Scott et al. 1997 (WO9738116).

Modulating, including lowering, the level of active gene products or of gene product activity can be achieved by administering or exposing cells, tissues, organs or organisms to said gene product, a homologue, analogue, derivative and/or immunologically active fragment thereof. Immunomodulation is another example of a technique capable of down-regulation levels of active gene product and/or of gene product activity and comprises administration of or exposing to or expressing antibodies to said gene product to or in cells, tissues, organs or organisms wherein levels of said gene product and/or gene product activity are to be modulated. Such antibodies comprise "plantibodies", single chain antibodies, IgG antibodies and heavy chain camel antibodies as well as fragments thereof.

Modulating, including lowering, the level of active gene products or of gene product activity can futhermore be-achieved by administering or exposing cells, tissues, organs or organisms to an inhibitor or activator of said gene product or the activity thereof. Such Inhibitors or activators include proteins (comprising e.g. proteinases and kinases) and chemical compounds identified according to the current invention as described supra. In the context of the invention the term "agonist" refers to a substance that can be either a protagonist or an antagonist, i.e. can have either positive or negative effects, can be an enhancer or an inhibitor or a modulator as well.

In the context of the current invention is envisaged the downregulation of the expression of a HOBBIT gene as defined higher. The invention further comprises downregulation of levels of a HOBBIT protein or of a HOBBIT protein activity whereby said HOBBIT protein has been defined supra. Further envisaged in the present invention is the downregulation of HOBBIT protein activity by enabling the expression of a mutant hobbit protein wherein said hobbit protein has been defined supra.

The term "endoreduplication" means recurrent DNA replication without consequent mitosis and cytokinesis. By manipulating the level of endorduplication one can increase the storage capacity of, for example, endosperm cells.

By "cell fate and/or plant development and/or plant morphology and/or biochemistry and/or physiology" is meant that one or more developmental and/or morphological and/or biochemical and/or physiological characteristics of a plant is altered by the performance of one or more steps pertaining to the invention described herein.

"Cell fate" refers to the cell-type or cellular characteristics of a particular cell that are produced during plant development or a cellular process therefor, in particular during the cell cycle or as a consequence of a cell cycle process.

"Plant development" or the term "plant developmental characteristic" or similar term shall, when used herein, be taken to mean any cellular process of a plant that is involved in determining the developmental fate of a plant cell, in particular the specific tissue or organ type into which a progenitor cell will develop. Cellular processes relevant to plant development will be known to those skilled in the art. Such processes include, for example, morphogenesis, photomorphogenesis, shoot development, root development, vegetative development, reproductive development, stem elongation, flowering, and regulatory mechanisms involved in determining cell fate, in particular a process or regulatory process involving the cell cycle.

"Plant morphology" or the term "plant morphological characteristic" or similar term will, when used herein, be understood by those skilled in the art to refer to the external appearance of a plant, including any one or more structural features or combination of structural features thereof. Such structural features include the shape, size, number, position, colour, texture, arrangement, and patternation of any cell, tissue or organ or groups of cells, tissues or organs of a plant, including the root, stem, leaf, shoot, petiole, trichome, flower, petal, stigma, style, stamen, pollen, ovule, seed, embryo, endosperm, seed coat, aleurone, fibre, fruit, cambium, wood, heartwood, parenchyma, aerenchyma, sieve element, phloem or vascular tissue, amongst others.

"Plant biochemistry" or the term "plant biochemical characteristic" or similar term will, when used herein, be understood by those skilled in the art to refer to the metabolic and catalytic processes of a plant, including primary and secondary metabolism and the products thereof, including any small molecules, macromolecules or chemical compounds, such as but not limited to starches, sugars, proteins, peptides, enzymes, hormones, growth factors, nucleic acid molecules, celluloses, hemicelluloses, calloses, lectins, fibres, pigments such as anthocyanins, vitamins, minerals, micronutrients, or macronutrients, that are produced by plants.

"Plant physiology" or the term "plant physiological characteristic" or similar term will, when used herein, be understood to refer to the functional processes of a plant, including developmental processes such as growth, expansion and differentiation, sexual development, sexual reproduction, seed set, seed development, grain filling, asexual reproduction, cell division, dormancy, germination, light adaptation, photosynthesis, leaf expansion, fiber production, secondary growth or wood production, amongst others; responses of a plant to externally-applied factors such as metals, chemicals, hormones, growth factors, environment and environmental stress factors (eg. anoxia, hypoxia, high temperature, low temperature, dehydration, light, daylength, flooding, salt, heavy metals, amongst others), including adaptive responses of plants to said externally-applied factors. "Patterning" or "pattern formation" or "cell pattern" or similar terms will, when used herein, be understood as the spatial arrangement of cells, groups of cells, tissues or organs of an organism within that organism. Preferably, said organism is a plant. This process is involved in influencing cell fate, plant development, plant morphology, plant biochemistry and plant physiology.

When used herein, the terms "domain" or "cell region" are to be understood as a single cell or a group of cells which collectively have the same fate or which can be treated such that they obtain said fate. In this context "fate" is to be understood as having the potential to develop into or as having developed into a certain tissue, organ or organism. The acquisition of fate can imply the occurrence of asymmetry in a population of previously uniform cells.

A "meristem" is a formative tissue of a plant which is distinguished from permanent plant tissues by the ability of meristem cells to divide and to form new cells. Meristems can be apical, i.e. determining the vertical shoot-root axis of plants and responsible for shoot (shoot apical meristems) or root (root apical meristems) growth. Meristems can furthermore be lateral, i.e. determining the horizontal branching off the shoot-root axis and responsible for growth of e.g. tree branches (shoot apical meristem) or lateral roots (root apical meristem). Several organs find their origin in meristems. Thus, with "organ emanation" is meant the conception and subsequent development of an organ from a meristem. Well-known organs emanating from vegetative meristems are e.g. leaves. Well-known organs emanating from floral meristems are e.g. flowers.

Means for introducing recombinant DNA into plant tissue or cells include, but are not limited to, transformation using $CaCl_2$ and variations thereof, in particular the method described by Hanahan (1983), direct DNA uptake into protoplasts (Krens et al, 1982; Paszkowski et al, 1984), PEG-mediated uptake to protoplasts (Armstrong at al, 1990) microparticle bombardment, electroporation (Fromm et al., 1985), microinjection of DNA (Crossway et al., 1986), microparticle bombardment of tissue explants or cells (Christou et al, 1988; Klein et al. 1992), vacuum-infiltration of tissue with nucleic acid, or in the case of plants, T-DNA-mediated transfer from Agrobacterium to the plant tissue as described essentially by An et al.(1985), Dodds et al. (1985), Herrera-Estrella et al. (1983a, 1983b). Methods for transformation of monocotyledonous plants are well known in the art and include Agrobacterium-mediated transformation (Cheng et al. 1997—WO9748814; Hansen 1998—WO9854961, Hiei et al. 1994—WO9400977; Hiei et al. 1998—WO9817813; Rikiishi et al. 1999—WO9904618; Saito et al. 1995—WO9506722), microprojectile bombardment (Adams et al. 1999—U.S. Pat. No. 5,969,213; Bowen et al. 1998—U.S. Pat No. 5,736,369; Chang et al. 1994—WO9413822; Lundquist et al. 1999—U.S. Pat. Nos. 5,874,265/5,990,390; Vasil and Vasil 1995—U.S. Pat. No. 5,405,765; Walker et al. 1999—U.S. Pat. No. 5,955,362), DNA uptake (Eyal et al. 1993—WO9318168), microinjection of *Agrobacterium* cells (von Holt 1994—DE4309203) and sonication (Finer et al. 1997—U.S. Pat. No. 5,693,512).

For microparticle bombardment of cells, a microparticle is propelled into a cell to produce a transformed cell. Any suitable ballistic cell transformation methodology and apparatus can be used in performing the present invention. Exemplary apparatus and procedures are disclosed by Stomp et al. (U.S. Pat. No. 5,122,466) and Sanford and Wolf (U.S. Pat. No. 4,945,050). When using ballistic transformation procedures, the gene construct may incorporate a plasmid capable of replicating in the cell to be transformed.

Examples of microparticles suitable for use in such systems include 1 to 5 µm gold spheres. The DNA construct may be deposited on the microparticle by any suitable technique, such as by precipitation.

A whole plant may be regenerated from the transformed or transfected cell, in accordance with procedures well known in the art. Plant tissue capable of subsequent clonal propagation, whether by organogenesis or embryogenesis, may be transformed with a gene construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem).

The term "organogenesis", as used herein, means a process by which shoots and roots are developed sequentially from meristematic centers.

The term "embryogenesis", as used herein, means a process by which shoots and roots develop together in a concerted fashion (not sequentially), whether from somatic cells or gametes.

Preferably, the plant is produced according to the inventive method is transfected or transformed with a genetic sequence, or amenable to the introduction of a protein, by any art-recognized means, such as microprojectile bombardment, microinjection, *Agrobacterium*-mediated transformation (including the 'flower dip' transformation method; Bechtold and Pelletier 1998, Trieu et al. 2000), protoplast fusion, or electroporation, amongst others. Most preferably said plant is produced by *Agrobacterium*-mediated transformation.

*Agrobacterium*-mediated transformation or agrolistic transformation of plants, yeast, moulds or filamentous fungi is based on the transfer of part of the transformation vector sequences, called the T-DNA, to the nucleus and on integration of said T-DNA in the genome of said eukaryote.

With "*Agrobacterium*" is meant a member of the Agrobacteriaceas, more preferably *Agrobacterium* or *Rhizobacterium* and most preferably *Agrobacterium tumefaciens*. With "T-DNA", or transferred DNA, is meant that part of the transformation vector flanked by T-DNA borders which is, after activation of the *Agrobacterium* vir genes, nicked at the T-DNA borders and is transferred as a single stranded DNA to the nucleus of an eukaryotic cell.

When used herein, with "T-DNA borders", "T-DNA border region", or "border reg" ion are meant either right T-DNA border (RB) or left T-DNA border (LB). Such a border comprises a core sequence flanked by a border inner region as part of the T-DNA flanking the border and/or a border outer region as part of the vector backbone flanking the border. The core sequences comprise 22 bp in case of octopine-type vectors and 25 bp in case of nopaline-type vectors. The core sequences in the right border region and left border region form imperfect repeats. Border core sequences are indispensable for recognition and processing by the Agrobacterium nicking complex consisting of at least VirD1 and VirD2. Core sequences flanking a T-DNA are sufficient to promote transfer of said T-DNA. However, efficiency of transformation using transformation vectors carrying said T-DNA solely flanked by said core sequences is low. Border inner and outer regions are known to modulate efficiency of T-DNA transfer (Wang et al. 1987). One element enhancing T-DNA transfer has been characterized and resides in the right border outer region and is called overdrive (Peralta et al. 1986, van Haaren et al. 1987).

With "T-DNA transformation vector" or "T-DNA vector" is meant any vector encompassing a T-DNA sequence flanked by a right and left T-DNA border consisting of at least the right and left border core sequences, respectively, and used for transformation of any eukaryotic cell.

With "T-DNA vector backbone sequence" or "T-DNA vector backbone sequences" is meant all DNA of a T-DNA containing vector that lies outside of the T-DNA borders and, more specifically, outside the nicking sites of the border core imperfect repeats.

The current invention includes optimized T-DNA vectors such that vector backbone integration in the genome of a eukaryotic cell is minimized or absent. With "optimized T-DNA vector" is meant a T-DNA vector designed either to decrease or abolish transfer of vector backbone sequences to the genome of a eukaryotic cell. Such T-DNA vectors are known to the one familiar with the art and include those described by Hanson et al. (1999) and by Stuiver et al. (1999—WO9901563).

The current invention clearly considers the inclusion of a DNA sequence encoding a HOBBIT or mutant HOBBIT protein, homologue, derivative or immunologically active fragment thereof as defined supra, in any T-DNA vector comprising binary transformation vectors, super-binary transformation vectors, co-integrate transformation vectors, Ri-derived transformation vectors as well as in T-DNA carrying vectors used in agrolistic transformation.

With "binary transformation vector" is meant a T-DNA transformation vector comprising at least one gene of interest and/or at least one selectable marker active in the eukaryotic cell to be transformed; and a vector backbone region comprising at least origins of replication active in *E coli* and *Agrobacterium* and markers for selection in *E. coli* and *Agro-* bacterium. Alternatively, replication of the binary transformation vector in *Agrobacterium* is dependent on the presence of a separate helper plasmid. The binary vector pGreen and the helper plasmid pSoup form an example of such a system as described in e.g. Hellens et al. (2000), Plant Mol. Biol. 42, 819-832, or as available on the internet site http://.pgreen-.ac.uk.

The T-DNA borders of a binary transformation vector can be derived from octopine-type or nopaline-type Ti plasmids or from both. The T-DNA of a binary vector is only transferred to a eukaryotic cell in conjunction with a helper plasmid. Also known in the art are multiple binary vector *Agrobacterium* strains for efficient co-transformation of plants (Bidney and Scelonge 2000—WO0018939).

With "helper plasmid" is meant a plasmid that is stably maintained in *Agrobacterium* and is at least carrying the set of vir genes necessary for enabling transfer of the T-DNA. Said set of vir genes can be derived from either octopine-type or nopaline-type Ti plasmids or from both.

With "super-binary transformation vector" is meant a binary transformation vector additionally carrying in the vector backbone region a vir region of the Ti plasmid pTiBo542 of the super-virulent *A. tumefaciens* strain A281 (Hiei et al. 1994—EP0604662, Hiei et al. 1995—EP0687730). Super-binary transformation vectors are used in conjunction with a helper plasmid.

With "co-integrate transformation vector" is meant a T-DNA vector at least comprising:

(a) a T-DNA region comprising at least one gene of interest and/or at least one selectable marker active in plants; and (b) a vector backbone region comprising at least origins of replication active in *Escherichia coli* and Agrobacterium, and markers for selection in *E. coli* and *Agrobacterium*, and a set of vir genes necessary for enabling transfer of the T-DNA.

The T-DNA borders and said of vir genes of a said T-DNA vector can be derived from either octopine-type or nopaline-type Ti plasmids or from both.

With "Ri-derived plant transformation vector" is meant a binary transformation vector in which the T-DNA borders are derived from a Ti plasmid and said binary transformation vector being used in conjunction with a 'helper' Ri-plasmid carrying the necessary set of vir genes.

As used herein, the term "selectable marker gene" or "selectable marker" or "marker for selection" includes any gene which confers a phenotype on a cell in which it is expressed to facilitate the identification and/or selection of cells which are transfected or transformed with a gene construct of the invention or a derivative thereof. Suitable selectable marker genes contemplated herein include the ampicillin resistance ($Amp^r$), tetracycline resistance gene ($Tc^r$), bacterial kanamycin resistance gene ($Kan^r$), phosphinothricin resistance gene, neomycin phosphotransferase gene (nptII), hygromycin resistance gene, β-glucuronidase (GUS) gene, chloramphenicol acetyltransferase (CAT) gene, green fluorescent protein (gfp) gene (Haseloff et al, 1997), and luciferase gene, amongst others.

With "agrolistics", "agrolistic transformation" or "agrolistic transfer" is meant here a transformation method combining features of *Agrobacterium*-mediated transformation and of biolistic DNA delivery. As such, a T-DNA containing target plasmid is co-delivered with DNA/RNA enabling in planta production of VirD1 and VirD2 with or without VirE2 (Hansen and Chilton 1996; Hansen et al. 1997; Hansen and Chilton 1997—WO9712046).

The present invention further describes an approach to remove from transformed cells a stably integrated foreign DNA sequence by recombination involving a recombinase and recombination sites.

With "foreign DNA" is meant any DNA sequence that is introduced in the host's genome by recombinant techniques. Said foreign DNA includes e.g. a T-DNA sequence or a part thereof such as the T-DNA sequence comprising the selectable marker in an expressible format. Foreign DNA furthermore include intervening DNA sequences as defined supra.

With "recombination event" is meant either a site-specific recombination event or a recombination event effected by transposon 'jumping'.

With "recombinase" is meant either a site-specific recombinase or a transposase.

With "recombination site" is meant either site-specific recombination sites or transposon border sequences.

With "site specific recombination event" is meant an event catalyzed by a system generally consisting of three elements: a pair of DNA sequences (the site-specific recombination sequences or sites) and a specific enzyme (the site-specific recombinase). The site-specific recombinase catalyzes a recombination reaction only between two site-specific recombination sequences depending on the orientation of the site-specific recombination sequences. Sequences intervening between two site-specific recombination sites will be inverted in the presence of the site-specific recombinase when the site-specific recombination sequences are oriented in opposite directions relative to one another (i.e. inverted repeats). If the site-specific recombination sequences are oriented in the same direction relative to one another (i.e. direct repeats), then any intervening sequences will be deleted upon interaction with the site-specific recombinase. Thus, if the site-specific recombination sequences are present as direct repeats at both ends of a foreign DNA sequence integrated into a eukaryotic genome, such integration of said sequences can subsequently be reversed by interaction of the site-specific recombination sequences with the corresponding site specific recombinase.

A number of different site specific recombinase systems can be used including but not limited to the Cre/lox system of bacteriophage P1, the FLP/FRT system of yeast, the Gin recombinase of phage Mu, the Pin recombinase of *E. coli*, the PinB, PinD and PinF from *Shigella*, and the R/RS system of *Zygosaccharomyces rouxii*. Recombinases generally are integrases, resolvases or flippases. Also dual-specific recombinases can be used in conjunction with direct or indirect repeats of two different site-specific recombination sites corresponding to the dual-specific recombinase (Baszczynski et al. 1999—WO9925840). The preferred site-specific recombinase systems are the bacteriophage P1 Cre/lox, the yeast FLP/FRT and the *Z. rouxii* R/RS systems. In these systems a recombinase (Cre, FLP or R) interact specifically with its respective site-specific recombination sequence (lox, FRT, or RS respectively) to invert or excise the intervening sequences. The site-specific recombination sequences for each of these two systems are relatively short (34 bp for lox and 47 bp for FRT). Some of these systems have already been used with high efficiency in plants such as tobacco (Dale et al. 1990, Onouchi et al. 1991, Sugita et al. 2000) and *Arabidopsis* (Osborne et al. 1995, Onouchi et al. 1995). Site-specific recombination systems have many applications in plant molecular biology including methods for control of homologous recombination (e.g. Hodges et al. 1996—U.S. Pat. No. 5,527,695), for targeted insertion, gene stacking, etc. (Baszczynski et al. 1999—WO9925821) and for resolution of complex T-DNA integration patterns or for excision of a selectable marker (Ow et al. 1999—WO9923202).

Although the site-specific recombination sequences must be linked to the ends of the DNA to be excised or to be inverted, the gene encoding the site specific recombinase may be located elsewhere. For example, the recombinase gene could already be present in the eukaryote's DNA or could be supplied by a later introduced DNA fragment either introduced directly into cells, through crossing or through cross-pollination. Alternatively, a substantially purified recombinase protein could be introduced directly into the eukaryotic cell, e.g. by micro-injection or particle bombardment. Typically, the site-specific recombinase coding region will be operably linked to regulatory sequences enabling expression of the site-specific recombinase in the eukaryotic cell.

With "recombination event effected by transposon jumping" or "transposase-mediated recombination" is meant a recombination event catalyzed by a system consisting of three elements: a pair of DNA sequences (the transposon border sequences) and a specific enzyme (the transposase). The transposase catalyzes a recombination reaction only between two transposon border sequences which are arranged as inverted repeats.

A number of different transposon/transposase systems can be used including but not limited to the Ds/Ac system, the Spm system and the Mu system. These systems originate from corn but it has been shown that at least the Ds/Ac and the Spm system also function in other plants (Fedoroff et al. 1993, Schlappi et al. 1993, Van Sluys et al. 1987). Preferred are the Ds- and the Spm-type transposons which are delineated by 11 bp- and 13 bp-border sequences, respectively.

Although the transposon border sequences must be linked to the ends of the DNA to be excised, the gene encoding the transposase may be located elsewhere. For example, the recombinase gene could already be present in the eukaryote's DNA or could be supplied by a later introduced DNA fragment either introduced directly into cells, through crossing or through cross-pollination. Alternatively, a substantially purified transposase protein could be introduced directly into cells, e.g. by microinjection or by particle bombardment.

As part of the current invention, transposon border sequences are included in a foreign DNA sequence such that they lie outside said DNA sequence and transform said DNA into a transposon-like entity that can move by the action of a transposase.

As transposons often reintegrate at another locus of the host's genome, segregation of the progeny of the hosts in which the transposase was allowed to act might be necessary to separate transformed hosts containing e.g. only the transposon footprint and transformed hosts still containing the foreign DNA.

In performing the present invention, the genetic element is preferably induced to mobilize, such as, for example, by the expression of a recombinase protein in the cell which contacts the integration site of the genetic element and facilitates a recombination event therein, excising the genetic element completely, or alternatively, leaving a "footprint", generally of about 20 nucleotides in length or greater, at the original integration site. Those hosts and host parts that have been produced according to the inventive method can be identified by standard nucleic acid hybridization and/or amplification techniques to detect the presence of the mobilizable genetic element or a gene construct comprising the same. Alternatively, in the case of transformed host cells, tissues, and hosts wherein the mobilizable genetic element has bene excised, it is possible to detect a footprint in the genome of the host which has been left following the excision event, using such techniques. As used herein, the term "footprint" shall be taken to refer to any derivative of a mobilizable genetic element or gene construct comprising the same as described herein which is produced by excision, deletion or other removal of the mobilizable genetic element from the genome of a cell transformed previously with said gene construct. A footprint generally comprises at least a single copy of the recombination loci or transposon used to promote excision. However, a footprint may comprise additional sequences derived from the gene construct, for example nucleotide sequences derived from the left border sequence, right border sequence, origin of replication, recombinase-encoding or transposase-encoding sequence if used, or other vector-derived nucleotide sequences. Accordingly, a footprint is identifiable according to the nucleotide sequence of the recombination locus or transposon of the gene construct used, such as, for example, a sequence of nucleotides corresponding or complementary to a lox site, frt site or RS site. The term "cell cycle" means the cyclic biochemical and structural events associated with growth and with division of cells, and in particular with the regulation of the replication of DNA and mitosis. Cell cycle includes phases called: G0, Gap1 (G1), DNA synthesis (S), Gap2 (G2), and mitosis (M). Normally these four phases occur sequentially, however, the cell cycle also includes modified cycles wherein one or more phases are absent resulting in modified cell cycle such as endomitosis, acytokinesis, polyploidy, polyteny, and endoreduplication.

The term "cell cycle interacting protein", "cell cycle protein" or "cell cycle control protein" as denoted herein means a protein which exerts control on or regulates or is required for the cell cycle or part thereof of a cell, tissue, organ or whole organism and/or DNA replication. It may also be capable of binding to, regulating or being regulated by cyclin dependent kinases or their subunits. The term also includes peptides, polypeptides, fragments, variant, homologs, alleles or precursors (eg preproproteins or preproteins) thereof.

Cell cycle control proteins and their role in regulating the cell cycle of eukaryotic organisms are reviewed in detail by John (1981) and the contributing papers therein (Norbury and Nurse 1992; Nurse 1990; Ormrod and Francis 1993) and the contributing papers therein (Doerner et 1996; Elledge 1996; Francis and Halford 1995; Francis et al. 1998; Hirt et al. 1991; Mironov et al. 1999) which are incorporated by reference.

The term "cell cycle control genes" refers to any gene or mutant thereof which exerts control on or are required for: chromosomal DNA synthesis and for mitosis (preprophase band, nuclear envelope, spindle formation, chromosome condensation, chromosome segregation, formation of new nuclei, formation of phragmoplast, duplication of microtubule organizing center, etc) meiosis, cytokinesis, cell growth, endoreduplication, cell cycle control genes are also all genes exerting control on the above: homologues of CDKs, cyclins, E2Fs, Rb, CKl, Cks, and also any genes which interfere with the above, cyclin D, cdc25, Wee1, Nim1, MAP kinases, etc.

More specifically, cell cycle control genes are all genes involved in the control of entry and progression through S phase. They include, not exclusively, genes expressing "cell cycle control proteins" such as cyclin dependent kinases (CDK), cyclin dependent kinase inhibitors (CKI), D, E and A cyclins, E2F and DP transcription factors, pocket proteins, CDC7/DBF4 kinase, CDC6, MCM2-7, Orc proteins, cdc45, components of SCF ubiquitin ligase, PCNA, DNA-polymerase.

The term "cell cycle control protein" include cyclins A, B, C, D and E including CYCA1;1, CYCA2;1, CYCA3;1, CYCB1;1, CYCB1;2, CYCB2;2, CYCD1 ;1, CYCD2;1, CYCD3;1, and CYCD4;1 (Evans et al. 1983; Francis et al.

1998; Labbe et al. 1989; Murray and Kirschner 1989; Renaudin et al. 1996; Soni et al. 1995; Sorrell et al. 1999; Swenson et al. 1986) cyclin dependent kinase inhibitor (CKI) proteins such as ICK1 (Wang et al. 1997), FL39, FL66, FL67 (PCT/EP98/05895), Sic1, Far1, Rum1, p21, p27, p57, p16, p15, p18, p19 (Elledge 1996; Pines 1995), p14 and p14ARF, p13suc1 or CKS1At (De Veylder et al. 1997; Hayles and Nurse 1986) and nim-1 (Russell and Nurse 1987a; Russell and Nurse 1987b; Fantes 1989; Russell and Nurse 1986; Russell and Nurse 1987a; Russell and Nurse 1987b) homologues of Cdc2 such as Cdc2MsB (Hirt et al. 1993) CdcMs kinase (Bogre et al. 1997) cdc2 T14Y15 phosphatases such as Cdc25 protein phosphatase or p80cdc25 (Bell et al. 1993; Elledge 1996; Kumagai and Dunphy 1991; Russell and Nurse 1986) and Pyp3 (Elledge 1996) cdc2 protein kinase or p34cdc2 (Colasanti et al. 1991 ; Feiler and Jacobs 1990; Hirt et al. 1991; John et al. 1989; Lee and Nurse 1987; Nurse and Bisset 1981 ; Ormrod and Francis 1993) cdc2a protein kinase (Hemerly et al. 1993) cdc2 T14Y15 kinases such as wee1 or p107wee1 (Elledge 1996; Russell and Nurse 1986; Russell and Nurse 1987a; Russell and Nurse 1987b; Sun et al. 1999) mik1 (Lundgren et al. 1991) and myt1 (Elledge 1996); cdc2 T161 kinases such as Cak and Civ (Elledge 1996); cdc2 T161 phosphatases such as Kap1 (Elledge 1996); cdc28 protein kinase or p34cdc28 (Nasmyth 1993; Reed et al. 1985) p40MO15 (Fesquet et al. 1993; Poon et al. 1993) chk1 kinase (Zeng et al. 1998) cds1 kinase (Zeng et al. 1998) growth-associated H1 kinase (Labbe et al. 1989; Lake and Salzman 1972; Langan 1978; Zeng et al. 1998) MAP kinases described by (Binarova et al. 1998; Bögre et al. 1999; Calderini et al. 1998; Wilson et al. 1999).

Other cell cycle control proteins that are involved in cyclin D-mediated entry of cells into G1 from G0 include pRb (Xie et al. 1996; Huntley et al. 1998) E2F, RIP, MCM7 and potentially the pRb-like proteins p107 and p130.

Other cell cycle control proteins that are involved in the formation of a pre-replicative complex at one or more origins of replication, such as, but not limited to, ORC, CDC6, CDC14, RPA and MCM proteins or in the regulation of formation of this pre-replicative complex, such as, but not limited to, the CDC7, DBF4 and MBF proteins.

For the present purpose, the term "cell cycle control protein" shall further be taken to include any, one or more of those proteins that are involved in the turnover of any other cell cycle control protein, or in regulating the half-life of said other cell cycle control protein. The term "protein turnover" is to include all biochemical modifications of a protein leading to the physical or functional removal of said protein. Although not limited to these, examples of such modifications are phosphorylation, ubiquitination and proteolysis. Particularly preferred proteins which are involved in the proteolysis of one or more of any other of the above-mentioned cell cycle control proteins include the yeast-derived and animal-derived proteins, Skp1, Skp2, Rub1, Cdc20, cullins, CDC23, CDC27, CDC16, and plant-derived homologues thereof (Cohen-Fix and Koshland 1997; Hochstrasser 1998; Krek 1998; Lisztwan et al. 1998) and Plesse et al in (Francis et al. 1998)).

For the present purpose, the term "cell cycle control genes" shall further be taken to include any one or more of those gene that are involved in the transcriptional regulation of cell cycle control gene expression such as transcription factors and upstream signal proteins. Additional cell cycle control genes are not excluded.

For the present purpose, the term "cell cycle control genes" shall further be taken to include any cell cycle control gene or mutant thereof, which is affected by environmental signals such as for instance stress, nutrients, pathogens, or by intrinsic signals such as the animal mitogens or the plant hormones (auxins, cytokinins, ethylene, gibberellic acid, abscisic acid and brassinosteroids).

The term "cell cycle progression" refers to the process of passing through the different cell cycle phases. The term "cell cycle progression rate" accordingly refers to the speed at which said cell cycle phases are run through or the time spans required to complete said cell cycle phases.

With "yeast two-hybrid assay" is meant an assay that is based on the observation that many eukaryotic transcription factors comprise two domains, a DNA-binding domain (DB) and an activation domain (AD) which, when physically separated (i.e. disruption of the covalent linkage) do not effectuate target gene expression. Two proteins able to interact physically with one of said proteins fused to DB and the other of said proteins fused to AD will re-unite the DB and AD domains of the transcription factor resulting in target gene expression. The target gene in the yeast two-hybrid assay is usually a reporter gene such as the β-galactosidase gene. Interaction between protein partners in the yeast two-hybrid assay can thus be quantified by measuring the activity of the reporter gene product (Bartel and Fields 1997). Alternatively, a mammalian two-hybrid system can be used which includes e.g. a chimeric green fluorescent protein encoding reporter gene (Shioda et al. 2000). Yet another alternative consists of a bacterial two-hybrid system using e.g. HIS as reporter gene (Joung et al. 2000).

The term "fragment of a sequence" or "part of a sequence" means a truncated sequence of the original sequence referred to. The truncated sequence (nucleic acid or protein sequence) can vary widely in length; the minimum size being a sequence of sufficient size to provide a sequence with at least a comparable function and/or activity or the original sequence referred to, while the maximum size is not critical. In some applications, the maximum size usually is not substantially greater than that required to provide the desired activity and/or function(s) of the original sequence. Typically, the truncated amino acid or nucleotide sequence will range from about 5 to about 60 amino acids in length. More typically, however, the sequence will be a maximum of about 50 amino acids in length, preferably a maximum of about 60 amino acids. It is usually desirable to select sequences of at least about 10, 12 or 15 amino acids or nucleotides, up to a maximum of about 20 or 25 amino acids or nucleotides.

Furthermore, folding simulations and computer redesign of structural motifs of the protein of the invention can be performed using appropriate computer programs (Olszewski et al. 1996, Hoffman et al. 1995). Computer modeling of protein folding can be used for the conformational and energetic analysis of detailed peptide and protein models (Monge et al. 1995, Renouf et al. 1995). In particular, the appropriate programs can be used for the identification of interactive sites of the HOBBIT protein and HOBBIT-interacting proteins by computer assistant searches for complementary peptide sequences (Fassina and Melli 1994). Further appropriate computer systems for the design of protein and peptides are described in the prior art, for example in Berry and Brenner (1994), Wodak (1987), Pabo and Suchanek (1986). The results obtained form the above-described computer analysis can be used for, e.g. the preparation of peptidomimetics of the protein of the invention or fragments thereof. Such pseudopeptide analogues of the natural amino acid sequence of the protein may very efficiently mimic the parent protein (Benkirane et al. 1996). For example, incorporation of easily available achiral ω-amino acid residues into a protein of the invention or a fragment thereof results in the substitution of amino bonds by polymethylene units of an aliphatic chain, thereby providing a convenient strategy for constructing a peptidomimetic (Banerjee et al. 1996). Superactive peptidomimetic analogues of small peptide hormones in other systems are described in the prior art (Zhang et al. 1996). Appropriate peptidomimetics of the protein of the present invention can also be identified by the synthesis of peptidomimetic combinatorial libraries through successive amine alkylation and testing the resulting compounds, e.g., for their binding, kinase inhibitory and/or immunlogical properties. Methods for the generation and use of peptidomimetic combinatorial libraries are described in the prior art, for example in Ostresh et al. (1996) and Domer et al. (1996).

Furthermore, a three-dimensional and/or crystallographic structure of the protein of the invention can be used for the design of peptidomimetic inhibitors of the biological activity of the protein of the invention (Rose et al. 1996, Ruterber et al. 1996).

The compounds to be obtained or identified in the methods of the invention can be compounds that are able to bind to any of the nucleic acids, peptides or proteins of the invention. Other interesting compounds to be identified are compounds that modulate the expression of the genes or the proteins of the invention in such a way that either the expression of said gene or protein is enhanced or decreased by the action of said compound. Alternatively the compound can exert his action by directly or indirectly enhancing or decreasing the activity of any of the proteins of the invention.

Said compound or plurality of compounds may be comprised in, for example, samples, e.g., cell extracts from, e.g., plants, animals or microorganisms. Furthermore, said compound(s) may be known in the art but hitherto not known to be capable of suppressing or activating cell cycle interacting proteins. The reaction mixture may be a cell free extract of may comprise a cell or tissue culture. Suitable set ups for the method of the invention are known to the person skilled in the art and are, for example, generally described in Alberts et al., Molecular Biology of the Cell, third edition (1994), in particular Chapter 17. The plurality of compounds may be, e.g., added to the reaction mixture, culture medium or injected into the cell.

If a sample containing a compound or a plurality of compounds is identified in the method of the invention, then it is either possible to isolate the compound form the original sample identified as containing the compound capable of acting as an agog or one can further subdivide the original sample, for example, if it consists of a plurality of different compounds, so as to reduce the number of different substances per sample and repeat the method with the subdivisions of the original sample. Depending on the complexity of the samples, the steps described above can be performed several times, preferably until the sample identified according to the method of the invention only comprises a limited number of or only one substance(s). Preferably said sample comprises substances or similar chemical and/or physical properties, and most preferably said substances are identical. Preferably, the compound identified according to the above described method or its derivative is further formulated in a form suitable for the application in plant breeding or plant cell and tissue culture.

The invention, now being generally described, will be more readily understood by reference to the following examples, which are included merely for purposes of illustration of certain aspects and embodiments of the present invention and are not intended to limit the invention.

All of the references mentioned herein are incorporated by reference.

FIGURE LEGENDS

FIG. 1. Phenotypic characteristics of hobbit (hbt) mutant *Arabidopsis thaliana* seedlings.

The hobbit seedling phenotype shows that the HOBBIT (HBT) gene is required for post-embryonic cell division in the root meristem and in the shoot apical meristems. Strong alleles lack cell division in the root meristem from the heart stage of embryogenesis onward. Appearance of seedlings 7 days after germination on 0,8% plantagar is shown (A) a wild-type *A. thaliana* (ecotype Columbia-O; Col-O) seedling, (B) a hbt$^{2311}$ homozygote mutant *A. thaliana* (Col-O) seedling, (C) a hbt$^{GVII-24/1}$ homozygote mutant *A. thaliana* (ecotype Landsberg erecta; Ler) seedling, and (D) a hbt$^{e56}$ mutant *A. thaliana* (ecotype Col-O) seedling. Mutants are shown at 4× magnification relative to the wild-type seedling (Willemsen et al. 1998).

FIG. 2. Root cap and lateral root cap marker gene expression

The distal root tip of *Arabidopsis* contains specialized cell types such as those building the columella root cap or the lateral root cap. These cell types are not specified in hbt seedlings, demonstrating that Hbt gene activity is required for cell fate specification in the distal root tip. Illustrated are the expression of the root cap specific marker gene comprising the 35S::B2 promoter operably linked to the GUS marker (A, C) and the expression of the lateral root cap specific marker gene comprising the LRC244 promoter operably linked to the GUS marker (B, D). Wild-type *A. thaliana* roots (ecotype Col-O) are shown in (A) and (B), the root tip of a hbt$^{2311}$ homozygous mutant *A. thaliana* seedling is depicted in (C) and (D) (Willemsen et al; 1998). The root cap is abundantly stained in (A) and the arrow in (B) points at the lateral root cap cell layers expressing GUS. No GUS-staining is apparent in (C) and (D). The bar represents approximately 45 μm.

FIG. 3. Ectopic root cap marker gene expression and ectopic root hair formation in hbt mutant *A. thaliana* seedlings.

Post-embryonic changes in gene expression patterns and cell identity in the epidermis demonstrate that the HBT gene is required for stable determination of cell fate in non-root cell types. This is illustrated by the expression of the root cap marker (35S::B2 operably linked to GUS) not only in the root cap but also ectopically in the hypocotyl and the cotyledons (A) of hbt$^{2311}$ mutant *A. thaliana* seedlings, and by the formation of ectopic root hairs on the hypocotyl of dark grown hbt$^{2311}$ mutant *A. thaliana* seedlings (B).

FIG. 4. Qui scent center root endodermis marker gene expression.

The root tip of *Arabidopsis* contains specialized cell types such as those building the quiescent center (QC) or the endodermis. The QC is not specified in hbt seedlings, demonstrating that HBT gene activity is required for specification of QC cells in the root tip. Illustrated are the expression of the QC specific marker gene comprising the QC46 promoter operably linked to the GUS marker (A, C) and the expression of the root endodermis marker gene comprising the SCARECROW (SCR) promoter operably linked to the GUS marker (B, D). Wild-type *A. thaliana* roots (ecotype Col-O) are shown in (A) and (B), the root tip of a hbt$^{2311}$ homozygous mutant *A. thaliana* seedling is depicted in (C) and (D). The QC is abundantly stained in (A) and the endodermis is visible in (B). No GUS-staining is apparent in (C) but is still visible in (D).

FIG. 5. Bloating of epidermal cells in hbt mutant *A. thaliana* seedlings.

Wild type *A. thaliana* seedlings and hbt[2311] homozygous mutant *A. thaliana* seedlings were cryo-fixed and a photograph taking by scanning electron microscopy. Clearly visible are the irregular arrays of swollen epidermal cells of cotyledons and hypocotyl of the mutant seedling (C) compared to cotyledons (A) and hypocotyl (B) of the wild-type seedling.

Figure 6:
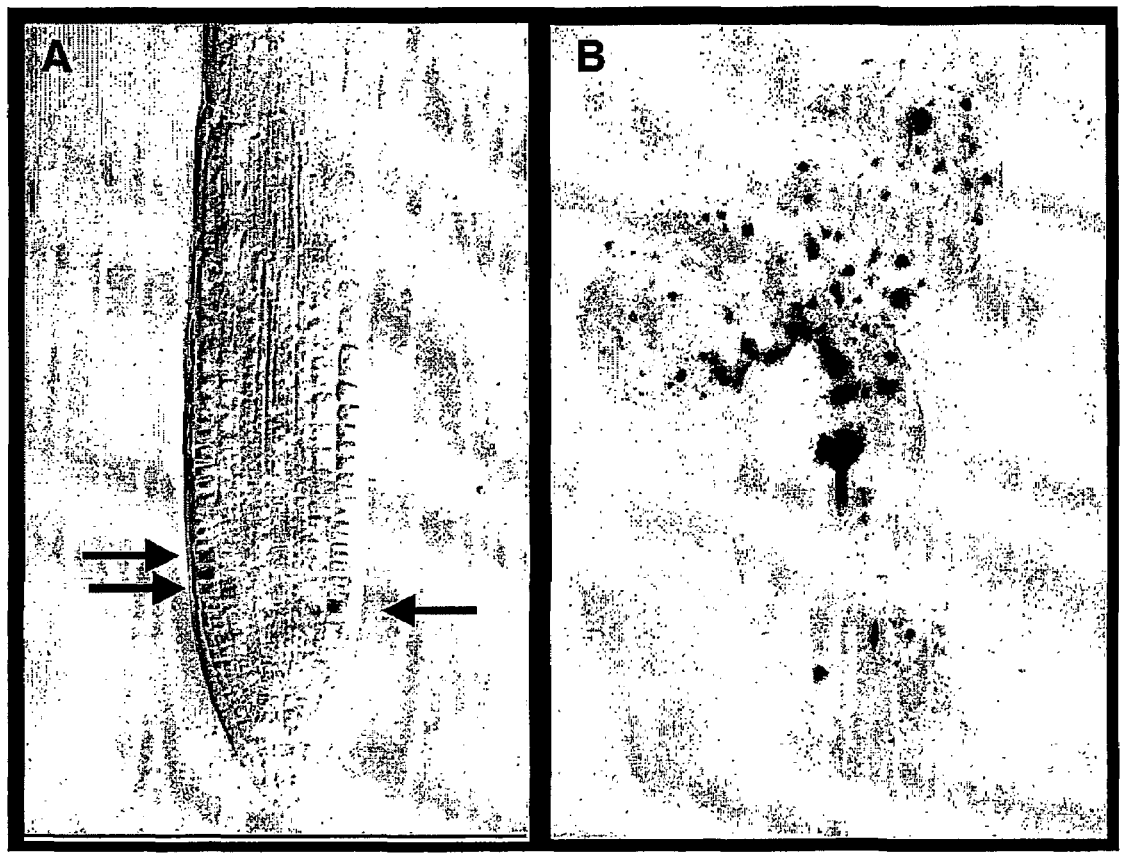

FIG. 6. Stabilization of cyclin B1 in hbt mutant *A. thaliana* seedlings.

Stability of cyclin B1 was indirectly assessed via GUS-staining. The *A. thaliana* cyclin B1 promoter was operably linked to the cyclin B1 instability domain, i.e. the destruction box, followed by GUS. Stabilization of GUS leads to increased GUS staining in the hbt[2311] homozygous mutant *A. thaliana* seedling (B) relative to a wild-type seedling (A). Whereas wild-type seedlings hardly show GUS-staining (indicated by arrows), a patchy pattern of GUS-staining is obvious in the hbt mutant genetic background.

Figure 7:
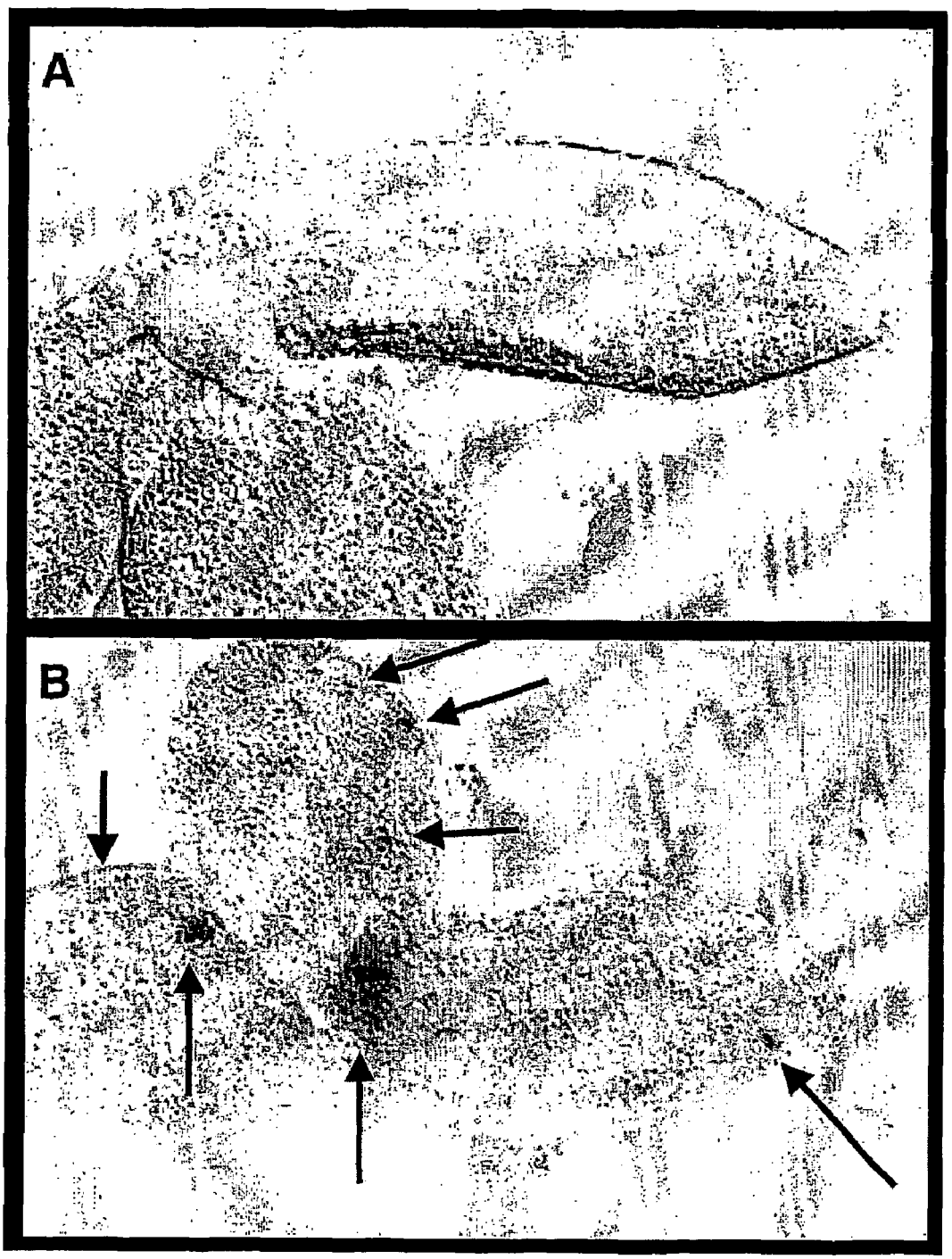

FIG. 7. Stabilization of AXR3 in hbt mutant *A. thaliana* seedlings.

Stability of AXR3 was indirectly assessed via GUS-staining. The tobacco heat shock promoter was operably linked to domain I and instability domain II of AXR3 followed by GUS. Stabilization of GUS leads to increased GUS staining in the hbt[2311] homozygous mutant *A. thaliana* seedling (B) relative to a wild-type seedling (A). Whereas wild-type, seedlings hardly show GUS-staining, a patchy pattern of GUS-staining (indicated by arrows) is obvious in the hbt mutant genetic background.

FIG. 8. Amino acid sequence alignment of Cdc27A and HBT/Cdc27B.

Aligned are the amino acid sequences of Cdc27A (GenBank accession number AC001645; protein ID AAB63645.1) and of HBT/Cdc27B2 from *A. thaliana* ecotype Columbia (Col-O). The $NH_2$-terminal part of the HBT/Cdc27B protein not annotated in GenBank (accession number AC006081; protein ID AAD24396.1) is underbraced and indicated by SEQ ID NO 5. Gaps (–) are introduced to ensure an optimal alignment. Identical amino acids are shaded in a black box. Similar amino acids (the groups M, I, V, L; R, K, H; F, W, Y; D, E; N, Q; S, T) are shaded in a grey box.

FIG. 9. Schematic representation of the HBT open reading frame and protein sequence and indication of the different hbt mutations.

Start and stop codons are underlined. On the amino acid level, the stop codon is represented by a '*'. Indicated between square brackets and shaded in a grey box are the different tetratricopeptide repeat domains (TPRs) of HBT based on the delineation of the TPRs in yeast Cdc27 (Lamb et al. 1994). Further indicated in boxes are the several characterized point mutations in different hbt mutants, the mutated nucleotide and amino acid are shaded in a black box. The mutant number is indicated outside the box, e.g. hbt5421. In one mutant, hbt2311, the glutamine residue is changed into a stop codon indicated by '*' and shaded in a black box. Three mutations occur in intron borders and result in deletion of part of the HBT protein. The insertion was independently isolated four times and is indicated by hbt5422, hbt5423, hbt5859, hbt9624. The inserted stretches of nucleotides and amino acids are delineated by square brackets and are underlined. The deletion mutants are hbt9620 and hbt5721 and the deletions are indicated between rounded brackets and the deleted nucleotide sequences are shaded in a black box. The amino acid numbering at the right is not taking into account the insertion or the deletions.

FIG. 10. Schematic representation of the HBT gene with indication of introns, exons and hbt point mutations.

Start and stop codons are underlined. Exons are shaded in a grey box. Point mutations are indicated below the nucleotide sequence and are shaded in a black box and with the mutant number, e.g. hbt5421.

FIG. 11. In situ hybridization analysis of HBT/CDC27B and AtCDC16 expression in wild-type *A. thaliana* embryos.

In situ hybridization was performed with gene-specific DIG-labeled antisense RNA probes. A patchy HBT expression pattern is visible in octant stage (A) and heart stage (B) of wild-type *A. thaliana* embryos. As a negative control, in situ hybridization was performed with a DIG-labeled sense RNA probe in octant stage embryos (C). A uniform AtCDC16 expression pattern is visible in both octant stage (D) and heart stage (E) wild-type *A. thaliana* embryos.

FIG. 12. In situ hybridization analysis of HBT/CDC27B, AtCDC16 and AtCDC27A expression in roots of wild-type *A. thaliana* seedlings.

In situ hybridization was performed with gene-specific DIG-labeled antisense RNA probes. A patchy Hbt expression pattern is visible in a cross-section of a root (A) and in a whole mount root (B) of wild-type *A. thaliana* seedlings. A uniform expression in a whole mount root of wild-type *A. thaliana* seedlings is observed for both AtCDC16 (C) and AtCDC27A (D).

FIG. 13. List of sequences (SEQ ID NOs).

FIG. 14. Outprint of GenBank accession number AC006081 on Nov. 13, 2000.

FIG. 15. Yeast complementation assay

Expression of AtCDC27A and HOBBIT compared to an empty pREP3 vector under the thiamine-repressible promoter in *S. pombe* nuc2ts, at the permissive temperature (25° C., A) and the restrictive temperature (37° C., B)

Figure 16:
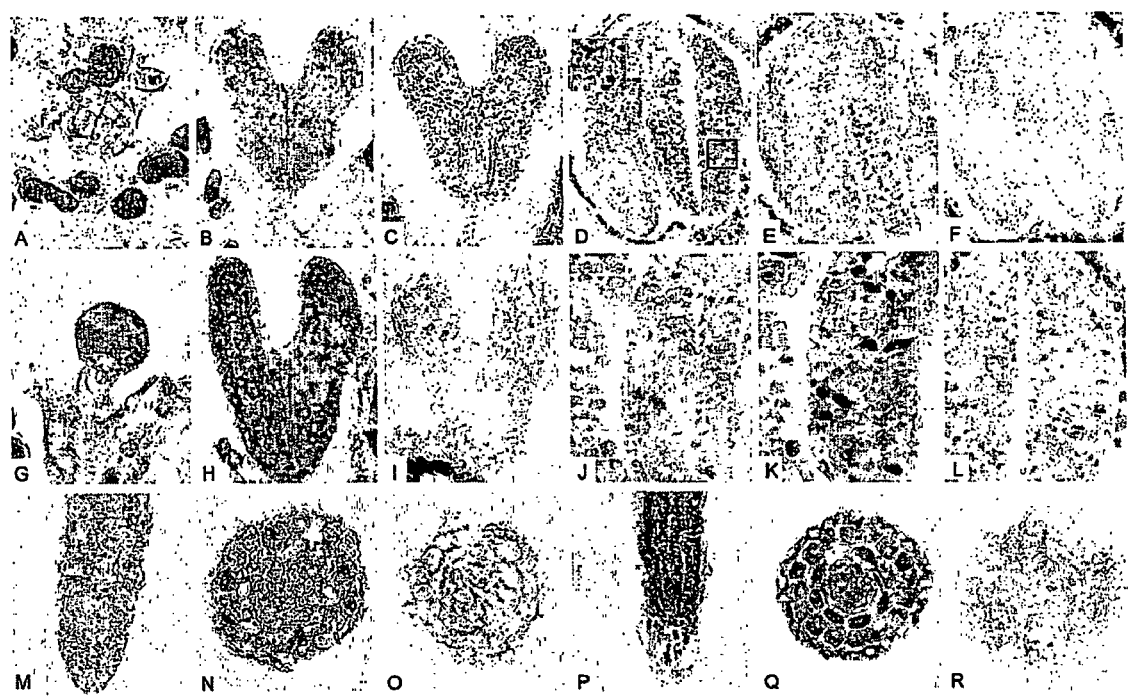

FIG. 16. Expression pattern of the HBT gene.

HBT expression during embryogenesis (A-D) and post embryonically (M-O) in wildtype roots using antisense (A, B, D, M and N) and sense (C and O) probes. HBT expression in a hbt mutant embryo with a antisense (E and sense (F) probe. AtCDC27At expression in wildtype embryos (G-I) and seedlings (P-R) with antisense (G, K, P and Q) and sense (I and R) probes. Double labeling of AtCYC2B (J) and HBT (K) in a single section (both antisense probes) and double labeling of AtCYC2B antisense and HBT sense probes in a single section as a control (L). In both cases the detection of the AtCYC2B antisense probe (fast red) was performed followed by an inactivation step of alkaline phoshatase and the labeling and detection of the (anti)sense HBT probe (NBT/BCIP).

FIG. 17. Exogenous auxin application.

DR5::GUS expression in wt roots (A-E) and in hbt seedlings (E-I). Three days post germination seedlings were transferred to 0.5 GM plates (A and F) and 0.5 GM plates containing $10^{-9}$ M 2,4 D (B and G), $10^{-8}$ M 2,4 D (C and H), $10^{-7}$ M 2,4 D (D and I) and $10^{-6}$ M 2,4 D (E and J) and incubated for another three days. Mutants are shown at 10× magnification of the wildtype seedling.

FIG. 18. Hypcotyl and epidermis cell length measurements.

(A) Hypocotyl lengths of hbt single mutants and hbt axr3-1T double mutants germinated in light.
(B) Hypocotyl lengths of hbt single mutants and hbt axr3-1T double mutants germinated in the dark.
(C) Epidermal cell length of hypocotyls of the hbt single mutants and the hbt axr3-1T double mutants. L: seedlings germinated in light, D: seedlings germinated in the dark.

FIG. 19: hbt mutants contain higher levels of ARX3 protein.

(A) RT-PCR analysis of AXR3 expression in wild-type Col-O *Arabidopsis* (WT) and hobbit mutant background ($hbt^{9620}$ and $hbt^{5722}$). RNA were extracted from wild-type and mutant seedlings. After cDNA synthesis, PCR were performed respectively using AXR3 specific primers, and ubiquitin (UBQ) as constitutive control. The results show that AXR3 mRNA levels are lower than in wild-type.

(B) Western blot analysis of AXR3/IAA17 expression in wild-type Col-0 Arabidopsis (WT) and hobbit background ($hbt^{2311}$, $hbt^{9620}$ and $hbt^{e56}$). Proteins were extracted from whole plants (10 d.p.g.), quantified, and 1 µg was separated on a 15% polyacrylamide gel. After transfer, membranes were incubated first with anti-AXR3/IAA17 antibody (upper blot), and then with anti-actin antibody (lower blot) as control of protein loading. The result shows that hbt mutants accumulate a band at the expected AXR3 size.

(C) Western blot analysis of AXR3/IAA17 expression in $hbt^{2311}$ and $hbt^{2311}$ $axr3^{GT3958}$ (individual plants from 3 independent crosses). Experiment was carried out in same conditions as B, except that plants were 25 d.p.g. The result shows that the vast majority of protein detected by the antiserum in hbt seedlings is AXR3/IAA17. Molecular weight markers in kilo Dalton (kDa) are indicated at the right side of panel B and C and. The expected band of ARX3 is indicated by an arrowhead) As a control the ACTIN protein was also stained in the same plant extracts.

FIG. 20: nuclear DNA content In hypocotyls after endoreduplication

Histogram of the DNA content of hypocotyls cells of wild-type (WT) arabidopsis plants and hbt mutant plants ($hbt^{2311}$). The ploidy distribution of the different cells is measured according to the DNA content.

EXAMPLES

For all molecular cloning steps, and unless otherwise stated, the standard protocols as described in Sambrook et al. 1989, were followed.

Example 1

Identification of hbt Mutant *Arabidopsis thaliana* Plants and Complementation Analysis.

Eleven alleles of the HBT gene have been identified, all with similar mutant phenotypes (Willemsen et al., 1998). Since all the mutations have been induced by EMS, the isolation of the HBT gene based on its map position was the most straightforward approach. Several factors influence the efficiency of the map based cloning procedure. First, the size of the mapping population is very important. When many recombinants are generated the chance that there is a crossing-over event close to the gene of interest increases and thus the number of candidate genes that have to be sequenced to identify the mutant gene decreases. Second, even though EMS usually introduces single base pair changes, there is a small chance for chromosomal rearrangements that strongly interfere with the quality of the mapping population. When such a rearrangement surrounds the mutant locus, there will be no recombination in this area, because rearrangements interfere with the correct aligning of homologous chromatids during meiosis needed for the precise breakage, swapping and reunion of the chromatids in the recombination process. We therefore generated two mapping populations, using different alleles. Third, the amount of information that is available about the chromosomal region of the mutated gene. If the chromosomal region in which the mutant gene is localized is covered by a large number of markers, they can be used for the fine mapping of the mutant locus. However, if available markers are scarce, new markers have to be developed, which is time-consuming. Several detailed maps have been generated combining available genetic and molecular marker data providing a framework for the mapping of the mutant locus (Chang et al., 1988; Nam et al., 1989; Talon et al., 1990; Reiter et al., 1992; Hauge et al., 1993). A large collection of single nucleotide polymorphisms (SNPs) between Col-0 and Ler has recently been published in the *Arabidopsis thaliana* Database that can be used to design new molecular markers. Although many classical markers depend on the presence of a polymorphism in a restriction site, various new molecular markers have been developed that distinguish different ecotypes by a single nucleotide polymorphism. And last, the information available about the sequence of the entire *Arabidopsis* genome facilitates a fast development of new molecular markers, since information about the position of genes is also provided. This is important when molecular markers have to be developed for ecotype combinations other than Col-0 and Ler, for which there is only a limited amount of SNPs known. In this case, selecting intragenic regions for marker generation will increase the chance of identifying polymorphisms.

We generated a set of recombinants and by screening this collection of recombinants with both published (morphological and molecular) markers and new (molecular) markers that were developed in our laboratory, we were able to position the hbt locus on a DNA interval of approximately 120 kb. At this point we started sequencing the open reading frames present in this interval in the mutant background of two Col-0 alleles and this revealed mutations in one of the transcription units. We confirmed that this transcription unit represents the HBT gene by sequencing all the mutant alleles and by complementation analysis. More in detail, these experiments were carried out as follows. For mutagenesis experiments the *Arabidopsis thaliana* ecotype Columbia-0 was used (containing a marker transgene consisting of the promoter of the vascular-expressed S-adenosyl-methionine-synthetase (SAM) gene fused to β-glucuronidase; Peleman et al., 1989). Dry seeds were mutagenised with freshly made 10 mM ethyl methane sulphonate (EMS) in water for 24 hours at 22'C. Seeds were sown on soil and grown in a plant chamber at 22'C, 75% humidity with a 16 hours light and 8 hours dark cycle. Single siliques representing 10,000 M1 families were harvested, then seeds were suspended in 0.1% agarose and plated on a medium containing 0.8% plant agar (Duchefa) and 50 µg/ml ampicillin.

M2 seedlings pooled in individual families were screened under a Zeiss stemi SV-6 dissecting microscope for root meristem defective mutants by pre-selecting mutants with severely reduced root length, and subsequent analysis of root cap structure in cleared specimens (see Example 3). The M3 progeny from siblings of candidate mutants with aberrant root cap structure was re-tested for mutant phenotype, and cleared ovule preparations (see Example 3) were examined using Nomarski optics to detect abnormalities in embryo development. Six hbt alleles, 2311, 5721, 5859, 8052, 9620 and 9624 were recovered. 7.7% of the M1 families segregated chlorophyll mutants, and 6 monopteros and 7 gnom alleles were recovered (complementation analysis by T. Berleth and U. Mayer, data not shown). The $hbt^{1611}$ allele was recovered from a separate mutagenesis experiment performed as above but using Landsberg erecta seeds. The hbt alleles GVI-20/1, GVII-24/1, G221-30/2 (ecotype Landsberg erecta) were provided by G. Jurgens (University of Tübingen) and the $hbt^{e56}$ allele (ecotype Columbia-0) was provided by C. Bellini and H. Höfte (INRA, Versailles).

In complementation tests we combined hobbit alleles (with the dominant SAM-GUS marker) as donors with the Ler or hbt$^{e56}$ alleles as acceptor, allowing selection of successful cross-pollination events. Non-complementation was observed in combinations of the reference allele hbt$^{2311}$ with hbt$^{e56}$, hbt$^{GVI-20/1}$, hbt$^{GVII-24/1}$, hbt$^{G221-30/2}$ and hbt$^{1611}$, in combinations of hbt$^{5859}$ with hbt$^{e56}$ and hbt$^{GVII-24/1}$, in combinations of hbt$^{5721}$ and hbt$^{9624}$ with hbt$^{GVI-20/1}$, and in combinations of hbt$^{8052}$ and hbt$^{9820}$ with hbt$^{GVII-24/1}$, thus placing all hbt alleles in a single complementation group (Willemsen et al. 1998).

Example 2

Recombination Mapping of the hbt Locus.

hbt$^{GVI-20/1}$ heterozygous plants (ecotype Ler) were used to pollinate Col-0 plants and F1 plants segregating mutants were selected. Individual F2 hbt mutants were ground in liquid nitrogen, and suspended in 200 µl ddH$_2$O. Two to ten µl of the DNA isolates were analysed using CAPS and micro satellite markers (Koorneef and Stam, 1992). Recombination frequencies in n hbt chromosomes were calculated as r=n$_{Col}$/(n$_{Col}$+n$_{Ler}$), and genetic distances were calculated using the Kosambi mapping function. Linkage was observed between hbt and the chromosome II markers m246 (8/52 recombinant chromosomes, 15.4±5.5 cM) and GPA1 (24/294 recombinant chromosomes, 8.2±1.6 cM). The Col-0 hbt allele 2311 was subsequently crossed to a Ler line with flanking markers sti and er. F2 lines with recombinant chromosomes were selected based on the appearance of "only sti" and "only er". DNA was prepared from F3 lines from these recombinants which segregated hbt, and a variety of CAPS and SNP markers were used to map the gene to a region on BACs F6F22 and T2G17.

Thus, the two nearest markers flanking the HBT gene were located on two partially overlapping BACs, F6F22 and T2G17. The physical distance between the two markers was approximately 120 kb. These two BACs are sequenced by the *Arabidopsis* Genome Initiative (AGI) and 30 putative open reading frames (ORFs) were predicted in this area. To amplify and sequence these candidate ORFS, primers were designed. DNA was isolated from two Col-0 hbt alleles (hbt$^{2311}$ and hbt$^{9620}$), PCR amplified and sequenced.

PCR primers consisting of 30 nucleotides were designed with an average melting temperature of 65.degree. C. using the Primer3 program (http:// genome.wi.mit.edu/cgibin/primer/primer.htm). 5-10 .mu.g DNA was mixed with a PCR mix (75 mM Tris-HCl pH 9.0; 20 mM (NH).sub.4SO.sub.4; 0.1% Tween 20; 2 mM MgCl.sub.2; 200 .mu.M dNTPs; 200 .mu.M primers; 1 u polymerase). The DNA was amplified through 35 cycles (94.degree. C. for 1 min, 60.degree. C. for 1 min and 72degree. C. for 1.5 min per cycle) and detected on a 1% agarose gel (Hispanagar). For sequencing products from two independent PCR amplifications were washed over a column (High Pure PCR Product Purification Kit: Boerhinger Mannheim). Sequence reactions were performed using Big Dye Terminator Sequencing Premix (GENPAK LTD) and analyzed on an ABI PRISM 310 Genetic Analyzer.

The obtained sequences were compared to the Col-0 sequence published on the National Center for Biotechnology database (http://.ncbi.nlm.nih.gov/). W identified mutations for these two alleles only in ORF T2G17.20 and decided to sequence this ORF in the mutant background of the other hbt alleles. Eight more hbt alleles revealed sequence changes in T2G17.20, therefore we concluded that this transcription unit represents the HBT gene.

Analysis of Mutant Alleles

Mutations in the hbt alleles were identified by sequencing products from two independent PCR reactions from mutant seedlings.

(Primers:

```
HBT AF:
AGAGTGACCTACTTACTACATTGGTACAAAACC;:    SEQ ID Nr.41

HBT AR:
CCCATTAAAGCGTAAACGCTGCTCTCTGAAG;:      SEQ ID Nr.42

HBT BF:
TATTCAAATGGTCAATTATAAAGCCCAATAAG;:     SEQ ID Nr.43

HBT BR:
TGAATGAATACTTTCTCAACTACTATTGAAGC;:     SEQ ID Nr.44

HBT CF:
TATGAGTCAACTGTTAGAGGAATGTCTCTG;:       SEQ ID Nr.45

HBT CR:
GAAGTTGACAGTTGTTGCATATACTGC;:          SEQ ID Nr.46

HBT DF:
TCTTACACTTTTCTGTCTGCTCAACTTTCA;:       SEQ ID Nr.47

HBT DR:
CAAAGAACTCAATTTAGAACCTCCCAAATAC;:      SEQ ID Nr.48

HBT EF:
CAGATTTCTGGCAGACTATTTTCTGATTCT;:       SEQ ID Nr.49

HBT ER:
AAGTAACTCAGCTTCATGTCTTCCTTCAAA;:       SEQ ID Nr.50

HBT FF:
GATATTTATTTGCAGCATTTGAAGGAAGAC;:       SEQ ID Nr.51

HBT FR:
GAATTTTCAGATTTAAAAACCATCATTGGA;:       SEQ ID Nr.52

HBT GF:
AGTCTTTAAAACAGAGTCGTCCAATGATG;:        SEQ ID Nr.53

HBT GR:
ATATTGCGATTAGGTAGTGTTACGGACAAC.:       SEQ ID Nr.54
``` cDNA from RNA of the splicing mutants (GVII-24/1, G221-30/2,5859, 9624, 9620 and 5721) was synthesized and the region of interest was PCR amplified and sequenced.

Example 3

Phenotypic Analysis of hbt Mutant *Arabidopsis thaliana* Plants.

The root cap marker line containing the 35S::B2 promoter fused with GUS (β-glucuronidase) (Benfey et al., 1990) (FIGS. 2 and 3) and the lateral root cap marker line containing the lateral root cap specific promoter LRC244 fused with GUS (Malamy and Benfey, 1997) (FIG. 2) were provided by P. Benfey (New York University). The marker line containing the chimeric gene comprising the quiescent center specific promoter GC46 and the GUS gene (FIG. 4) was obtained from the INRA-Versailles collection. The marker line containing the SCARECROW (SCR) promoter fused with GUS (pSCR::GUS) (FIG. 4) was provided by Dr. Philip Benfey (Wysocka-Diller et al., 2000). The pGL2::GUS (Masucci et al., 1996) was used.

The marker line containing the Soy bean heat shock promoter HSP19 driving the expression of the fusion protein comprising the AXR3 domains I and II followed by GUS (FIG. 7) was obtained from O. Leyser (University of California at Davis). The marker line containing the *A. thaliana* cyclin B1 promoter (Ferreira et al. 1994) driving the expression of the fusion protein comprising the cyclinB1 destruction box followed by GUS (FIG. 6) was provided by Dr. Peter Doerner (Salk Institute for biological studies, La Jolla).

All marker lines were crossed with hbt heterozygotes. F2 lines derived from these crosses segregating hbt and homozygous for the markers were selected and analyzed by X-gluc staining as described below. Expression of the AXR3-GUS fusion protein was activated by applying a heat shock (2 h at 37° C.).

Fixation, embedding, sectioning and microscopy for histological analysis of seedlings and embryos were performed as described previously (Scheres et al., 1994, 1995). For quantitave analysis of embryo phenotypes, ovules were cleared for 10 minutes in an 8:3:1 mixture of chloral hydrate: distilled water:glycerol (Mayer et al., 1991) and embryos were visualised using Nomarski optics on a Zeiss photomicroscope III.

The shoot apical meristem in mature embryos of $hbt^{2311}$, $hbt^{5859}$, $hbt^{5721}$, $hbt^{8052}$, $hbt^{9620}$, $hbt^{GVII-24/1}$ and $hbt^{G221-30/2}$ was visualised by confocal laser scanning microscopy (CSLM) as described previously (Clark et al., 1995).

Cell numbers of the root were determined in chloral-hydrate-cleared seedlings by counting the cortical cells in files extending from the quiescent centre to the uppermost root hair. For root length measurements the seedlings were grown at ½ GM (8 g/l Duchefa plant agar, 2.2 g/l Murashige, and Skoog salts incl. vitamins, 1% sucrose) for 10 days. After clearing of the seedlings the roots were measured from the tip to the uppermost root hair using a VIDAS RT image analysis system (Zeiss/Kontron) with a software package that is available on request (M. Terlou, Department of Image Processing and Design, Padualaan 8, 3584 CH Utrecht).

Starch granules in the columella root cap were visualised with 1% lugol solution (Merck) in 3-day-old seedlings grown on ½ GM. Seedlings were stained for 3 minutes, rinsed with water, cleared with chloral hydrate and photographed with Nomarski optics on a Zeiss photomicroscope III with a Agfa APX-25 film.

Cell numbers in the hypocotyl were determined in 10-day-old chloral hydrate cleared seedlings. Cortical cells were counted in files from the uppermost root hair to the cotyledon bifurcation point. Numbers of cells in the cotyledon epidermis of the mature embryo were counted in circumference and in median longitudinal sections showing both the cotyledons and the shoot apical meristem. β-glucuronidase activity in transgenic marker lines was visualised by staining for 2-16 hours at 37° C. in 0.5 mg/ml X-gluc (5bromo-4-chloro-3-indolyl-glucuronide; Biosynth AG) dissolved in n-dimethylformamide, 0.1% Triton X-100, 0.5 mM $K_4Fe(CN)_6.H_2O$, 0.5 mM $K_3Fe(CN)_6$, and 50 mM sodium phosphate buffer, pH 7.2.

Example 4

In Situ Hybridization.

In situ hybridization was performed using a digoxigenin RNA labeling and detection system (Roche) (FIGS. 11 and 12).

Probe Synthesis

HOBBIT RNA probe was synthesized using a 600 pb fragment of the N terminal region of the cDNA. The fragment was cloned in PGMT vector, which contain promoters of Sp6 and T7 RNA polymerase. The antisense HBT RNA was synthesized using T7 RNA polymerase and the sense control with the Sp6 RNA polymerase.

Preparation of the Material

The fresh tissues were fixed 4 hours at 4° C. in 4% of formaldehyde following vacuum infiltration (2 min), after which they were submitted to gradual step of ethanol 10%, 30%, 50% and left overnight at 70% of ethanol. The samples were then treated with 95% ethanol 0.1% eosin overnight and after several incubations in 100% ethanol 0.1% eosin; gradual steps of xylem (25%, 50% and 75%) were performed. The material was finally embedded in paraffin. The sections of 8μm were performed and mounted on coated slides.

Pretreatment Prior to Hybridization

The paraffin was removed by treatment with xylem and the tissues were incubated in differents concentrations of ethanol (100%, 95%, 80%, 60%, 30% and 10%). Incubations in NaCl 0.83% 5 min, PBS 5 min, 4% formaldehyde in PBS followed these steps. After which a treatment with proteinase K has been performed, this step was followed by a gradual dehydration with ethanol (10%, 30%, 50%, 80%, 95% and 100%).

Hybridization

The slides were hybridized overnight at 62° C.

Washing and Detection

The washing steps were performed using a washing solution (2×SSC, Formamide 50%) at 65° C. during 30 min, after which incubations in NT buffer (500 mM NaCl, 10 mM Tris, pH 8) were performed. The slides were treated with Rnase A and after incubation with the washing solution, the samples were treated with a blocking solution (antibody buffer 150 mM NaCl, 100 mM Tris, BSA and plant extract) during 1 hour. A 1:1000 dilution of antibody was prepared in the same blocking solution where the samples were incubated for 2 hours. To the staining Buffer (100 mM NaCl, 100 mM T, pH9, 5) the following staining reagents were added BCIP and NBT (provided by Roche). Incubate overnight at room temperature and after checking the staining reaction is stopped by incubation in ethanol 95% and the slides were mounted in glycerol 1:1.

Example 5

Ectopic Expression of the HOBBIT Gene.

The HOBBIT cDNA as identified by SEQ ID NO 2 or 3 is operably linked to a promoter operational in plants Expression constructs are inserted into a suitable binary plant transformation vector further comprising in its T-DNA an appropriate selectable marker. After transfer of said plant transformation vectors to *Agrobacterium tumefaciens* by means of electroporation, and subsequently plants are transformed with standard plant transformation procedures. Transformed are selected on a medium containing the appropriate selective agent. T2 plants homozygous for the introduced transgenes are selected in an analogous way. Preferred plants to be transformed are *Arabidopsis thaliana* and crop plants.

Overexpresion

Several promoter systems are used to drive the expression of the Hobbit gene in the transgenic plants, such as the constitutive ubiquitin promoter, the yeast UAS promoter activated by the GAL4 transcription factor and the Hsp19 promoter.

The GAL4 responsive promoter allows the tissue specific expression of the gene as follows: Transgenic *A. thaliana* lines containing the GAL4 ORF operably linked to a wide variety of e.g. tissue-specific or cell cycle-specific gene promoters are obtained from the Nottingham *Arabidopsis* stock center (J. Haseloff collection). The GAL4 element is cloned in between the Cre-Lox recombination sites. Said GAL4-expressing lines are crossed with the earlier obtained *A. thaliana* plants transgenic for the yeast UAS promoter responsive to GAL4.

The Hsp19 promoter will allow inducible Hobbit expression.

Also cell cycle specific promoter cdc2a promoter, which allows specific expression in meristem cells. The 2S2 promoter is also used to direct expression in storage cells. For expression in monocots, oleosin promoter is used to direct expression in embryonic cells, the prolamin for storage cells and GOS2 for constitutive expression. In a preferred application of ectopic hobbit expression, these constructs are transformed to rice plants via *agrobacterium* mediated transformation.

Phenotypic effects of ectopic HOBBIT expression are studied in the transgenic *A. thaliana* plants constitutively expressing HOBBIT under the control of the constitutive ubiquitin promoter or in the offspring of the crossings including *A. thaliana* plants ectopically expressing HOBBIT in e.g. a tissue-specific or a cell cycle-specific fashion. Alternatively, the HOBBIT expression under the control of a heat shock promoter is induced in a post-embryonic stage.

When extra Hobbit activity is added to the plant cells, the plant cells are more sensitive or more responsive to auxin. Alternatively, the plants cells are normally not responsive to auxin and upon altered Hobbit activity, they are rendered responsive to auxin. This higher responsiveness results in phenotypic effects such as, formation of more organs such as formation of more lateral roots or different branching patterns.

Other phenotypic effects are also envisaged by the technique of the present invention because of the pleiotropic effect of the auxin hormone.

Downregulation

Ectopic expression of the antisense RNA of the Hobbit gene results in downregulation of the Hobbit activity in the cell. Lower Hobbit activity in a cell results in a lower responsiveness to auxin. The downtuning of auxin related effects in these cells results in phenotypic effects such as elimination or retardation of organ formation such as elimination of lateral roots.

Other phenotypic effects are also envisaged because of the pleiotropic effect of the auxin hormone.

Co-expression

The Hobbit gene is also ectopically expressed (overexpression or downregulation) in concert with the modulation of other genes or proteins. This is particularly interesting to design a particular phenotypic effect, based on the combination of the effects mediated by each of the genes. For example, the Hobbit gene is co-expressed with a gene involved in cytokinin effects. It is known that both auxins, acting in the S-phase, and cytokinin, acting in the M-phase are necessary to induce normal cell division in plants.

Also, the Hobbit gene is co-expressed with other genes that encode a limiting factor in the cell-cycle process, more particularly a limiting factor of the APC. Herewith, an equilibrium of of both proteins is re-established, but now on a higher level than normal.

Alteration of Endogenous Expression

Another application of the present invention is the CRE-lox mediated recombination that creates loss of function clones in wildtype background. With this method plants are transformed with a construct carrying a wildtype copy of the HBT gene driven by its own promoter in between two lox sites. These transgenic plants are then treated with a short heat shock, activating CRE driven recombination and deletion of the HBT gene. Introducing this construct in a hbt mutant background results in a complemented wildtype plant. Subsequent heat shock CRE activation thus creates mutant clones in an otherwise heterozygous wildtype plant. This Is a powerful system because in these mutant clones the function of the gene is studied, without long-term and possible indirect defects. Such effects likely are present in the hbt mutant. It is also possible to induce these clones in adult plants, to study HBT function in the adult plant for example during flower development. Together these experiments provide proof and important information of how the HBT gene links cell cycle progression to developmental competence.

Example 6

Yeast Complementation: Role of HOBBIT in the APC

The coding region of the HBT cDNA was amplified by PCR using the following primers: SEQ ID No. 55: YC F: GAAGTCGACACAAACTATGGAAGCT and SEQ ID No. 56: YC R: AATCATACCCAAGGATCCTGGAG. PCR was carried out using the ELONGASE Amplification System essentially as recommended by the manufacture (Life Technologies), except that the reactions were cycled automatically through time/temperature cycles as follows: denaturation 94° C./1 min; annealing 50° C./1 min, and extension 68° C. The resulting amplified DNA fragment was purified through agarose gel, and introduced in pGEM-T (Promega). The resulting plasmid was sequenced. The approximately 2,4 kb insert was released by digestion with SalI and BamHI and transcriptionally fused to the thiamine repressible promoter (nmt1) in the yeast shuttle vector pREP3 (Maundrell, 1990), containing LEU2 as a selectable marker. The plasmid construct was transformed in *Schizosaccharomyces pombe* strain nuc2-663 (Hirano et al., 1988), using the lithium acetate method (Okasaki et al., 1990). The Leu+resulting colonies were inoculated in minimal liquid medium (Moreno et al., 1991) containing 5 μM thiamine and grown overnight at 25° C. Cells were washed in minimal medium without thiamine, divided in two flasks and grown at 25° C. for 16 hr to induce the promoter. One flask was shifted to 37° C., the other kept at 25° C. and samples taken every two hours to measure optical density.

HBT cDNA partially complemented a nuc2ts mutation in *S. pombe* (see FIG. 15).

Example 7

In Sity Hybridization

Expression of HBT is cell cycle regulated and the expression of the HBT gene was cell cycle regulated with a peak of expression at the G2/M phase.

In situ hybridizations were performed using a digoxigenine RNA labeling and detection system (Roche). Sense and antisense probes from different cDNA regions of both the HBT gene and CDC27At were synthesized (FIG. 16): N terminal, central, and C terminal part of the ORF. The following primers were used:

```
HBT   GCAACAACTGTCAACTTCCCTCGGCTT:       SEQ ID Nr.57
NF:

HBT   AGAACCAGTCGTTGAGGCAGTATTAGGCC;:    SEQ ID Nr.58
NR:
```

SEQ ID No. 33: HBT 2F and SEQ ID No. 34: HBT 2R; SEQ ID No. 35: HBT 3F and SEQ ID No. 36: HBT 3R;

```
CDC27   ATGATGGAGAATCTACTGGCGAATTG;:     SEQ ID Nr.59
1F:

CDC27   CATCGAGGAAAGAGAAGGTGCATAG;:      SEQ ID Nr.60
1R:

CDC27   ATCCTAGTGAATCTTCCCCGGATCG;:      SEQ ID Nr.61
2F:

CDC27   AGCCAGTTGAAATTGATGCTGCG;:        SEQ ID Nr.62
2R:

CDC27   GATGCAGAGAGATGCTACCGGAAGGC;:     SEQ ID Nr.63
3F:

CDC27   CTAAATGCAAAATGTGACCATGATTG:      SEQ ID Nr.64
3R:
```

Tissues were fixed, dehydrated and embedded as described (Wilkinson and Nieto, 1993). Hybridisation were performed at 62° C. and the washing steps were carried out under stringent conditions (2×SSC, 50% formamide at 65° C.). Double labelings were performed according to Long and Barton (1998). The antisense AtCYC2B probe was labeled with digoxigen-11-UTP and both HBT antisense and sense probes with fluorescein-12-UTP. AtCYC2B was first detected first using anti-digoxigen antibody (1:1250) to which alkline phosphatase (Boehringer Mannheim) was conjugated. Fast Red was used as a substrate. Then HBT transcripts were detected using anti-fluorescein antibody (1:6000) also conjugated to alkaline phosptatase. NBT/BCIP was used as a substrate.

For fight microscopy plant material was cleared and mounted according to Scheres et al., 1994 and photographed using an Axioskope 2 microscope with Nomarski optics (Zeiss) and a Nikon Digital Camera (Nikon, DXM1200). For the scanning EM tissues were fixed according to (Bowman et al., 1989) and visualized with a Philips XL30labs microscope from Feicompagny.

Example 8

HBT Transcript Structure

To determine the correct transcript sequence of the hobbit gene, RNA was isolated from Col-0 seedlings using a Purescript kit (Gentra) and a RT-PCR was performed (Ready-to-go kit; Pharmacia) using the following primers:

```
HBT GAAGAAAGGCAACAACTATGGAAGCTATG;:     SEQ ID Nr.31
1F

HBT GAACTGTCAGTAATAAGGGAGTTTGGGTTT;:    SEQ ID Nr.32
1R:

HBT ATGCAACAACTGTCAACTTCCCTCG;:         SEQ ID Nr.33
2F:

HBT TATCCATTCCTTCTAAGCAATAAGGAGAAGC;:   SEQ ID Nr.34
2R:

HBT AAATTTTAAACCTCCTTAGGACACTCGGA;:     SEQ ID Nr.35
3F:

HBT TCACGGGCTCTCATCGATCTCATCT.:         SEQ ID Nr.36
3R:
```

In addition, the product obtained with primers HBT 1F and HBT 1R was used as a probe to screen a cDNA library (Giraudat et al., 1992). The cDNA identified was sequenced together with the RT-PCR products. The 3' end of the identified cDNA of HBT was confirmed using a 5'/3' RACE kit (Boehringer Mannheim; primers: SEQ ID No. 37: HBT 3'2F: GTTCTTGAGGAGCTCAAGAGTATG and SEQ ID No. 38: HBT 3'1F: GCTTTAATGGGCAGGATCTATAAG) and by sequencing the RACE product.

HBT transcription start site was determined using RNase Protection on 20 µg of total RNA from roots and cotelydons and on 1 µg of poly A RNA from seedlings. A 350 bp HBT DNA fragment (primers: SEQ ID No. 39: HBT BF: TAT-TCAAATGGTCAATTATAAAGCCCAATAAG and SEQ ID No. 40: HBT 5'1R: ACATGAAAATAGCATTTTTGTA-GAC), including the putative ATG and transcription start, was subcloned into a pGEMT vector (Promega). RNA antisense and sense probes were synthesized using T7 and Sp6 RNA polymerase and the RNase protection experiment was carried out using the Ambion RPA II RNase Protection Kit, according to the manufacturers instructions.

In this experiment the endogenous control probe used was the 18S RNA provided by Ambion. Comparisons with the deduced protein sequence were performed using BLAST program.

Example 9

Auxin Sensitivity Test

DR5::GUS constructs was used (Ulmasov et al., 1997b). Seedlings were germinated on 0.5 GM medium as described, 3 dpg transferred to fresh 0.5 GM plates containing different concentrations of 2,4 D or IAA ($5.10^{-9}$ M until $5.10^{-6}$ M) (see FIG. 17) and incubated for an additional 3 days. After that the b-glucuronidase was visualized as described (Willemsen et al., 1998).

Example 10 axr3-1 T Crosses to hbt$^{2311}$

Homozygous axr3-1T plants were crossed with heterozygous hbt$^{2311}$ plants. The F1 was allowed to self-pollinate and in the F2 seedlings were analysed. To measure the hypocotyls of the hbt single mutants, seedlings were analysed that arose from the cross with axr3-1T but did not segregate axr3-1T. Hypocotyl and epidermal cell lengths (dee FIG. 18) were measured using a Zeiss Mikroscope II, a CCD camera (Panasonic, WC-CD50) and an image analysis system (IBAS, Kontron/Zeiss).

Example 11

Level of ARX3 in hbt Mutants

Plant Material hbt alleles are described herein. axr3$^{GT3958}$ null allele (see FIG. 9) (seed line GT3958, NASC database) contains a single Ds element insertion in the first exon of the axr3 gene and is in L-er background. All plants were grown on ½ GM.

RT-PCR Analysis

AXR3 primers: SEQ ID No. 65: AXR3-F: TCT TCC CGG TGG AGA TAC AG and SEQ ID Nr. 66: AXR3-R:GCC CAT GGT AAA AGA GCT GA Western Blot Analysis Crude protein extract was proceeded from whole seedlings using EZ procedure as described in Martinez-Garcia et al. (1999). Total proteins were quantified using D$_C$ reagent (Bio-Rad, Hercules, USA). 1 μg of extract was separated on 15% polyacrylamide gel, transferred on Immobilon-P membranes following manufacturer instructions (Millipore Corp., Bedford, USA). Membranes were blocked, incubated with anti-AXR3/IAA17 purified antibody (1/500; Ouellet et al., 2001) and anti-rabbit IgG conjugated to HRP (1/5000; Bio-Rad, Hercules, USA), and revealed as described in ECL kit (Amersham Pharmacia biotech., Roosendaal, Netherlands). Membranes were then incubated with anti-actin IgG (1/3000; ICN Pharmaceuticals Inc., Costa Mesa, USA) and anti-mouse IgG conjugated to HRP (1/5000; Bio-Rad, Hercules, USA), following same procedure.

Example 12

Flow Cytometric Analysis

Ten to twelve hypocotyls (from seedlings grown either in light or dark conditions, 2 to 7 d.p.g.) were chopped with a razor blade in the extraction buffer (pH 7.0, 45 mM magnesium chloride, 30 mM sodium citrate, 20 mM 4-morpholinepropane sulfonate, sodium metabisulfite 1 M and Triton X-100 0,5% containing 5 □g/ml of DAPI. The nuclei were filtered (30 μm) and 1000-2500 nuclei were analysed on a cytometer (EPICS V, Coulter) with laser excitation (40 mW) at 357 nm. Each result is the mean value of at least two independent measurements (i.e. at least 20 hypocotyls). In contrast to wildtype, a high percentage of hbt nuclei has a DNA content between 2C and 4C, which suggests slow S-phase progression—which has been linked in the literature to reduced APC activity (see FIG. 20).

REFERENCES

Abel, S., Nguyen, M. D., and Theologis, A. (1995). The PS-IAA4/5-like family of early auxin-inducible mRNAs in *Arabidopsis thaliana*. *J.Mol.Biol.* 251, 533-549.

Abel, S., Oeller, P. W., and Theologis, A. (1994). Early auxin-induced genes encode short-lived nuclear proteins. *Proc..Natl.Acad.Sci.U.S.A* 91, 326-330.

Ainley, W. M., Walker, J. C., Nagao, R. T., and Key, J. L. (1988). Sequence and characterization of two auxin-regulated genes from soybean. *J.Biol.Chem.* 263, 10658-10666.

Alberts, B., Bray, D., Lewis, J., Raff, M., Roberts, K., and Watson, J. D. (1994). "Molecular Biology of the Cell." Garland Publishing Inc.

An, G., Watson, B. D., Stachel, S., Gordon, M. P., and Nester, E. W. (1985). New cloning vehicles for transformation of higher plants. *EMBO J.* 4, 277-284.

Armstrong, C. L., Petersen, W. P., Buchholz, W. G., Bowen, B. A., and Sulc, S. L. (1990). Factors affecting PEG-mediated stable transformation of maize protoplasts. *Plant Cell Reports* 9, 335-339.

Aukerman, M. J., Lee, I., Weigel, D., and Amasino, R. M. (1999). The *Arabidopsis* flowering-time gene LUMINIDEPENDENS is expressed primarily in regions of cell proliferation and encodes a nuclear protein that regulates LEAFY expression. *Plant J.* 18, 195-203.

Banerjee, A., Pramanik, A., Bhattacharijya, S., and Balaram, P. (1996). Omega amino acids in peptide design: incorporation into helices. *Biopolymers* 39, 769-777.

Baron, M. H. and Baltimore, D. (1982). Antibodies against the chemically synthesized genome-linked protein of poliovirus react with native virus-specific proteins. *Cell* 28, 395-404.

Bartel, P. L. and Fields, S. (1997). "The Yeast Two-Hybrid System." Oxford University Press.

Bechtold, N. and Pelletier, G. (1998). In planta *Agrobacterium*-mediated transformation of adult *Arabidopsis thaliana* plants by vacuum infiltration. *Methods Mol.Biol.* 82, 259-266.

Benfey, P. N. (1999). Is the shoot a root with a view? *Curr.Opin.Plant Biol.* 2, 39-43.

Benfey, P. N., Ren, L., and Chua, N. H. (1990). Tissue-specific expression from CaMV 35S enhancer subdomains in early stages of plant development. *EMBO J.* 9, 1677-1684.

Benkirane, N., Guichard, G., Briand, J. P., and Muller, S. (1996). Exploration of requirements for peptidomimetic immune recognition. Antigenic and immunogenic properties of reduced peptide bond pseudopeptide analogues of a histone hexapeptide. *J.Biol Chem.* 271, 33218-33224.

Berry, A. and Brenner, S. E. (1994). A prototype computer system for de novo protein design. *Biochem.Soc.Trans.* 22,1033-1036.

Bowman, J. L., Smydh, D. R. and Meyerowtz, E. M. (1989). Genes directing flower development in *Arabidopsis*. *Plant cell* 1, 37-52

Bowman, J. L. and Eshed, I. (2000). Formation and maintenance of the shoot apical meristem. *Trends Plant Sci.* 5,110-115.

Brandeis, M. and Hunt, T. (1996). The proteolysis of mitotic cyclins in mammalian cells persists from the end of mitosis until the onset of S phase. *EMBO J.* 15, 5280-5289.

Carabelli M, Morelli G, Whitelam G and Ruberti I (1996). Twilight-zone and canopy shade induction of the Athb-2 homeobox gene in green plants. Proc. Natl. Acad. Sci. USA 93, 3530-3535.

Chang, C., Bowman, J. L., DeJohn, A. W., Lander, E. S. and Meyerowitz, E. M. (1988) Restriction length polymorphism linkage map of *Arabidopsis thaliana* Proc. Natl. Acad. Sci. U.S.A. 85, 6856-6860.

Christou, P., McCabe, D. E., and Swain, W. F. (1988). Stable transformation of soybean callus by DNA-coated gold particles. *Plant Physiol.* 87, 671-674.

Clark, S. E., Running, M. P., and Meyerowiz, E. M. (1995). CLAVATA3 is a specific regulator of shoot and floral meristem development affecting the same processes as CLAVATA 1. *Development* 121, 1567-1575.

Conner, T. W., Goekjian, V. H., LaFayette, P. R., and Key, J. L. (1990). Structure and expression of two auxin-inducible genes from *Arabidopsis*. *Plant Mol.Biol.* 15, 623-632.

Crossway, A., Oakes, J. V., Irvine, J. M., Ward, B., Knauf, V. C., and Shewmaker, C. K. (1986). Integration of foreign DNA following microinjection of tobacco mesophyll protoplasts. *Mol.Gen.Genet.* 202,179-185.

Dale, E. C. and Ow, D. W. (1990). Intra- and intermolecular site-specific recombination in plant cells mediated by bacteriophage P1 recombinase. *Gene* 91, 79-85.

del Pozo, J. C. and Estelle, M. (1999). Function of the ubiquitin-proteosome pathway in auxin response. *Trends Plant Sci.* 4, 107-112.

Di Laurenzio, L., Wysocka-Diller, J., Malamy, J. E., Pysh, L., Helariutta, Y., Freshour, G., Hahn, M. G., Feldmann, K. A., and Benfey, P. N. (1996). The SCARECROW gene regulates an asymmetric cell division that is essential for generating the radial organization of the *Arabidopsis* root. *Cell* 86, 423-433.

Dodds, J. H. (1985). "Plant genetic engineering." Cambridge University Press.

Doerner, P. (1999). Shoot meristems: Intercellular signals keep the balance. *Curr.Biol.* 9, R377-R380.

Dorner, B., Husar, G. M., Ostresh, J. M., and Houghten, R. A. (1996). The synthesis of peptidomimetic combinatorial libraries through successive amide alkylations. *Bioorg.Med.Chem.* 4, 709-715.

Ellis, J. G., Llewellyn, D. J., Dennis, E. S., and Peacock, W. J. (1987). Maize Adh-1 promoter sequences control anaerobic regulation: addition of upstream promoter elements from constitutive genes is necessary for expression in tobacco. *EMBO J.* 6, 11-16.

Fassina, G. and Melli, M. (1994). Identification of interactive sites of proteins and protein receptors by computer-assisted searches for complementary peptide sequences. *Immunomethods.* 5,114-120.

Fedoroff, N. V. and Smith, D. L. (1993). A versatile system for detecting transposition in *Arabidopsis*. *Plant J.* 3, 273-289.

Ficcadenti, N., Sestili, S., Pandolfini, T., Cirillo, D., Rotino, G. L., and Spena, A. (1999). Genetic engineering of parthenocarpic fruit development in tomato. *Mol.Breeding* 5, 463-470.

Fromm, M., Taylor, L. P., and Walbot, V. (1985). Expression of genes transferred into monocot and dicot plant cells by electroporation. *Proc.Natl.Acad.Sci.U.S.A* 82, 5824-5828.

Giraudat, J., Hauge, B. M., Valon, C., Smalle, J., Parcy, F, and Goodman, H. F. (1992) Isolation of the *Arabidopsis* ABI3 gene by positional cloning. *Plant cell* 4: 1251-1261.

Gray, W. M. and Estelle, I. (2000). Function of the ubiquitin-proteasome pathway in auxin response. *Trends Biochem.Sci.* 25,133-138.

Guilfoyle, T. J., Ulmasov, T., and Hagen, G. (1998). The ARF family of transcription factors and their role in plant hormone—responsive transcription. Cell Mol. Life Sci. 54, 619-627.

Hamann, T., Mayer, U., and Jurgens, G. (1999a). The auxin-insensitive bodenlos mutation affects primary root formation and apical-basal patterning in the *Arabidopsis* embryo. Development 126,1387-1395.

Hanahan, D. (1983). Studies on transformation of *Escherichia coli* with plasmids. *J.Mol.Biol* 66, 557-580.

Hansen, G. and Chilton, M. D. (1996). "Agrolistic" transformation of plant cells: integration of T-strands generated in planta. *Proc.Natl.Acad.Sci.U.S.A* 93, 14978-14983.

Hansen, G., Shillito, R. D., and Chilton, M. D. (1997). T-strand integration in maize protoplasts after codelivery of a T-DNA substrate and virulence genes. *Proc.Natl.Acad.Sci.U.S.A* 94, 11726-11730.

Hanson, B., Engler, D., Moy, Y., Newman, B., Ralston, E., and Gutterson, N. (1999). A simple method to enrich an Agrobacterium-transformed population for plants containing only T-DNA sequences. *Plant J.* 19, 727-734.

Hardtke, C. S. and Berleth, T. (1998). The Arabidopsis gene MONOPTEROS encodes a transcription factor mediating embryo axis formation and vascular development. EMBO J. 17,1405-1411.

Harlow, E. and Lane, D. (1988). "Antibodies: A Laboratory Manual." Cold Spring Harbor Laboratory Press.

Haseloff, J., Siemering, K. R., Prasher, D. C., and Hodge, S. (1997). Removal of a cryptic intron and subcellular localization of green fluorescent protein are required to mark transgenic Arabidopsis plants brightly. *Proc.Natl.Acad.Sci.U.S.A* 94, 2122-2127.

Hauge, B., Hanley, S., Cartinhours, S et al. (1993) An integrated genetic/RFLP map of the *Arabidopsis thaliana* genome. The Plant Journal, 395, 745-754.

Helariutta, Y., Fukaki, H., Wysocka-Diller, J., Nakajima, K., Jung, J., Sena, G., Hauser, M. T., and Benfey, P. N. (2000). The SHORT-ROOT gene controls radial patterning of the *Arabidopsis* root through radial signaling. *Cell* 101, 555-567.

Herrera-Estrella, L., De Block, M., Messens, E. H. J. P., Van Montagu, M., and Schell, J. (1983). Chimeric genes as dominant selectable markers in plant cells. *EMBO J.* 2, 987-995.

Herrera-Estrella, L., Depicker, A., Van Montagu, M., and Schell, J. (1983). Expression of chimaeric genes transferred into plant cells using a Ti-plasmid-derived vector. *Nature* 303, 209-213.

Hirano, T., Hiraoka, Y., Yanagida, M. (1988). A temperature-sensitive mutation of the *Schizosaccharomyces pombe* gene nuc2+ that encodes a nuclear scaffold-like protein blocks spindle elongation in mitotic anaphase. J. Cell Biol. Apr; 106(4): 1171-83.

Hirano, T., Kinoshita, N., Morikawa, K., Yanagida, M. (1990) Snap helix with knob and hole: essential repeats in *S. pombe* nuclear protein nuc2+. Cell. Jan 26; 60(2): 319-28.

Hobbie, L., McGovern, M., Hurwitz, L. R., Pierro, A., Lieu, N.Y., Bandyophadhyay, A., and Estelle, M. (2000). The axr6 mutants of *Arabidopsis thaliana* define a gene involved in auxin response and early development. Development 127, 23-32.

Hoffman, D. L., Laiter, S., Singh, R. K., Vaisman, I. I., and Tropsha, A. (1995). Rapid protein structure classification using one-dimensional structure profiles on the bioSCAN parallel computer. *Comput.Appl.Biosci.* 11, 675-679.

Joung, J. K., Ramm, E. I., and Pabo, C. O. (2000). A bacterial two-hybrid selection system for studying protein-DNA and protein-protein interactions. *Proc.Natl.Acad.Sci.U.S.A* 97, 7382-7387.

Kim, J., Harter, K., and Theologis, A. (1997). Protein-protein interactions among the Aux/IAA proteins. *Proc.Natl.Acad.Sci.U.S.A* 94, 11786-11791.

King, R. W., Peters, J. M., Tugendreich, S., Rolfe, M., Hieter, P., and Kirschner, M. W. (1995). A 20S complex containing CDC27 and CDC16 catalyzes the mitosis-specific conjugation of ubiquitin to cyclin B. *Cell* 81, 279-288.

Klein, R. M., Wolf, E. D., Wu, R., and Sanford, J. C. (1992). High-velocity microprojectiles for delivering nucleic acids into living cells. 1987 [classical article]. *Biotechnology* 24, 384-386.

Koornneef, M. and Stam, P. (1992). Genetic Analysis. In "Methods in *Arabidopsis* Research" (C. C. N. H. Koncz and J. Schell, Eds.), pp. 85-99. World Scientific, Singapore.

Krens, F. A., Molendijk, L., Wullems, G. J., and Schilperoort, R. A. (1982). In vitro transformation of plant protoplasts with Ti-plasmid DNA. *Nature* 296, 72-74.

Lamb, J. R., Michaud, W. A., Sikorski, R. S., and Hieter, P. A. (1994). Cdc16p, Cdc23p and Cdc27p form a complex essential for mitosis. *EMBO J.* 13, 4321-4328.

Langdale, J. A. (1998). Cellular differentiation in the leaf. *Curr.Opin.Cell Biol.* 10, 734-738.

Lenhard, M. and Laux, T. (1999). Shoot meristem formation and maintenance. *Curr.Opin.Plant Biol.* 2, 44-50.

Lerner, R. A. (1982). Tapping the immunological repertoire to produce antibodies of predetermined specificity. *Nature* 299, 593-596.

Lerner, R. A., Green, N., Alexander, H., Liu, F. T., Sutcliffe, J. G., and Shinnick, T. M. (1981). Chemically synthesized peptides predicted from the nucleotide sequence of the hepatitis B virus genome elicit antibodies reactive with the native envelope protein of Dane particles. *Proc.Natl.Acad. .Sci.U.S.A* 78, 3403-3407.

Leyser, H. M., Pickett, F. B., Dharmasiri, S., and Estelle, M. (1996). Mutations in the AXR3 gene of Arabidopsis result in altered auxin response including ectopic expression from the SAUR-AC1 promoter. Plant J. 10, 403-143.

Liddle, J. E. and Cryer, A. (1991). "A Practical Guide to Monoclonal Antibodies." Wiley New York.

Loffler, J., Langui, D., Probst, A., and Huber, G. (1994). Accumulation of a 50 kDa N-terminal fragment of beta-APP695 in Alzheimers disease hippocampus and neocortex. *Neurochem.Int.* 24, 281-288.

Long J. A. and Barton, M. K. (1998). The development of apical embryonic pattern in *Arabidopsis*. Development 125, 3027-3035.

Malamy, J. E. and Benfey, P. N. (1997). Organization and cell differentiation in lateral roots of *Arabidopsis thaliana*. Development 124, 33-44.

Martinez-Garcia, J. F., Monte, E. and Quail, P. H. 1999. A simple, rapid and quantitative method for preparing Arabidopsis protein extracts for immunoblot analysis. Plant J. 20: 251-257.

Masucci, J. D., Rerie, W. G., Foreman, D. R., Zhang M., Galway, M. E., Marks, M. D., and Schiefelbein, J. W. (1996). The homebox gene GLABRA2 is required for position-dependent cell differentiation in the root epidermis of *Arabidopsis thaliana*. Development 122, 1253-1260.

Maundrell K. (1990). nmt1 of fission yeast. J. Biol. Chem. 265:10857-10864.

Mayer, U., Torres Ruiz, R., Berleth, T., Misera, S., and Jürgens, G. (1991). Mutations affecting body organization in the Arabidopsis embryo. *Nature* 353, 402-407.

McSteen, P. and Hake, S. (1998). Genetic control of plant development. *Curr.Opin.Biotechnol.* 9,189-195.

Merrifield, R. B. (1963). Solid phase peptide synthesis. I. The synthesis of a tetrapeptide. *J.Amer.Chem.Soc.* 85, 2149-2154.

Mironov, V., De Veyider, L. Van Montagu, M., and Inze, D. (1999). Cyclin-dependent kinases and cell division in plants—the nexus. *Plant Cell* 11, 509-522.

Monge, A., Lathrop, E. J., Gunn, J. R., Shenkin, P. S., and Friesner, R. A. (1995). Computer modeling of protein folding: conformational and energetic analysis of reduced and detailed protein models. *J.Mol.Biol*247, 995-1012.

Morelli, G. and Ruberti, I. (2000). Shade avoidance responses. Driving auxin along lateral routes. *Plant Physiol* 122, 621-626.

Moreno, S., Klar, A., and Nurse, P. (1991). Molecular Genetic Analysis of fission yeast *Schizosaccharomyces pombe*. Methods in Enzimol. 194, 795-823.

Murakami, T., Simonds, W. F., and Spiegel, A. M. (1992). Site-specific antibodies directed against G protein beta and gamma subunits: effects on alpha and beta gamma subunit interaction. *Biochemistry* 31, 2905-2911.

Nam, H-G., Giraudat, J., den Boer, B., Moonan, F., Loos, W. D. B., Hauge, B. M. and Goodman, H (1989) Restriction fragment length polymorphism linkage map of *Arabidopsis thaliana* Plant Cell, 1, 699-705.

Nemhauser, J. L., Zambryski, P. C., and Roe, J. L. (1998). Auxin signaling in Arabidopsis flower development? *Curr.Opin.Plant Biol.* 1, 531-535.

Okasaki, K., Okasaki, N., Kume, K., Jinno, S., Tanaka, K. And Okayama, H. (1990). High-frequency transformation method and library transducing vectors for cloning mammalian cDNA by trans-complementation of *Schizosaccharomyces pombe*. Nucl. Acids Res. 18, 6485-6489.

Olszewski, K. A., Kolinski, A., and Skolnick, J. (1996). Folding simulations and computer redesign of protein A three-helix bundle motifs. *Proteins* 25, 286-299.

Onouchi, H., Nishihama, R., Kudo, M., Machida, Y., and Machida, C. (1995). Visualization of site-specific recombination catalyzed by a recombinase from *Zygosaccharomyces rouxii* in *Arabidopsis thaliana*. *Mol.Gen.Genet.* 247, 653-660.

Onouchi, H., Yokoi, K., Machida, C., Matsuzaki, H., Oshima, Y., Matsuoka, K., Nakamura, K., and Machida, Y. (1991). Operation of an efficient site-specific recombination system of *Zygosaccharomyces rouxii* in tobacco cells. *Nucleic Acids Res.* 19, 6373-6378.

Osborne, B. I., Wirtz, U., and Baker, B. (1995). A system for insertional mutagenesis and chromosomal rearrangement using the Ds transposon and Cre-lox. *Plant J.* 7, 687-701.

Ostresh, J. M., Blondelle, S. E., Domer, B., and Houghten, R. A. (1996). Generation and use of nonsupport-bound peptide and peptidomimetic combinatorial libraries. *Methods Enzymol.* 267, 220-234.

Pabo, C. O. and Suchanek, E. G. (1986). Computer-aided model-building strategies for protein design. *Biochemistry* 25, 5987-5991.

Palme, K. and Galweiler, L. (1999). PIN-pointing the molecular basis of auxin transport. *Curr.Opin.Plant Biol.* 2, 375-381.

Paszkowski, J., Shillito, R. D., Saul, M., Mandak, V., and Hohn, T. H. B. P. I. (1984). Direct gene transfer to plants. *EMBO J.* 3, 2717-2722.

Peleman, J., Boerjan, W., Engler, G., Seurinck, J., Botterman, J., Alliotte, T., Van Montagu, M., and Inze, D. (1989). Strong cellular preference in the expression of a housekeeping gene of *Arabidopsis thaliana* encoding S-adenosylmethionine synthetase. *Plant Cell* 1, 81-93.

Peralta, E. G., Hellmiss, R., and Ream, W. (1986). Overdrive, a T-DNA transmission enhancer on the A. tumefaciens tumour-inducing plasmid. *EMBO J.* 5, 1137-1142.

Peters, J. M., King, R. W., Hoog, C., and Kirschner, M. W. (1996). Identification of BIME as a subunit of the anaphase-promoting complex. *Science* 274, 1199-1201.

Pnueli, L., Carmel-Goren, L., Hareven, D., Guffinger, T., Alvarez, J., Ganal, M., Zamir, D., and Lifschitz, E. (1998). The SELF-PRUNING gene of tomato regulates vegetative to reproductive switching of sympodial meristems and is the ortholog of CEN and TFL1. *Development* 125, 1979-1989.

Ouellet, F., Overvoorde, P. J. and Theologis, A. 2001. IAA17/AXR3: biochemical insight into an auxin mutant phenotype. Plant Cell 13: 829-841.

Reed, S. I. (1996). G1/S regulatory mechanisms from yeast to man. *Prog.Cell Cycle Res.* 2,15-27.

Reiter, R. S., Williams, J. G., Feldman, K. A., Rafalski, J. A., Tingey, S. V. and Scolnik, P. A. (1992) Global and local genome mapping in *Arabidopsis thaliana* by using recombinant inbred lines and random amplified polymorphic DNA's. Proc. Natl. Acad. Sci. U.S.A. 89, 1477-1481

Renouf, D. V. and Hounsell, E. F. (1995). Molecular modelling of glycoproteins by homology with non-glycosylated protein domains, computer simulated glycosylation and molecular dynamics. *Adv.Exp.Med.Biol* 376, 37-45.

Rose, R. B., Craik, C. S., Douglas, N. L., and Stroud, R. M. (1996). Three-dimensional structures of HIV-1 and SIV protease product complexes. *Biochemistry* 35, 12933-12944.

Rotino, G. L., Perri, E., Zottini, M., Sommer, H., and Spena, A. (1997). Genetic engineering of parthenocarpic plants [see comments]. *Nat.Biotechnol.* 15,1398-1401.

Rouse, D., Mackay, P., Stirnberg, P., Estelle, M., and Leyser, O. (1998). Changes in auxin response from mutations in an AUX/IAA gene. *Science* 279,1371-1373.

Rutenber, E. E., McPhee, F., Kaplan, A. P., Gallion, S. L., Hogan, J. C., Jr., Craik, C. S., and Stroud, R. M. (1996). A new class of HIV-1 protease inhibitor: the crystallographic structure, inhibition and chemical synthesis of an aminimide peptide isostere. *Bioorg.Med.Chem.* 4,1545-1558.

Sabatini, S., Beis, D., Wokenfelt, H., Murfett J., Guilfoyle, T., Malamy J., Benfey, P., Leyser, O., Bechtold, N., Weisbeek, P., and Scheres, B. (1999). An auxin-dependent distal organizer of pattern and polarity in the Arabidopsis root. *Cell* 99, 463-472.

Sambrook, J., and Russel (2001). "Molecular Cloning: A Laboratory Manual." Third edition. Cold Spring Harbor Laboratory Press.

Sambrook, J., Fritsch, E. F., and Maniatis, T. (1989). "Molecular Cloning: A Laboratory Manual." Cold Spring Harbor Laboratory Press.

Scheres, B. and Berleth, T. (1998). Root development: new meanings for root canals? *Curr.Opin.Plant Biol.* 1, 32-36.

Scheres, B., Di Laurenzio, L., Willemsen, V., Hauser, M.-T., Janmaat, K., Weisbeek, P., and Benfey, P. N. (1995). Mutations affecting the radial organisation of the Arabidopsis root display specific defects throughout the embryonic axis. *Development* 121, 53-62.

Scheres, B., Wolkenfelt, H., Willemsen, V., Terlouw, M., Lawson, E., Dean, C., and Weisbeek, P. (1994). Embryonic origin of the Arabidopsis primary root and root meristem initials. *Development* 120, 2475-2487.

Schlappi, M., Smith, D., and Fedoroff, N. (1993). TnpA trans-activates methylated maize Suppressor-mutator transposable elements in transgenic tobacco. *Genetics* 133, 1009-1021.

Semler, B. L., Anderson, C. W., Hanecak, R., Dorner, L. F., and Wimmer, E. (1982). A membrane-associated precursor to poliovirus VPg identified by immunoprecipitation with antibodies directed against a synthetic heptapeptide. *Cell* 28, 405-412.

Sessions, A., Nemhauser, J. L., McColl, A., Roe, J. L., Feldmann, K. A., and Zambryski, P. C. (1997). ETTIN patterns the Arabidopsis floral meristem and reproductive organs. *Development* 124, 4481-4491.

Shioda, T., Andriole, S., Yahata, T., and Isselbacher, K. J. (2000). A green fluorescent protein-reporter mammalian two-hybrid system with extrachromosomal maintenance of a prey expression plasmid: Application to interaction screening. *Proc.Natl.Acad.Sci.U.S.A* 97, 5220-5224.

Small, I. D. and Peeters, N. (2000). The PPR motif—a TPR-related motif prevalent in plant organellar proteins. *Trends Biochem.Sci.* 25, 46-47.

Steinmann, T., Geldner, N., Grebe, M., Mangold, S., Jackson, C. L., Paris, S., Galweiler, L., Palme, K., and Jurgens, G. (1999). Coordinated polar localization of auxin efflux carrier PIN1 by GNOM ARF GEF. *Science* 286, 316-318.

Sudakin, V., Ganoth, D., Dahan, A., Heller, H., Hershko, J., Luca, F. C., Ruderman, J. V., and Hershko, A. (1995). The cyclosome, a large complex containing cyclin-selective ubiquitin ligase activity, targets cyclins for destruction at the end of mitosis. *Mol.Biol.Cell* 6,185-197.

Sugita, K., Kasahara, T., Matsunaga, E., and Ebinuma, H. (2000). Technical advance: A transformation vector for the production of marker-free transgenic plants containing a single copy transgene at high frequency [In Process Citation]. *Plant J.* 22, 461-469.

Talon, M., Koornneef, M. And Zeevaart, J. A. (199) Endogenous gibberilins in *Arabidopsis thaliana* and possible steps blocked in the biosynthetic pathway of the semidwarf ga4 and ga5 mutants. Proc. Natl. Acad.Sci. U.S.A. 87, 7983-7987.

Tamura, R. N., Cooper, H. M., Collo, G., and Quaranta, V. (1991). Cell type-specific integrin variants with alternative alpha chain cytoplasmic domains. *Proc.Natl.Acad.Sci.U.S.A* 88, 10183-10187.

Theologis, A., Huynh, T. V., and Davis, R. W. (1985). Rapid induction of specific mRNAs by auxin in pea epicotyl tissue. *J.Mol.Biol.* 183, 53-68.

Trieu, A. T., Burleigh, S. H., Kardailsky, I. V., Maldonado-Mendoza, I. E., Versaw, W. K., Blaylock, L. A., Shin, H., Chiou, T. J., Katagi, H., Dewbre, G. R., Weigel, D., and Harrison, M. J. (2000). Technical Advance: Transformation of Medicago truncatula via infiltration of seedlings or flowering plants with Agrobacterium. *Plant J.* 22, 531-541.

Tyers, M. and Jorgensen, P. (2000). Proteolysis and the cell cycle: In this RING I do thee destroy. *Curr.Opin.Genet.Dev.* 10, 54-64.

Ulmasov, T., Murfett, J., Hagen, G., and Guilfoyle, T. J. (1997). Aux/IAA proteins repress expression of reporter genes containing natural and highly active synthetic auxin response elements. *Plant Cell* 9, 1963-1971.

Ulmasov, T., Hagen G., and Guilfoyle, T. J. (1997b). ARF1, a transcription factor that binds to auxin response elements. *Science* 276,1865-1868.

van Haaren, M. J., Sedee, N. J., Schilperoort, R. A., and Hooykaas, P. J. (1987). Overdrive is a T-region transfer enhancer which stimulates T-strand production in *Agrobacterium tumefaciens*. *Nucleic Acids Res.* 15, 8983-8997.

Van Sluys, M. A., Tempe, J., and Fedoroff, N. (1987). Studies on the introduction and mobility of the maize Activator element in *Arabidopsis thaliana* and *Daucus carota*. *EMBO J.* 6, 3881-3889.

Walker, L. and Estelle, M. (1998). Molecular mechanisms of auxin action. *Curr.Opin.Plant Biol.* 1, 434-439.

Wang, K., Genetello, C., Van Montagu, M., and Zambryski, P. C. (1987). Sequence context of the T-DNA border repeat element determines its relative activity during T-DNA transfer to plant cells. *Mol.Gen.Genet.* 210, 338-346.

Wang, M. and Sternberg, P. W. (1999). Competence and commitment of *Caenorhabditis elegans* vulval precursor cells. Dev. Biol. 212,12-24.

Wilkinson, D. G. and Nieto, M. A. (1993). Detection of messenger RNA by in situ hybridization to tissue sections and whole mounts. Methods Enzymol. 225, 361-373.

Willemsen, V., Wolkenfelt, H., de Vrieze, G., Weisbeek, P., and Scheres, B. (1998). The HOBBIT. gene is required for formation of the root meristem in the Arabidopsis embryo. *Development* 125, 521-531.

Wodak, S. J. (1987). Computer-aided design in protein engineering. *Ann.N.Y.Acad.Sci.* 501,1-13.

Worley, C. K., Zenser, N., Ramos, J., Rouse, D., Leyser, O., Theologis, A., and Callis, J. (2000). Degradation of Aux/IAA proteins is essential for normal auxin signalling. *Plant J.* 21, 553-562.

Woulfe, J., Lafortune, L., de Nadai, F., Kitabgi, P., and Beaudet, A. (1994). Post-translational processing of the neurotensin/neuromedin N precursor in the central nervous system of the rat-II. Immunohistochemical localization of maturation products. *Neuroscience* 60, 167-181.

Yamamoto, K. T., Mori, H., and Imaseki, H. (1992). Novel mRNA sequences induced by indole-3-acetic acid in sections of elongating hypocotyls of mung bean (*Vigna radiata*). *Plant Cell. Physiol.* 33, 13-20.

Zhang, Y. L., Dawe, A. L., Jiang, Y., Becker, J. M., and Naider, F. (1996). A superactive peptidomimetic analog of a farnesylated dodecapeptide yeast pheromone. *Biochem.Biophys.Res.Commun.* 224, 327-331.

The invention claimed is:

1. A method for modulating or mimicking auxin-related effects in a plant or a plant cell, said method comprising introducing and expressing a nucleic acid molecule encoding the amino acid sequence of SEQ ID NO:9 in the plant cell or in cells of a plant, wherein the transformed plant or plant cell exhibits auxin-related effects.

2. The method of claim 1, wherein the modulating or mimicking of auxin-related effects in a plant results in an increased yield in the transformed plant compared to a non-transformed plant.

3. The method of claim 1, wherein the modulating or mimicking of auxin related effects in a plant results in an increased survival rate of transformed plants compared to non-transformed plants.

4. The method of claim 1, wherein the modulating or mimicking of auxin related effects in a plant results in an increased survival rate of transformed plants under drought conditions compared to non-transformed plants.

5. The method of claim 1, wherein the modulating or mimicking of auxin related effects in a plant results in an increase in seedling emergence compared to non-transformed plants.

6. The method of claim 1, wherein the modulating or mimicking of auxin related effects in a plant cell results in the mimicking of root generation in tissue cultures of the transformed cell compared to a non-transformed cell.

7. The method of claim 1, wherein the modulating or mimicking of auxin related effects in a plant results in an increased shade avoidance response in the transformed plant compared to a non-transformed plant.

8. The method of claim 1, wherein the modulating or mimicking of auxin related effects in a plant results in stimulating vascular strand formation and patterning in the transformed plant compared to a non-transformed plant.

9. The method of claim 1, wherein the modulating or mimicking of auxin related effects in a plant results in the production of parthenocarpic fruits in the transformed plant.

10. The method of claim 1, wherein the plant cell or cells are cycling cell or cells.

11. The method of claim 10, wherein the cycling cells are in particular domains, tissues, or organs of the plant.

12. The method of any one of claims 1 or 2-10, wherein the nucleic acid molecule encoding the amino acid sequence of SEQ ID NO:9 is set forth in SEQ ID NO:3.

* * * * *